United States Patent
Koenen et al.

(10) Patent No.: US 12,279,521 B2
(45) Date of Patent: Apr. 15, 2025

(54) MATERIALS FOR ORGANIC ELECTROLUMINESCENT DEVICES

(71) Applicant: Merck Patent GmbH, Darmstadt (DE)

(72) Inventors: Nils Koenen, Griesheim (DE); Anna Hayer, Darmstadt (DE); Florian Maier-Flaig, Weinheim (DE); Jochen Pfister, Seeheim-Jugenheim (DE); Holger Heil, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 789 days.

(21) Appl. No.: 17/423,686

(22) PCT Filed: Jan. 15, 2020

(86) PCT No.: PCT/EP2020/050845
§ 371 (c)(1),
(2) Date: Jul. 16, 2021

(87) PCT Pub. No.: WO2020/148303
PCT Pub. Date: Jul. 23, 2020

(65) Prior Publication Data
US 2022/0140245 A1    May 5, 2022

(30) Foreign Application Priority Data
Jan. 17, 2019 (EP) .................................. 19152285

(51) Int. Cl.
*H10K 85/60*      (2023.01)
*C07C 13/567*   (2006.01)
*H10K 50/11*     (2023.01)
*H10K 101/10*   (2023.01)

(52) U.S. Cl.
CPC ......... *H10K 85/615* (2023.02); *C07C 13/567* (2013.01); *H10K 85/654* (2023.02); *H10K 85/6572* (2023.02); *C07C 2603/18* (2017.05); *H10K 50/11* (2023.02); *H10K 2101/10* (2023.02)

(58) Field of Classification Search
CPC ............... H10K 85/615; C07C 13/567; C07C 2603/18
See application file for complete search history.

(56) References Cited

U.S. PATENT DOCUMENTS

| | | | |
|---|---|---|---|
| 2011/0037027 A1* | 2/2011 | Stoessel ................ | C07C 255/51 548/440 |
| 2012/0228554 A1* | 9/2012 | Franz ................... | C07D 251/24 252/301.16 |
| 2013/0200359 A1* | 8/2013 | Stoessel ................ | C07D 405/14 548/440 |
| 2018/0354931 A1* | 12/2018 | He ....................... | C07D 407/10 |

FOREIGN PATENT DOCUMENTS

| CN | 105254561 A | 1/2016 | |
|---|---|---|---|
| CN | 107353281 A | 11/2017 | |
| CN | 108203417 A | 6/2018 | |
| KR | 10-2015-0113642 A1 | 10/2015 | |
| KR | 20150113642 A | * 10/2015 | |
| KR | 20170126691 A | * 11/2017 | |
| WO | WO-2009124627 A1 | * 10/2009 | ........... C07C 13/567 |
| WO | 2010/108579 A1 | 9/2010 | |
| WO | WO-2016184540 A1 | * 11/2016 | ........... C07C 13/567 |
| WO | 2019/000494 A1 | 1/2019 | |

OTHER PUBLICATIONS

Machine Translation of KR20150113642A (Year: 2015).*
Machine Translation of KR20170126691A (Year: 2017).*
Machine Translation of WO2009124627A1 (Year: 2009).*
International Search Report and Written Opinion received for PCT Patent Application No. PCT/EP2020/050845, mailed on Feb. 28, 2020, 14 pages (6 pages of English Translation and 8 pages of Original Document).
International Preliminary Report on Patentability received for PCT Patent Application No. PCT/EP2020/087423, mailed on Jul. 29, 2021, 12 pages (6 pages of English Translation and 6 pages of Original Document).

\* cited by examiner

*Primary Examiner* — Jenna N Chandhok

(74) *Attorney, Agent, or Firm* — Faegre Drinker Biddle & Reath LLP

(57) ABSTRACT

The invention relates to fluorene derivatives and electronic devices, particularly organic electroluminescent devices in which said compounds are used, particularly as a matrix material for phosphorescent emitters.

17 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2020/050845, filed Jan. 15, 2020, which claims benefit of European Application No. 19152285.3, filed Jan. 17, 2019, both of which are incorporated herein by reference in their entirety.

The present invention relates to materials for use in electronic devices, especially in organic electroluminescent devices.

Emitting materials used in organic electroluminescent devices (OLEDs) are frequently phosphorescent organometallic complexes. In general terms, there is still a need for improvement in OLEDs, especially also in OLEDs which exhibit triplet emission (phosphorescence), for example with regard to efficiency, operating voltage and lifetime. The properties of phosphorescent OLEDs are not just determined by the triplet emitters used. More particularly, the other materials used, such as matrix materials, are also of particular significance here. Improvements to these materials can thus also lead to improvements in the OLED properties. For instance, there is still a need for improvement especially in the lifetime and efficiency of solution-processed or at least partly solution-processed organic electroluminescent devices. An additional requirement is for the compounds to have sufficiently high solubility in standard organic solvents for processing from solution. In order to be able to bake the device after application of a layer from solution and also for application at elevated temperature, a high glass transition temperature is essential. There is therefore still a need for improved materials.

Matrix materials used for phosphorescent emitters are typically compounds having hole- and/or electron-transporting properties. It may be advantageous, in addition to these materials, to use further matrix materials that have neither hole- nor electron-conducting properties and hence are not involved to a significant degree, if at all, in charge transport within the OLED (WO 2010/108579). WO 2009/124627 and WO 2016/184540 disclose 9,9-diphenylfluorene derivatives substituted on the phenyl groups by further aryl groups. There is no disclosure of fluorene derivatives substituted in the 4 position of the fluorene.

It has been found that, surprisingly, 9,9-diphenylfluorene derivatives which are each substituted in the 3' position on at least one phenyl group and preferably on both phenyl groups and which simultaneously have an aromatic substituent in the 4 position on the fluorene base skeleton are of very good suitability for use in organic electroluminescent devices and lead to distinct improvements over the prior art therein. The present invention therefore provides these compounds and for the use thereof in electronic devices. These compounds are especially suitable as wide bandgap materials for use in the emitting layer of a phosphorescent OLED.

The materials according to the invention have a higher glass transition temperature than corresponding materials that otherwise have the same structure but have no aromatic group bonded in the 4 position of the fluorene base skeleton. As a result, the layer can be baked at a higher temperature after production from solution. In addition, the compounds have improved solubility. By comparison with OLEDs comprising compounds containing a corresponding aromatic group bonded in the 2 position rather than in the 4 position of the fluorene, OLEDs comprising the compounds according to the invention have an improved lifetime.

For the sake of clarity, the numbering of 9,9-diphenylfluorene is shown below:

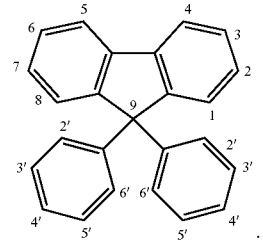

The invention provides compounds of the following formula (1):

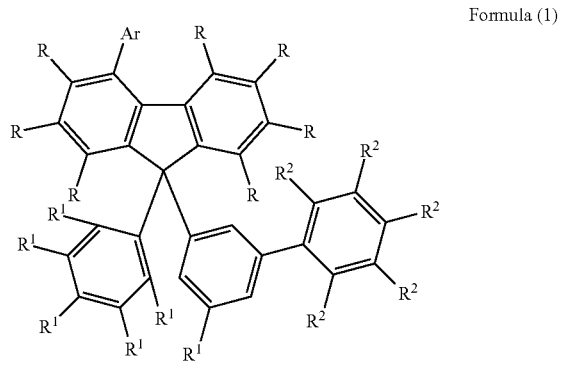

Formula (1)

where the symbols used are as follows:

Ar is an aromatic ring system which has 6 to 30 aromatic ring atoms and may be substituted by one or more $R^3$ radicals, or a dibenzofuran or dibenzothiophene group, each of which may be substituted by one or more $R^3$ radicals, or a combination of an aromatic ring system having 6 to 18 aromatic ring atoms and a dibenzofuran or dibenzothiophene group, where these groups may each be substituted by one or more $R^3$ radicals; Ar here may form a ring system together with the adjacent substituent R;

R is the same or different at each instance and is H, D, a straight-chain alkyl or alkoxy group having 1 to 20 carbon atoms or a branched or cyclic alkyl or alkoxy group having 3 to 20 carbon atoms or an alkenyl group having 2 to 20 carbon atoms, where the alkyl, alkoxy or alkenyl group may in each case be substituted by one or more $R^3$ radicals, where one or more hydrogen atoms may be replaced by D, or an aromatic ring system which has 6 to 30 aromatic ring atoms and may be substituted by one or more $R^3$ radicals, or a dibenzofuran or dibenzothiophene group, each of which may be substituted by one or more $R^3$ radicals; it is also possible here for two or more adjacent substituents R together to form a mono- or polycyclic aliphatic ring system; in addition, it is possible for R with an adjacent Ar group to form a ring system;

$R^1$, $R^2$ is the same or different at each instance and is H, D, a straight-chain alkyl or alkoxy group having 1 to 20 carbon atoms or a branched or cyclic alkyl or alkoxy group having 3 to 20 carbon atoms or an alkenyl group having 2 to 20 carbon atoms, where the alkyl, alkoxy or alkenyl group may in each case be substituted by one or more $R^3$ radicals, where one or more hydrogen atoms may be replaced by D, or an aromatic ring system which has 6 to 30 aromatic ring atoms and may be substituted by one or more $R^3$ radicals, or a dibenzofuran or dibenzothiophene group, each of which may be substituted by one or more $R^3$ radicals; it is possible here for multiple adjacent substituents $R^1$ together to form a ring system; in addition, it is possible for multiple adjacent substituents $R^2$ together to form a ring system;

$R^3$ is the same or different at each instance and is H, D, a straight-chain alkyl or alkoxy group having 1 to 20 carbon atoms or a branched or cyclic alkyl or alkoxy group having 3 to 20 carbon atoms, where the alkyl or alkoxy group may in each case be substituted by one or more $R^4$ radicals, where one or more hydrogen atoms may be replaced by D, or an aromatic ring system which has 6 to 30 aromatic ring atoms and may be substituted by one or more $R^4$ radicals, or a dibenzofuran or dibenzothiophene group, each of which may be substituted by one or more $R^4$ radicals; it is also possible here for two or more adjacent substituents $R^3$ together to form a ring system;

$R^4$ is the same or different at each instance and is H, D or an aliphatic and/or aromatic hydrocarbyl radical having 1 to 20 carbon atoms.

An aryl group in the context of this invention contains 6 to 30 carbon atoms. An aryl group is understood to mean either a simple aromatic cycle, i.e. benzene, or a fused aryl group, for example naphthalene, anthracene, pyrene, etc. An aromatic ring system in the context of this invention contains 6 to 30 carbon atoms in the ring system. An aromatic ring system in the context of this invention is understood to mean a system which does not necessarily contain only aryl groups, but in which it is also possible for multiple aryl groups to be interrupted by a short nonaromatic unit (preferably less than 10% of the atoms other than H), for example an sp³-hybridized carbon atom. For example, systems such as 9,9'-spirobifluorene or 9,9-diarylfluorene, etc. shall also be regarded as aromatic ring systems in the context of this invention. An aromatic ring system is likewise understood to mean systems in which multiple aryl groups are joined to one another by single bonds, for example biphenyl or terphenyl.

In the context of the present invention, a $C_1$- to $C_{20}$-alkyl group in which individual hydrogen atoms or $CH_2$ groups may also be replaced by the abovementioned groups is more preferably understood to mean methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl and 2-ethylhexyl. In the context of this invention, an alkenyl group is especially understood to mean ethenyl, propenyl, butenyl, pentenyl, cyclopentenyl, hexenyl, cyclohexenyl, heptenyl, cycloheptenyl, octenyl and cyclooctenyl. A $C_1$- to $C_{20}$-alkoxy group is more preferably understood to mean methoxy, trifluoromethoxy, ethoxy, n-propoxy, i-propoxy, n-butoxy, i-butoxy, s-butoxy, t-butoxy or 2-methylbutoxy. An aromatic ring system which has 5 to 30 aromatic ring atoms and may be joined to the aromatic system via any positions is especially understood to mean groups derived from benzene, naphthalene, anthracene, phenanthrene, benzanthracene, pyrene, chrysene, perylene, fluoranthene, naphthacene, pentacene, benzpyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene or spiroisotruxene.

When multiple adjacent substituents together form a ring system, this may be mono- or polycyclic, and it may be aliphatic or aromatic. The wording that two or more radicals together may form a ring, in the context of the present description, should be understood to mean, inter alia, that the two radicals are joined to one another by a chemical bond with formal elimination of two hydrogen atoms. This is illustrated by the following scheme:

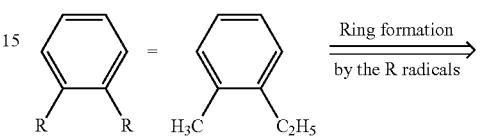

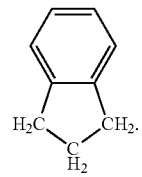

In addition, however, the abovementioned wording should also be understood to mean that, if one of the two radicals is hydrogen, the second radical binds to the position to which the hydrogen atom was bonded, forming a ring. This shall be illustrated by the following scheme:

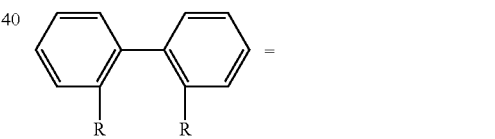

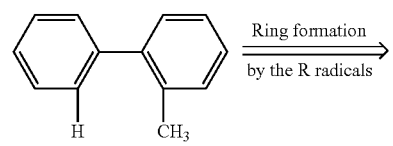

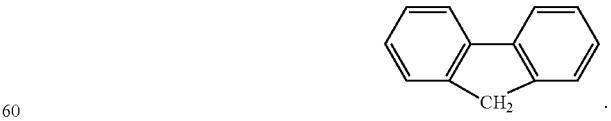

In a preferred embodiment of the invention, the compound of the formula (1) is selected from the compounds of the following formulae (2a), (2b) and (2c):

Formula (2a)

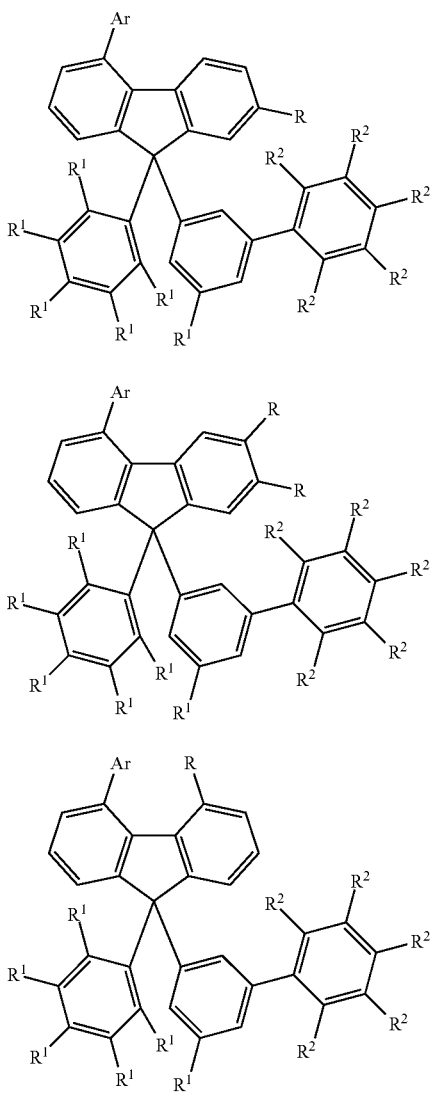

Formula (2b)

Formula (2c)

where the symbols used have the meanings given above.

In a further preferred embodiment of the invention, the compound of the formula (1) is selected from the compounds of the following formulae (3a) and (3b):

Formula (3a)

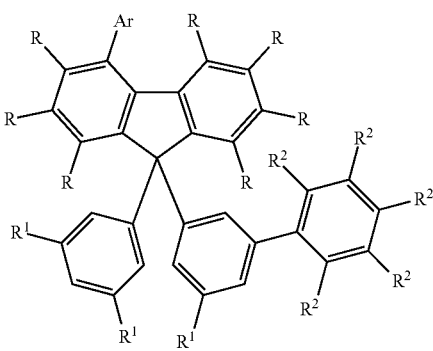

Formula (3b)

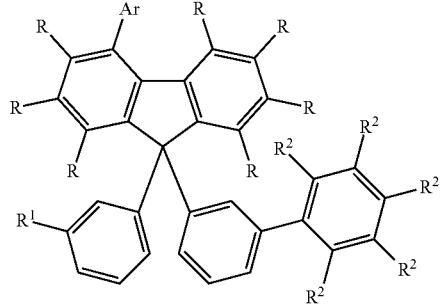

where the symbols used have the meanings given above.

More preferably, the compound of the formula (1) is selected from the compounds of the following formulae (4a) to (4f):

Formula (4a)

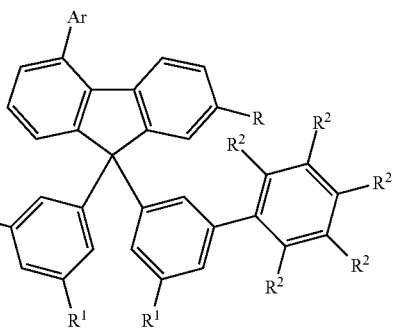

Formula (4b)

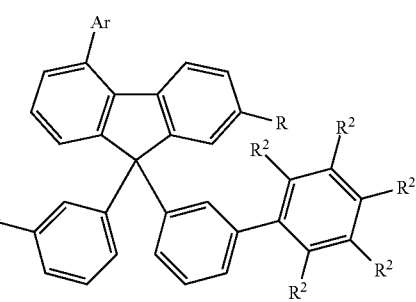

Formula (4c)

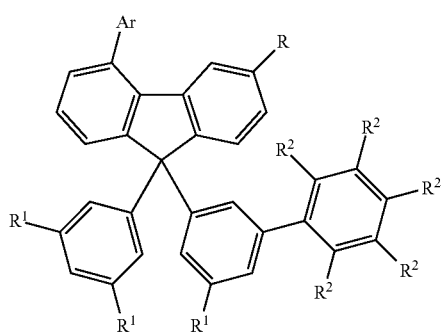

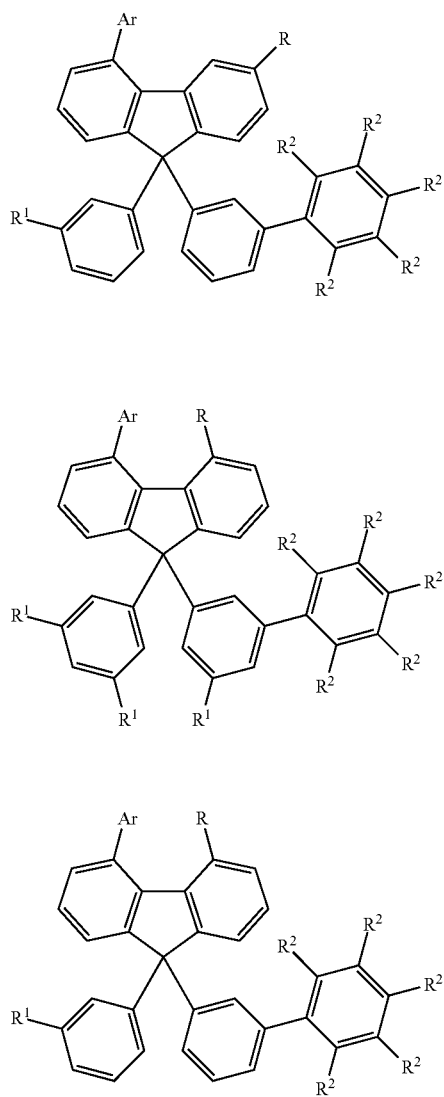

Formula (4d)

Formula (4e)

Formula (4f)

where the symbols used have the meanings given above.

In a further preferred embodiment of the invention, the compound of the formula (1) is selected from the compounds of the following formula (5):

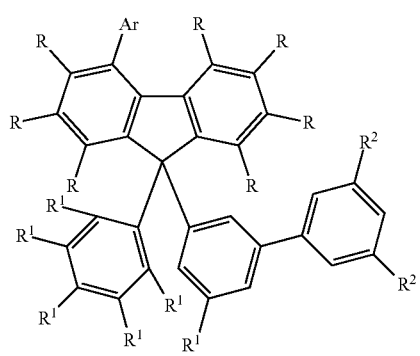

Formula (5)

where the symbols used have the meanings given above.

Particular preference is given to the compounds of the following formulae (6a) to (6f):

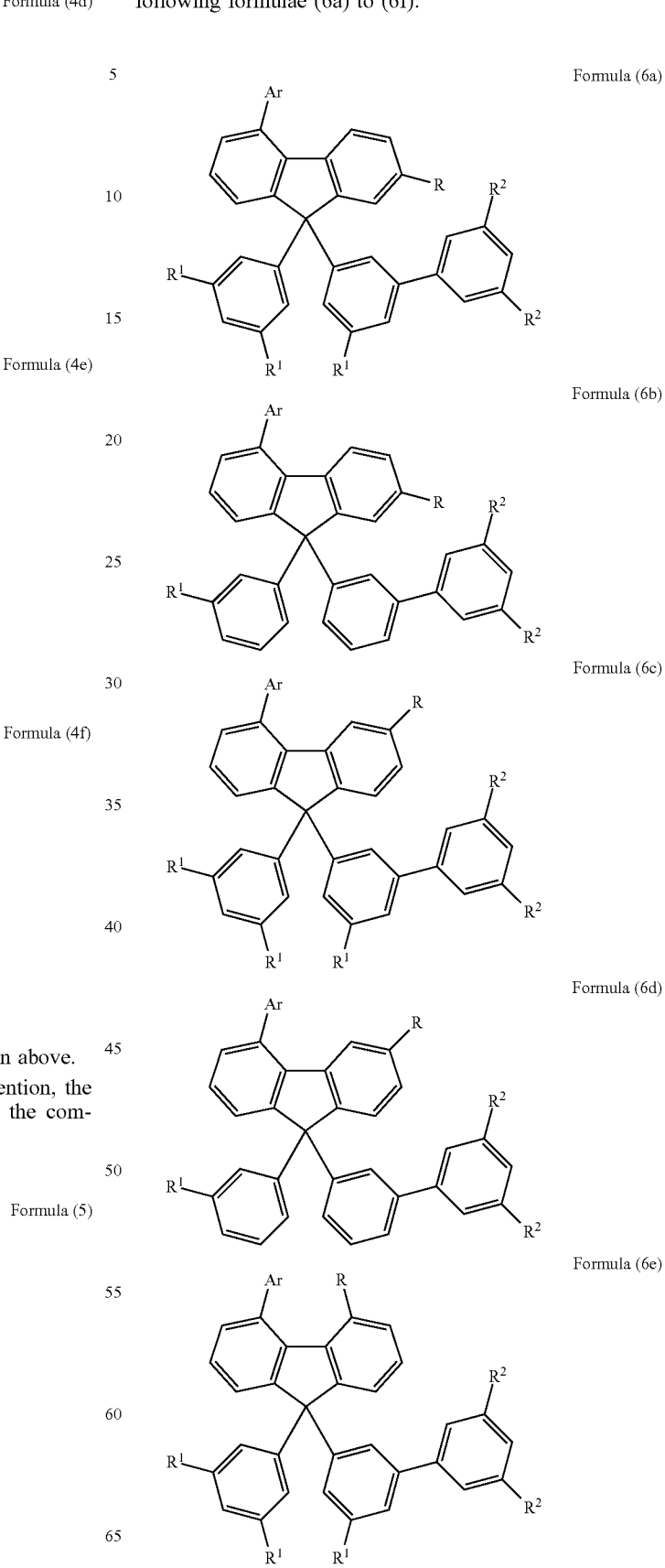

Formula (6a)

Formula (6b)

Formula (6c)

Formula (6d)

Formula (6e)

Formula (6f)

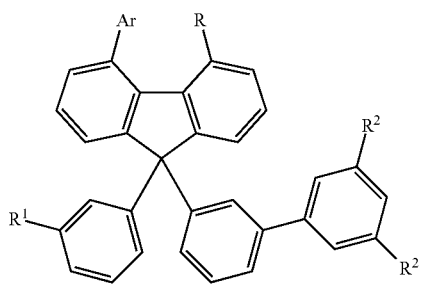

where the symbols used have the meanings given above.

There follows a description of preferred embodiments of the Ar, R, $R^1$, $R^2$, $R^3$ and $R^4$ groups. In a particularly preferred embodiment of the invention, the preferences specified hereinafter for Ar, R, $R^1$, $R^2$, $R^3$ and $R^4$ occur simultaneously and are applicable to the structures of the formula (1) and to all preferred embodiments detailed above.

In a preferred embodiment of the invention, Ar is an aromatic ring system which has 6 to 24 aromatic ring atoms and may be substituted by one or more preferably nonaromatic $R^3$ radicals, or a dibenzofuran or dibenzothiophene group which may be substituted in each case by one or more preferably nonaromatic $R^3$ radicals. In a particularly preferred embodiment of the invention, Ar is an aromatic ring system which has 6 to 18 aromatic ring atoms, especially 6 to 12 aromatic ring atoms, and may be substituted in each case by one or more preferably nonaromatic $R^3$ radicals.

Suitable Ar groups are selected from the group consisting of phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene which may be joined via the 1 or 2 position, dibenzofuran which may be joined via the 1, 2, 3 or 4 position, dibenzothiophene which may be joined via the 1, 2, 3 or 4 position, phenanthrene, triphenylene or a combination of these groups, each of which may be substituted by one or more preferably nonaromatic $R^3$ radicals.

Ar here is preferably selected from the groups of the following formulae Ar-1 to Ar-26:

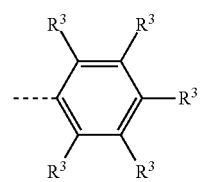
Ar-1

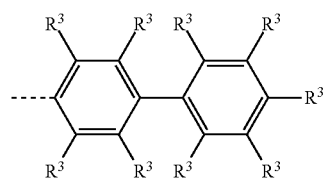
Ar-2

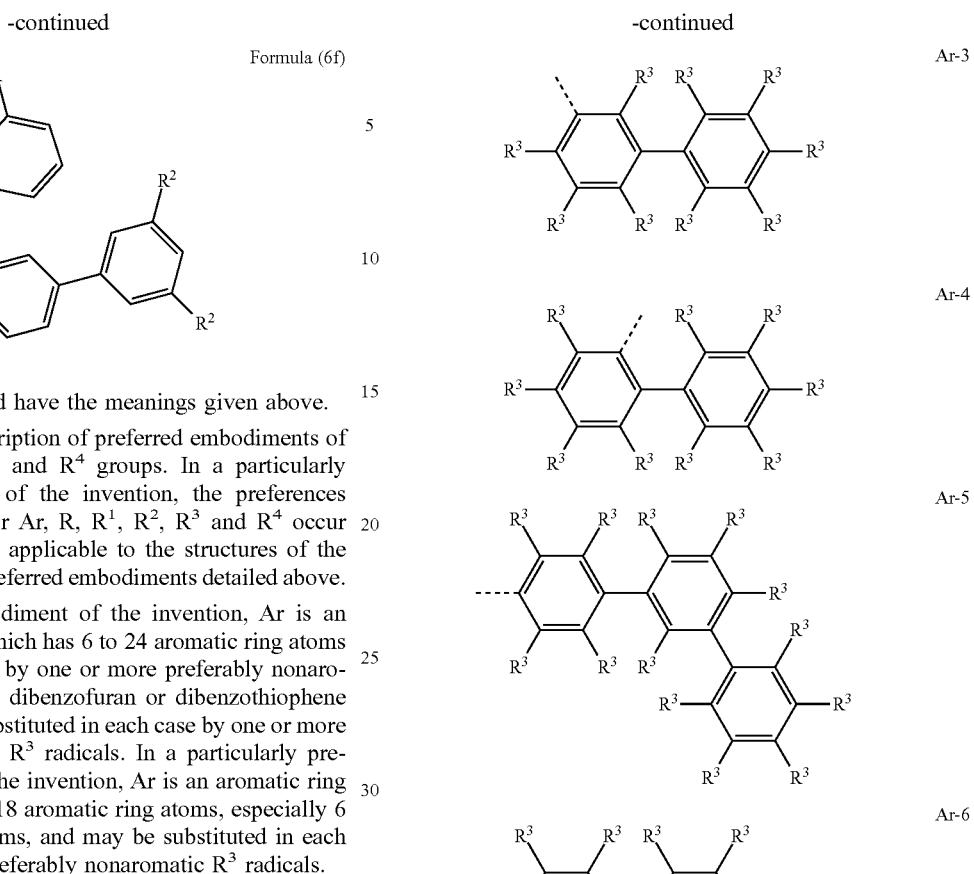

Ar-3

Ar-4

Ar-5

Ar-6

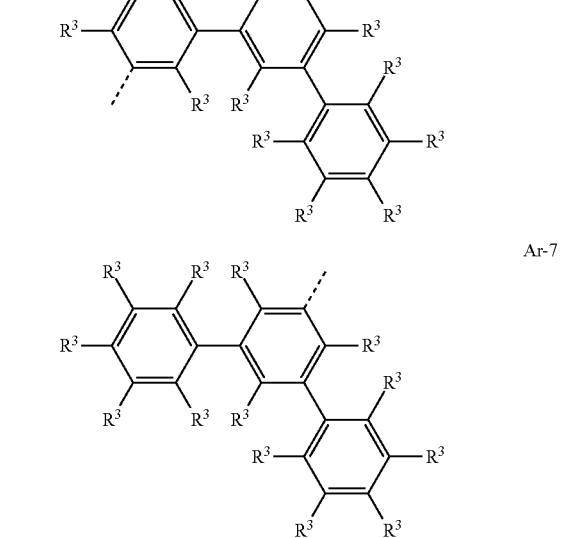
Ar-7

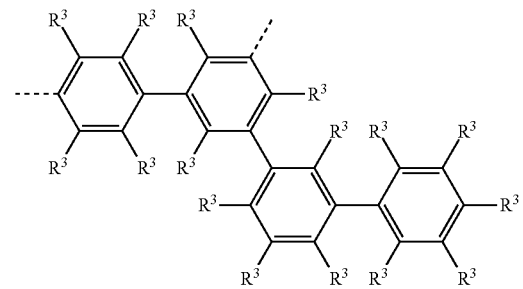
Ar-8

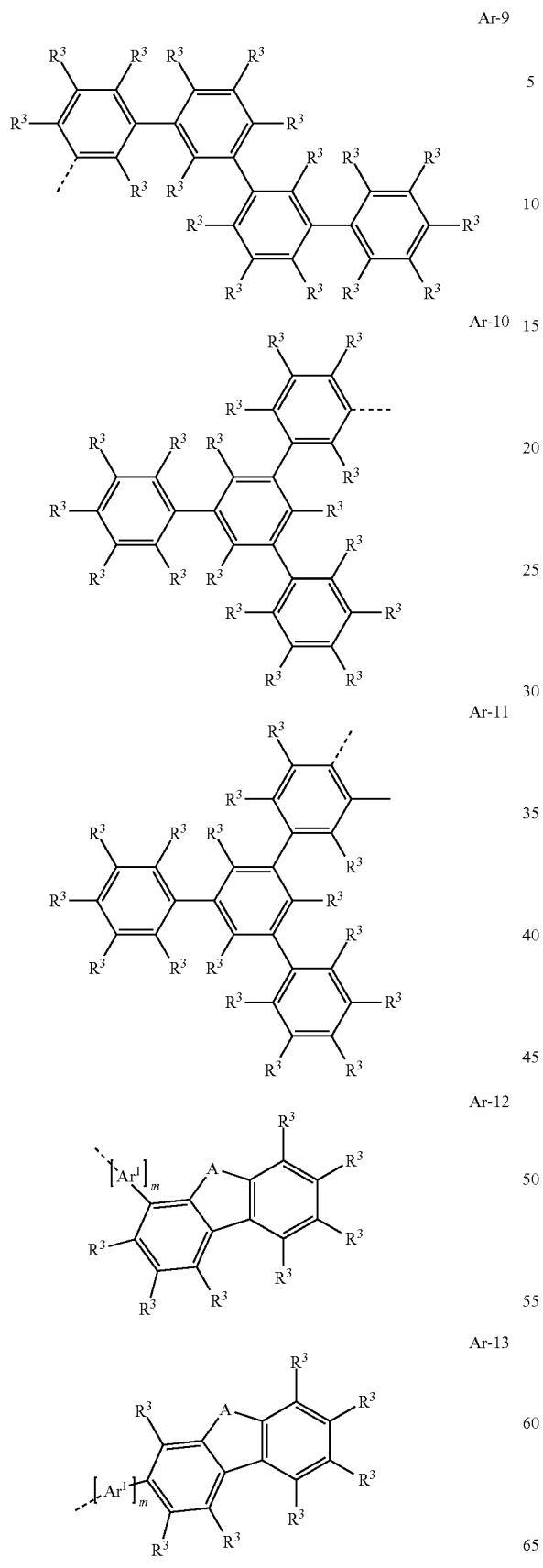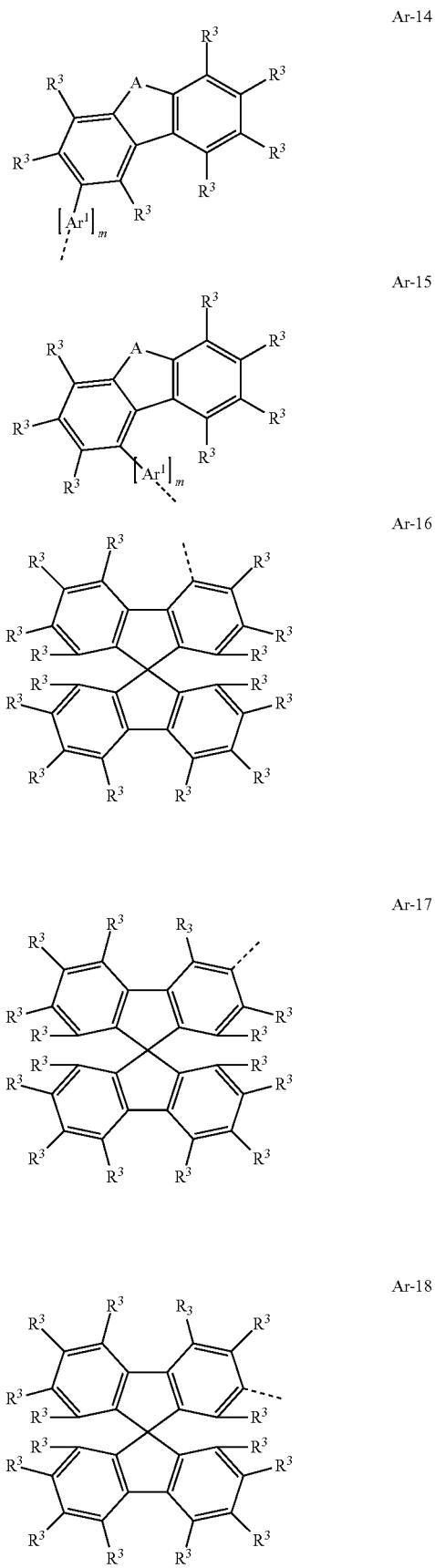

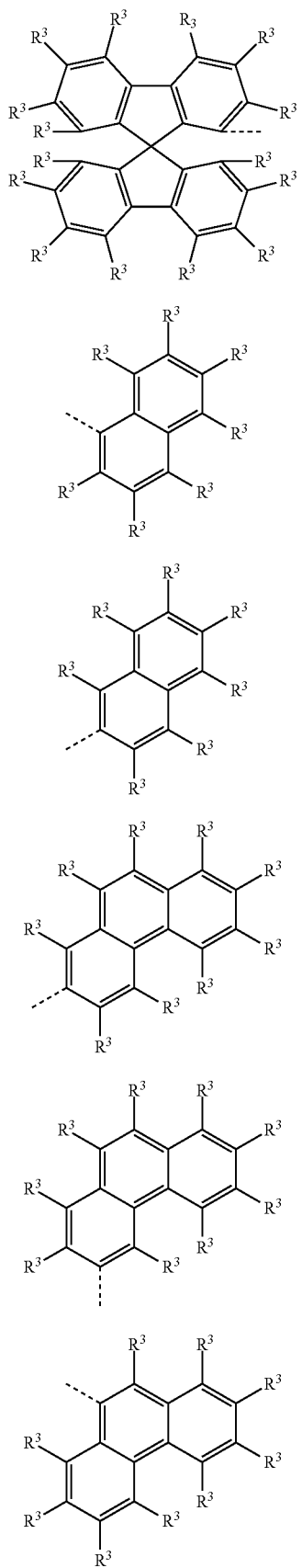

Ar-19
Ar-20
Ar-21
Ar-22
Ar-23
Ar-24

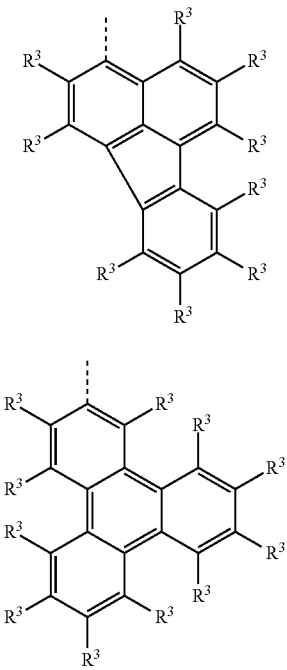

Ar-25
Ar-26 where $R^3$ is as defined above, the dotted bond represents the bond to the fluorene base skeleton and, in addition:

Ar$^1$ is the same or different at each instance and is a bivalent aromatic ring system which has 6 to 12 aromatic ring atoms and may be substituted in each case by one or more $R^3$ radicals;

A is the same or different at each instance and is $C(R^3)_2$, O or S;

m is 0 or 1, where m=0 means that the Ar$^1$ group is absent and that the corresponding aromatic or heteroaromatic group is bonded directly to the fluorene base skeleton.

In a further embodiment of the invention, Ar is a phenyl group, the R group adjacent to the Ar group is a $CH(R^3)_2$ group, and Ar and R together form a ring system, so as to form a compound of the following formula (7a) or (7b):

Formula (7a)

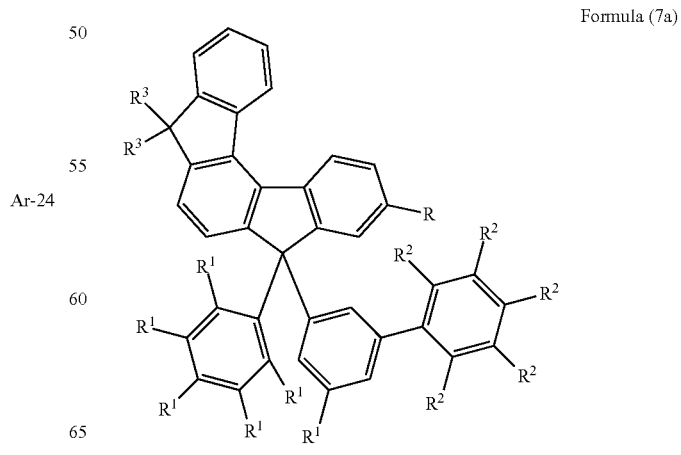

-continued

Formula (7b)

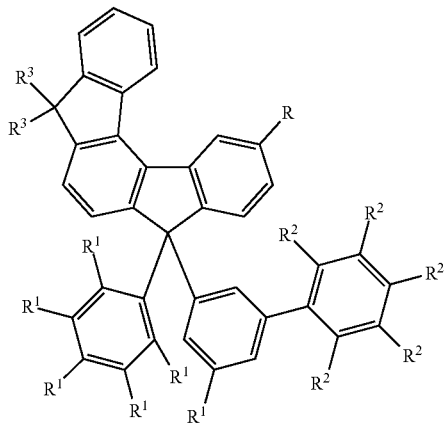

where the symbols used have the meanings given above.

In a further preferred embodiment of the invention, R is the same or different at each instance and is selected from the group consisting of H, D, a straight-chain alkyl group having 1 to 10 carbon atoms or a branched or cyclic alkyl group having 3 to 10 carbon atoms, where the alkyl group may be substituted in each case by one or more $R^3$ radicals, or an aromatic ring system which has 6 to 18 aromatic ring atoms, preferably 6 to 12 aromatic ring atoms, and may be substituted by one or more substituents $R^3$. More preferably, R is the same or different at each instance and is selected from the group consisting of H, D, a straight-chain alkyl group having 1 to 4 carbon atoms or a branched alkyl group having 3 or 4 carbon atoms, where the alkyl group in each case may be substituted by one or more $R^3$ radicals, but is preferably unsubstituted. Most preferably, R is the same or different at each instance and is H or D, especially H.

Particular preference is thus given to the compounds of the following formulae (2d), (6g) and (6h):

Formula (2d)

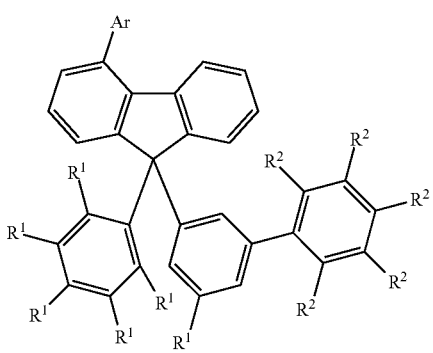

Formula (6g)

Formula (6h)

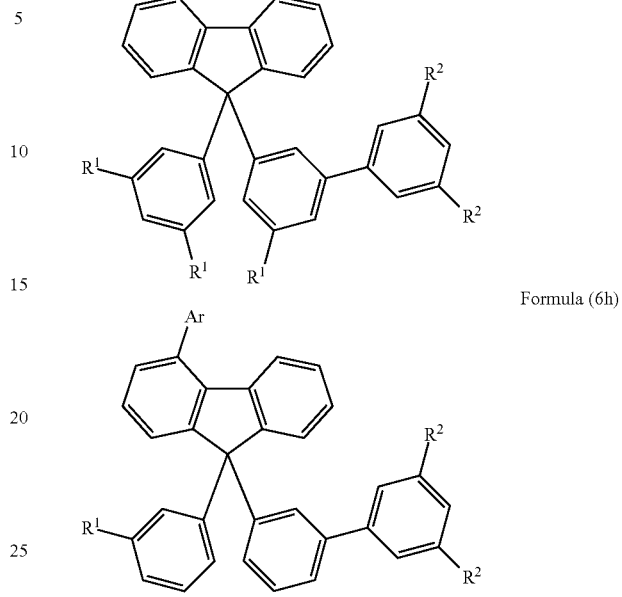

where the symbols used have the meanings given above.

In a further preferred embodiment of the invention, $R^1$ is the same or different at each instance and is selected from the group consisting of H, D, a straight-chain alkyl group having 1 to 10 carbon atoms or a branched or cyclic alkyl group having 3 to 10 carbon atoms, where the alkyl group may be substituted in each case by one or more $R^3$ radicals, but is preferably unsubstituted, or an aromatic ring system which has 6 to 24 aromatic ring atoms and may be substituted by one or more $R^3$ radicals, or dibenzofuran or dibenzothiophene, each of which may be substituted by one or more $R^3$ radicals. More preferably, $R^1$ is the same or different at each instance and is selected from the group consisting of H, D, a straight-chain alkyl group having 1 to 4 carbon atoms or a branched alkyl group having 3 or 4 carbon atoms, or an aromatic ring system which has 6 to 18 aromatic ring atoms and may be substituted by one or more preferably nonaromatic $R^3$ radicals, but is preferably unsubstituted.

In a further preferred embodiment of the invention, $R^2$ is the same or different at each instance and is selected from the group consisting of H, D, a straight-chain alkyl group having 1 to 10 carbon atoms or a branched or cyclic alkyl group having 3 to 10 carbon atoms, where the alkyl group may be substituted in each case by one or more $R^3$ radicals, but is preferably unsubstituted, or an aromatic ring system which has 6 to 24 aromatic ring atoms and may be substituted by one or more $R^3$ radicals, or dibenzofuran or dibenzothiophene, each of which may be substituted by one or more $R^3$ radicals. More preferably, $R^2$ is the same or different at each instance and is selected from the group consisting of H, D, a straight-chain alkyl group having 1 to 4 carbon atoms or a branched alkyl group having 3 or 4 carbon atoms, or an aromatic ring system which has 6 to 18 aromatic ring atoms and may be substituted by one or more preferably nonaromatic $R^3$ radicals, but is preferably unsubstituted.

When $R^1$ or $R^2$ is an aromatic ring system or dibenzofuran or dibenzothiophene or a combination of these groups, preferred $R^1$ or $R^2$ groups are selected from the group consisting of phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene which may be joined via the 1 or 2 position, dibenzofuran which may be joined via the 1, 2, 3 or 4 position, dibenzothiophene which may be joined via the 1, 2, 3 or 4 position, phenanthrene, triphenylene or a combination of these groups, each of which may be substituted by one or more $R^3$ radicals, preferably nonaromatic $R^3$ radicals.

Aromatic or heteroaromatic $R^1$ or $R^2$ groups are preferably the same or different at each instance and are selected from the groups of the following formulae R-1 to R-26:

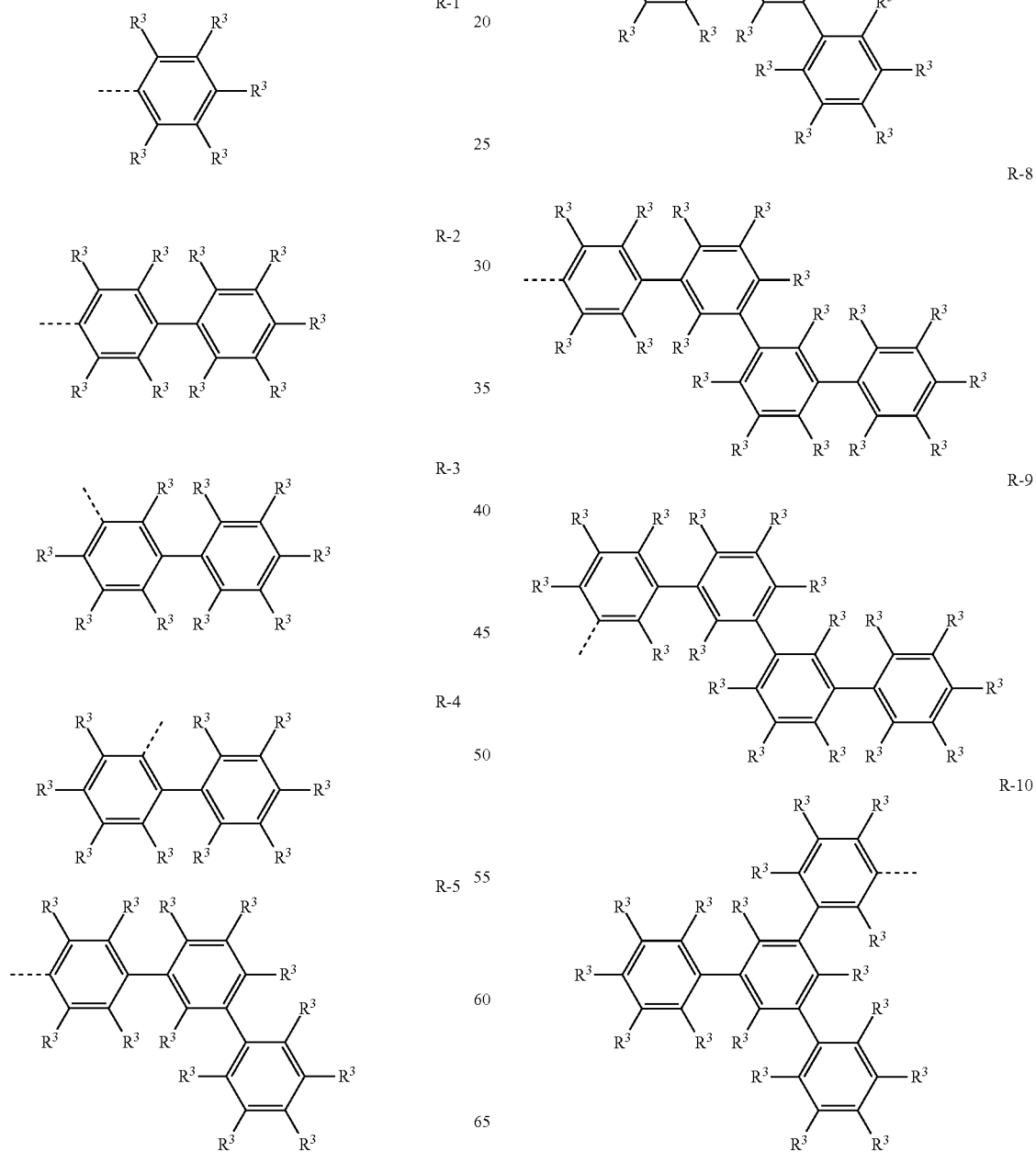

-continued
R-11
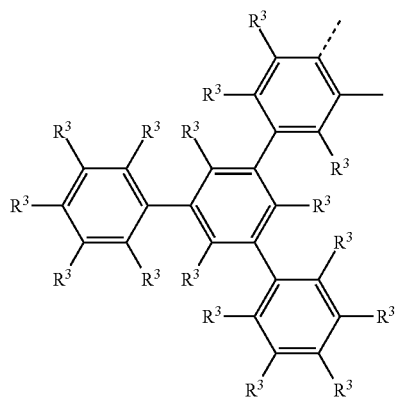
R-12
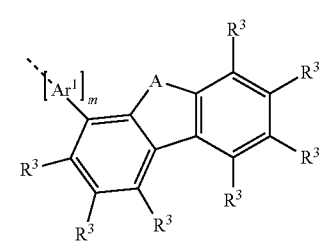
R-13
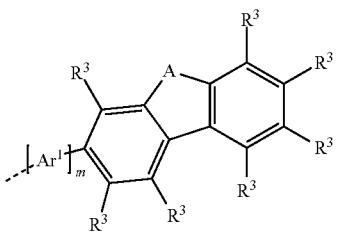
R-14
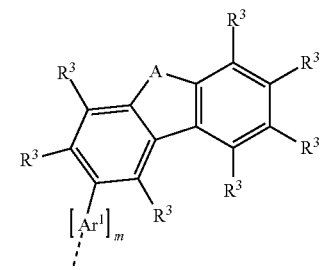
R-15
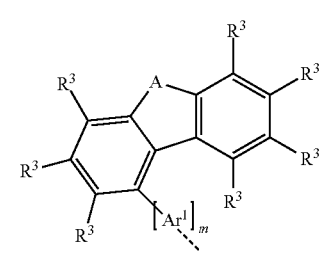
-continued
R-16
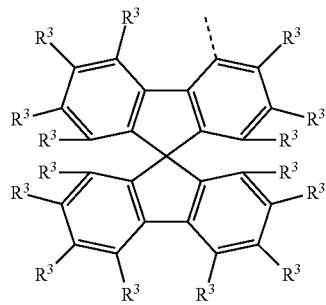
R-17
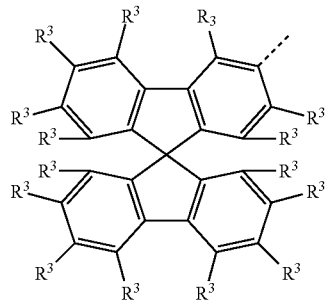
R-18
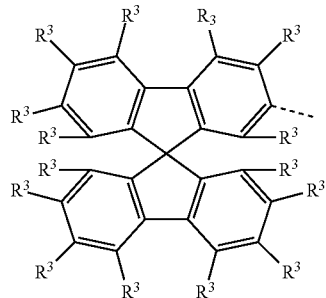
R-19
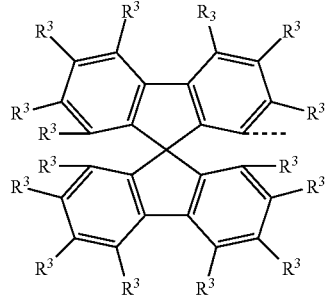
R-20
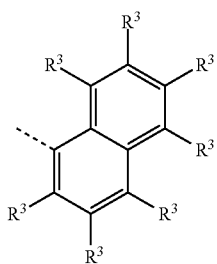

R-21
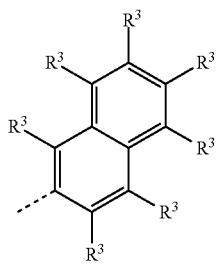

R-22
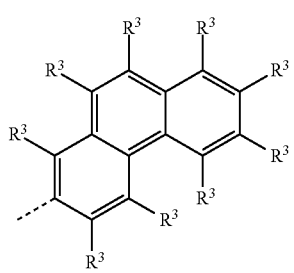

R-23
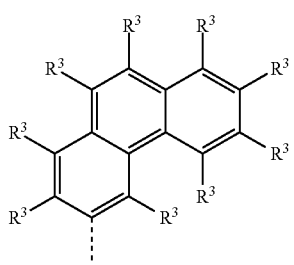

R-24
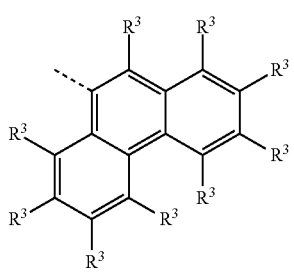

R-25
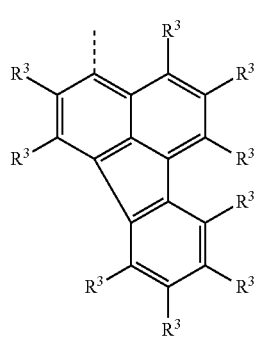

R-26
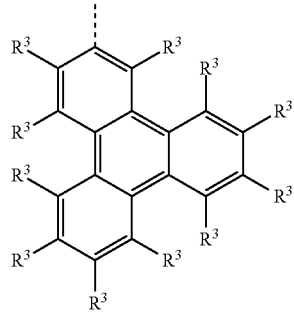

where $R^3$, $Ar^1$, A and m have the definitions given above, the dotted bond represents the bond to the phenyl group and m=0 means that the $Ar^1$ group is absent and that the corresponding aromatic or heteroaromatic group is bonded directly to the phenyl group.

In a further preferred embodiment of the invention, $R^3$ is the same or different at each instance and is selected from the group consisting of H, D, a straight-chain alkyl group having 1 to 10 carbon atoms or a branched or cyclic alkyl group which has 3 to 10 carbon atoms and may be substituted in each case by one or more $R^4$ radicals, but is preferably unsubstituted, or an aromatic ring system which has 6 to 24 aromatic ring atoms and may be substituted by one or more $R^4$ radicals, but is preferably unsubstituted. More preferably, $R^3$ is the same or different at each instance and is selected from the group consisting of H, D, a straight-chain alkyl group having 1 to 4 carbon atoms or a branched alkyl group having 3 or 4 carbon atoms or an aromatic ring system which has 6 to 18 aromatic ring atoms, preferably 6 to 12 aromatic ring atoms, and may be substituted in each case by one or more $R^4$ radicals, but is preferably unsubstituted.

$R^4$ is preferably the same or different at each instance and is H, D, an aliphatic hydrocarbyl radical having 1 to 4 carbon atoms or an aromatic hydrocarbyl radical having 6 to 12 carbon atoms.

A particularly preferred embodiment of the invention is the compounds of the following formulae (8a) and (8b):

Formula (8a)

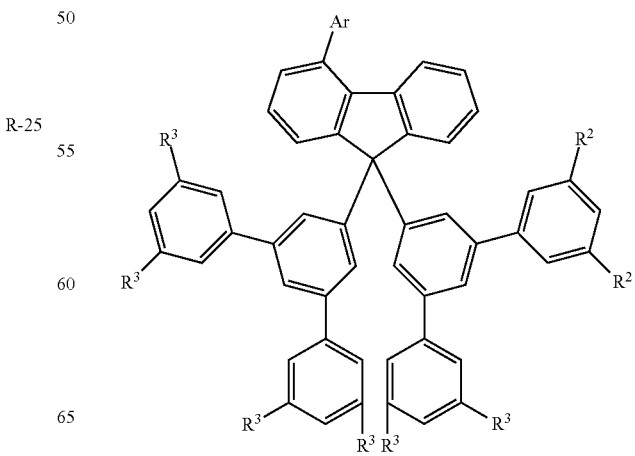

Formula (8b)

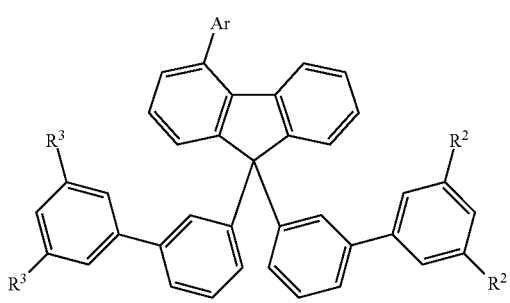

where the symbols used have the meanings given above.

Very particular preference is given to the compounds of the following formulae (9a) and (9b):

Formula (9a)

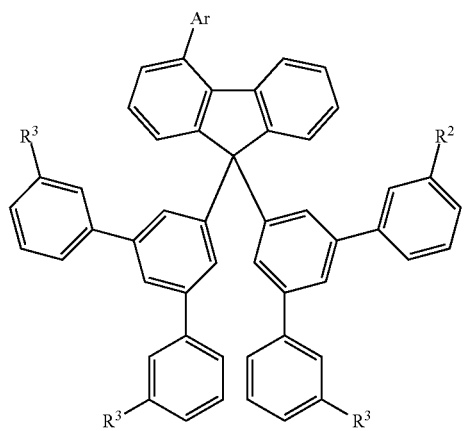

Formula (9b)

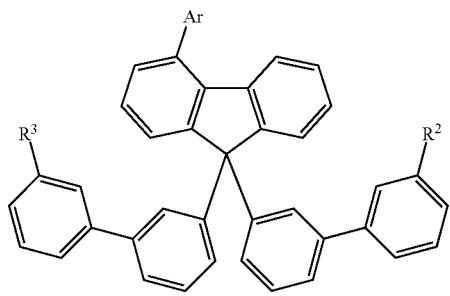

where the symbols used have the meanings given above.

$R^2$ and $R^3$ here in the formulae (8a), (8b), (9a) and (9b) are preferably an aromatic ring system having 6 to 18 aromatic ring atoms, more preferably having 6 to 12 aromatic ring atoms, where $R^2$ may be substituted by one or more substituents $R^3$, and $R^3$ may be substituted by one or more substituents $R^4$, but are preferably unsubstituted.

In a preferred configuration, the compounds of the formula (1) or the preferred embodiments have a molecular weight of not more than 5000 g/mol, preferably not more than 4000 g/mol, particularly preferably not more than 3000 g/mol, especially preferably not more than 2000 g/mol and most preferably not more than 1200 g/mol. Further preferably, the compounds of the formula (1) or the preferred embodiments have a molecular weight of not less than 750 g/mol.

In addition, it is a feature of preferred compounds of the invention that they have a high solubility in standard organic solvents, preferably a solubility of ≥10 mg/ml in toluene.

Preferably, the compound of the formula (1) or of the preferred embodiments is a hydrocarbon, i.e. does not contain any heteroatoms.

In a particular embodiment, a compound of the formula (1) or of the preferred embodiments has a glass transition temperature of at least 110° C., more preferably of at least 120° C., even more preferably of at least 140° C. and especially preferably of at least 160° C., determined in accordance with DIN EN ISO 11357-1 and DIN EN ISO 11357-2.

More preferably, the compound of the formula (1) or of the preferred embodiments is a wide bandgap material. It is preferable here when the compound has a band gap of 2.5 eV or more, preferably 3.0 eV or more, very preferably of 3.5 eV or more. A "wide bandgap" material in the context of the present invention refers to a material having a band gap of 3.0 eV or more. The band gap can be calculated via the energy levels of the highest occupied molecular orbital (HOMO) and the lowest unoccupied molecular orbital (LUMO). The optimization of the ground state geometry of the isolated gas phase molecules is conducted here by the B3PW91/6-31G(d) method. The TD-DFT calculations of the vertical singlet and triplet excitation energies (absorption energies) that follow are conducted using the same method (i.e. B3PW91/6-31G(d)). For this purpose, the Gaussian software package (E.01 edition) is used.

The compounds of the invention can be prepared by synthesis steps that are common knowledge to the person skilled in the art, as shown in Schemes 1 to 3. In a first step, an aromatic alkyl ortho-bromophenylbenzoate is coupled to an ortho-aryl-substituted phenylboronic acid or a corresponding boronic ester (Scheme 1). The phenyl groups may also each be substituted by substituent R, and it is also possible to use a different leaving group rather than bromine in the reactant. The resultant biphenyl derivative can be reacted with a meta-bromo-substituted phenyllithium compound to give a 9,9-diphenylfluorene substituted by bromine on the phenyl groups (Scheme 2). Rather than a bromine group, the phenyllithium may also bear two or more bromine groups or else other leaving groups. This fluorene derivative is reacted in a last step, in a Suzuki coupling, with a phenylboronic acid derivative that may also have further substitution, or in another coupling reaction, to give the product (Scheme 3).

Scheme 1

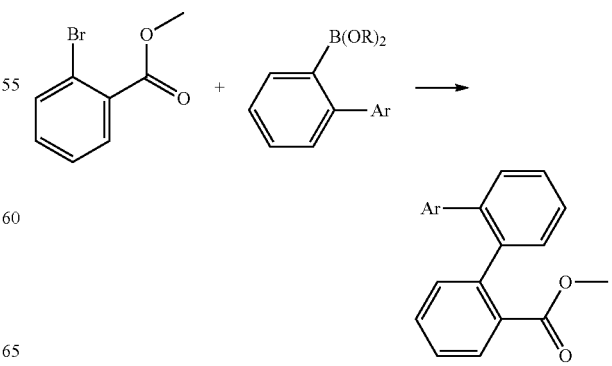

Scheme 2

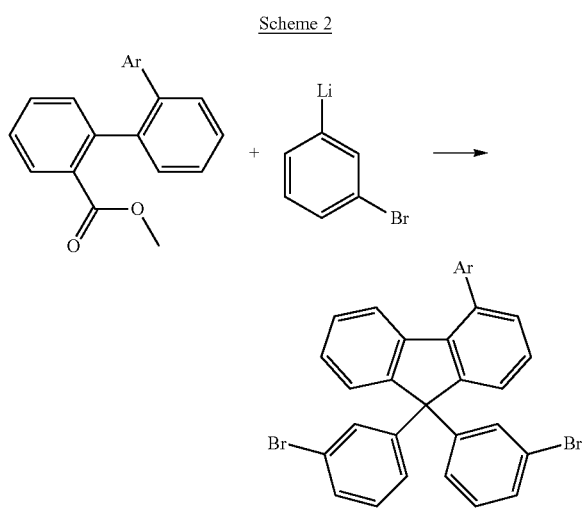

Scheme 3

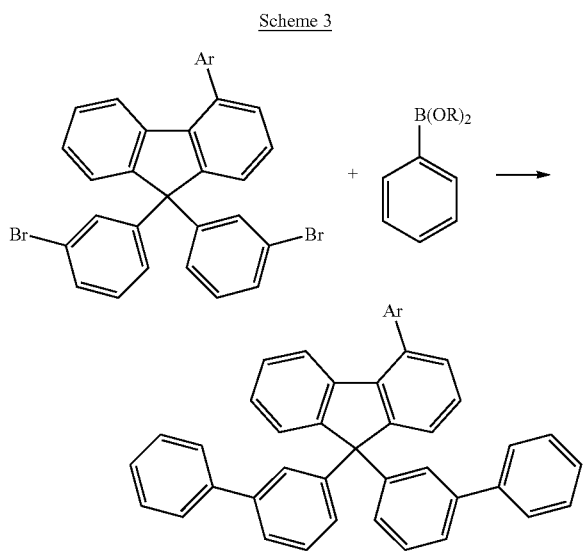

The present invention still further provides a composition comprising a compound of the invention and at least one further functional material that differs from the compounds of the invention. Functional materials are generally the organic or inorganic materials introduced between the anode and cathode. Preferably, the functional material is selected from the group consisting of fluorescent emitters, phosphorescent emitters, host materials (matrix materials), electron transport materials, electron injection materials, hole conductor materials, hole injection materials, electron blocker materials and hole blocker materials, especially phosphorescent emitters and further matrix materials.

The present invention further provides a composition comprising at least one compound of formula (1) or the preferred embodiments and at least one emitter and at least one matrix material selected from the group consisting of electron transport materials, hole transport materials and bipolar materials. Emitters include fluorescent emitters, phosphorescent emitters and emitters that exhibit TADF (thermally activated delayed fluorescence). Preference is given to phosphorescent emitters. The matrix material is preferably an electron transport material or a bipolar material, especially an electron transport material.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation comprising at least one compound of formula (1) or according to the preferred embodiments and one or more solvents, especially organic solvents, for example the solvents listed above. This formulation preferably comprises solutions, suspensions or miniemulsions, especially solutions. The way in which such solutions can be prepared is known to those skilled in the art and is described, for example, in WO 2002/072714, WO 2003/019694 and the literature cited therein.

The compounds of formula (1) or according to the preferred embodiments are suitable for use in electronic devices, especially in organic electroluminescent devices (OLEDs).

The invention therefore further provides for the use of compounds of formula (1) or the preferred embodiments in an electronic device, especially in an organic electroluminescent device.

The invention further provides an electronic device comprising at least one compound of formula (1) or the preferred embodiments, wherein the electronic device is preferably selected from the group consisting of organic electroluminescent devices (OLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photoreceptors.

The invention still further provides organic electroluminescent devices comprising anode, cathode and at least one emitting layer, characterized in that at least one organic layer, preferably an emitting layer, comprises at least one compound of formula (1) or the preferred embodiments.

In addition, the invention further provides an organic electroluminescent device comprising an emitting layer comprising at least one compound of formula (1) or the preferred embodiments and at least one phosphorescent emitter and at least one matrix material which differs from the compounds of the invention. Preferably, the further matrix material may be a hole- and/or electron-conducting matrix material or a bipolar matrix material having both hole-conducting and electron-conducting properties. More preferably, the compound of the invention has the properties of a wide bandgap material and the further matrix material is electron-conducting.

Apart from the cathode, anode and emitting layer, the organic electroluminescent device may also comprise further layers. These are selected, for example, from in each case one or more hole injection layers, hole transport layers, hole blocker layers, electron transport layers, electron injection layers, electron blocker layers, exciton blocker layers, charge generation layers and/or organic or inorganic p/n junctions. In addition, the layers, especially the charge transport layers, may also be doped. The doping of the layers may be advantageous for improved charge transport. However, it should be pointed out that not necessarily every one of these layers must be present and the choice of layers always depends on the compounds used.

Materials used for hole-transporting layers of OLEDs may especially be indenofluoreneamine derivatives, amine derivatives, hexaazatriphenylene derivatives, amine derivatives with fused aromatic systems, monobenzoindenofluoreneamines, dibenzoindenofluoreneamines, spirobifluoreneamines, fluoreneamines, spirodibenzopyranamines, dihydroacridine derivatives, spirodibenzofurans and spirodibenzothiophenes, phenanthrene diarylamines, spirotribenzotropolones, spirobifluorenes having meta-phenyldiamine groups, spirobisacridines, xanthene diarylamines, and 9,10-dihydroanthracene spiro compounds having diarylamino groups.

The following compounds HT-1 to HT-72 are additionally suitable for use in a layer having hole-transporting function, especially in a hole injection layer, a hole transport layer and/or an electron blocker layer, or for use in an emitting layer as matrix material, especially as matrix material in an emitting layer comprising one or more phosphorescent emitters:

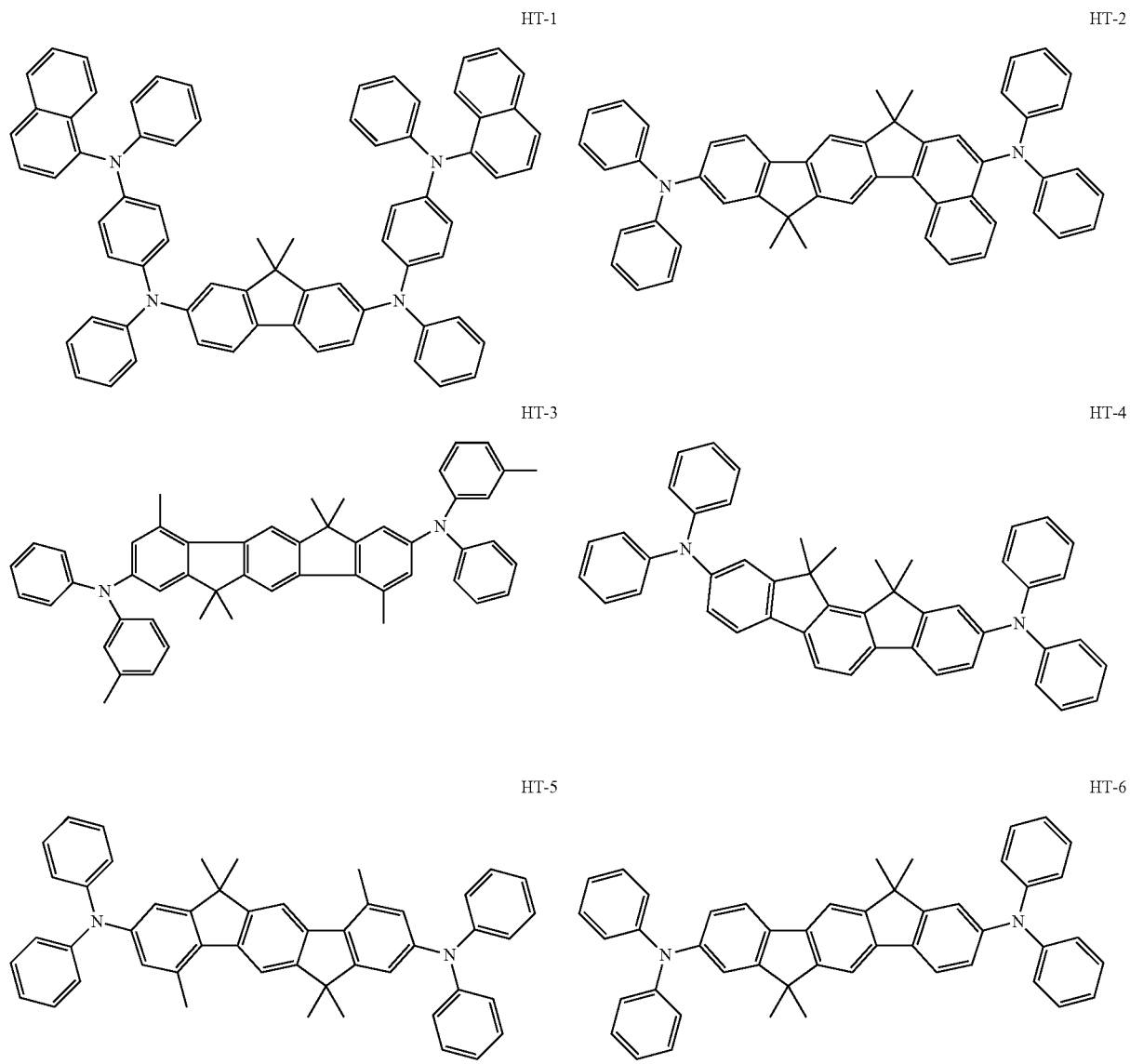

HT-7
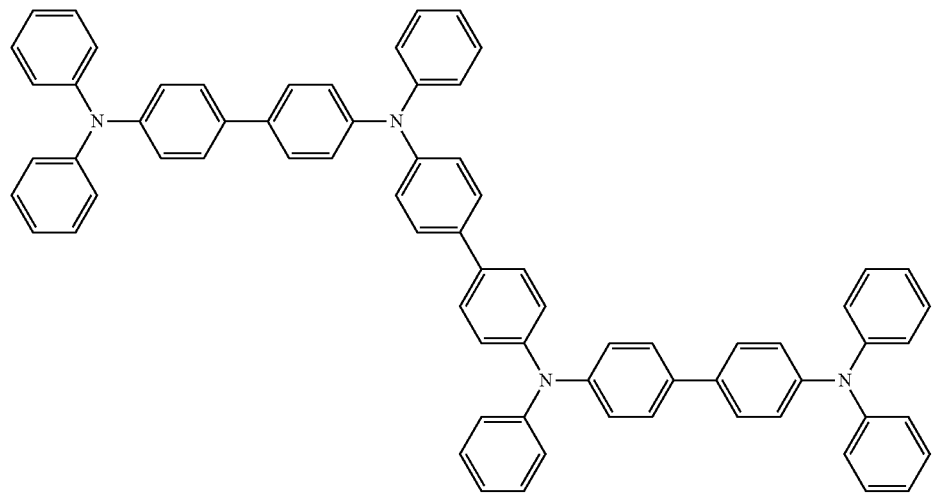
HT-8
HT-9
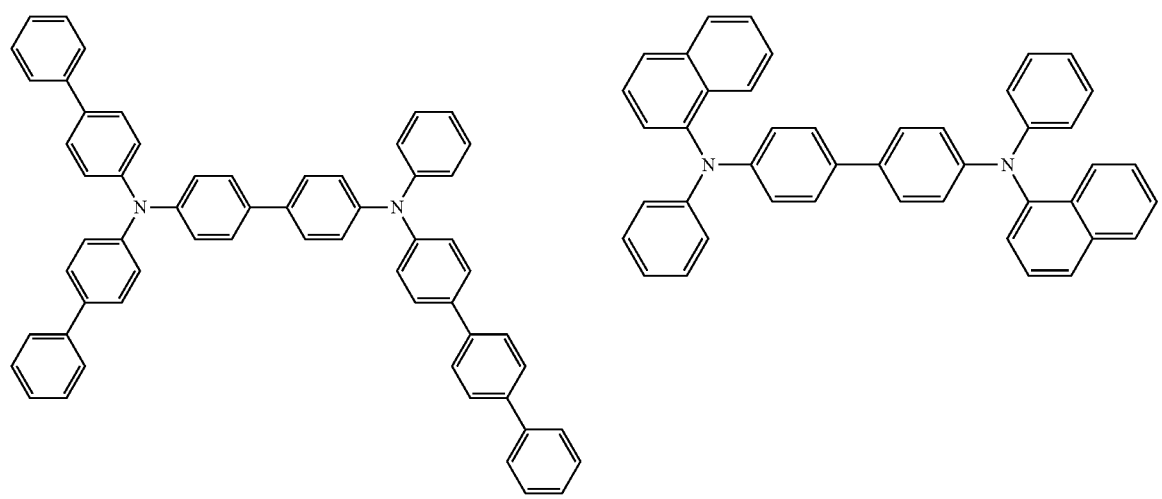
HT-10
HT-11
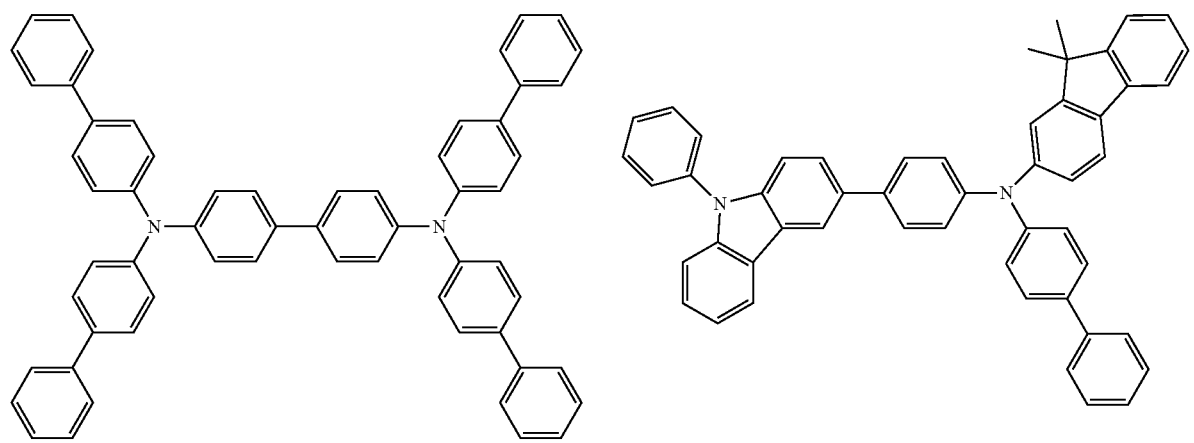

-continued
HT-12
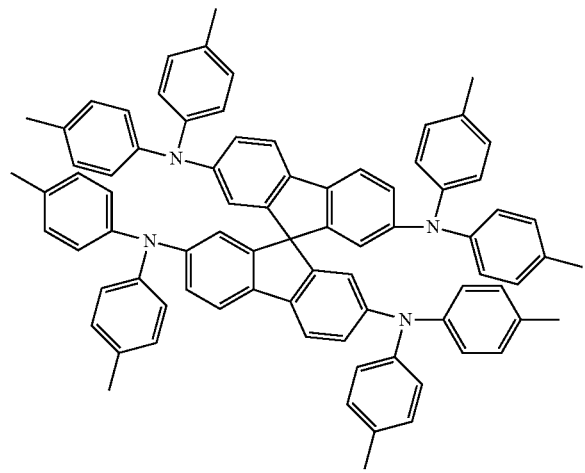
HT-13
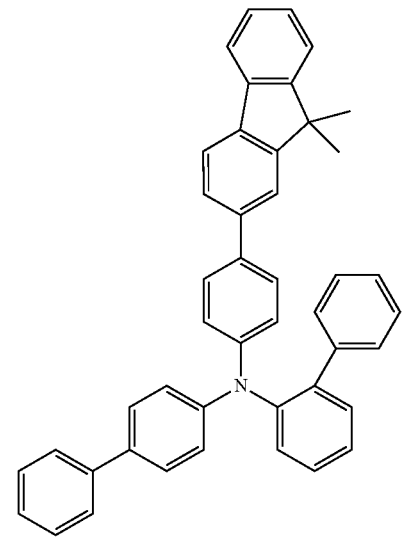
HT-14
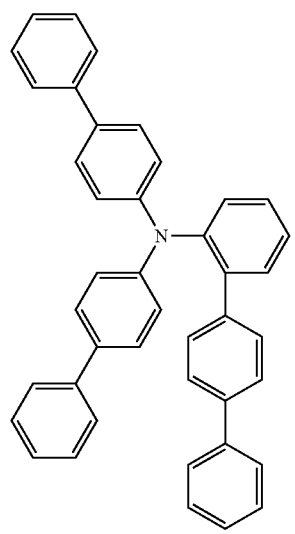
HT-15
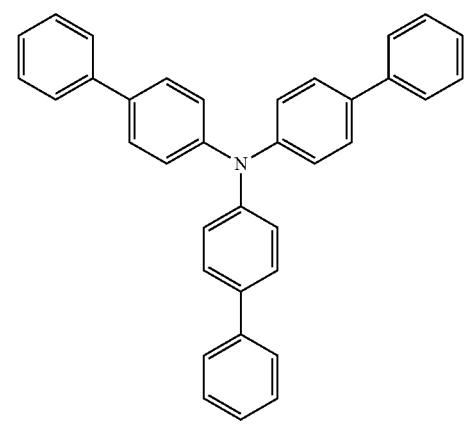
HT-16
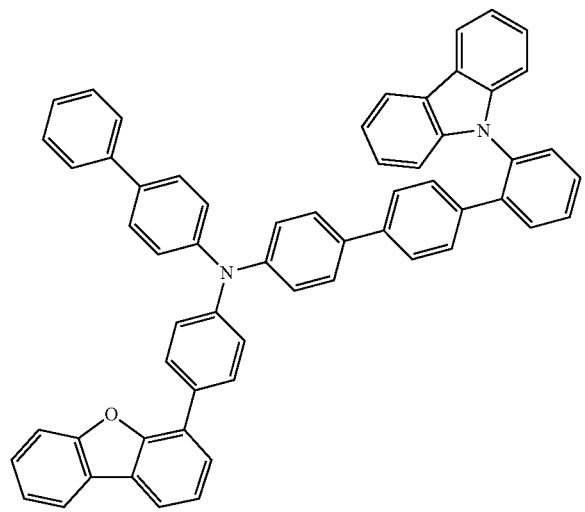
HT-17
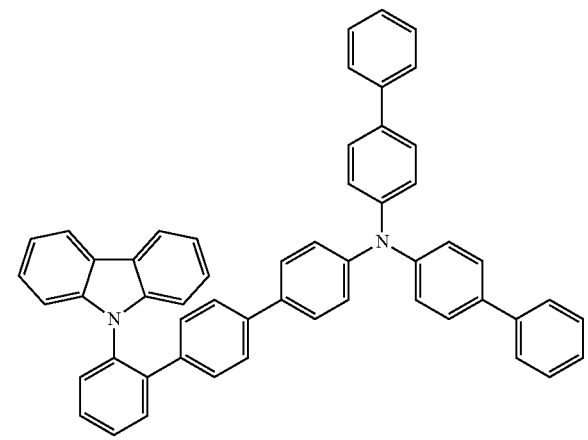

HT-18
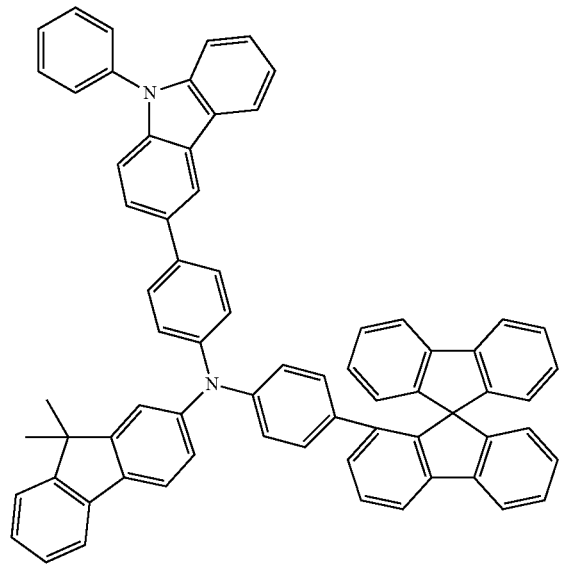
HT-19
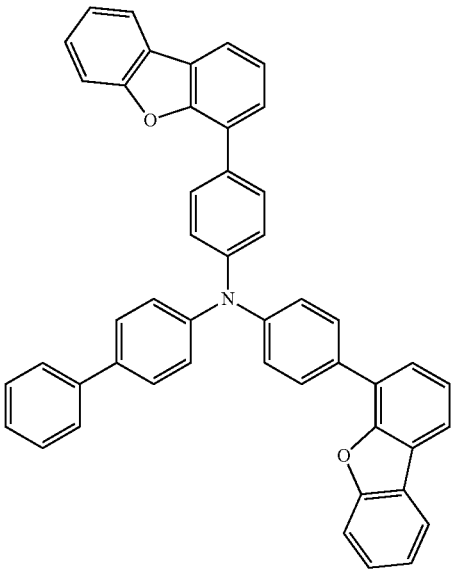
HT-20
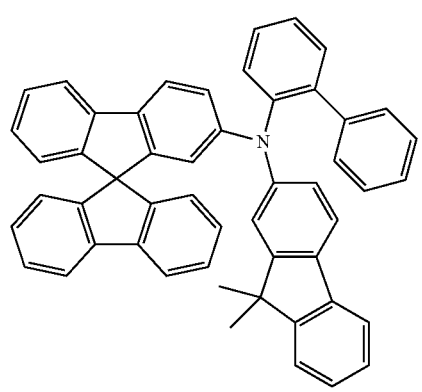
HT-21
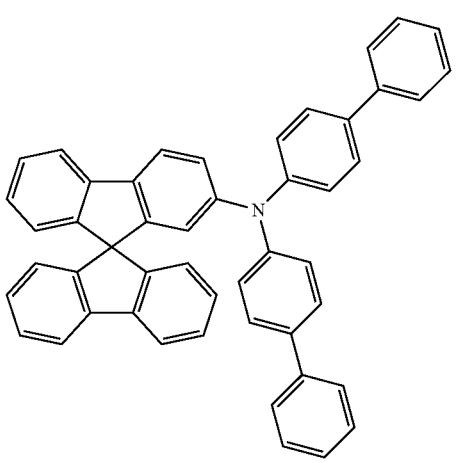
HT-22
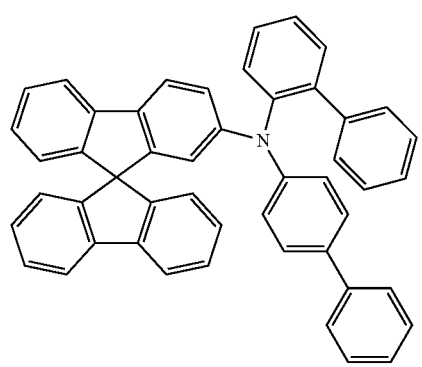
HT-23
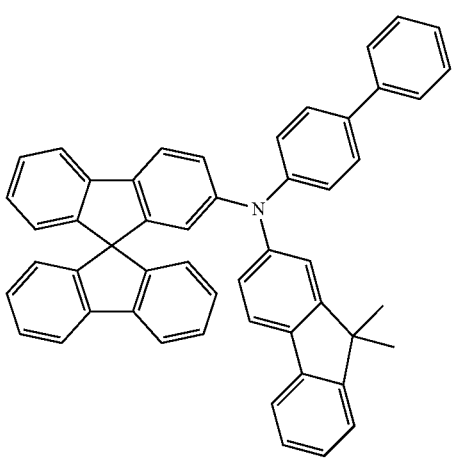

-continued
HT-24
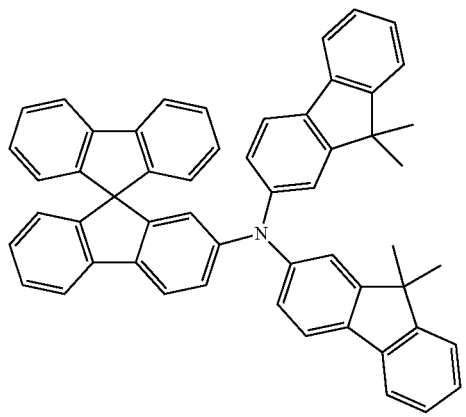
HT-25
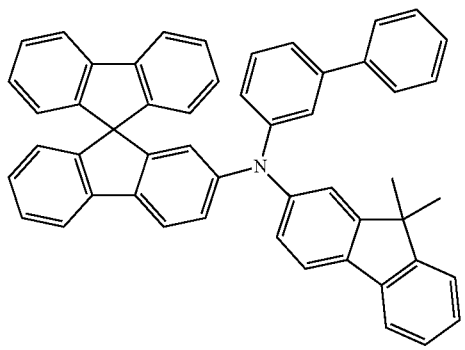
HT-26
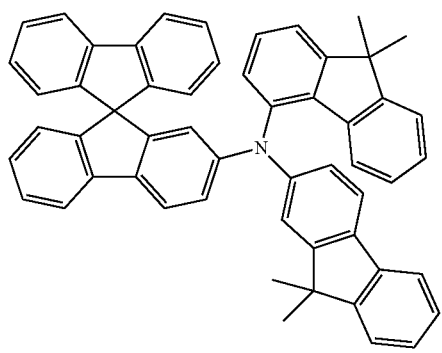
HT-27
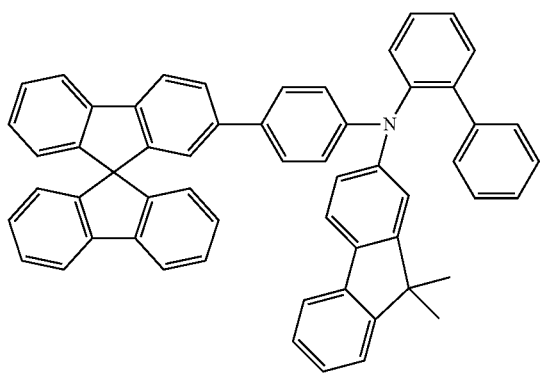
HT-28
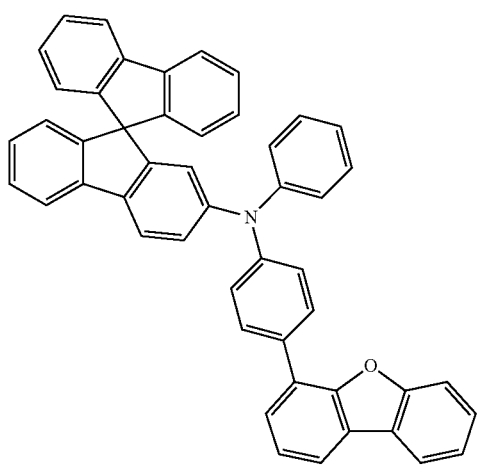
HT-29
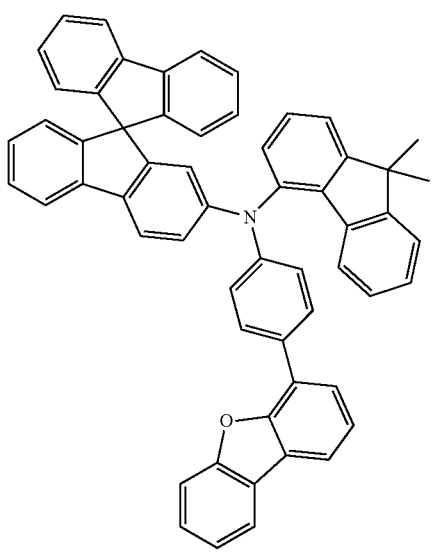

-continued
HT-30
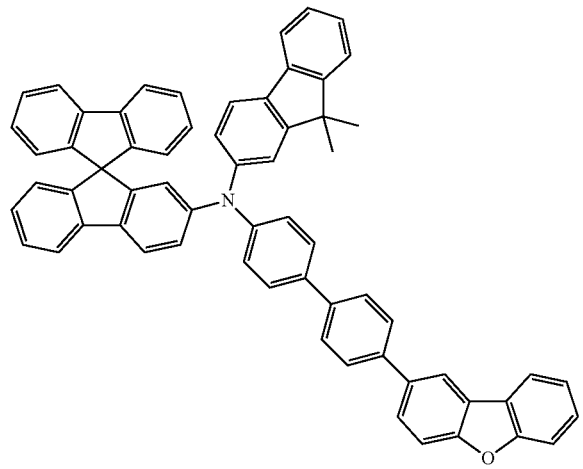
HT-31
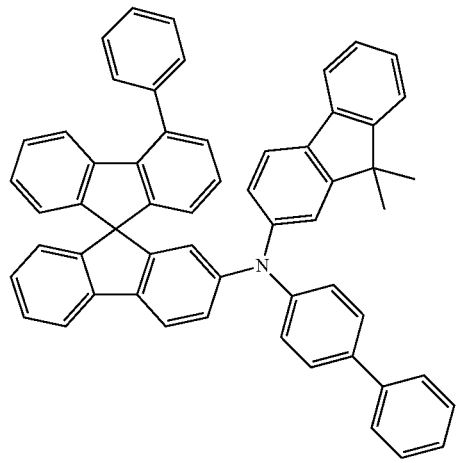
HT-32
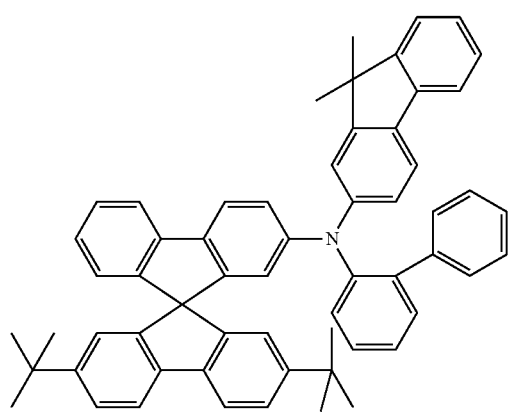
HT-33
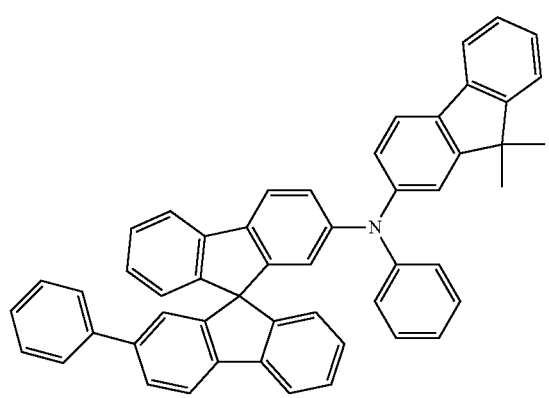
HT-34
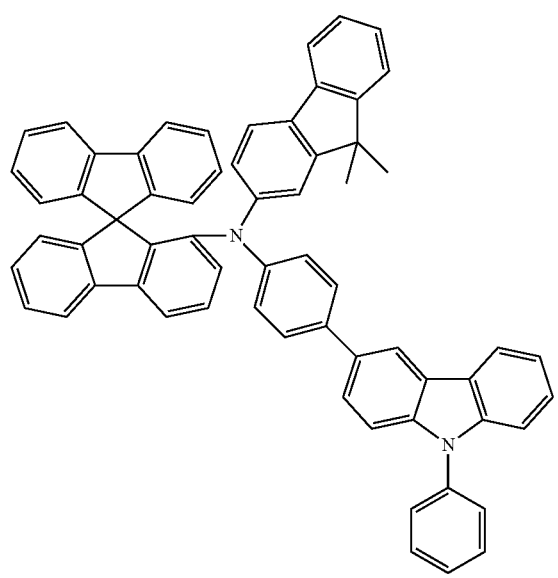
HT-35
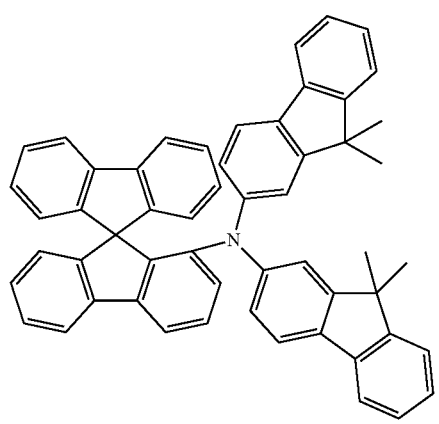

-continued
HT-36
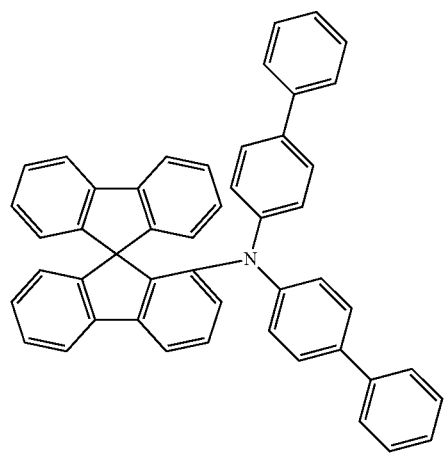
HT-37
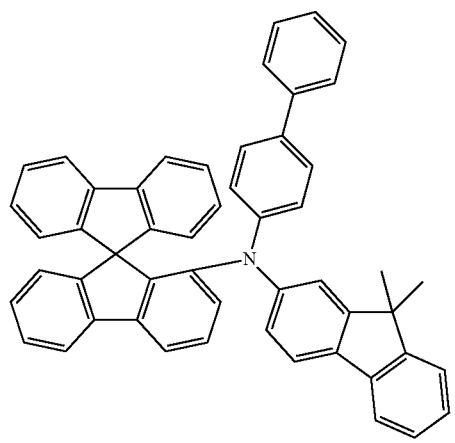
HT-38
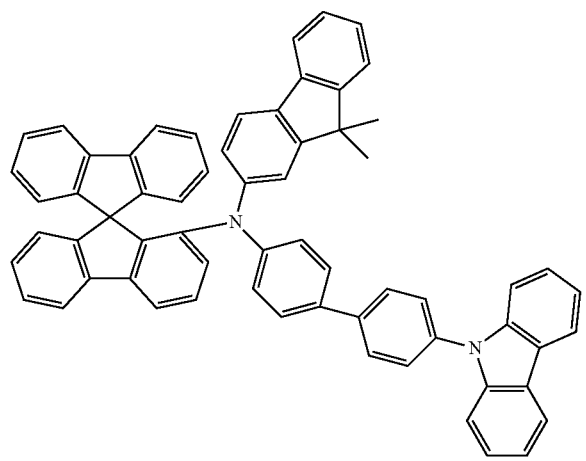
HT-39
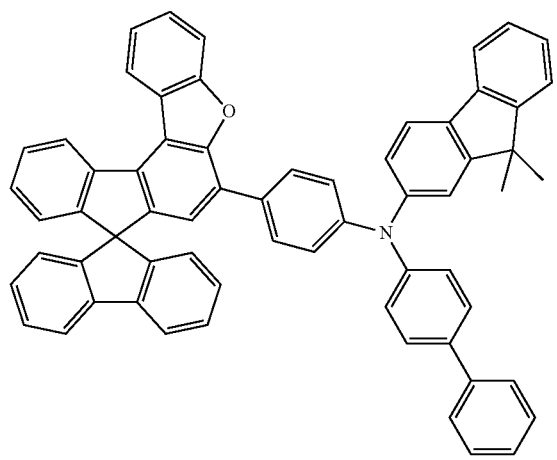
HT-40
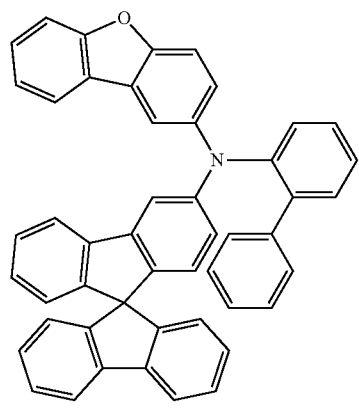
HT-41
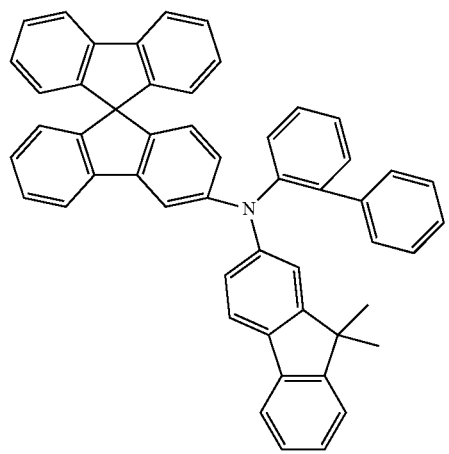

-continued
HT-42
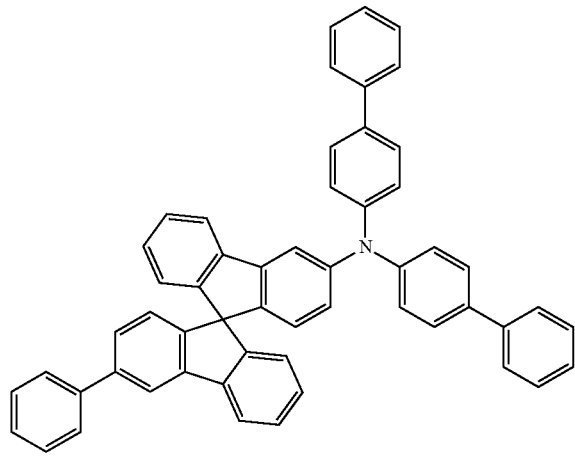
HT-43
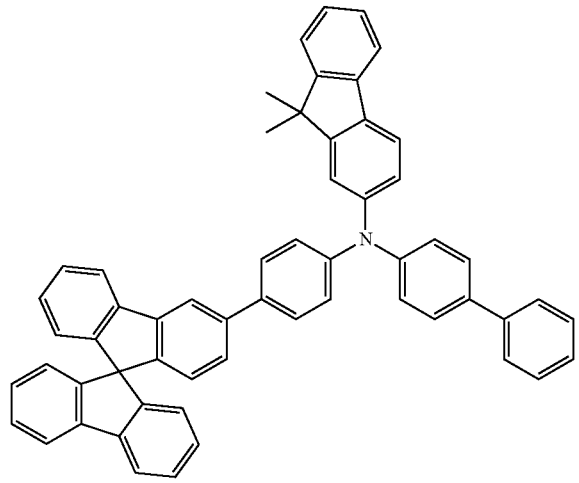
HT-44
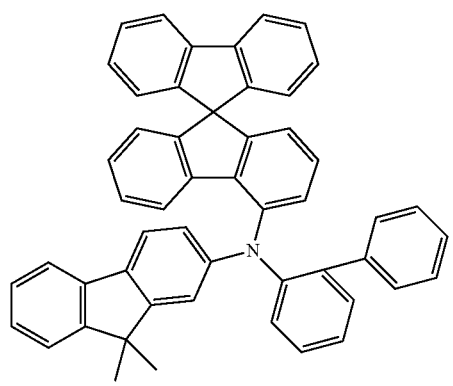
HT-45
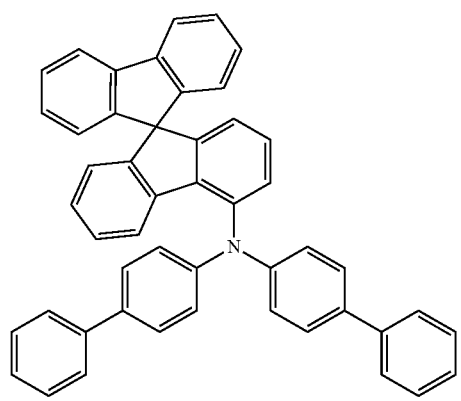
HT-46
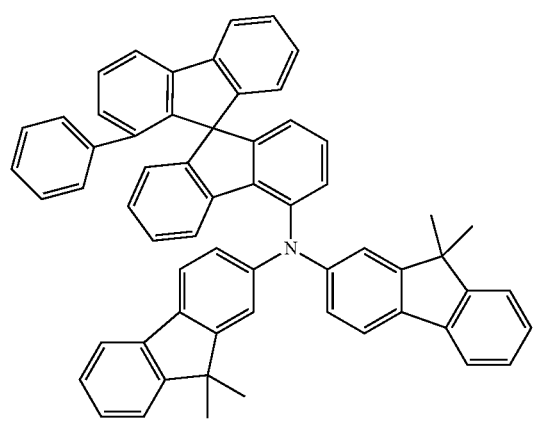
HT-47
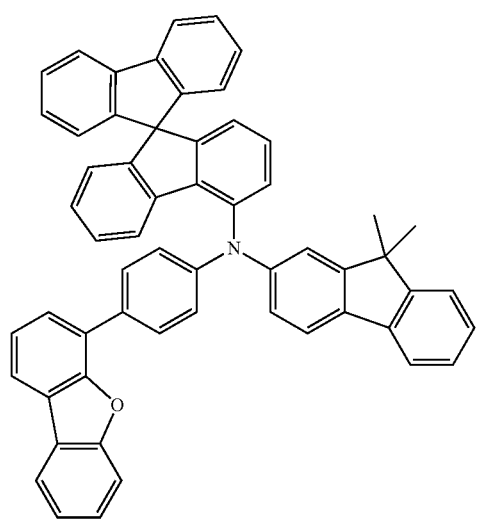

-continued
HT-48
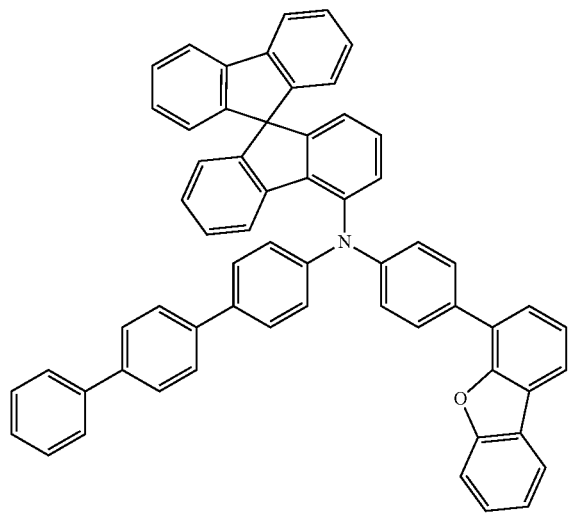
HT-49
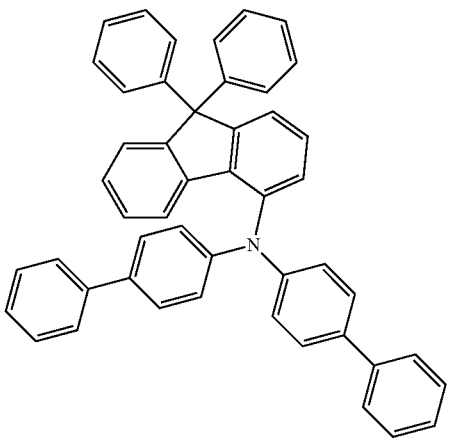
HT-50
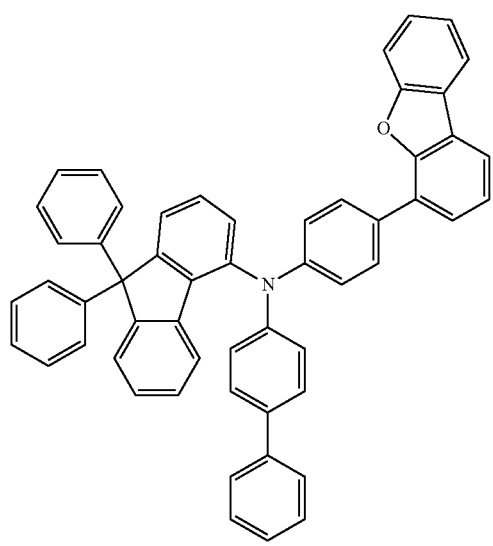
HT-51
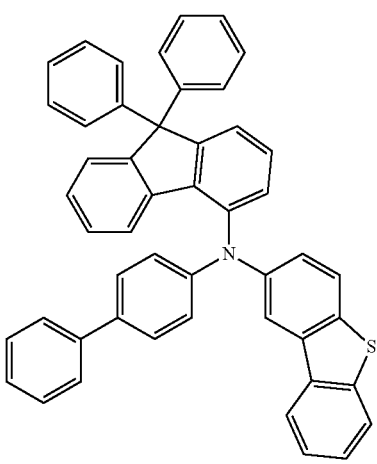
HT-52
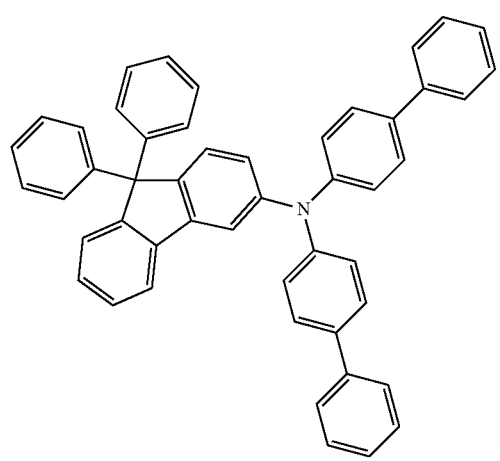
HT-53
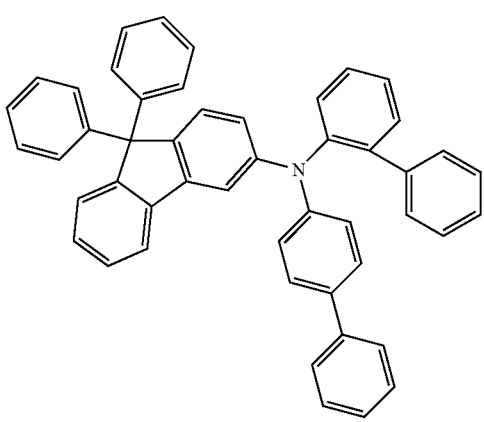

-continued
HT-54
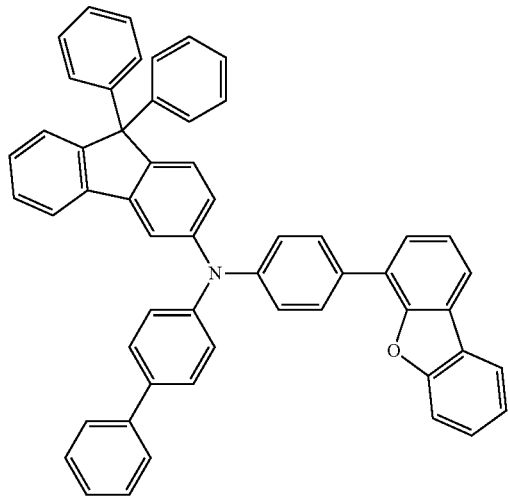
HT-55
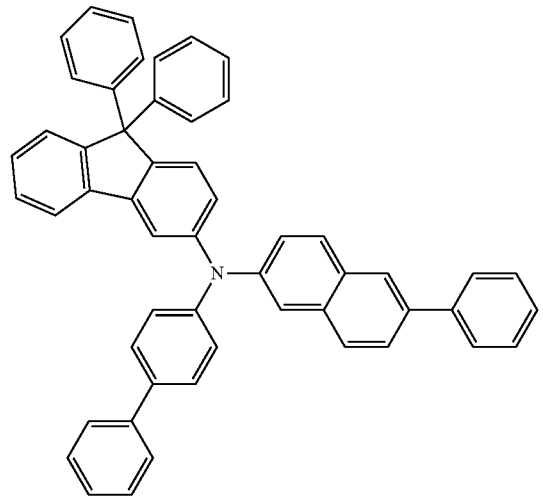
HT-56
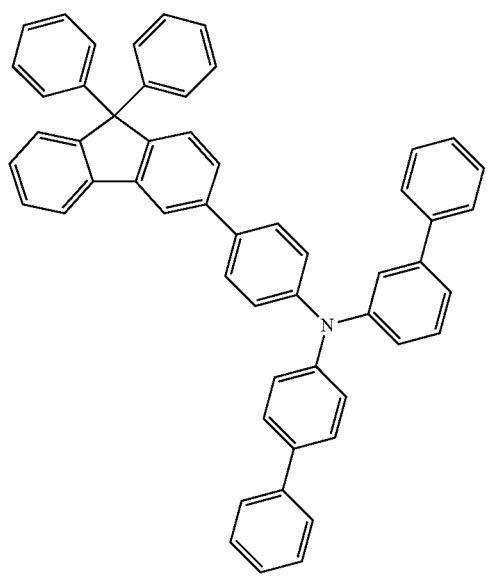
HT-57
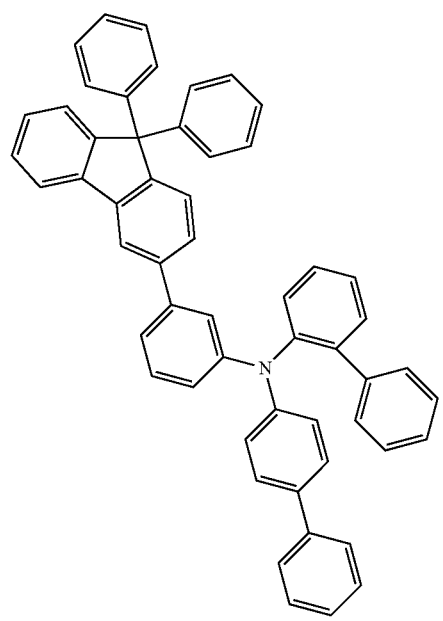
HT-58
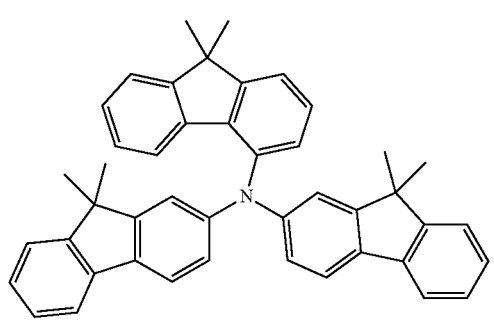
HT-59
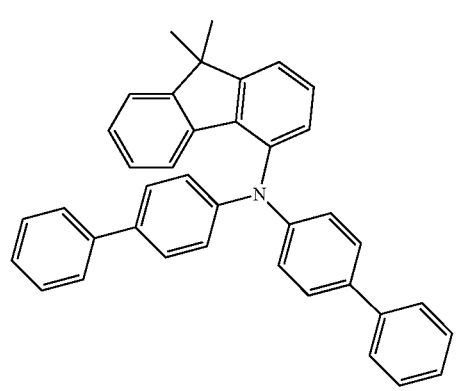

-continued
HT-60
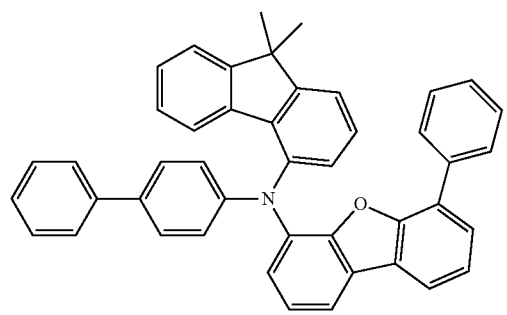
HT-61
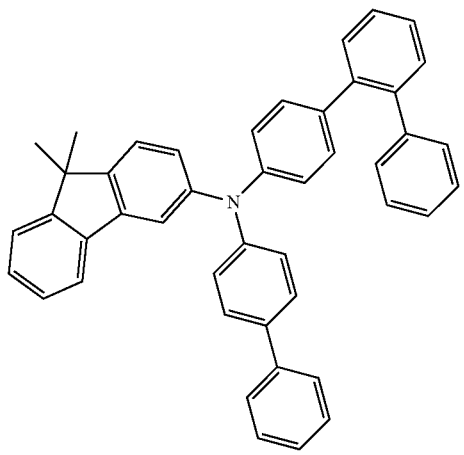
HT-62
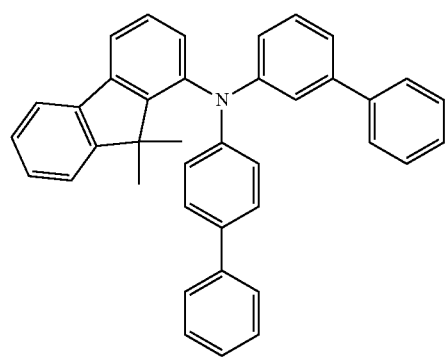
HT-63
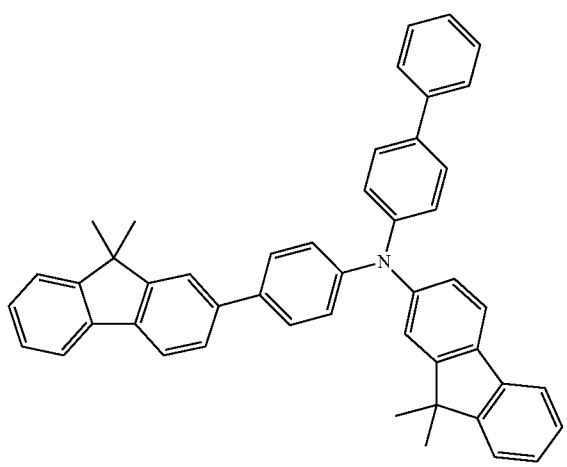
HT-64
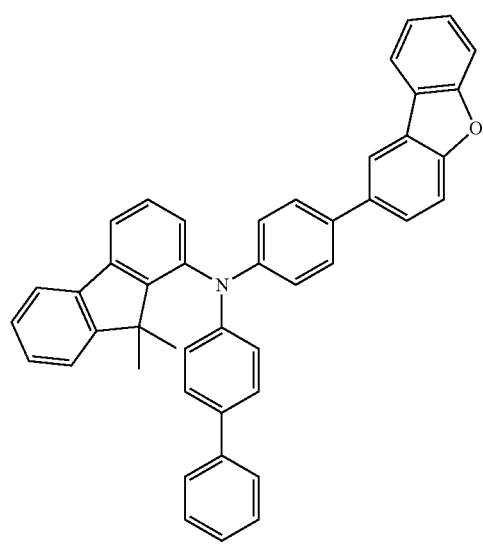
HT-65
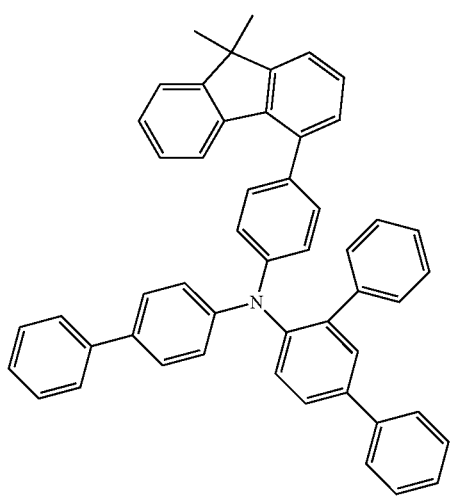

-continued
HT-66
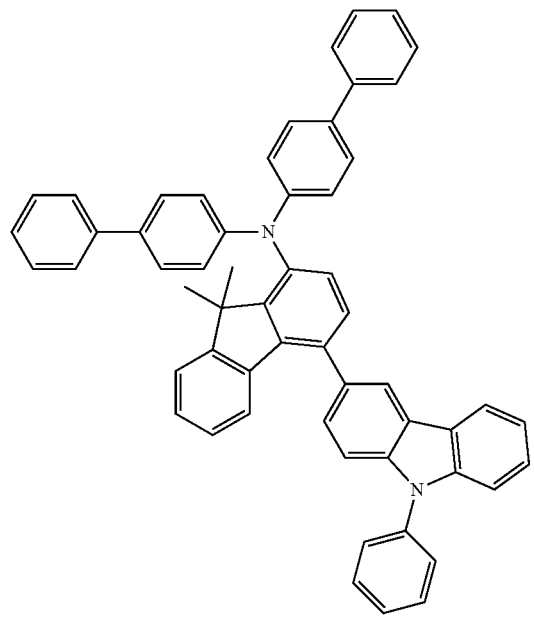
HT-67
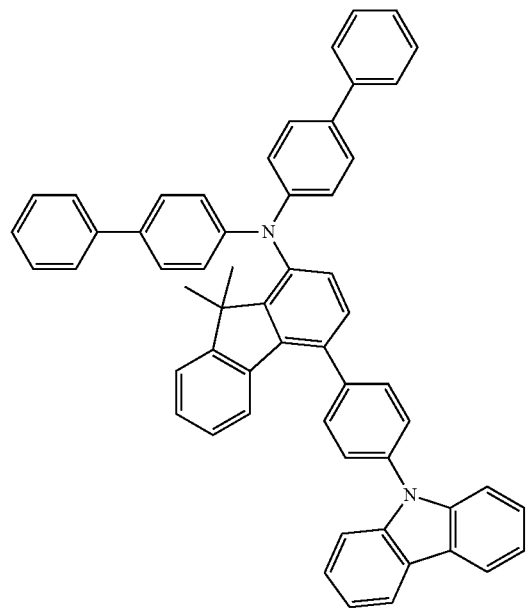
HT-68
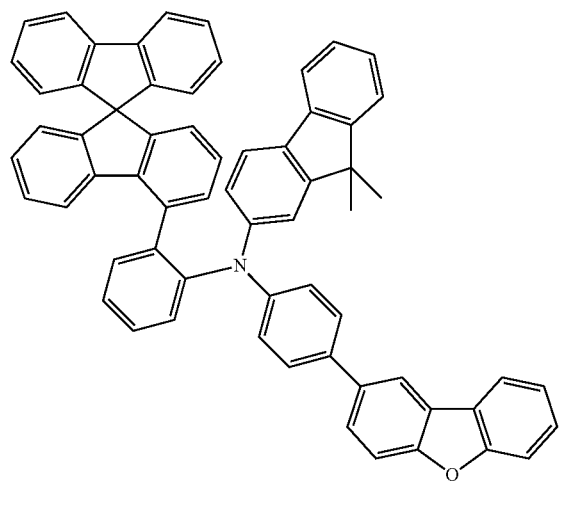
HT-69
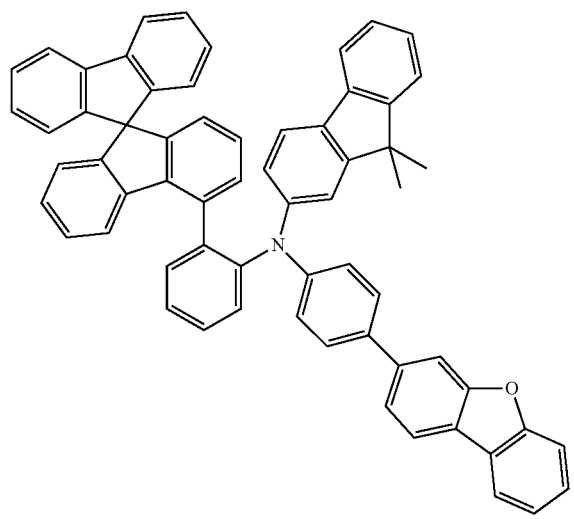

HT-70

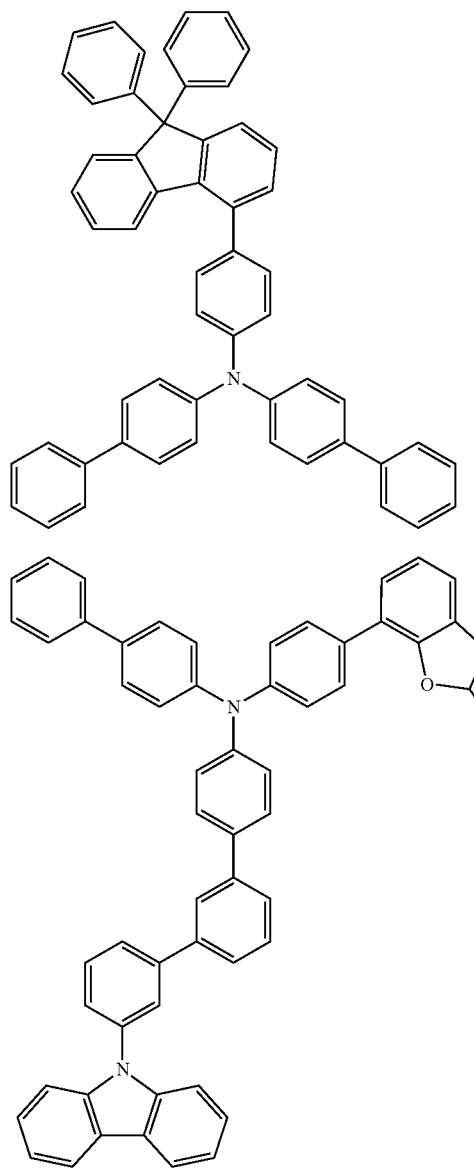

HT-71

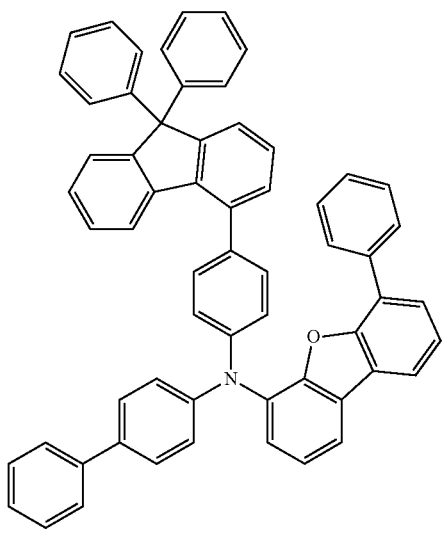

HT-72

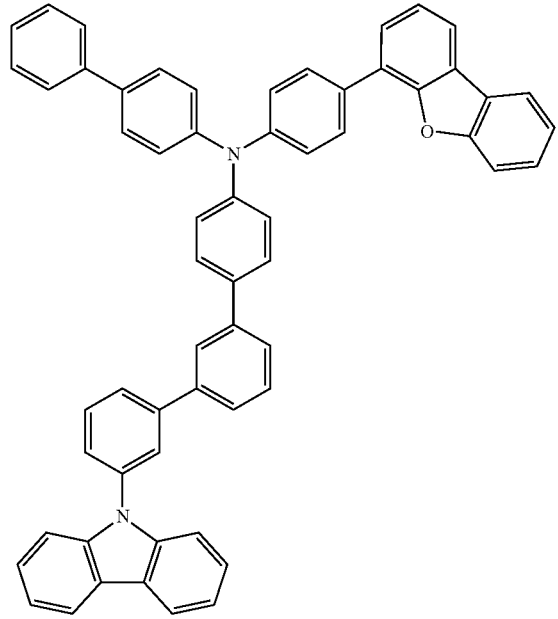

Compounds HT-1 to HT-72 are generally of good suitability for the abovementioned uses in OLEDs of any design and composition, not just in OLEDs according to the present application that contain a compound of formula (1). Compounds HT-1 to HT-72 lead to good performance data in OLEDs, especially good lifetime and good efficiency.

Processes for preparing the compounds HT-1 to HT-72 are known in the prior art. For example, processes for preparing compounds HT-16, HT-17 and HT-72 are disclosed in WO2014/079527, on pages 32-33 and in the working examples therein. Processes for preparing compound HT-18 are disclosed in WO 2013/120577 and WO2017/144150 in the description and the working examples. Processes for preparing compounds HT-20 to HT-32 are disclosed in WO2012/034627, on pages 39-40 and in the working examples therein.

In one embodiment of the invention, the organic electroluminescent device comprises two or more emitting layers, at least one organic layer comprising at least one compound of formula (1) or the preferred compounds. More preferably, these emission layers have several emission maxima between 380 nm and 750 nm overall, such that the overall result is white emission; in other words, various emitting compounds which may fluoresce or phosphoresce and which emit blue and yellow, orange or red light are used in the emitting layers. Especially preferred are three-layer systems, i.e. systems having three emitting layers, where at least one of these layers comprises at least one compound of formula (1) or according to the preferred embodiments and where the three layers show blue, green and orange or red emission.

In a preferred embodiment of the invention, the compounds of formula (1) or according to the preferred embodiments are used as matrix material for phosphorescent compounds in an emitting layer. In this case, the matrix used is preferably a mixture, wherein at least one component of this mixture is a compound of formula (1) or the preferred embodiments. Preferably, the other component of this mixture is a hole transport compound and/or an electron transport compound and/or a bipolar compound, especially an electron transport compound. Preferred electron transport compounds are triazine derivatives, quinazoline derivatives, pyrimidine derivatives and lactams, as set out in detail hereinafter.

The proportion of the inventive matrix material of formula (1) is preferably in the range from 5% to 95% by weight, more preferably in the range from 20% to 85% by weight and most preferably in the range from 50% to 75% by weight, based on the matrix material. Correspondingly, the proportion of the compound used as electron- and/or hole-conducting matrix material is 95% to 5% by weight, more preferably 80% to 15% by weight and most preferably 50% to 25% by weight, based on the matrix material.

Preferred triazine, quinazoline or pyrimidine derivatives that can be used as a mixture together with the compounds of the invention are the compounds of the following formulae (10), (11) and (12):

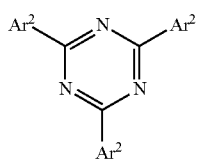

Formula (10)

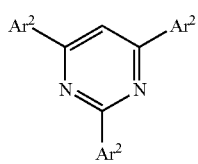

Formula (11)

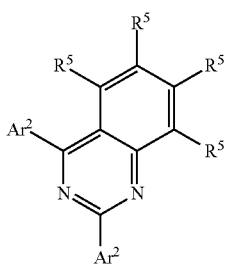

Formula (12)

where $R^3$ has the definitions given above and the other symbols used are as follows:

$Ar^2$ is the same or different at each instance and is an aromatic or heteroaromatic ring system which has 5 to 40 aromatic ring atoms and may be substituted by one or more $R^5$ radicals;

$R^5$ is the same or different at each instance and is H, D, F, Cl, Br, I, CN, $NO_2$, $N(R^3)_2$, $OR^3$, $SR^3$, $COOR^3$, $C(=O)N(R^3)_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl or alkoxy group having 1 to 20 carbon atoms or an alkenyl or alkynyl group having 2 to 20 carbon atoms or a branched or cyclic alkyl or alkoxy group having 3 to 20 carbon atoms, where the alkyl, alkoxy, alkenyl or alkynyl group may in each case be substituted by one or more $R^3$ radicals, where one or more nonadjacent $CH_2$ groups may be replaced by $Si(R^3)_2$, C=O, $NR^3$, O, S or $CONR^3$, or an aromatic or heteroaromatic ring system which has 5 to 30 aromatic ring atoms and may be substituted in each case by one or more $R^3$ radicals; at the same time, two $R^5$ radicals together may also form an aliphatic, heteroaliphatic, aromatic or heteroaromatic ring system.

Particular preference is given to the triazine derivatives of the formula (10) and the quinazoline derivatives of the formula (12), especially the triazine derivatives of the formula (10).

In a preferred embodiment of the invention, $Ar^2$ is the same or different at each instance and is an aromatic or heteroaromatic ring system which has 6 to 30 aromatic ring atoms, especially 6 to 24 aromatic ring atoms, and may be substituted by one or more $R^5$ radicals.

Suitable aromatic or heteroaromatic ring systems $Ar^2$ are the same or different at each instance and are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene which may be joined via the 1 or 2 position, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, quinazoline, benzimidazole, phenanthrene, triphenylene or a combination of two or three of these groups, each of which may be substituted by one or more $R^5$ radicals, preferably nonaromatic $R^5$ radicals. When $Ar^2$ is a heteroaryl group, especially triazine, pyrimidine, quinazoline or carbazole, preference may also be given to aromatic or heteroaromatic $R^5$ radicals on this heteroaryl group.

$Ar^2$ here is preferably the same or different at each instance and is selected from the groups of the following formulae $Ar^2$-1 to $Ar^2$-76:

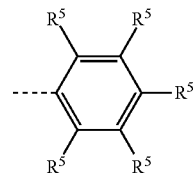

Ar²-1

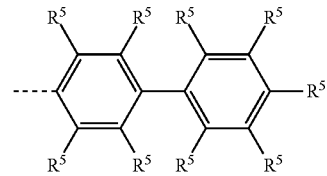

Ar²-2

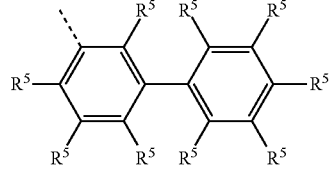

Ar²-3

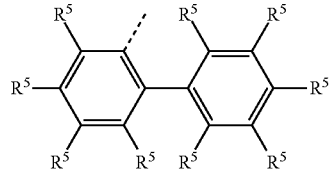

Ar²-4

-continued
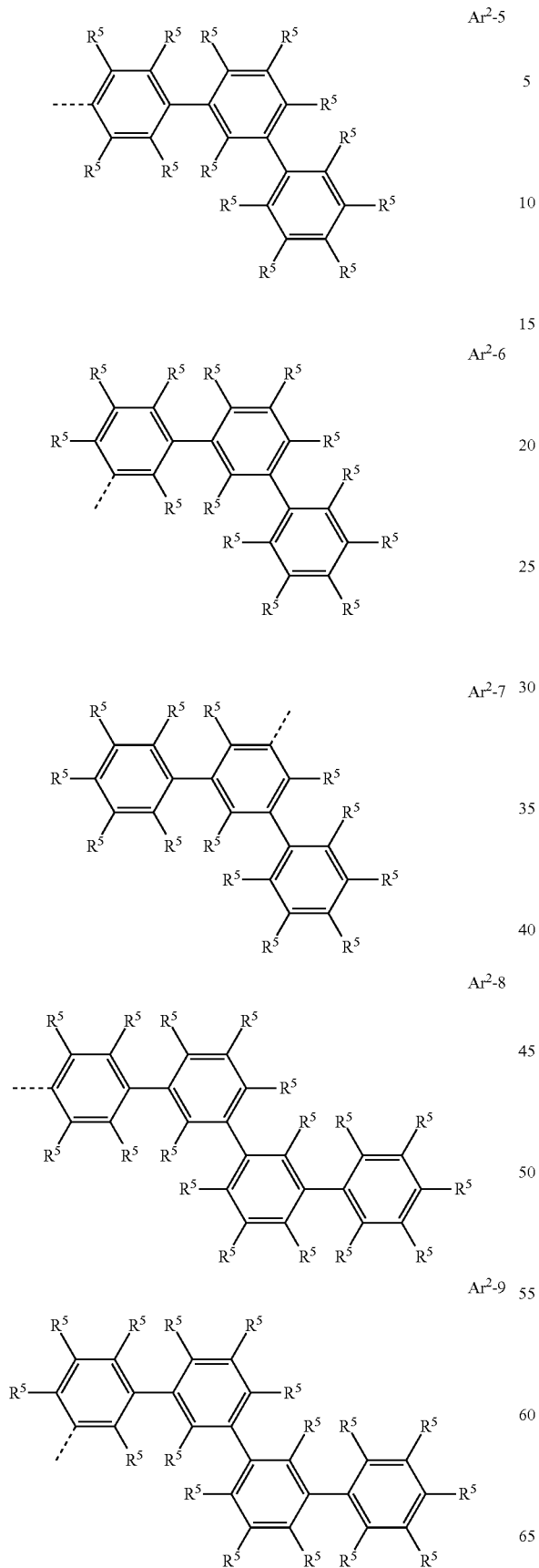
Ar²-5
Ar²-6
Ar²-7
Ar²-8
Ar²-9
-continued
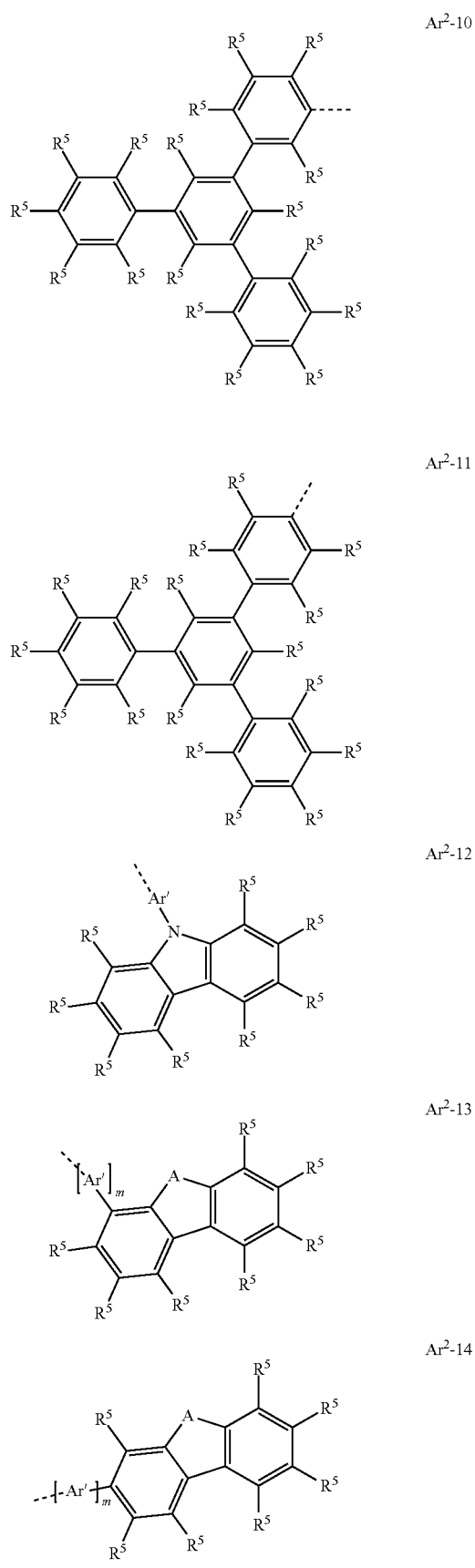
Ar²-10
Ar²-11
Ar²-12
Ar²-13
Ar²-14

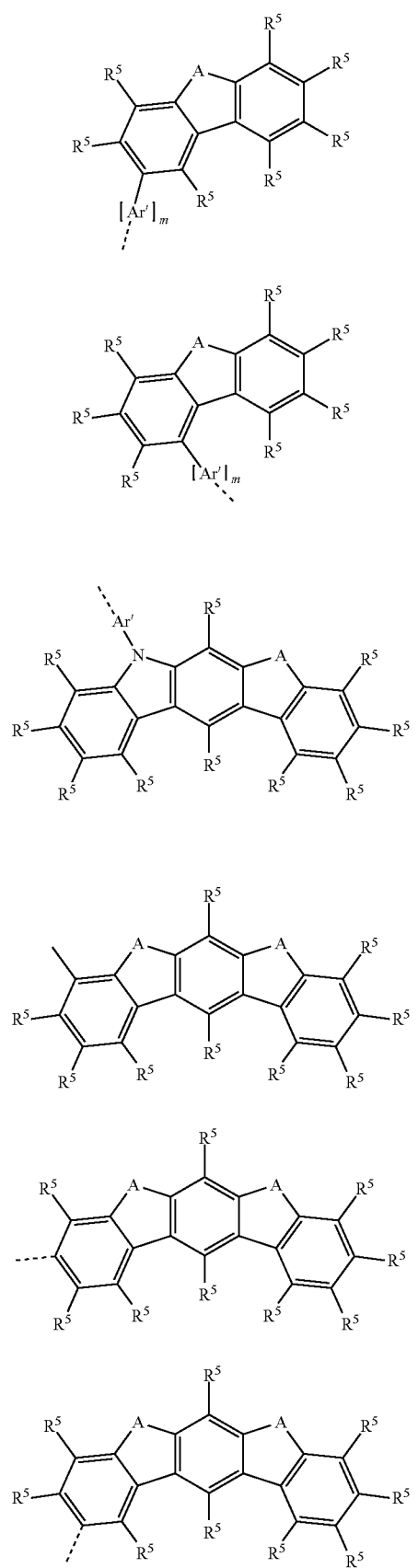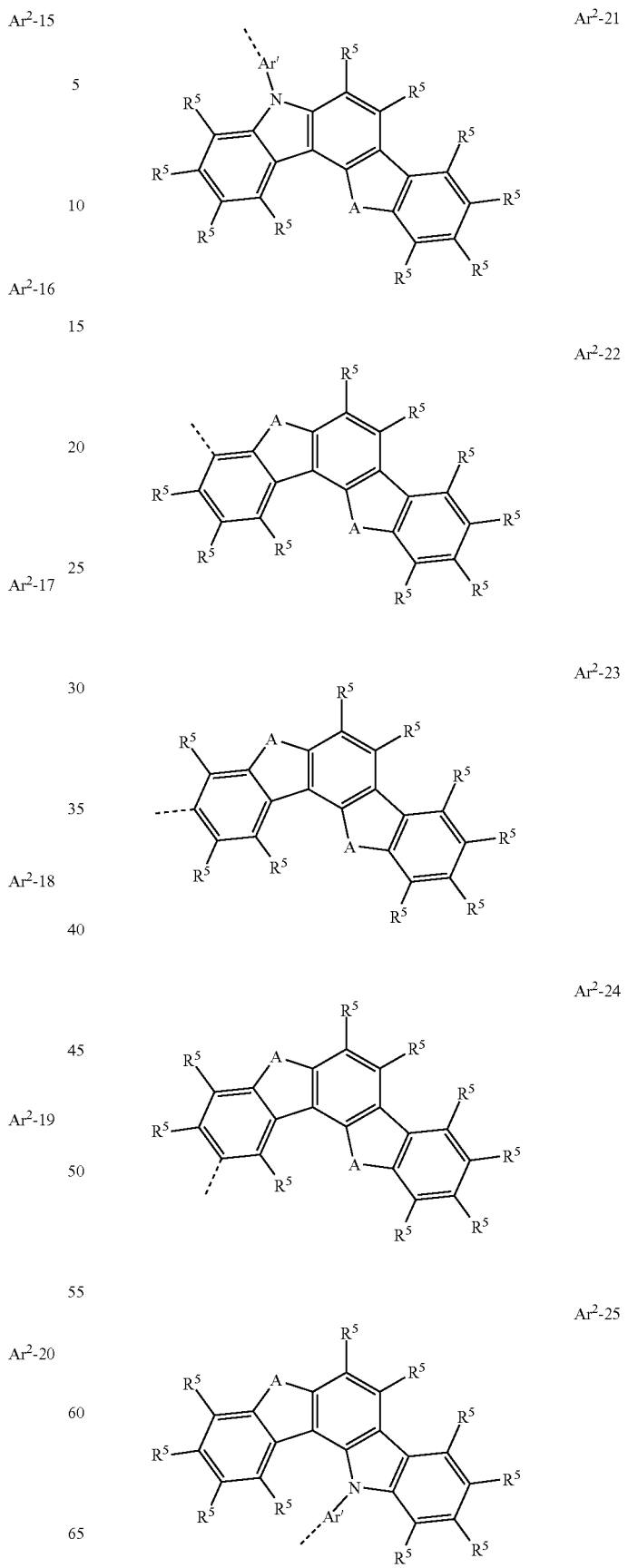

-continued
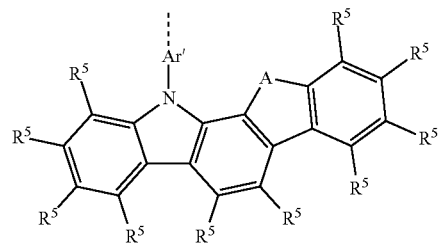
Ar²-26
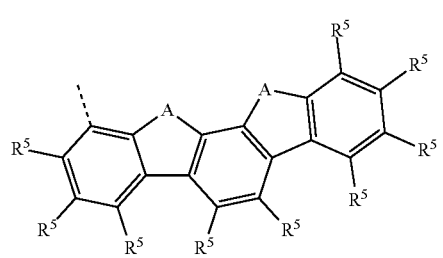
Ar²-27
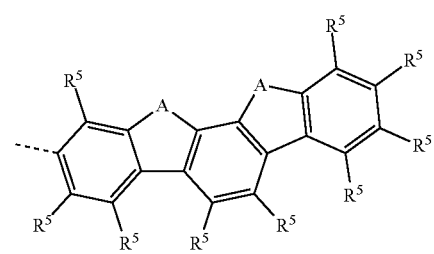
Ar²-28
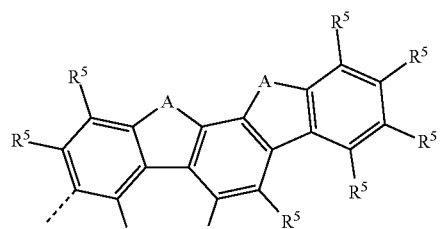
Ar²-29
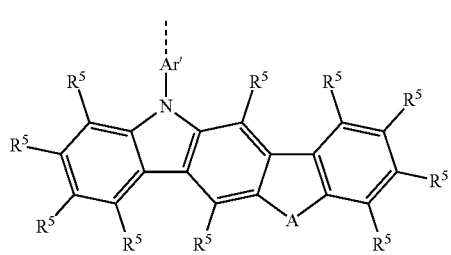
Ar²-30
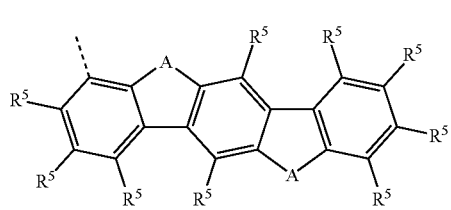
Ar²-31
-continued
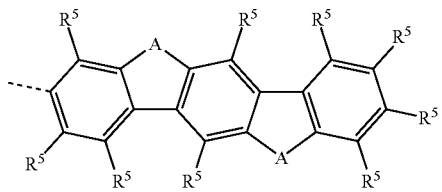
Ar²-32
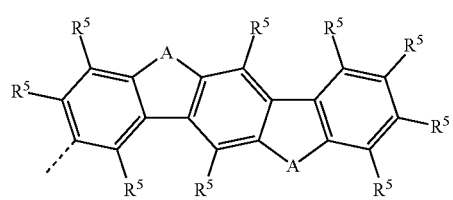
Ar²-33
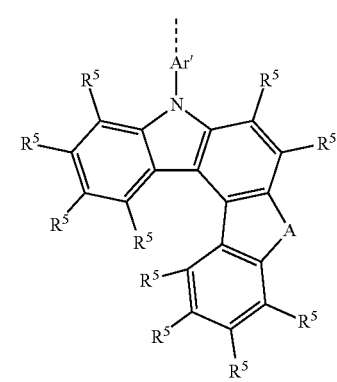
Ar²-34
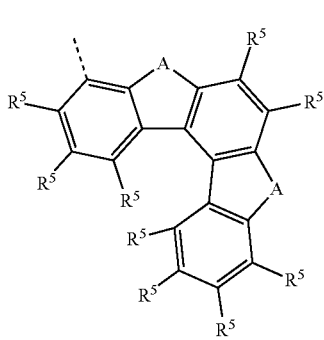
Ar²-35
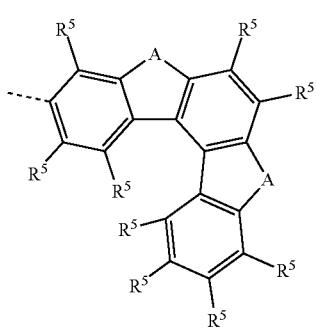
Ar²-36

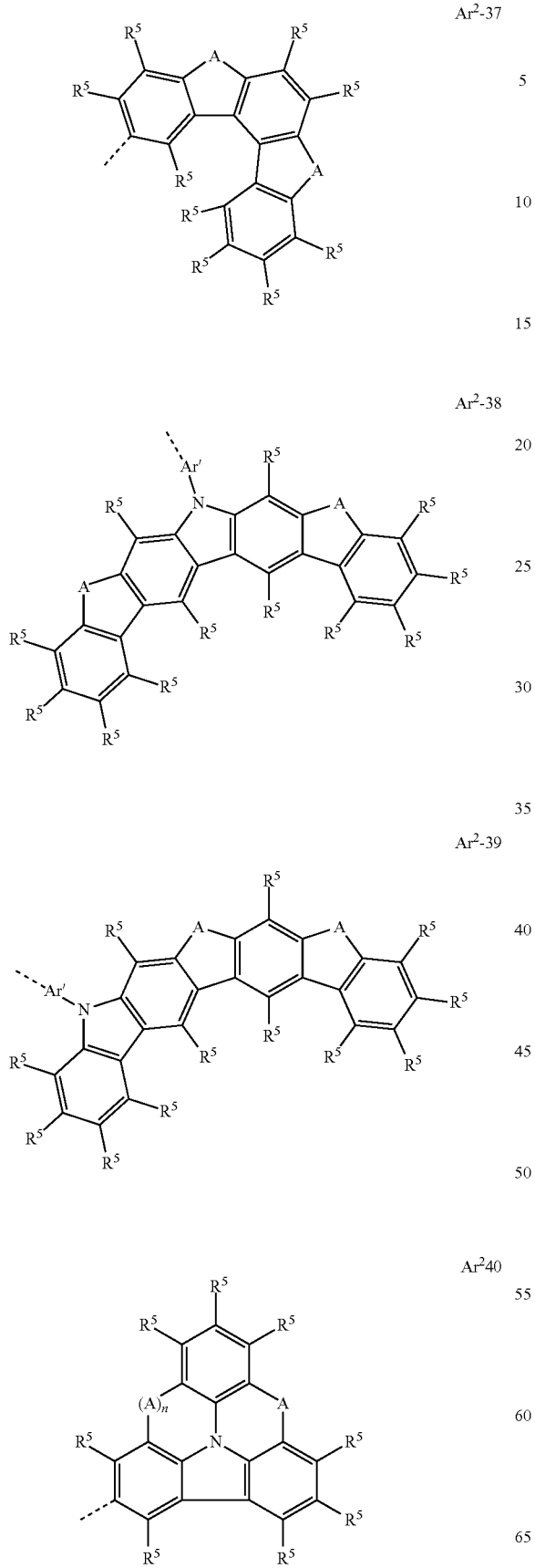
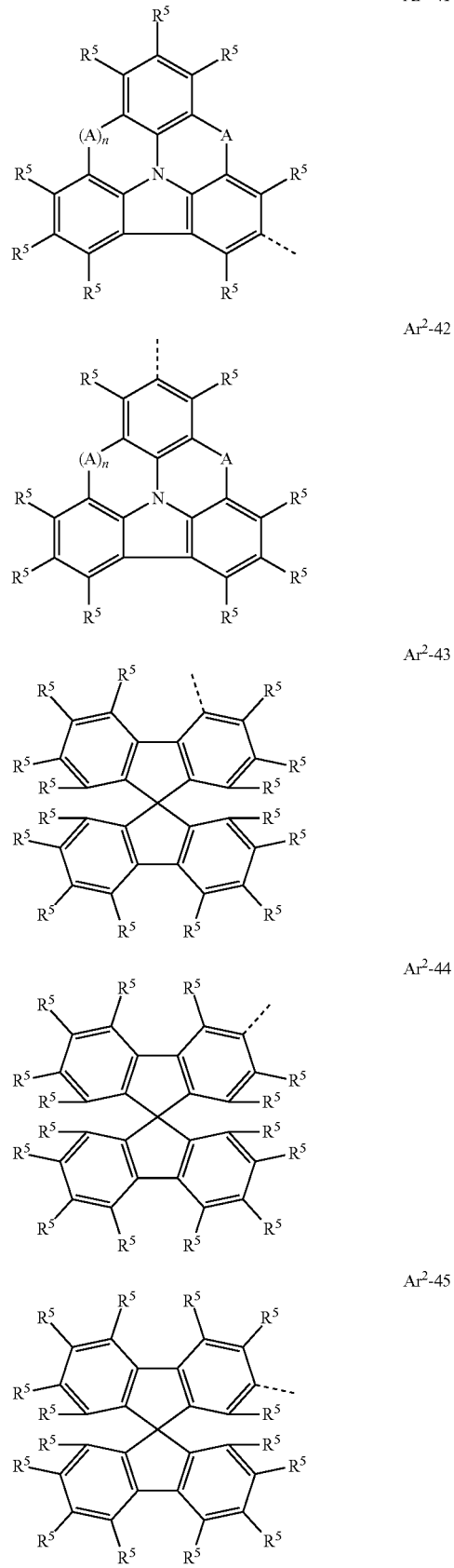

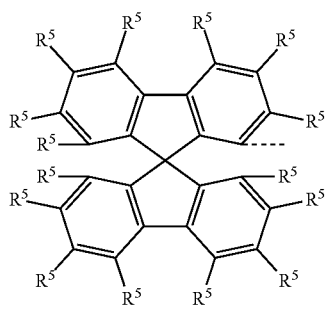
Ar²-46
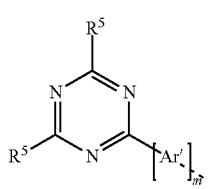
Ar²-47
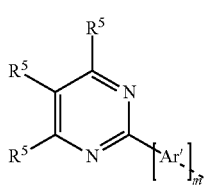
Ar²-48
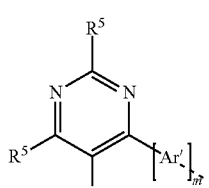
Ar²-49
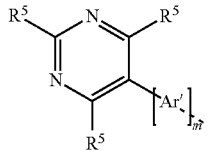
Ar²-50
Ar²-51
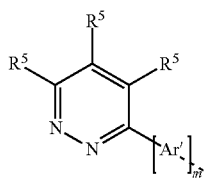
Ar²-52
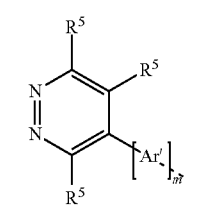
Ar²-53
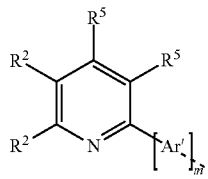
Ar²-54
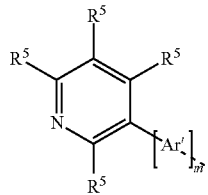
Ar²-55
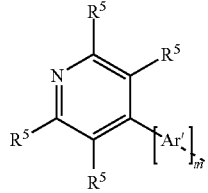
Ar²-56
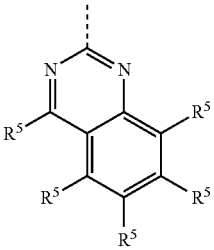
Ar²-57
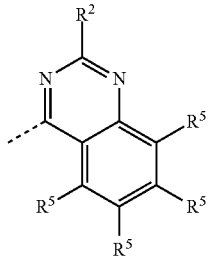
Ar²-58
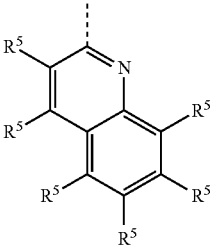
Ar²-59

-continued
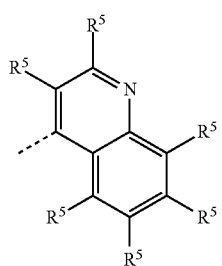
Ar²-60
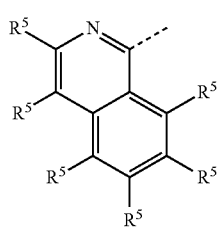
Ar²-61
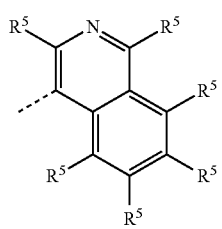
Ar²-62
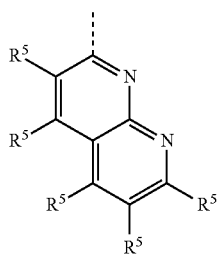
Ar²-63
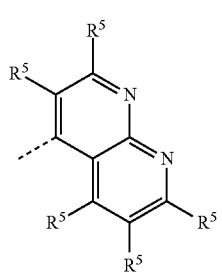
Ar²-64
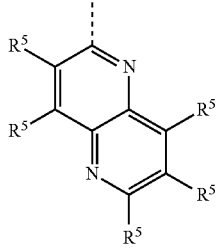
Ar²-65
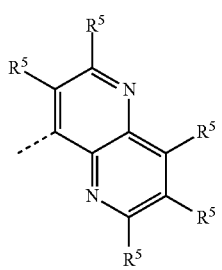
Ar²-66
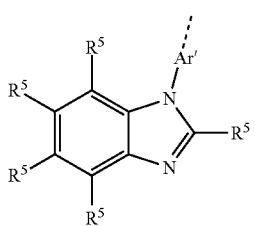
Ar²-67
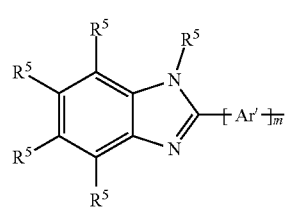
Ar²-68
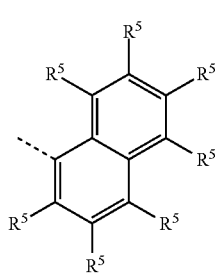
Ar²-69

Ar²-70 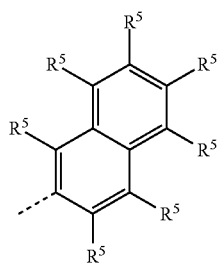

Ar²-71 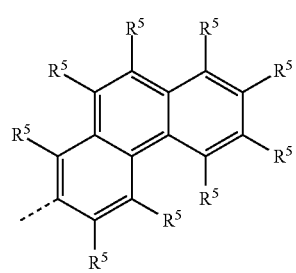

Ar²-72 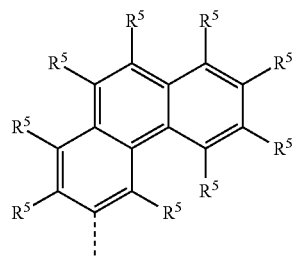

Ar²-73 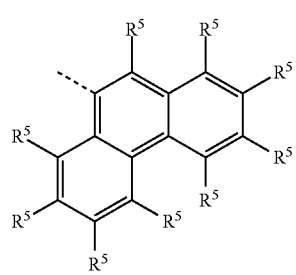

Ar²-74 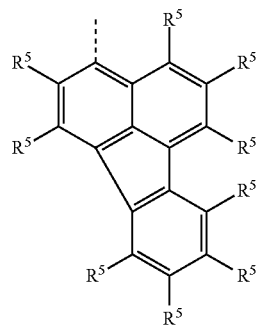

Ar²-75 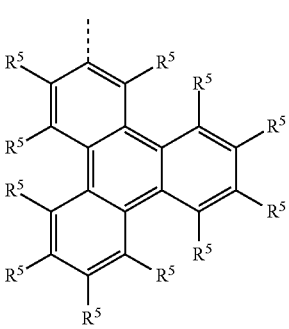

Ar²-76 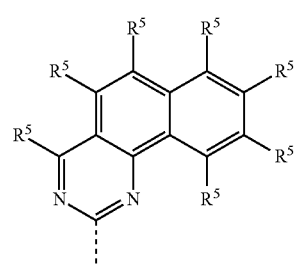

where $R^5$ has the definitions given above, the dotted bond represents the bond to the triazine or pyrimidine or quinazoline and, in addition:

Ar' is the same or different at each instance and is a divalent aromatic or heteroaromatic ring system which has 6 to 18 aromatic ring atoms, preferably 6 to 13 aromatic ring atoms, and may be substituted in each case by one or more $R^5$ radicals;

A is the same or different at each instance and is $C(R^5)_2$, $NR^5$, O or S;

n is 0 or 1, where n=0 means that no A group is bonded at this position and $R^5$ radicals are bonded to the corresponding carbon atoms instead;

m is 0 or 1, where m=0 means that the Ar' group is absent and that the corresponding aromatic or heteroaromatic group is bonded directly to the triazine or pyrimidine or quinazoline.

Examples of suitable triazine compounds that may be used as matrix materials together with the compounds of the invention are the compounds depicted in the following table:

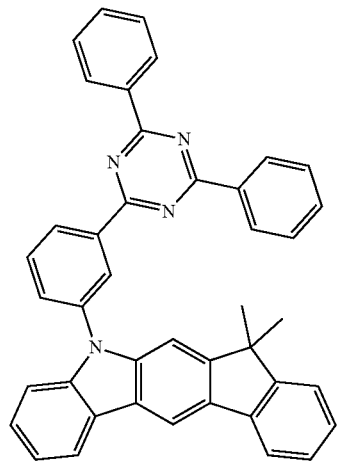 [SMILES: CC1(C)c2ccccc2-c2cc3c4ccccc4n(-c4cccc(-c5nc(-c6ccccc6)nc(-c6ccccc6)n5)c4)c3cc21]
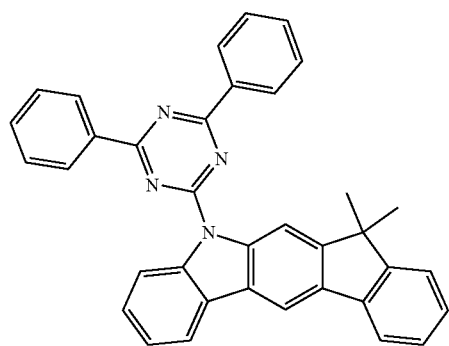 [SMILES: CC1(C)c2ccccc2-c2cc3c4ccccc4n(-c4nc(-c5ccccc5)nc(-c5ccccc5)n4)c3cc21]
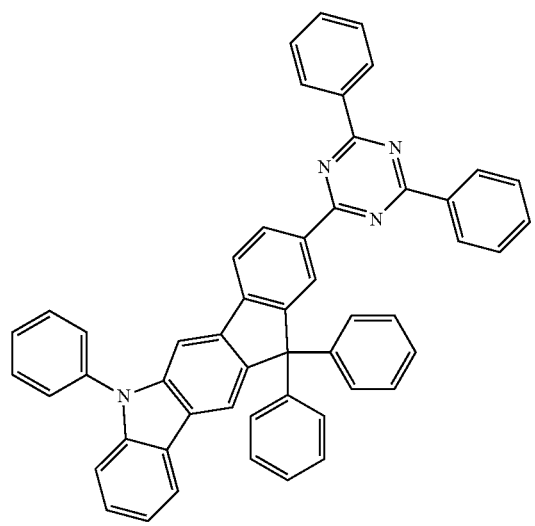 [SMILES: c1ccc(-c2nc(-c3ccccc3)nc(-c3ccc4c(c3)C(c3ccccc3)(c3ccccc3)c3cc5c6ccccc6n(-c6ccccc6)c5cc3-4)n2)cc1]

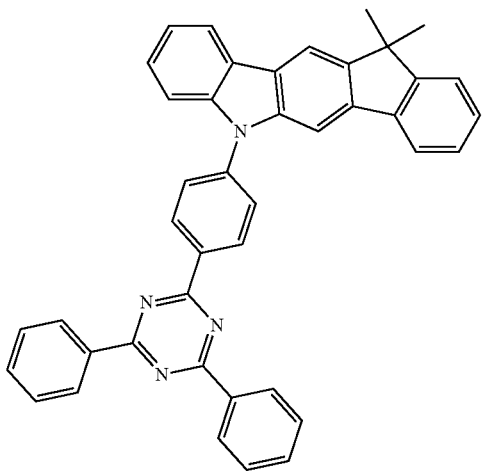 [SMILES: CC1(C)c2ccccc2-c2cc3c(cc21)c1ccccc1n3-c1ccc(-c2nc(-c3ccccc3)nc(-c3ccccc3)n2)cc1]
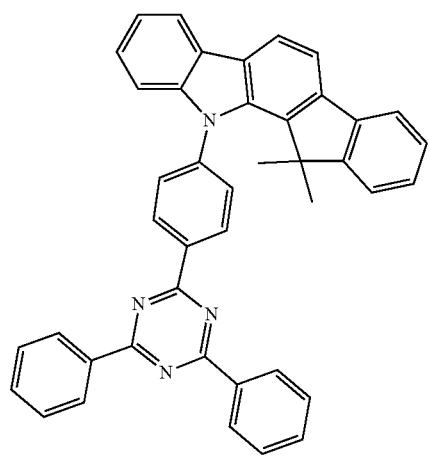 [SMILES: CC1(C)c2ccccc2-c2ccc3c4ccccc4n(-c4ccc(-c5nc(-c6ccccc6)nc(-c6ccccc6)n5)cc4)c3c21]
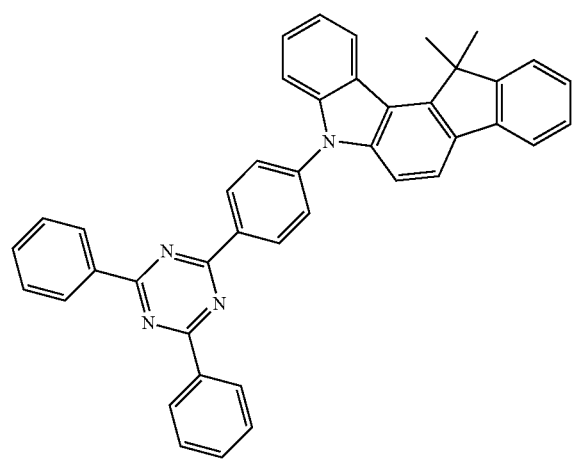 [SMILES: CC1(C)c2ccccc2-c2ccc3c(c21)c1ccccc1n3-c1ccc(-c2nc(-c3ccccc3)nc(-c3ccccc3)n2)cc1]

-continued
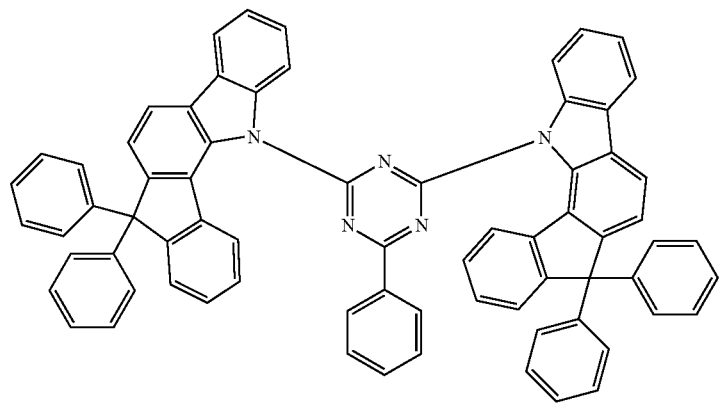 [SMILES: c1ccc(-c2nc(-n3c4ccccc4c4ccc5c(c43)-c3ccccc3C5(c3ccccc3)c3ccccc3)nc(-n3c4ccccc4c4ccc5c(c43)-c3ccccc3C5(c3ccccc3)c3ccccc3)n2)cc1]
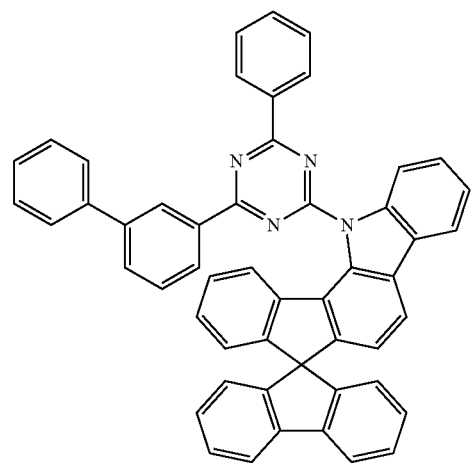 [SMILES: c1ccc(-c2cccc(-c3nc(-c4ccccc4)nc(-n4c5ccccc5c5ccc6c(c54)-c4ccccc4C64c5ccccc5-c5ccccc54)n3)c2)cc1]
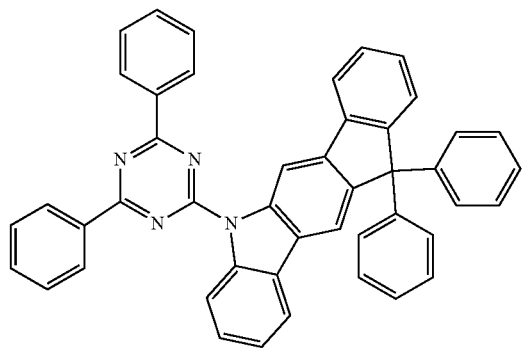 [SMILES: c1ccc(-c2nc(-c3ccccc3)nc(-n3c4ccccc4c4cc5c(cc43)-c3ccccc3C5(c3ccccc3)c3ccccc3)n2)cc1]
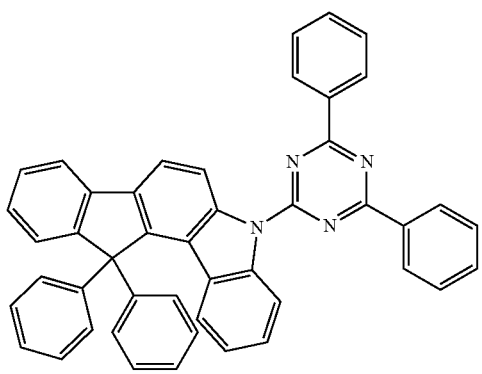 [SMILES: c1ccc(-c2nc(-c3ccccc3)nc(-n3c4ccccc4c4c5c(ccc43)-c3ccccc3C5(c3ccccc3)c3ccccc3)n2)cc1]

-continued
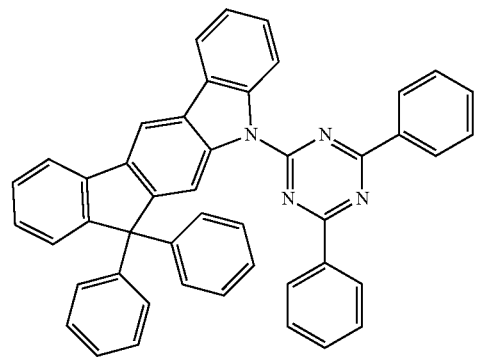 [SMILES: c1ccc(-c2nc(-c3ccccc3)nc(-n3c4ccccc4c4cc5c(cc43)C(c3ccccc3)(c3ccccc3)c3ccccc3-5)n2)cc1]
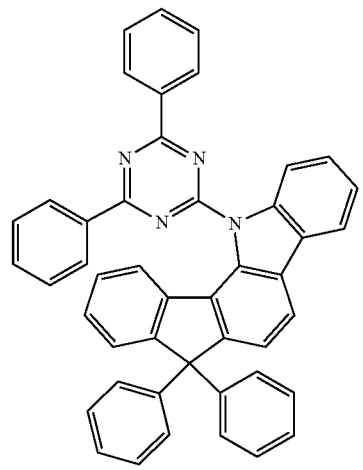 [SMILES: c1ccc(-c2nc(-c3ccccc3)nc(-n3c4ccccc4c4ccc5c(c43)-c3ccccc3C5(c3ccccc3)c3ccccc3)n2)cc1]
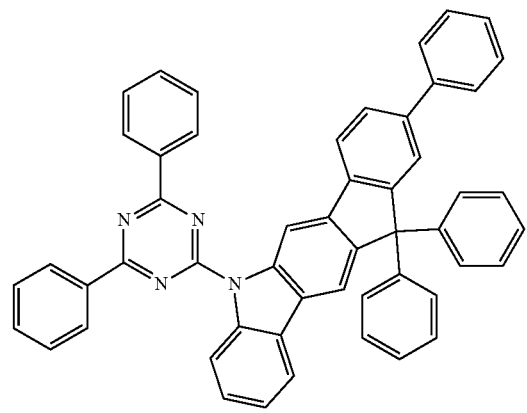 [SMILES: c1ccc(-c2ccc3c(c2)C(c2ccccc2)(c2ccccc2)c2cc4c5ccccc5n(-c5nc(-c6ccccc6)nc(-c6ccccc6)n5)c4cc2-3)cc1]
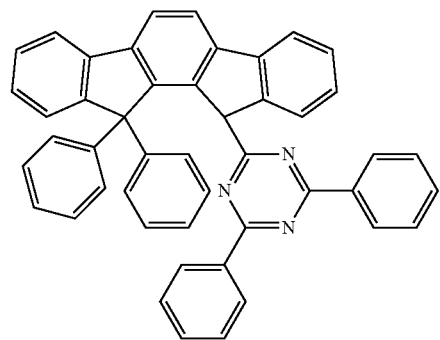 [SMILES: c1ccc(-c2nc(-c3ccccc3)nc(C3c4ccccc4-c4ccc5c(c43)C(c3ccccc3)(c3ccccc3)c3ccccc3-5)n2)cc1]

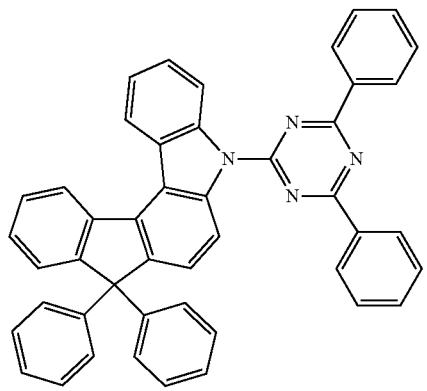 [SMILES: c1ccc(-c2nc(-c3ccccc3)nc(-n3c4ccccc4c4c5c(ccc43)C(c3ccccc3)(c3ccccc3)c3ccccc3-5)n2)cc1]
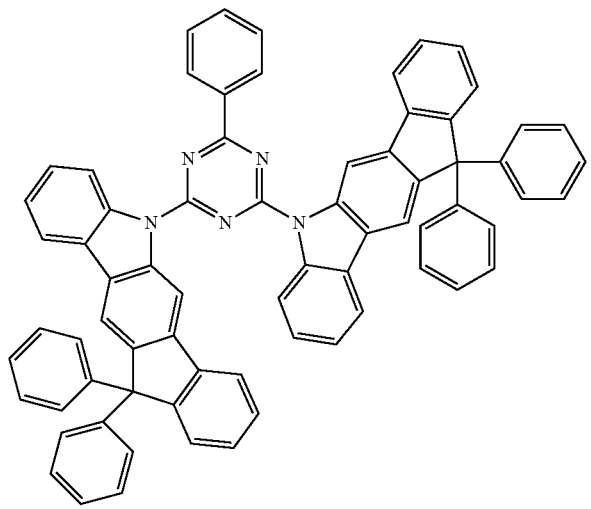 [SMILES: c1ccc(-c2nc(-n3c4ccccc4c4cc5c(cc43)-c3ccccc3C5(c3ccccc3)c3ccccc3)nc(-n3c4ccccc4c4cc5c(cc43)-c3ccccc3C5(c3ccccc3)c3ccccc3)n2)cc1]
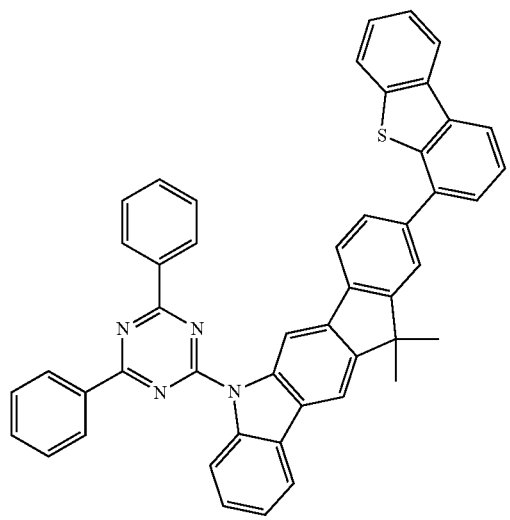 [SMILES: CC1(C)c2cc(-c3cccc4c3sc3ccccc34)ccc2-c2cc3c(cc21)c1ccccc1n3-c1nc(-c2ccccc2)nc(-c2ccccc2)n1]

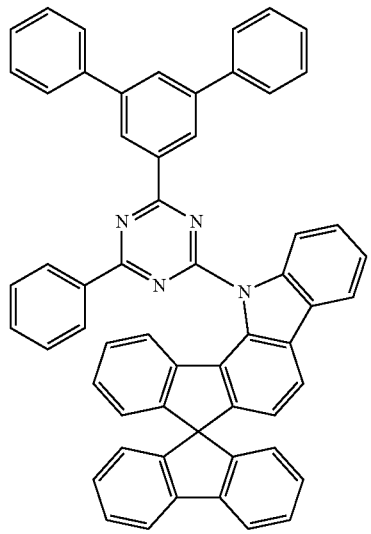 [SMILES: c1ccc(-c2cc(-c3ccccc3)cc(-c3nc(-c4ccccc4)nc(-n4c5ccccc5c5ccc6c(c54)-c4ccccc4C64c5ccccc5-c5ccccc54)n3)c2)cc1]
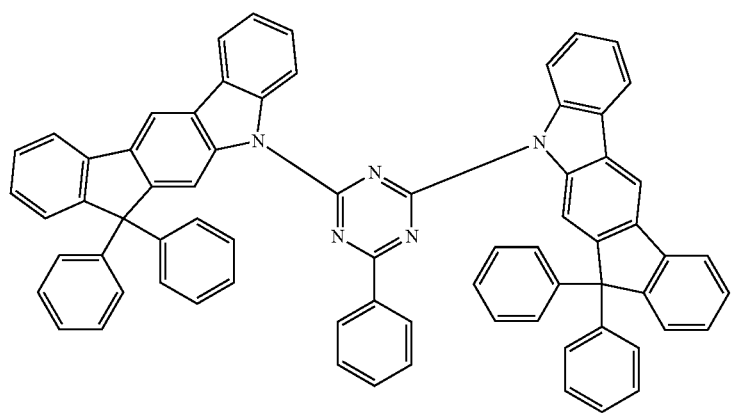 [SMILES: c1ccc(-c2nc(-n3c4ccccc4c4cc5c(cc43)C(c3ccccc3)(c3ccccc3)c3ccccc3-5)nc(-n3c4ccccc4c4cc5c(cc43)C(c3ccccc3)(c3ccccc3)c3ccccc3-5)n2)cc1]
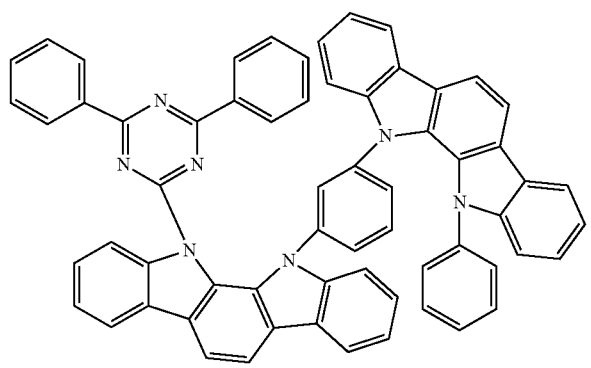 [SMILES: c1ccc(-c2nc(-c3ccccc3)nc(-n3c4ccccc4c4ccc5c6ccccc6n(-c6cccc(-n7c8ccccc8c8ccc9c%10ccccc%10n(-c%10ccccc%10)c9c87)c6)c5c43)n2)cc1]

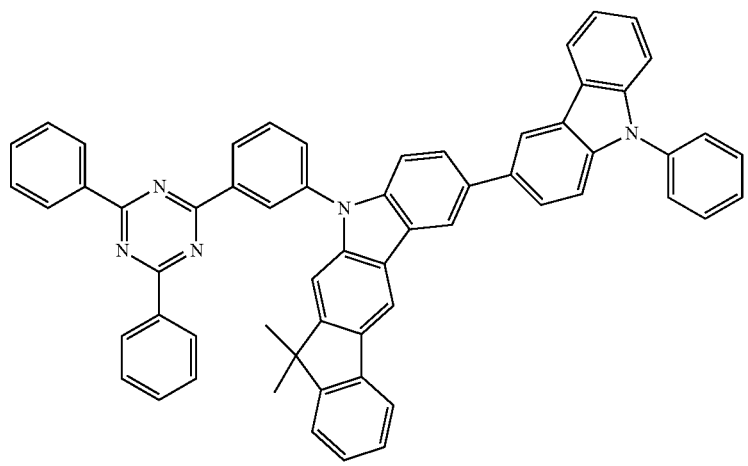 [SMILES: CC1(C)c2ccccc2-c2cc3c4cc(-c5ccc6c(c5)c5ccccc5n6-c5ccccc5)ccc4n(-c4cccc(-c5nc(-c6ccccc6)nc(-c6ccccc6)n5)c4)c3cc21]
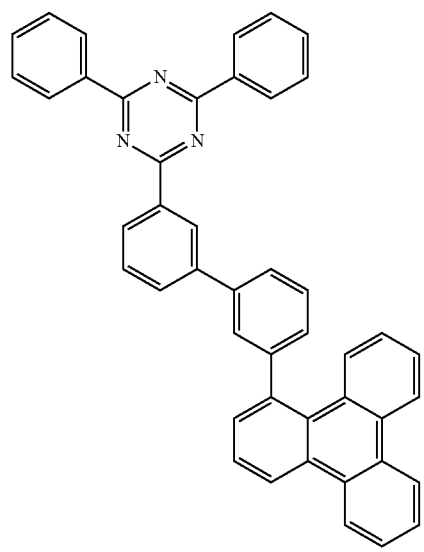 [SMILES: c1ccc(-c2nc(-c3ccccc3)nc(-c3cccc(-c4cccc(-c5cccc6c7ccccc7c7ccccc7c56)c4)c3)n2)cc1]
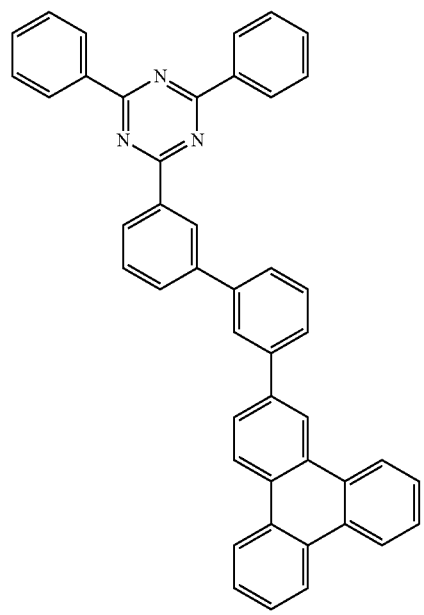 [SMILES: c1ccc(-c2nc(-c3ccccc3)nc(-c3cccc(-c4cccc(-c5ccc6c7ccccc7c7ccccc7c6c5)c4)c3)n2)cc1]

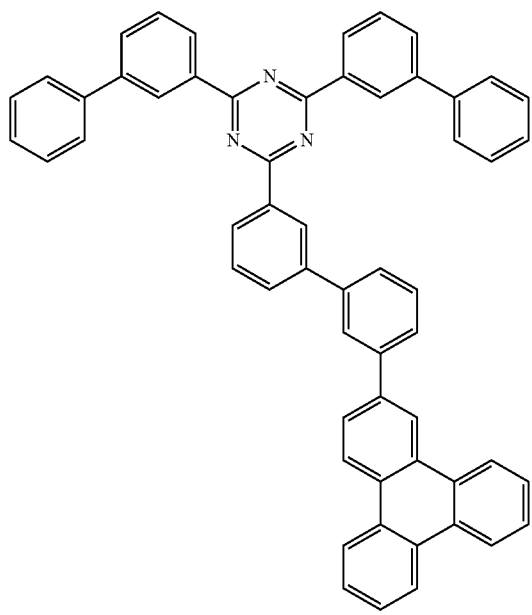 [SMILES: c1ccc(-c2cccc(-c3nc(-c4cccc(-c5ccccc5)c4)nc(-c4cccc(-c5cccc(-c6ccc7c8ccccc8c8ccccc8c7c6)c5)c4)n3)c2)cc1]
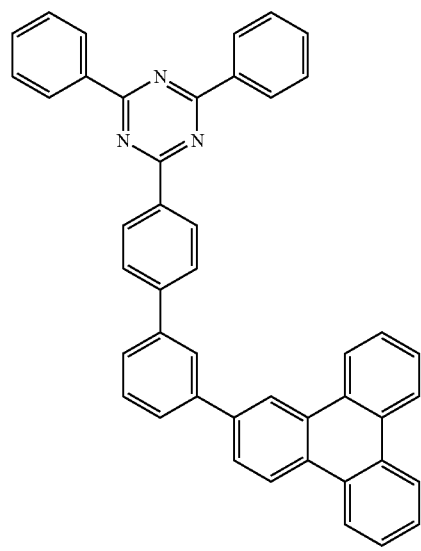 [SMILES: c1ccc(-c2nc(-c3ccccc3)nc(-c3ccc(-c4cccc(-c5ccc6c7ccccc7c7ccccc7c6c5)c4)cc3)n2)cc1]
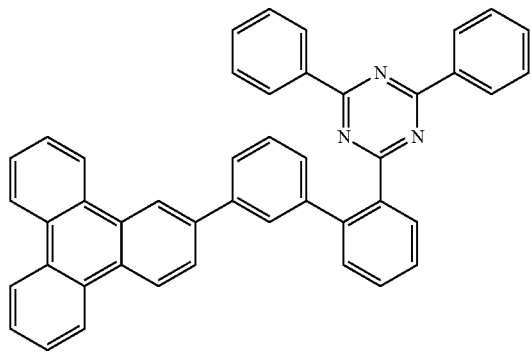 [SMILES: c1ccc(-c2nc(-c3ccccc3)nc(-c3ccccc3-c3cccc(-c4ccc5c6ccccc6c6ccccc6c5c4)c3)n2)cc1]

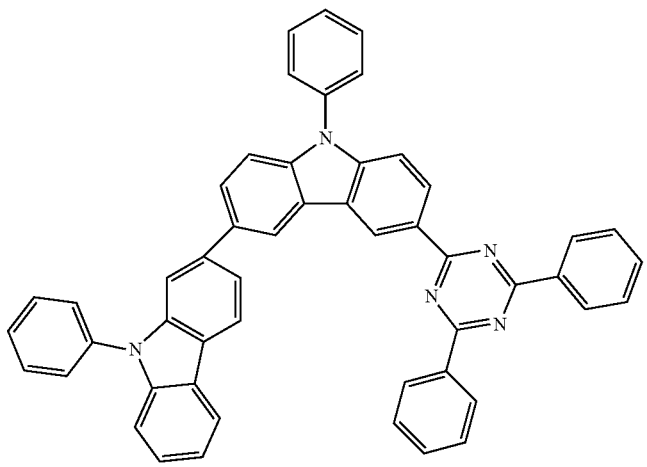 [SMILES: c1ccc(-c2nc(-c3ccccc3)nc(-c3ccc4c(c3)c3cc(-c5ccc6c7ccccc7n(-c7ccccc7)c6c5)ccc3n4-c3ccccc3)n2)cc1]
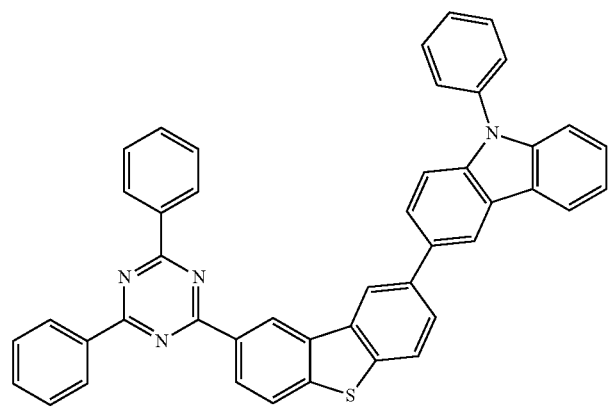 [SMILES: c1ccc(-c2nc(-c3ccccc3)nc(-c3ccc4sc5ccc(-c6ccc7c(c6)c6ccccc6n7-c6ccccc6)cc5c4c3)n2)cc1]
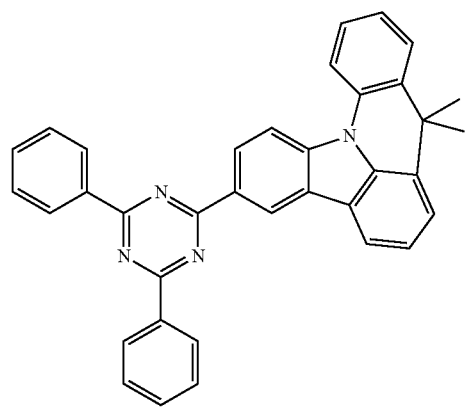 [SMILES: CC1(C)c2ccccc2-n2c3ccc(-c4nc(-c5ccccc5)nc(-c5ccccc5)n4)cc3c3cccc1c32]

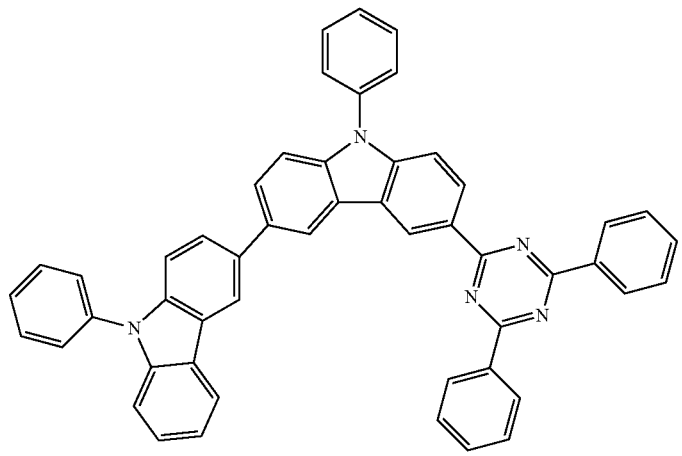 [SMILES: c1ccc(-c2nc(-c3ccccc3)nc(-c3ccc4c(c3)c3cc(-c5ccc6c(c5)c5ccccc5n6-c5ccccc5)ccc3n4-c3ccccc3)n2)cc1]
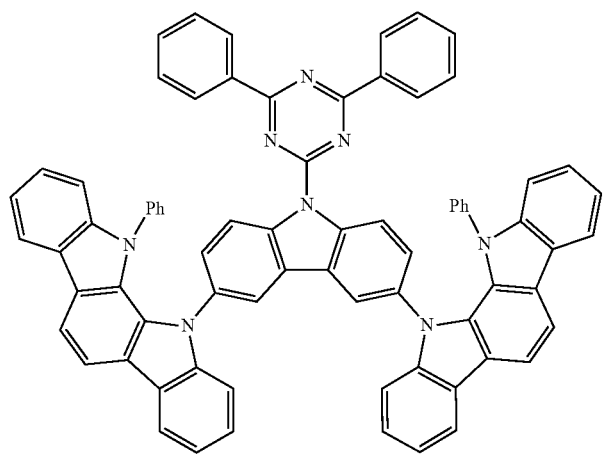 [SMILES: c1ccc(-c2nc(-c3ccccc3)nc(-n3c4ccc(-n5c6ccccc6c6ccc7c8ccccc8n(-c8ccccc8)c7c65)cc4c4cc(-n5c6ccccc6c6ccc7c8ccccc8n(-c8ccccc8)c7c65)ccc43)n2)cc1]
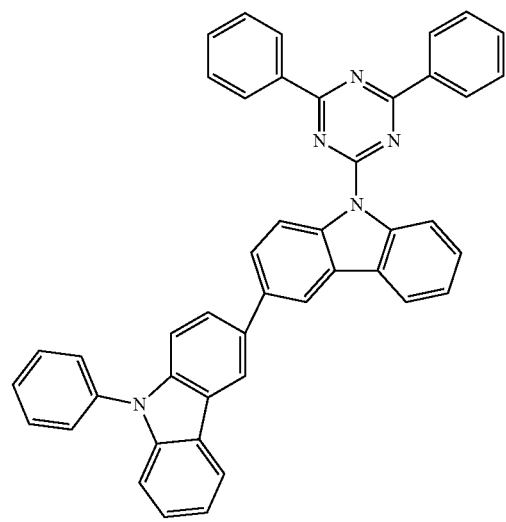 [SMILES: c1ccc(-c2nc(-c3ccccc3)nc(-n3c4ccccc4c4cc(-c5ccc6c(c5)c5ccccc5n6-c5ccccc5)ccc43)n2)cc1]

-continued
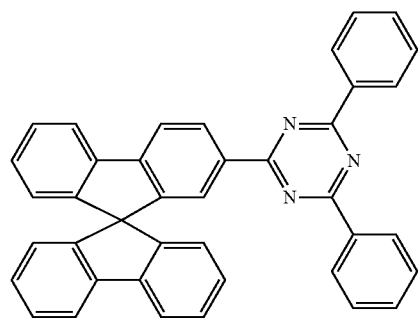 [SMILES: c1ccc(-c2nc(-c3ccccc3)nc(-c3ccc4c(c3)C3(c5ccccc5-c5ccccc53)c3ccccc3-4)n2)cc1]
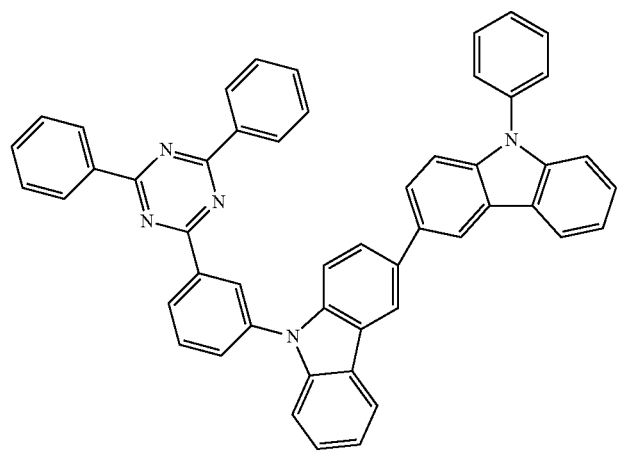 [SMILES: c1ccc(-c2nc(-c3ccccc3)nc(-c3cccc(-n4c5ccccc5c5cc(-c6ccc7c(c6)c6ccccc6n7-c6ccccc6)ccc54)c3)n2)cc1]
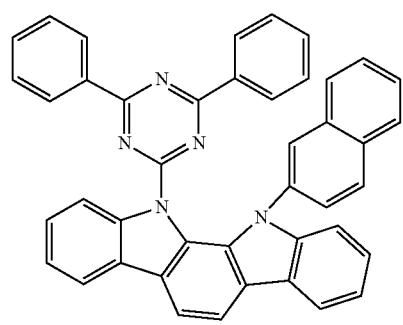 [SMILES: c1ccc(-c2nc(-c3ccccc3)nc(-n3c4ccccc4c4ccc5c6ccccc6n(-c6ccc7ccccc7c6)c5c43)n2)cc1]
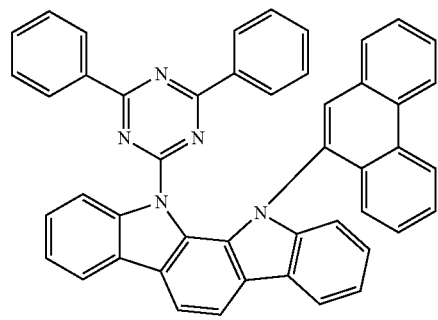 [SMILES: c1ccc(-c2nc(-c3ccccc3)nc(-n3c4ccccc4c4ccc5c6ccccc6n(-c6cc7ccccc7c7ccccc67)c5c43)n2)cc1]

-continued
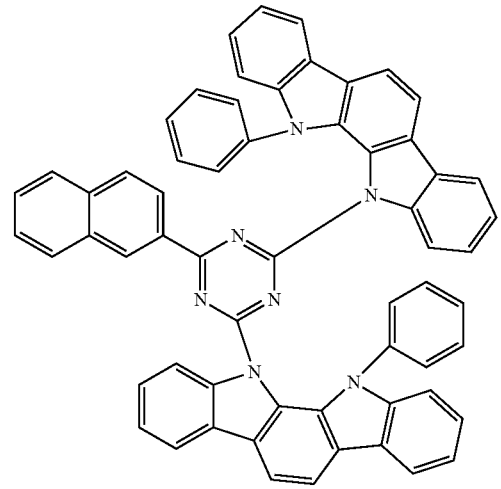 [SMILES: c1ccc(-n2c3ccccc3c3ccc4c5ccccc5n(-c5nc(-c6ccc7ccccc7c6)nc(-n6c7ccccc7c7ccc8c9ccccc9n(-c9ccccc9)c8c76)n5)c4c32)cc1]
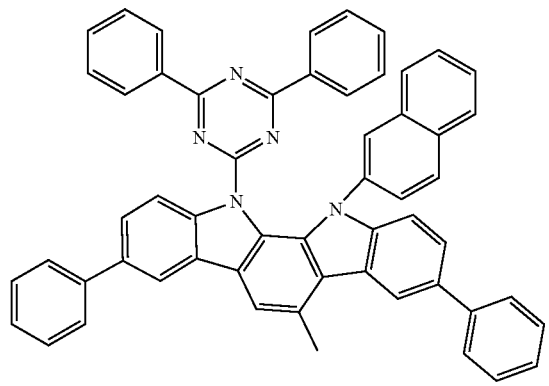 [SMILES: Cc1cc2c3cc(-c4ccccc4)ccc3n(-c3nc(-c4ccccc4)nc(-c4ccccc4)n3)c2c2c1c1cc(-c3ccccc3)ccc1n2-c1ccc2ccccc2c1]
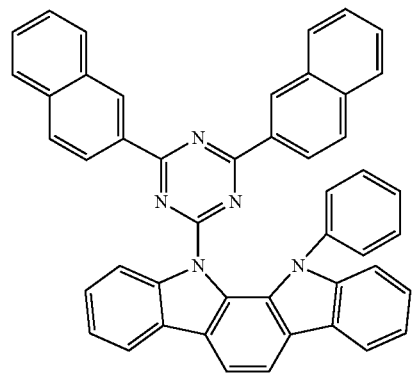 [SMILES: c1ccc(-n2c3ccccc3c3ccc4c5ccccc5n(-c5nc(-c6ccc7ccccc7c6)nc(-c6ccc7ccccc7c6)n5)c4c32)cc1]
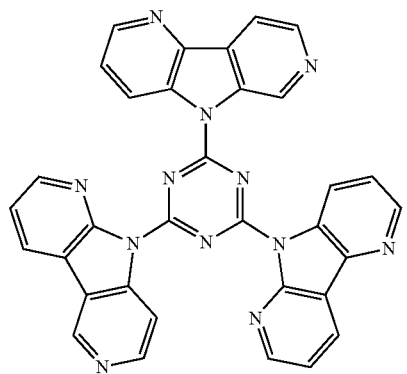 [SMILES: c1cnc2c(c1)c1cnccc1n2-c1nc(-n2c3cnccc3c3ncccc32)nc(-n2c3cccnc3c3cccnc32)n1]

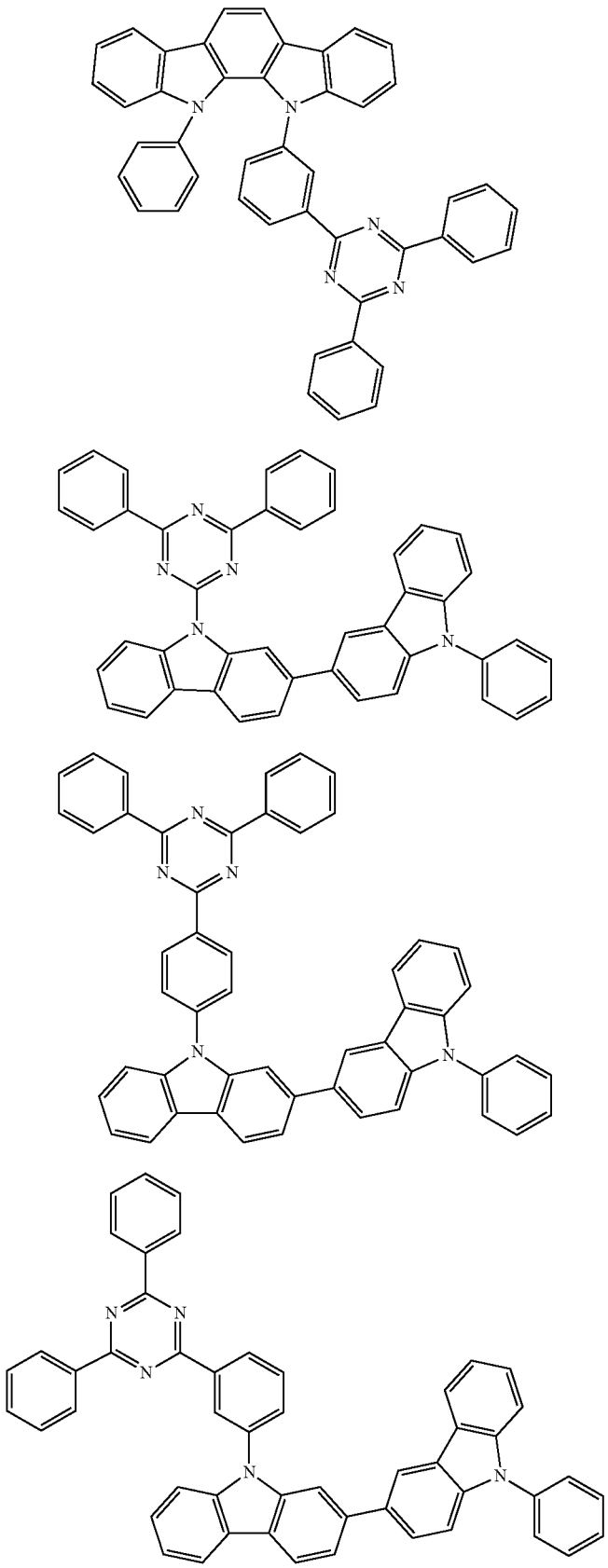

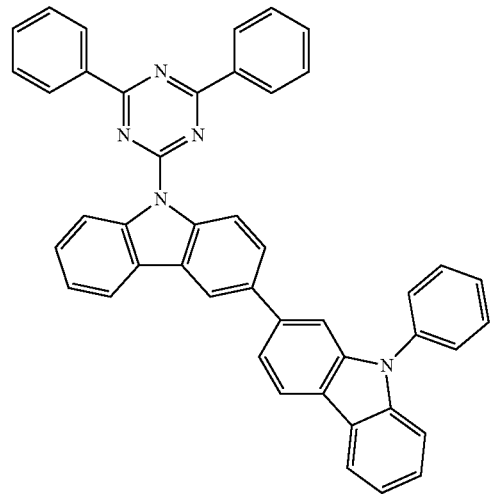 [SMILES: c1ccc(-c2nc(-c3ccccc3)nc(-n3c4ccccc4c4cc(-c5ccc6c7ccccc7n(-c7ccccc7)c6c5)ccc43)n2)cc1]
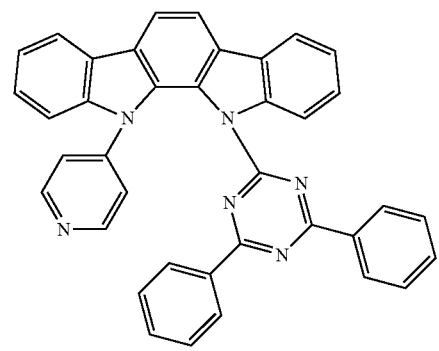 [SMILES: c1ccc(-c2nc(-c3ccccc3)nc(-n3c4ccccc4c4ccc5c6ccccc6n(-c6ccncc6)c5c43)n2)cc1]
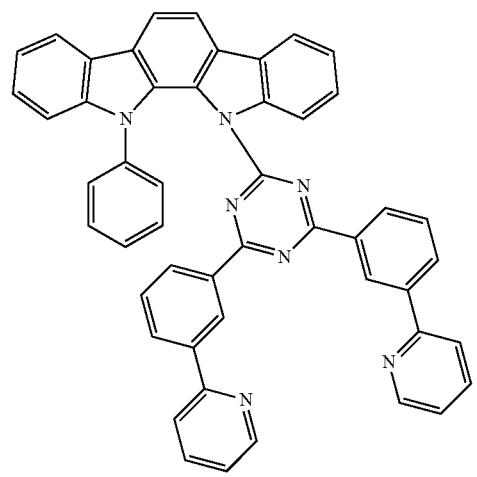 [SMILES: c1ccc(-n2c3ccccc3c3ccc4c5ccccc5n(-c5nc(-c6cccc(-c7ccccn7)c6)nc(-c6cccc(-c7ccccn7)c6)n5)c4c32)cc1]

-continued
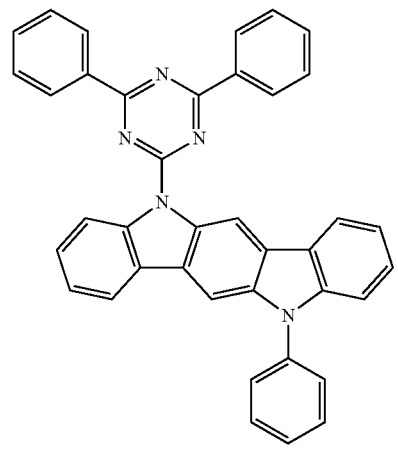 [SMILES: c1ccc(-c2nc(-c3ccccc3)nc(-n3c4ccccc4c4cc5c(cc43)c3ccccc3n5-c3ccccc3)n2)cc1]
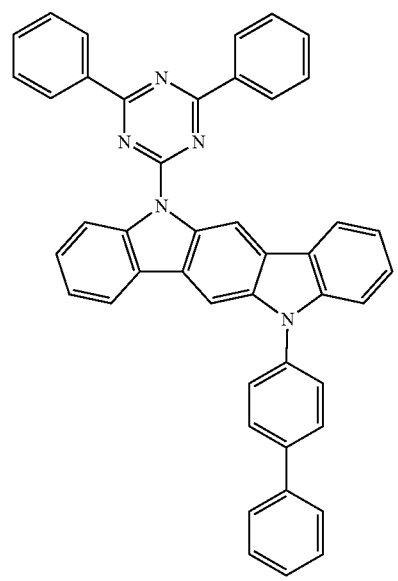 [SMILES: c1ccc(-c2ccc(-n3c4ccccc4c4cc5c(cc43)c3ccccc3n5-c3nc(-c4ccccc4)nc(-c4ccccc4)n3)cc2)cc1]
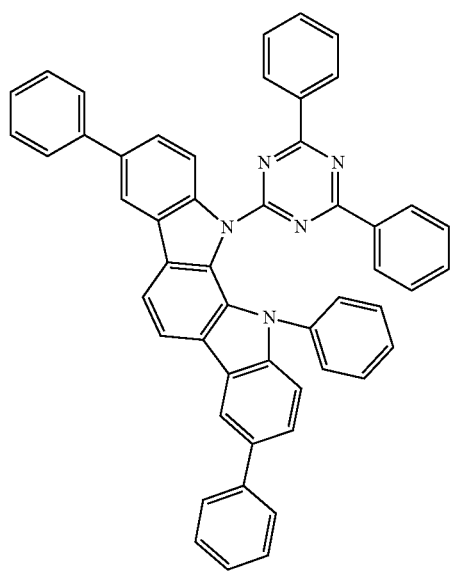 [SMILES: c1ccc(-c2ccc3c(c2)c2ccc4c5cc(-c6ccccc6)ccc5n(-c5nc(-c6ccccc6)nc(-c6ccccc6)n5)c4c2n3-c2ccccc2)cc1]

-continued
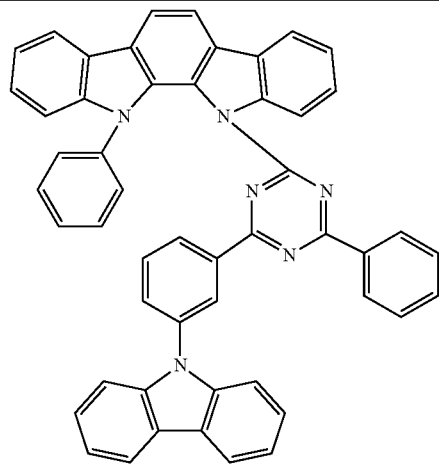
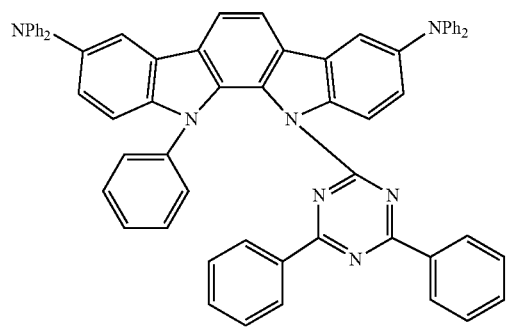
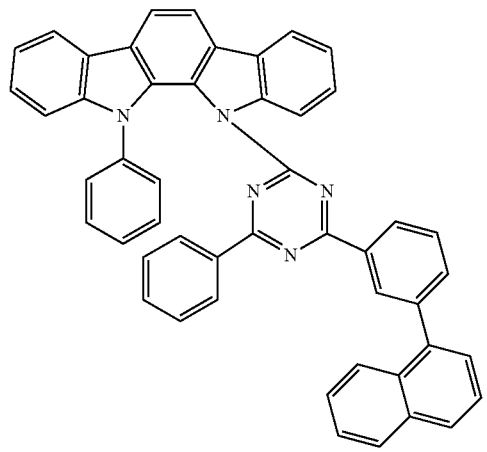 [SMILES: c1ccc(-c2nc(-c3cccc(-c4cccc5ccccc45)c3)nc(-n3c4ccccc4c4ccc5c6ccccc6n(-c6ccccc6)c5c43)n2)cc1]
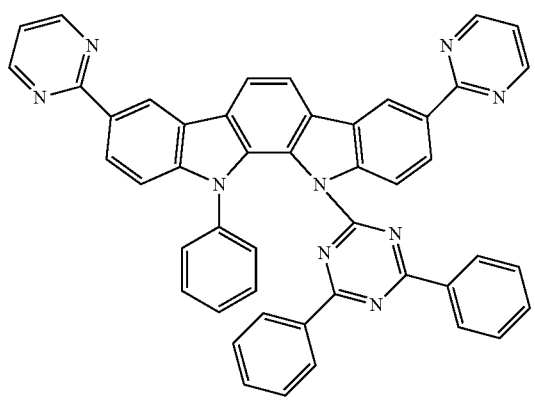 [SMILES: c1ccc(-c2nc(-c3ccccc3)nc(-n3c4ccc(-c5ncccn5)cc4c4ccc5c6cc(-c7ncccn7)ccc6n(-c6ccccc6)c5c43)n2)cc1]

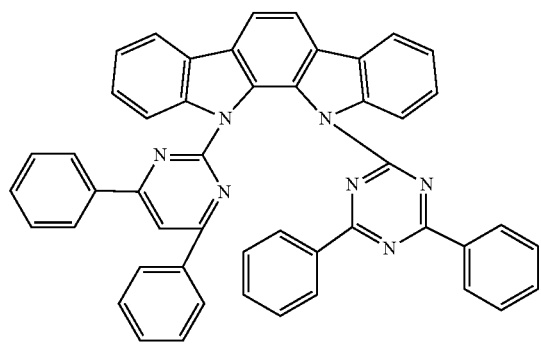 [SMILES: c1ccc(-c2cc(-c3ccccc3)nc(-n3c4ccccc4c4ccc5c6ccccc6n(-c6nc(-c7ccccc7)nc(-c7ccccc7)n6)c5c43)n2)cc1]
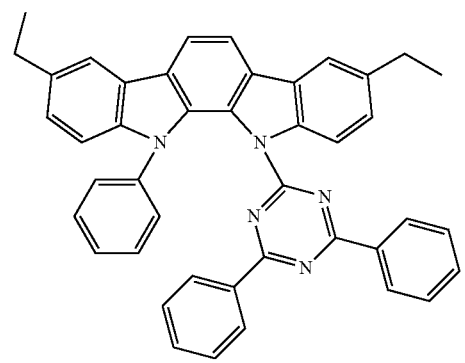 [SMILES: CCc1ccc2c(c1)c1ccc3c4cc(CC)ccc4n(-c4nc(-c5ccccc5)nc(-c5ccccc5)n4)c3c1n2-c1ccccc1]
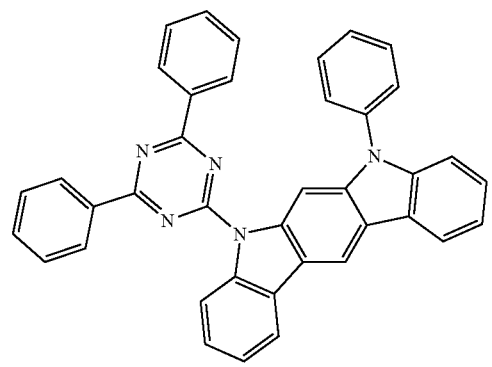 [SMILES: c1ccc(-c2nc(-c3ccccc3)nc(-n3c4ccccc4c4cc5c6ccccc6n(-c6ccccc6)c5cc43)n2)cc1]
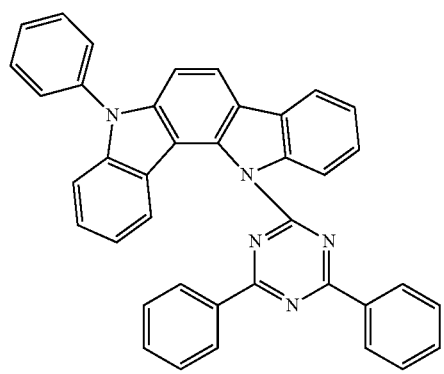 [SMILES: c1ccc(-c2nc(-c3ccccc3)nc(-n3c4ccccc4c4ccc5c(c6ccccc6n5-c5ccccc5)c43)n2)cc1]

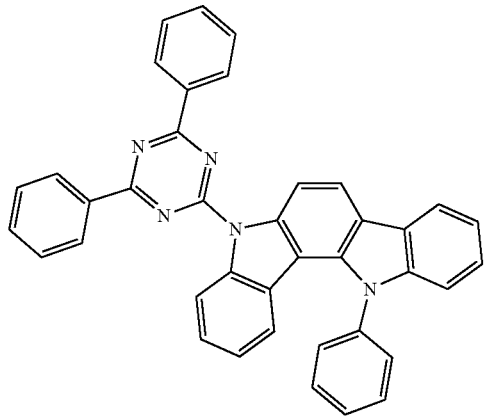 [SMILES: c1ccc(-c2nc(-c3ccccc3)nc(-n3c4ccccc4c4c3ccc3c5ccccc5n(-c5ccccc5)c34)n2)cc1]
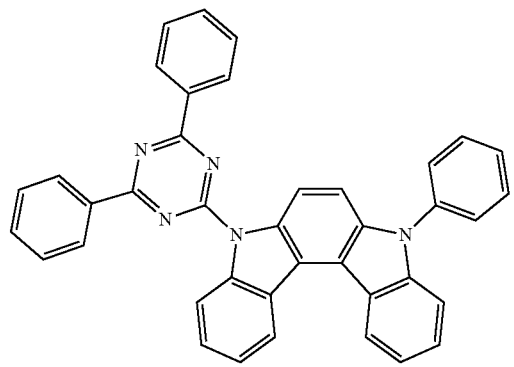 [SMILES: c1ccc(-c2nc(-c3ccccc3)nc(-n3c4ccccc4c4c5c6ccccc6n(-c6ccccc6)c5ccc43)n2)cc1]
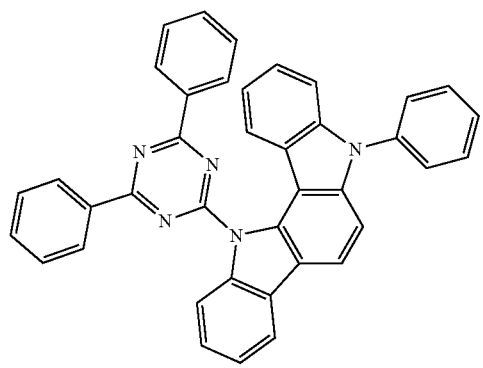 [SMILES: c1ccc(-c2nc(-c3ccccc3)nc(-n3c4ccccc4c4ccc5c(c6ccccc6n5-c5ccccc5)c43)n2)cc1]
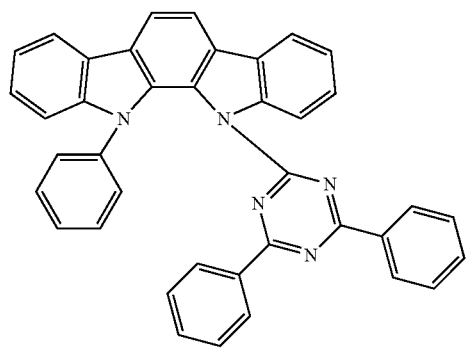 [SMILES: c1ccc(-c2nc(-c3ccccc3)nc(-n3c4ccccc4c4ccc5c6ccccc6n(-c6ccccc6)c5c43)n2)cc1]

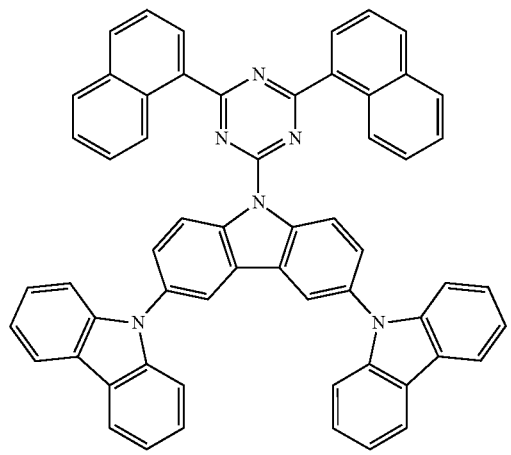 [SMILES: c1ccc2c(-c3nc(-c4cccc5ccccc45)nc(-n4c5ccc(-n6c7ccccc7c7ccccc76)cc5c5cc(-n6c7ccccc7c7ccccc76)ccc54)n3)cccc2c1]
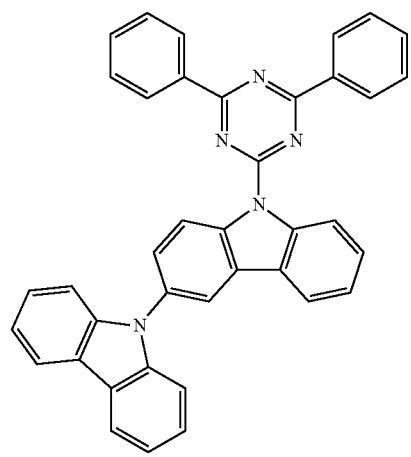 [SMILES: c1ccc(-c2nc(-c3ccccc3)nc(-n3c4ccccc4c4cc(-n5c6ccccc6c6ccccc65)ccc43)n2)cc1]
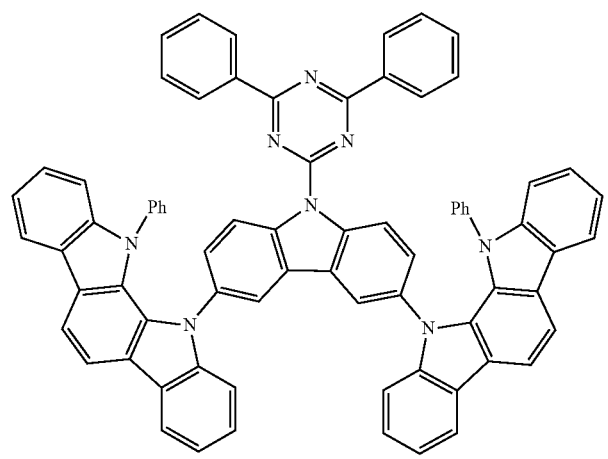 [SMILES: c1ccc(-c2nc(-c3ccccc3)nc(-n3c4ccc(-n5c6ccccc6c6ccc7c8ccccc8n(-c8ccccc8)c7c65)cc4c4cc(-n5c6ccccc6c6ccc7c8ccccc8n(-c8ccccc8)c7c65)ccc43)n2)cc1]

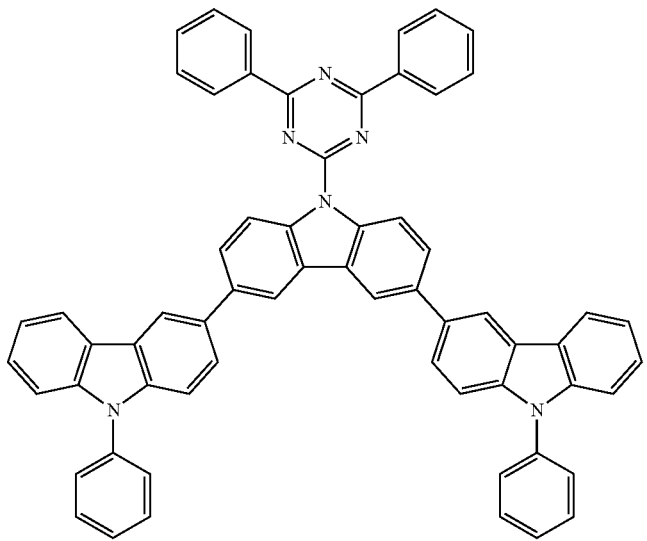 [SMILES: c1ccc(-c2nc(-c3ccccc3)nc(-n3c4ccc(-c5ccc6c(c5)c5ccccc5n6-c5ccccc5)cc4c4cc(-c5ccc6c(c5)c5ccccc5n6-c5ccccc5)ccc43)n2)cc1]
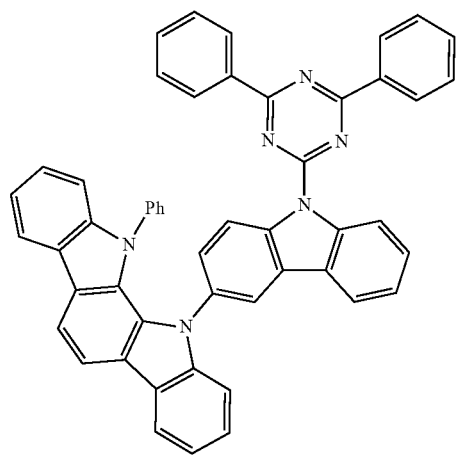 [SMILES: c1ccc(-c2nc(-c3ccccc3)nc(-n3c4ccccc4c4cc(-n5c6ccccc6c6ccc7c8ccccc8n(-c8ccccc8)c7c65)ccc43)n2)cc1]
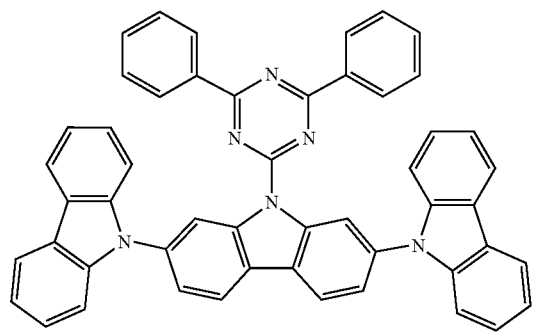 [SMILES: c1ccc(-c2nc(-c3ccccc3)nc(-n3c4cc(-n5c6ccccc6c6ccccc65)ccc4c4ccc(-n5c6ccccc6c6ccccc65)cc43)n2)cc1]

-continued
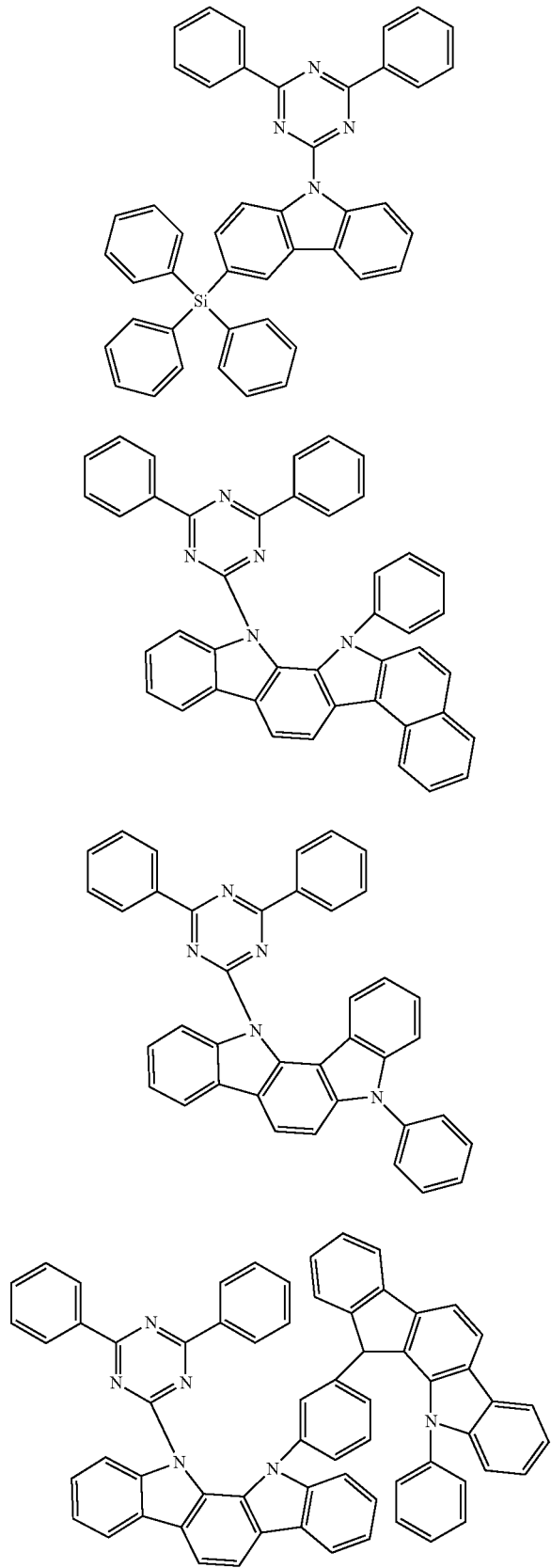

-continued
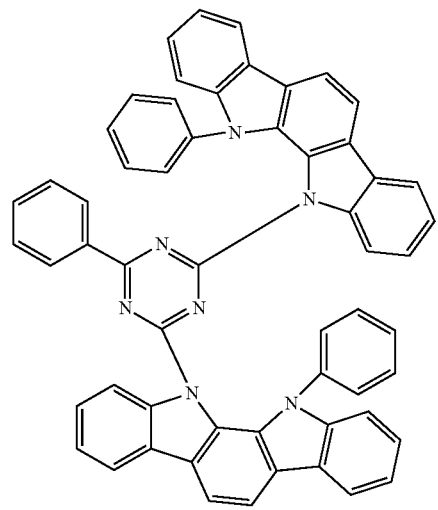 [SMILES: c1ccc(-c2nc(-n3c4ccccc4c4ccc5c6ccccc6n(-c6ccccc6)c5c43)nc(-n3c4ccccc4c4ccc5c6ccccc6n(-c6ccccc6)c5c43)n2)cc1]
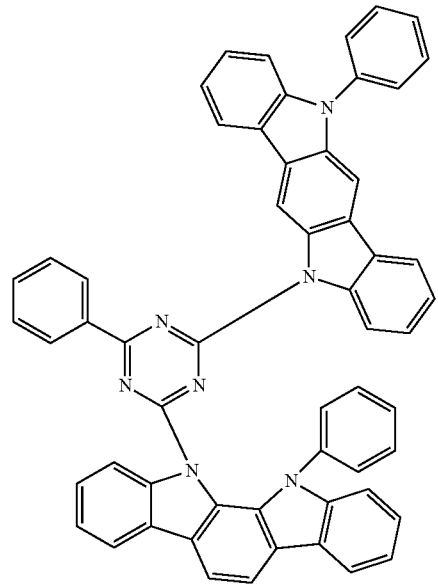 [SMILES: c1ccc(-c2nc(-n3c4ccccc4c4cc5c(cc43)c3ccccc3n5-c3ccccc3)nc(-n3c4ccccc4c4ccc5c6ccccc6n(-c6ccccc6)c5c43)n2)cc1]
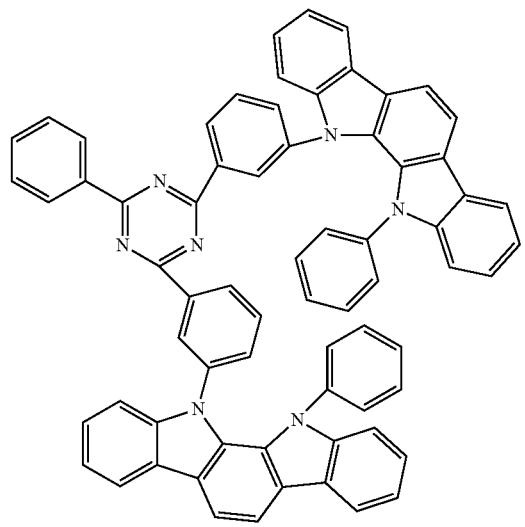 [SMILES: c1ccc(-c2nc(-c3cccc(-n4c5ccccc5c5ccc6c7ccccc7n(-c7ccccc7)c6c54)c3)nc(-c3cccc(-n4c5ccccc5c5ccc6c7ccccc7n(-c7ccccc7)c6c54)c3)n2)cc1]

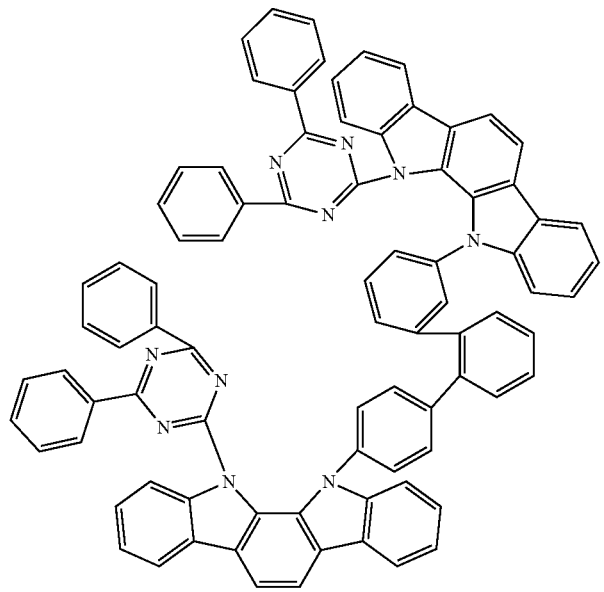 [SMILES: c1ccc(-c2nc(-c3ccccc3)nc(-n3c4ccccc4c4ccc5c6ccccc6n(-c6ccc(-c7ccccc7-c7cccc(-n8c9ccccc9c9ccc%10c%11ccccc%11n(-c%11nc(-c%12ccccc%12)nc(-c%12ccccc%12)n%11)c%10c98)c7)cc6)c5c43)n2)cc1]
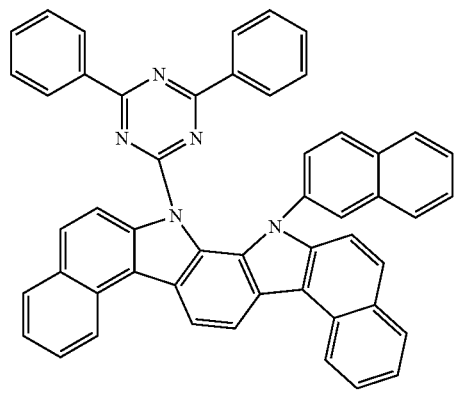 [SMILES: c1ccc(-c2nc(-c3ccccc3)nc(-n3c4ccc5ccccc5c4c4ccc5c6c7ccccc7ccc6n(-c6ccc7ccccc7c6)c5c43)n2)cc1]
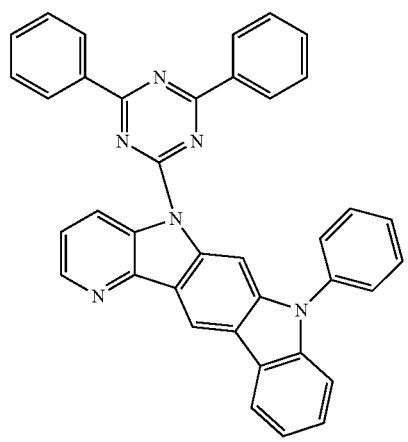 [SMILES: c1ccc(-c2nc(-c3ccccc3)nc(-n3c4cc5c(cc4c4ncccc43)c3ccccc3n5-c3ccccc3)n2)cc1]

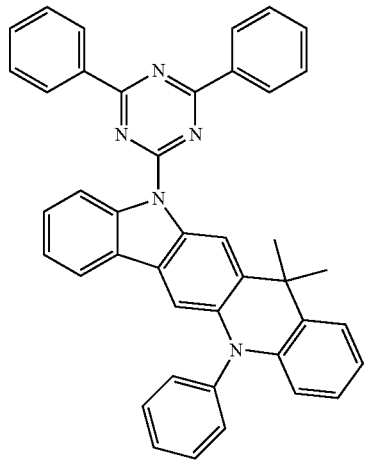 [SMILES: CC1(C)c2ccccc2N(c2ccccc2)c2cc3c4ccccc4n(-c4nc(-c5ccccc5)nc(-c5ccccc5)n4)c3cc21]
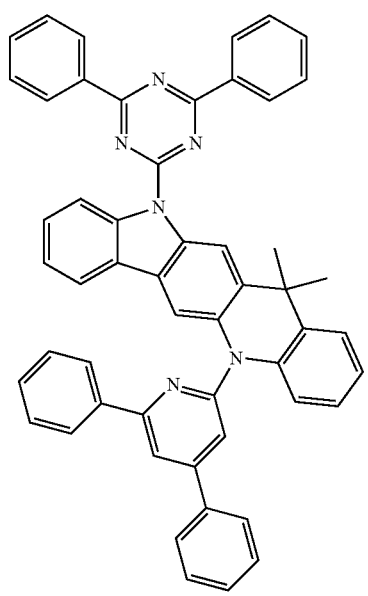 [SMILES: CC1(C)c2ccccc2N(c2cc(-c3ccccc3)cc(-c3ccccc3)n2)c2cc3c4ccccc4n(-c4nc(-c5ccccc5)nc(-c5ccccc5)n4)c3cc21]
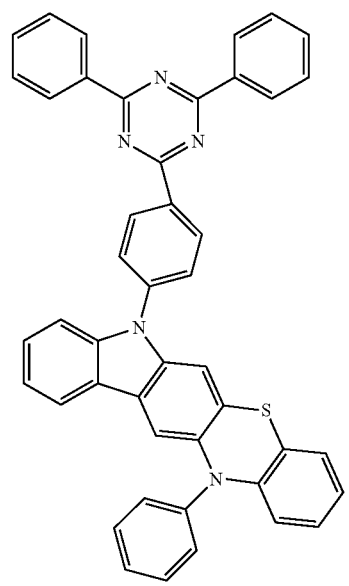 [SMILES: c1ccc(-c2nc(-c3ccccc3)nc(-c3ccc(-n4c5ccccc5c5cc6c(cc54)Sc4ccccc4N6c4ccccc4)cc3)n2)cc1]

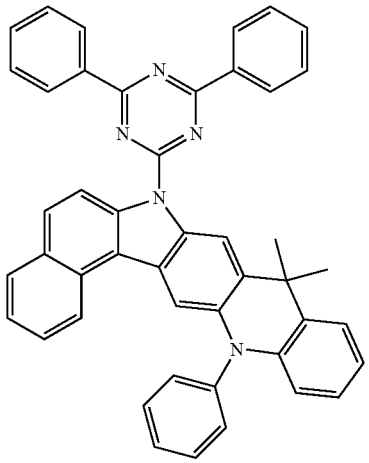 [SMILES: CC1(C)c2ccccc2N(c2ccccc2)c2cc3c4c5ccccc5ccc4n(-c4nc(-c5ccccc5)nc(-c5ccccc5)n4)c3cc21]
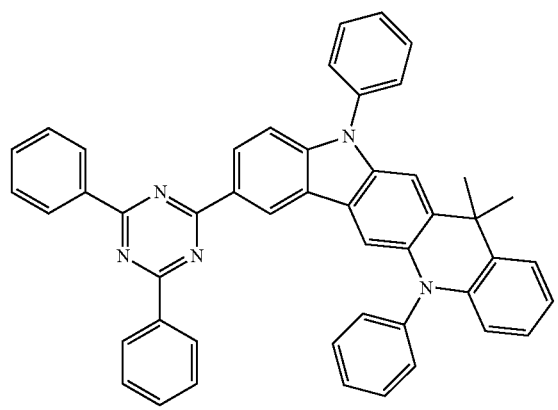 [SMILES: CC1(C)c2ccccc2N(c2ccccc2)c2cc3c4cc(-c5nc(-c6ccccc6)nc(-c6ccccc6)n5)ccc4n(-c4ccccc4)c3cc21]
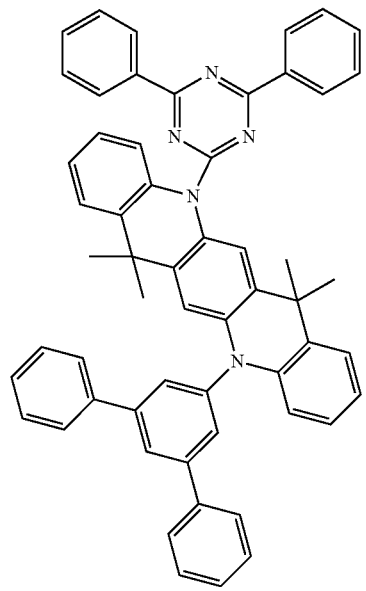 [SMILES: CC1(C)c2ccccc2N(c2cc(-c3ccccc3)cc(-c3ccccc3)c2)c2cc3c(cc21)N(c1nc(-c2ccccc2)nc(-c2ccccc2)n1)c1ccccc1C3(C)C]

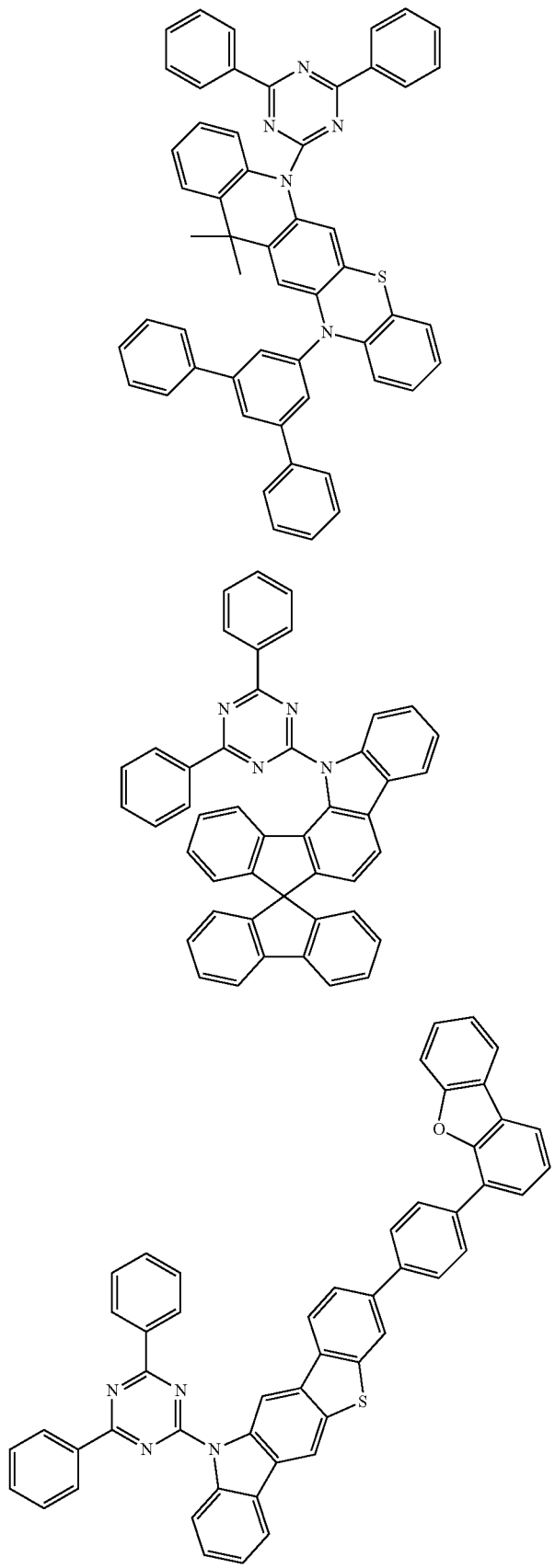

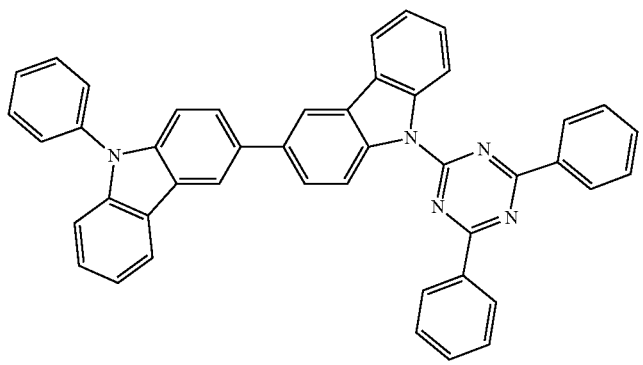 [SMILES: c1ccc(-c2nc(-c3ccccc3)nc(-n3c4ccccc4c4cc(-c5ccc6c(c5)c5ccccc5n6-c5ccccc5)ccc43)n2)cc1]
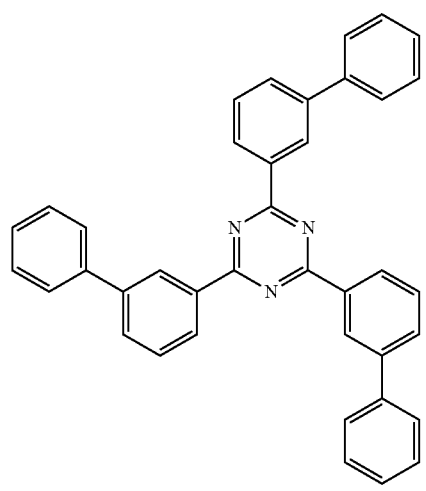 [SMILES: c1ccc(-c2cccc(-c3nc(-c4cccc(-c5ccccc5)c4)nc(-c4cccc(-c5ccccc5)c4)n3)c2)cc1]
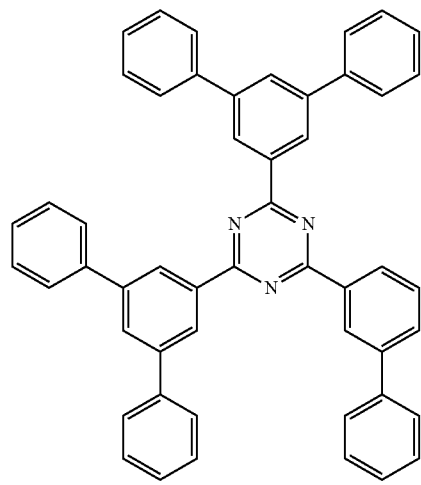 [SMILES: c1ccc(-c2cccc(-c3nc(-c4cc(-c5ccccc5)cc(-c5ccccc5)c4)nc(-c4cc(-c5ccccc5)cc(-c5ccccc5)c4)n3)c2)cc1]

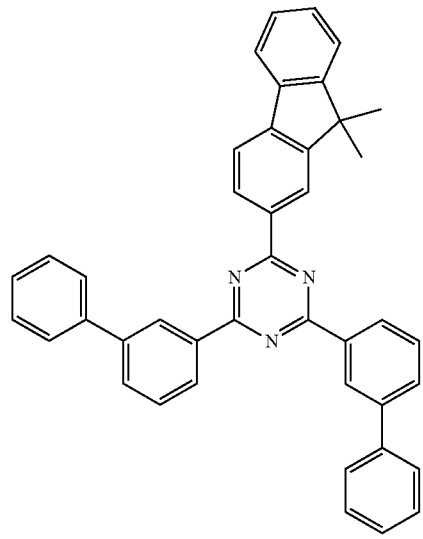 [SMILES: CC1(C)c2ccccc2-c2ccc(-c3nc(-c4cccc(-c5ccccc5)c4)nc(-c4cccc(-c5ccccc5)c4)n3)cc21]
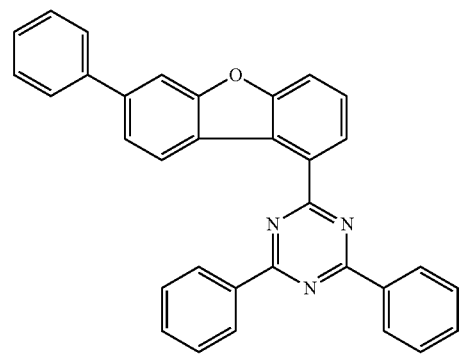 [SMILES: c1ccc(-c2ccc3c(c2)oc2cccc(-c4nc(-c5ccccc5)nc(-c5ccccc5)n4)c23)cc1]
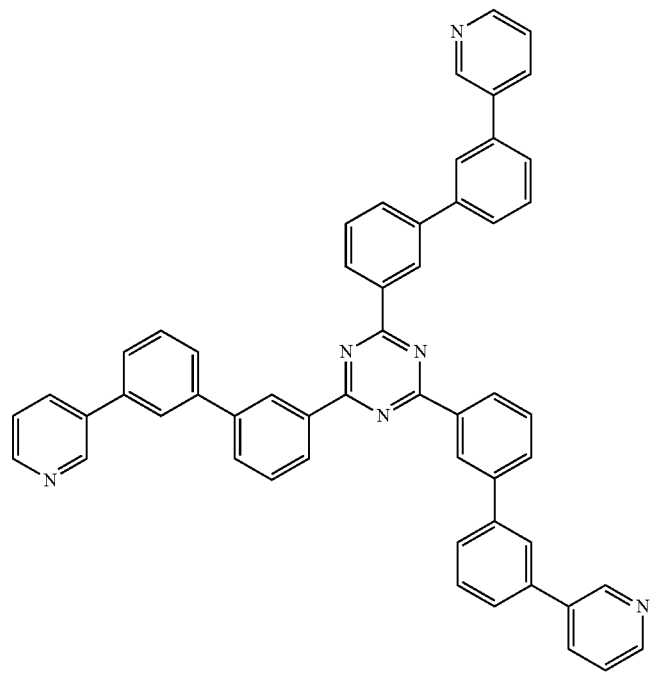 [SMILES: c1cncc(-c2cccc(-c3cccc(-c4nc(-c5cccc(-c6cccc(-c7cccnc7)c6)c5)nc(-c5cccc(-c6cccc(-c7cccnc7)c6)c5)n4)c3)c2)c1]

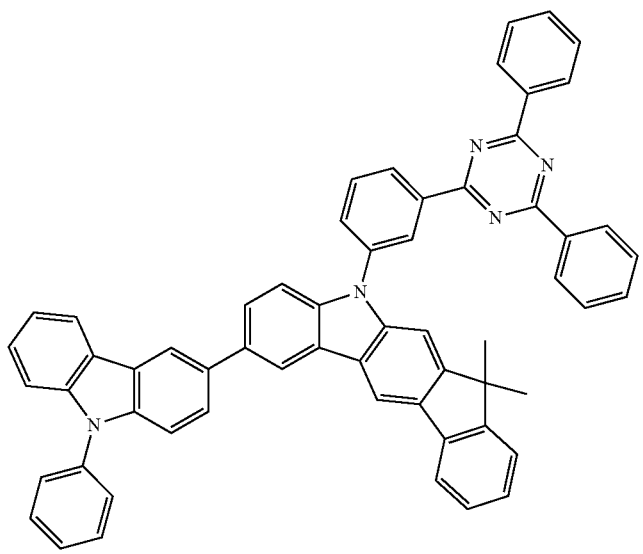 [SMILES: CC1(C)c2ccccc2-c2cc3c4cc(-c5ccc6c(c5)c5ccccc5n6-c5ccccc5)ccc4n(-c4cccc(-c5nc(-c6ccccc6)nc(-c6ccccc6)n5)c4)c3cc21]
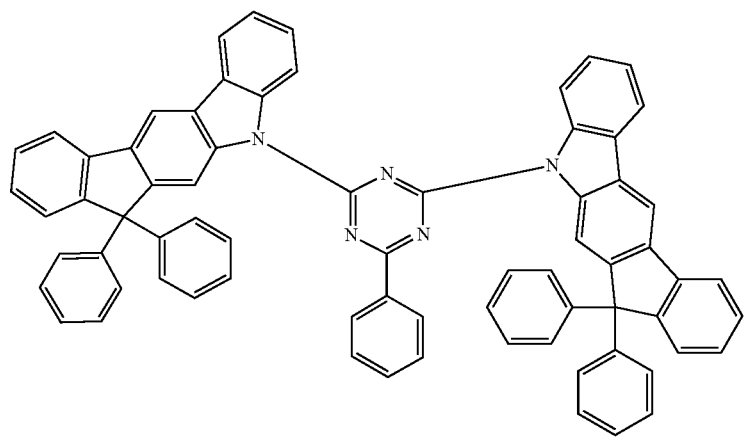 [SMILES: c1ccc(-c2nc(-n3c4ccccc4c4cc5c(cc43)C(c3ccccc3)(c3ccccc3)c3ccccc3-5)nc(-n3c4ccccc4c4cc5c(cc43)C(c3ccccc3)(c3ccccc3)c3ccccc3-5)n2)cc1]
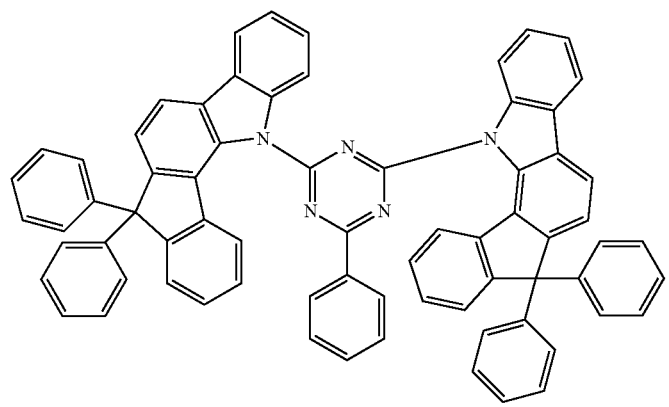 [SMILES: c1ccc(-c2nc(-n3c4ccccc4c4ccc5c(c43)-c3ccccc3C5(c3ccccc3)c3ccccc3)nc(-n3c4ccccc4c4ccc5c(c43)-c3ccccc3C5(c3ccccc3)c3ccccc3)n2)cc1]

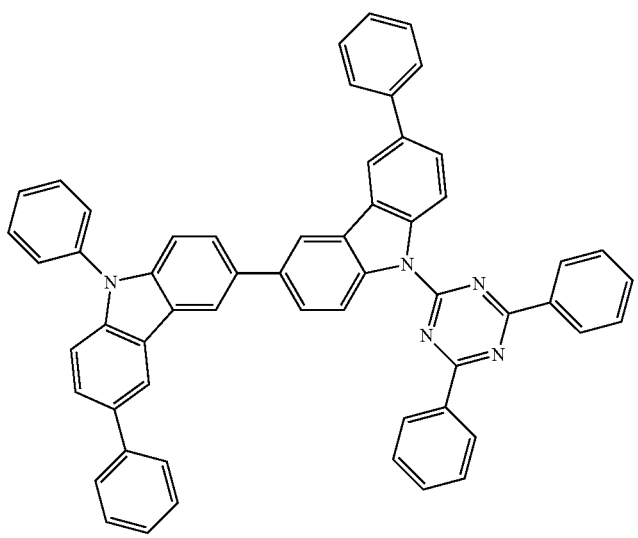 [SMILES: c1ccc(-c2ccc3c(c2)c2cc(-c4ccc5c(c4)c4cc(-c6ccccc6)ccc4n5-c4nc(-c5ccccc5)nc(-c5ccccc5)n4)ccc2n3-c2ccccc2)cc1]
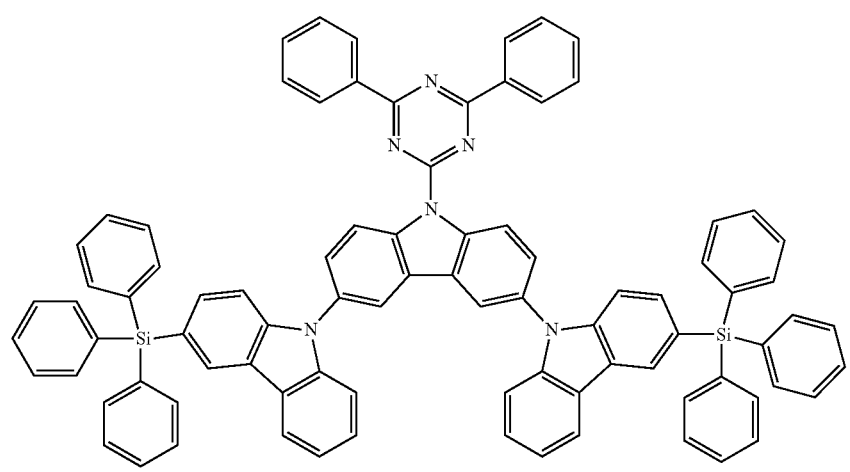 [SMILES: c1ccc(-c2nc(-c3ccccc3)nc(-n3c4ccc(-n5c6ccccc6c6cc([Si](c7ccccc7)(c7ccccc7)c7ccccc7)ccc65)cc4c4cc(-n5c6ccccc6c6cc([Si](c7ccccc7)(c7ccccc7)c7ccccc7)ccc65)ccc43)n2)cc1]
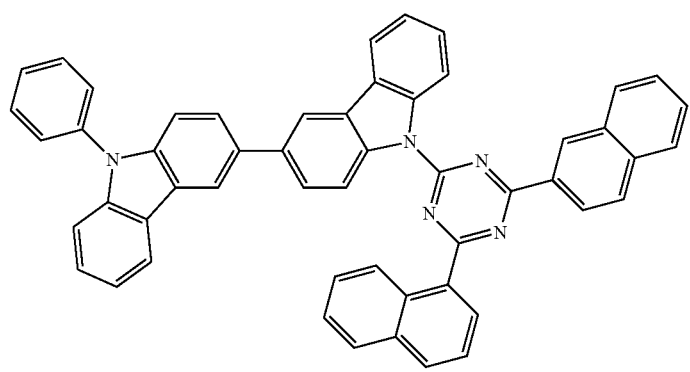 [SMILES: c1ccc(-n2c3ccccc3c3cc(-c4ccc5c(c4)c4ccccc4n5-c4nc(-c5ccc6ccccc6c5)nc(-c5cccc6ccccc56)n4)ccc32)cc1]

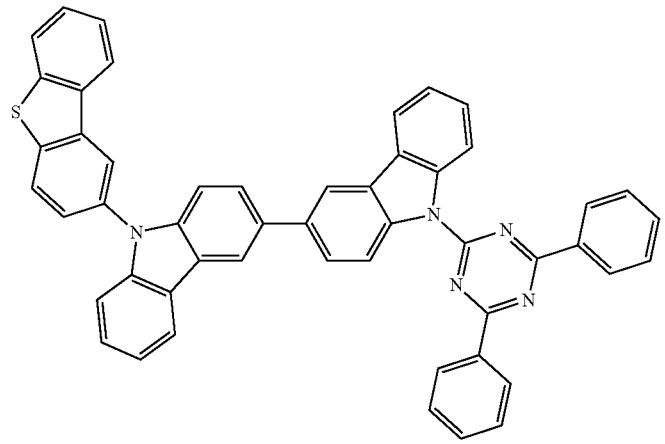 [SMILES: c1ccc(-c2nc(-c3ccccc3)nc(-n3c4ccccc4c4cc(-c5ccc6c(c5)c5ccccc5n6-c5ccc6sc7ccccc7c6c5)ccc43)n2)cc1]
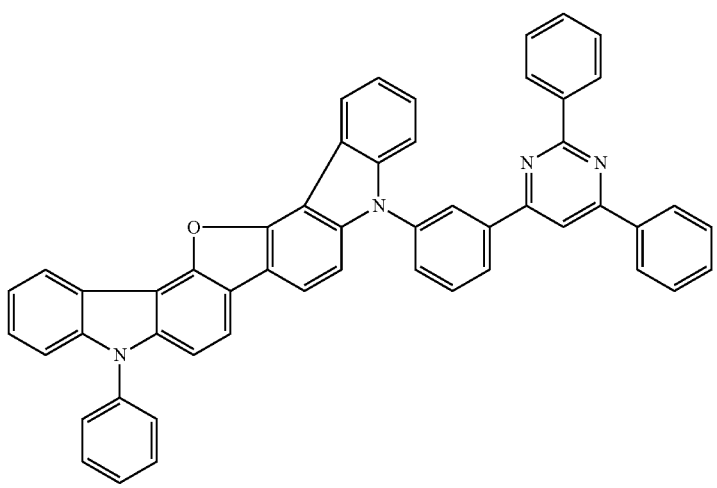 [SMILES: c1ccc(-c2cc(-c3cccc(-n4c5ccccc5c5c6oc7c(ccc8c7c7ccccc7n8-c7ccccc7)c6ccc54)c3)nc(-c3ccccc3)n2)cc1]
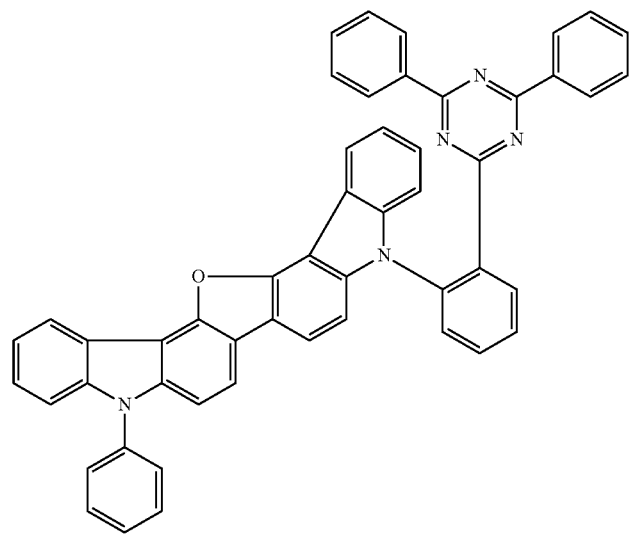 [SMILES: c1ccc(-c2nc(-c3ccccc3)nc(-c3ccccc3-n3c4ccccc4c4c5oc6c(ccc7c6c6ccccc6n7-c6ccccc6)c5ccc43)n2)cc1]

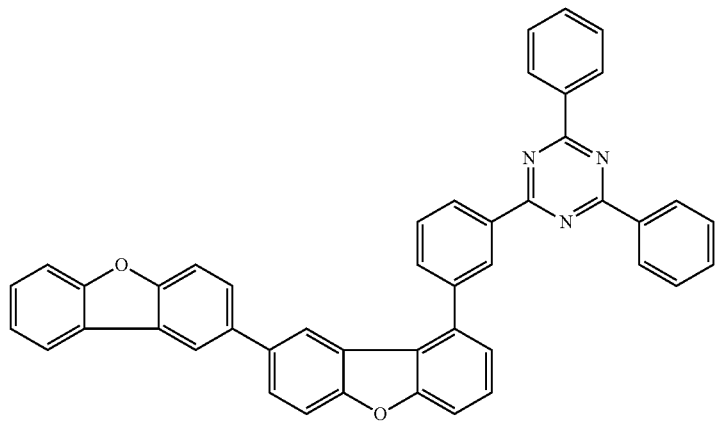 [SMILES: c1ccc(-c2nc(-c3ccccc3)nc(-c3cccc(-c4cccc5oc6ccc(-c7ccc8oc9ccccc9c8c7)cc6c45)c3)n2)cc1]
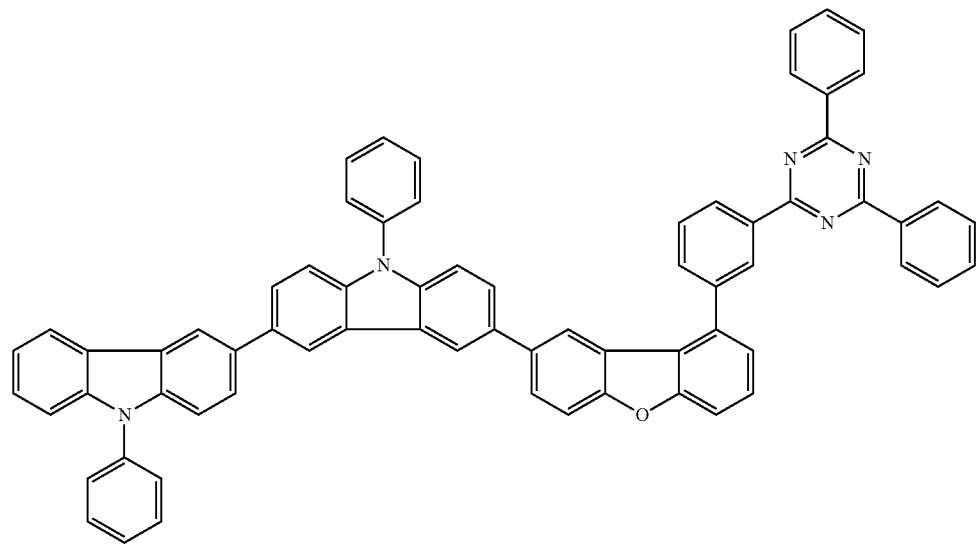 [SMILES: c1ccc(-c2nc(-c3ccccc3)nc(-c3cccc(-c4cccc5oc6ccc(-c7ccc8c(c7)c7cc(-c9ccc%10c(c9)c9ccccc9n%10-c9ccccc9)ccc7n8-c7ccccc7)cc6c45)c3)n2)cc1]
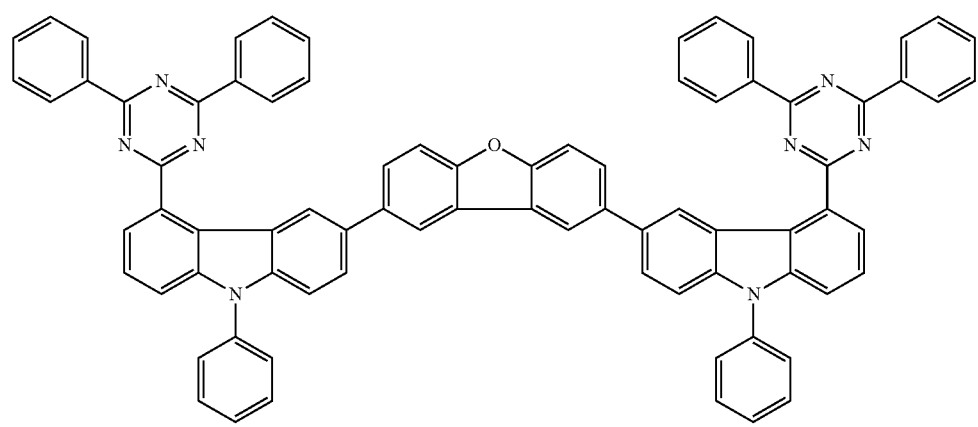 [SMILES: c1ccc(-c2nc(-c3ccccc3)nc(-c3cccc4c3c3cc(-c5ccc6sc7ccc(-c8ccc9c(c8)c8c(-c%10nc(-c%11ccccc%11)nc(-c%11ccccc%11)n%10)cccc8n9-c8ccccc8)cc7c6c5)ccc3n4-c3ccccc3)n2)cc1]

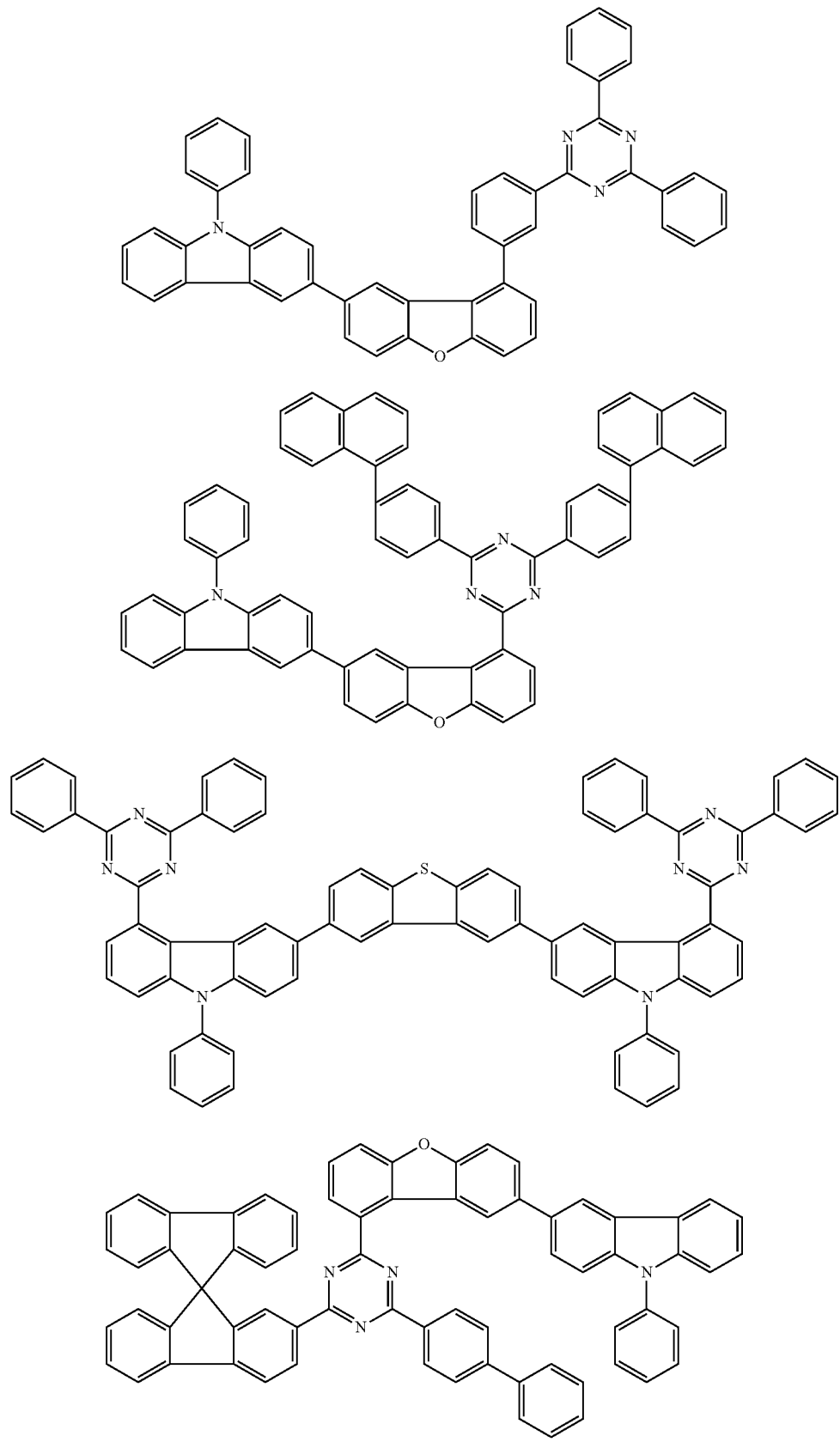

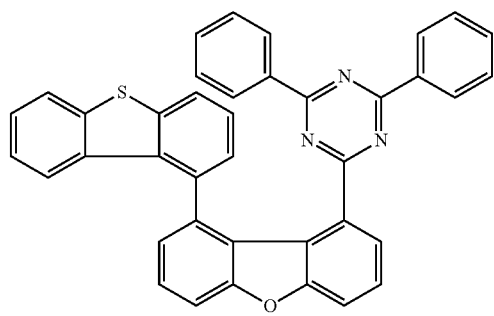 [SMILES: c1ccc(-c2nc(-c3ccccc3)nc(-c3cccc4oc5cccc(-c6cccc7sc8ccccc8c67)c5c34)n2)cc1]
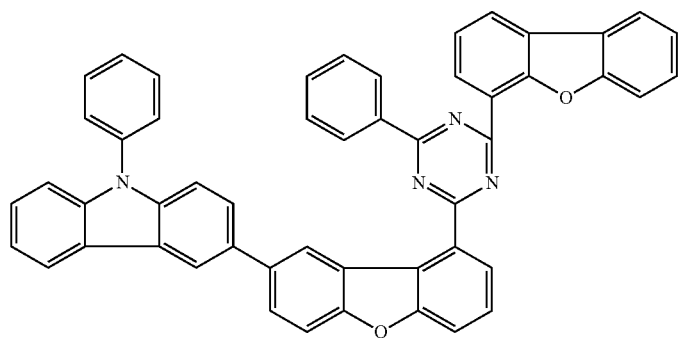 [SMILES: c1ccc(-c2nc(-c3cccc4c3oc3ccccc34)nc(-c3cccc4oc5ccc(-c6ccc7c(c6)c6ccccc6n7-c6ccccc6)cc5c34)n2)cc1]
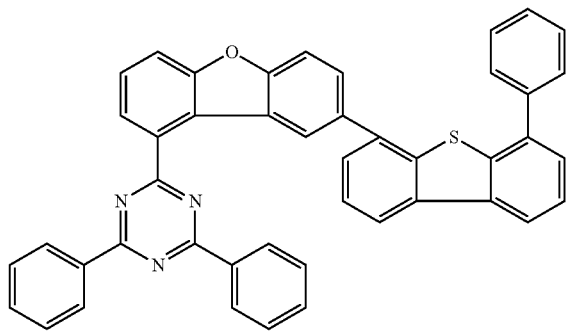 [SMILES: c1ccc(-c2nc(-c3ccccc3)nc(-c3cccc4oc5ccc(-c6cccc7c6sc6c(-c8ccccc8)cccc67)cc5c34)n2)cc1]
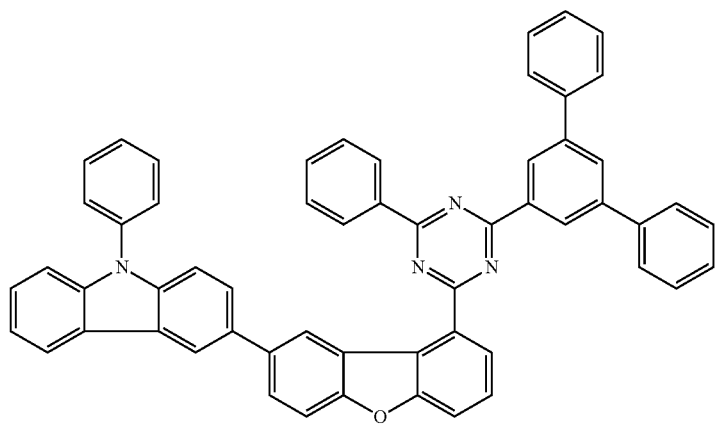 [SMILES: c1ccc(-c2cc(-c3ccccc3)cc(-c3nc(-c4ccccc4)nc(-c4cccc5oc6ccc(-c7ccc8c(c7)c7ccccc7n8-c7ccccc7)cc6c45)n3)c2)cc1]

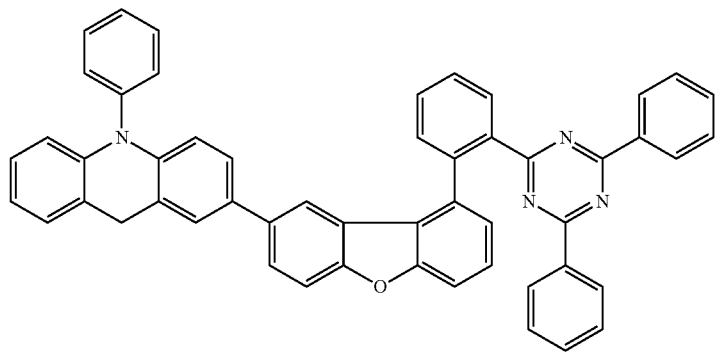 [SMILES: c1ccc(-c2nc(-c3ccccc3)nc(-c3ccccc3-c3cccc4oc5ccc(-c6ccc7c(c6)Cc6ccccc6N7c6ccccc6)cc5c34)n2)cc1]
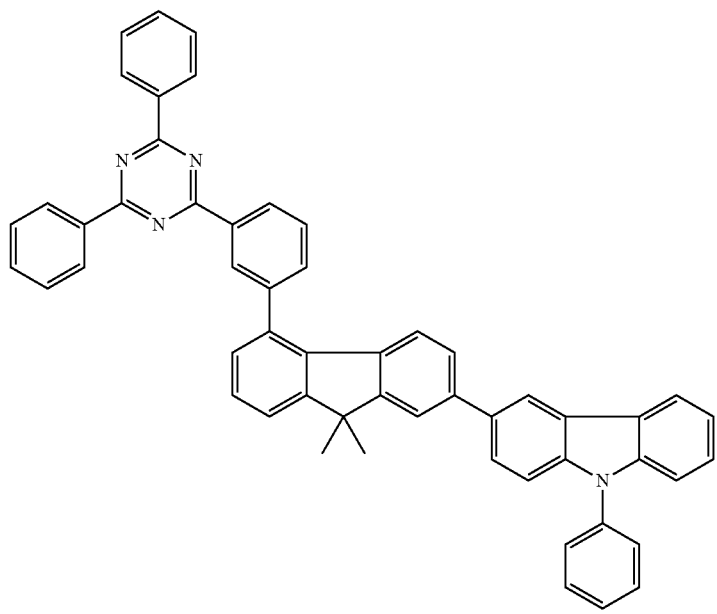 [SMILES: CC1(C)c2cc(-c3ccc4c(c3)c3ccccc3n4-c3ccccc3)ccc2-c2c(-c3cccc(-c4nc(-c5ccccc5)nc(-c5ccccc5)n4)c3)cccc21]
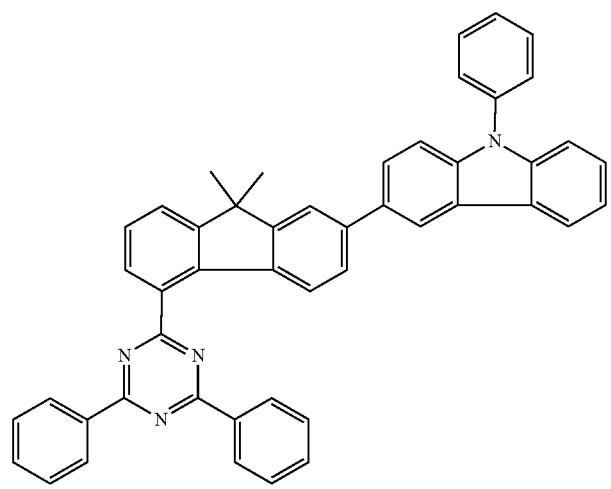 [SMILES: CC1(C)c2cc(-c3ccc4c(c3)c3ccccc3n4-c3ccccc3)ccc2-c2c(-c3nc(-c4ccccc4)nc(-c4ccccc4)n3)cccc21]

-continued
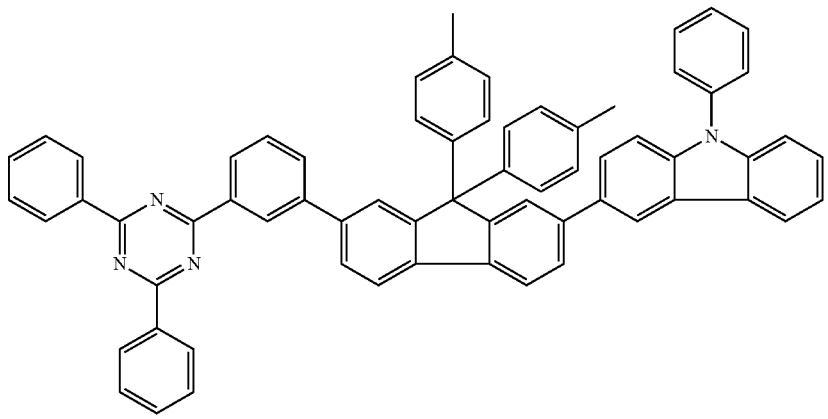 [SMILES: Cc1ccc(C2(c3ccc(C)cc3)c3cc(-c4cccc(-c5nc(-c6ccccc6)nc(-c6ccccc6)n5)c4)ccc3-c3ccc(-c4ccc5c(c4)c4ccccc4n5-c4ccccc4)cc32)cc1]
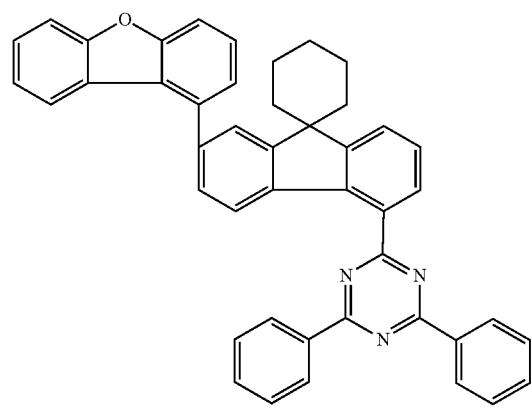 [SMILES: c1ccc(-c2nc(-c3ccccc3)nc(-c3cccc4c3-c3ccc(-c5cccc6oc7ccccc7c56)cc3C43CCCCC3)n2)cc1]
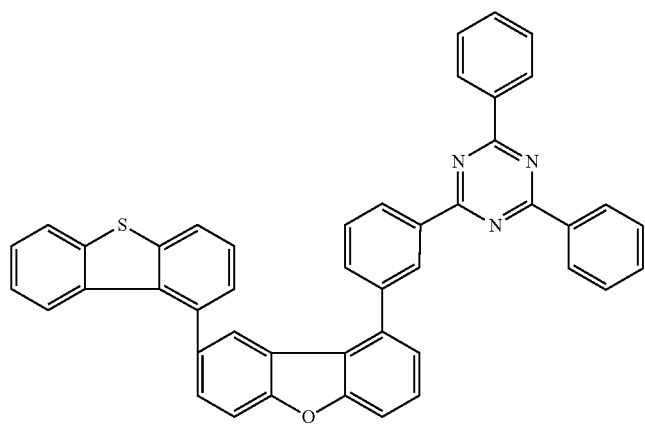 [SMILES: c1ccc(-c2nc(-c3ccccc3)nc(-c3cccc(-c4cccc5oc6ccc(-c7cccc8sc9ccccc9c78)cc6c45)c3)n2)cc1]

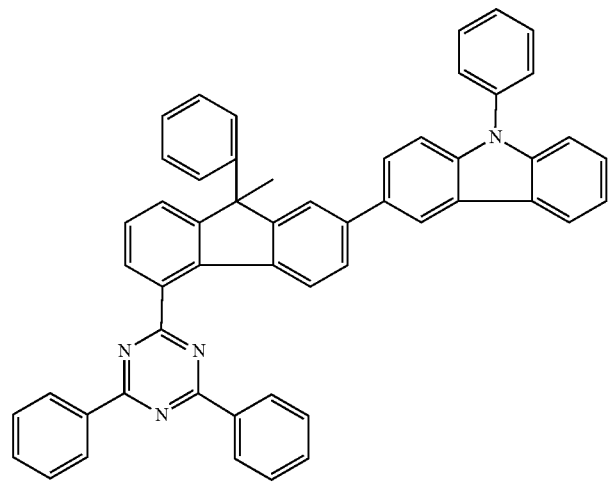 [SMILES: CC1(c2ccccc2)c2cc(-c3ccc4c(c3)c3ccccc3n4-c3ccccc3)ccc2-c2c(-c3nc(-c4ccccc4)nc(-c4ccccc4)n3)cccc21]
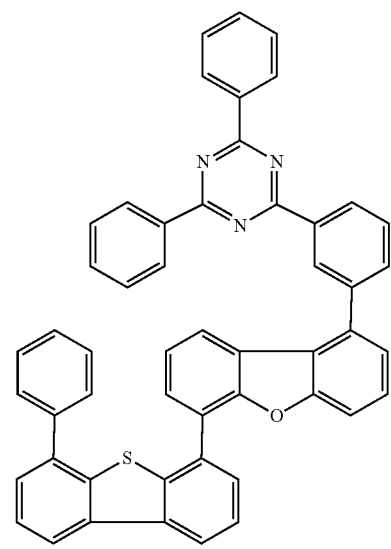 [SMILES: c1ccc(-c2nc(-c3ccccc3)nc(-c3cccc(-c4cccc5oc6c(-c7cccc8c7sc7c(-c9ccccc9)cccc78)cccc6c45)c3)n2)cc1]
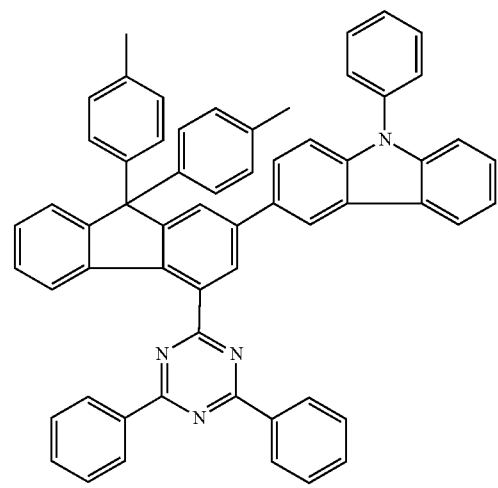 [SMILES: Cc1ccc(C2(c3ccc(C)cc3)c3ccccc3-c3c(-c4nc(-c5ccccc5)nc(-c5ccccc5)n4)cc(-c4ccc5c(c4)c4ccccc4n5-c4ccccc4)cc32)cc1]

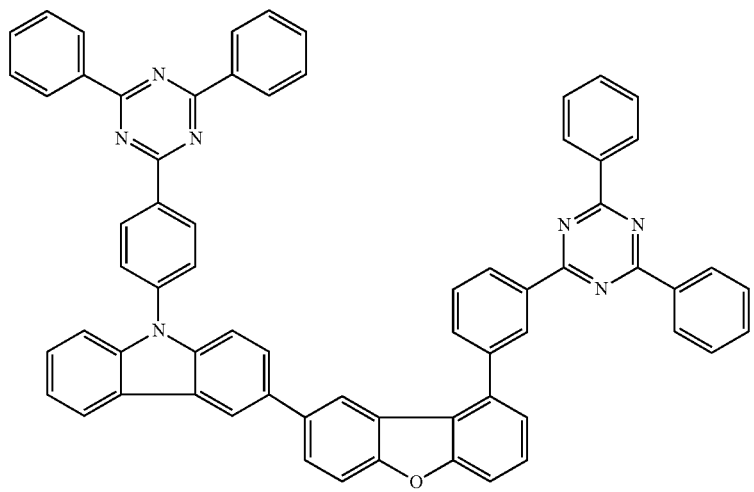 [SMILES: c1ccc(-c2nc(-c3ccccc3)nc(-c3ccc(-n4c5ccccc5c5cc(-c6ccc7oc8cccc(-c9cccc(-c%10nc(-c%11ccccc%11)nc(-c%11ccccc%11)n%10)c9)c8c7c6)ccc54)cc3)n2)cc1]
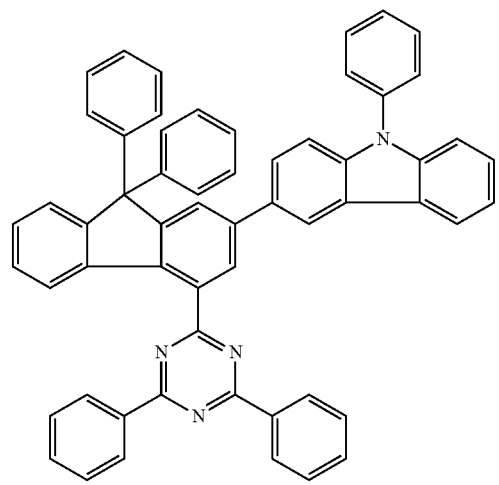 [SMILES: c1ccc(-c2nc(-c3ccccc3)nc(-c3cc(-c4ccc5c(c4)c4ccccc4n5-c4ccccc4)cc4c3-c3ccccc3C4(c3ccccc3)c3ccccc3)n2)cc1]
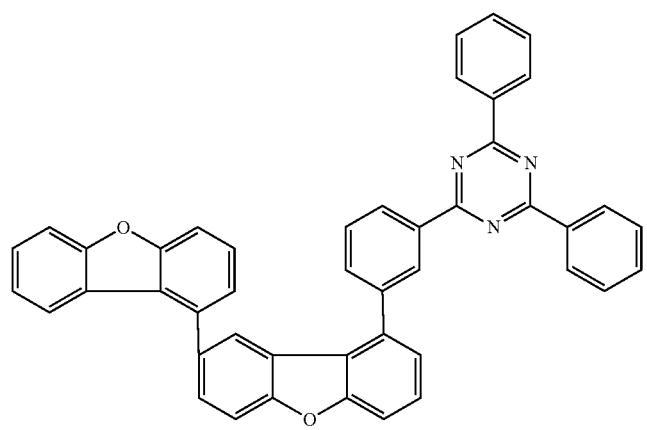 [SMILES: c1ccc(-c2nc(-c3ccccc3)nc(-c3cccc(-c4cccc5oc6ccc(-c7cccc8oc9ccccc9c78)cc6c45)c3)n2)cc1]

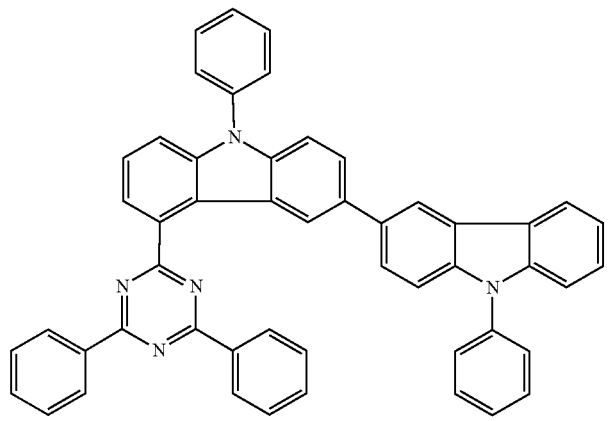 [SMILES: c1ccc(-c2nc(-c3ccccc3)nc(-c3cccc4c3c3cc(-c5ccc6c(c5)c5ccccc5n6-c5ccccc5)ccc3n4-c3ccccc3)n2)cc1]
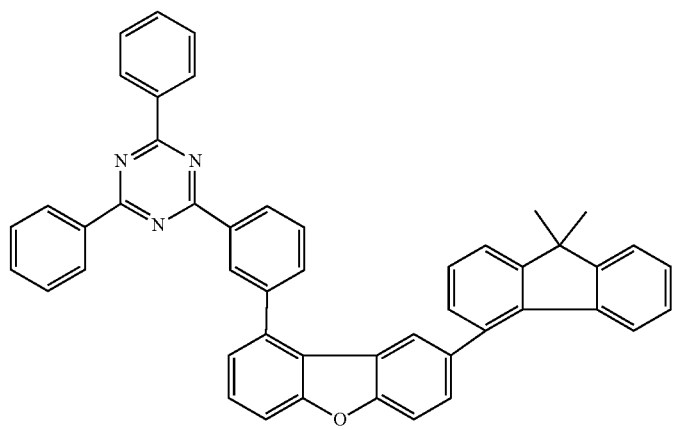 [SMILES: CC1(C)c2ccccc2-c2c(-c3ccc4oc5cccc(-c6cccc(-c7nc(-c8ccccc8)nc(-c8ccccc8)n7)c6)c5c4c3)cccc21]
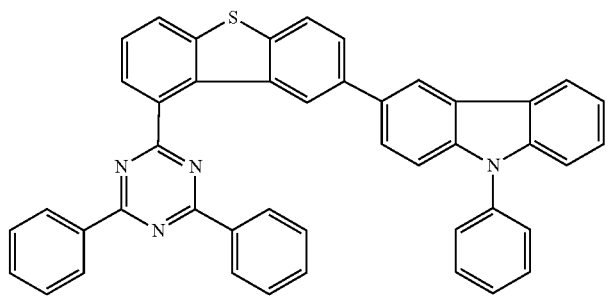 [SMILES: c1ccc(-c2nc(-c3ccccc3)nc(-c3cccc4sc5ccc(-c6ccc7c(c6)c6ccccc6n7-c6ccccc6)cc5c34)n2)cc1]
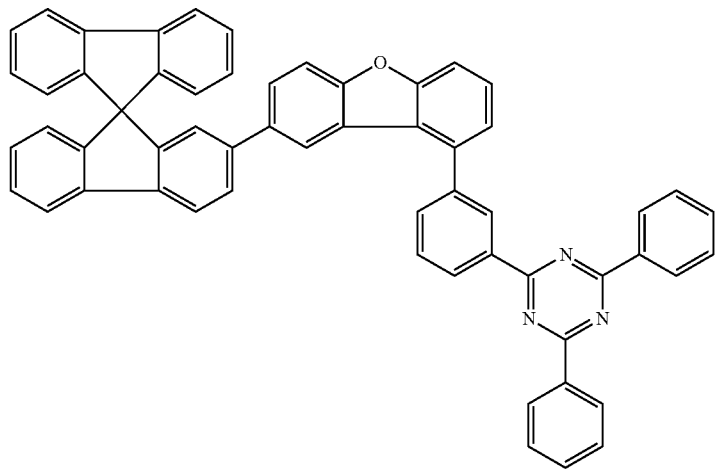 [SMILES: c1ccc(-c2nc(-c3ccccc3)nc(-c3cccc(-c4cccc5oc6ccc(-c7ccc8c(c7)C7(c9ccccc9-c9ccccc97)c7ccccc7-8)cc6c45)c3)n2)cc1]

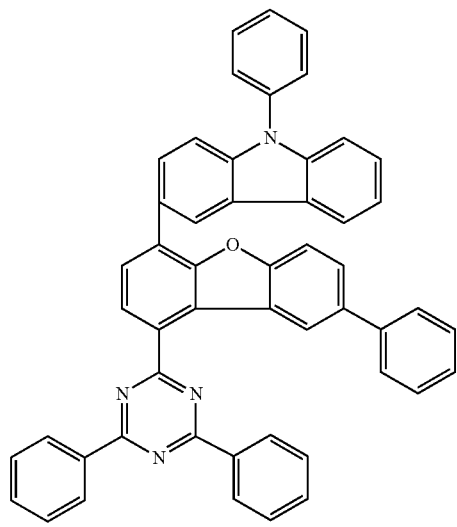 [SMILES: c1ccc(-c2ccc3oc4c(-c5ccc6c(c5)c5ccccc5n6-c5ccccc5)ccc(-c5nc(-c6ccccc6)nc(-c6ccccc6)n5)c4c3c2)cc1]
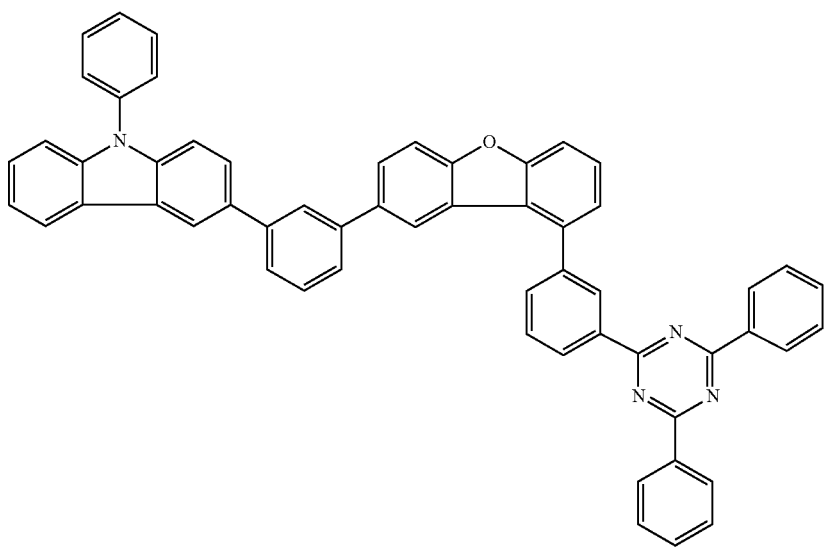 [SMILES: c1ccc(-c2nc(-c3ccccc3)nc(-c3cccc(-c4cccc5oc6ccc(-c7cccc(-c8ccc9c(c8)c8ccccc8n9-c8ccccc8)c7)cc6c45)c3)n2)cc1]
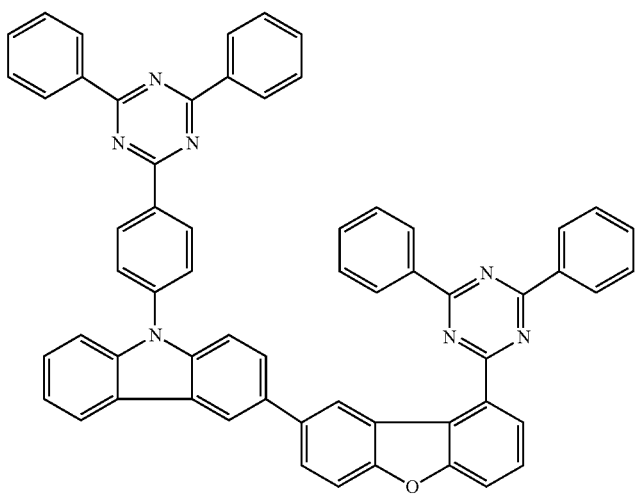 [SMILES: c1ccc(-c2nc(-c3ccccc3)nc(-c3ccc(-n4c5ccccc5c5cc(-c6ccc7oc8cccc(-c9nc(-c%10ccccc%10)nc(-c%10ccccc%10)n9)c8c7c6)ccc54)cc3)n2)cc1]

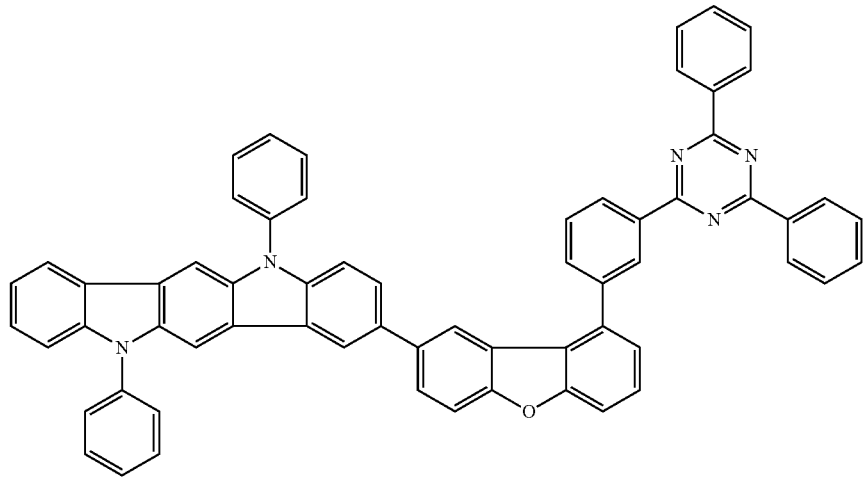 [SMILES: c1ccc(-c2nc(-c3ccccc3)nc(-c3cccc(-c4cccc5oc6ccc(-c7ccc8c(c7)c7cc9c(cc7n8-c7ccccc7)c7ccccc7n9-c7ccccc7)cc6c45)c3)n2)cc1]
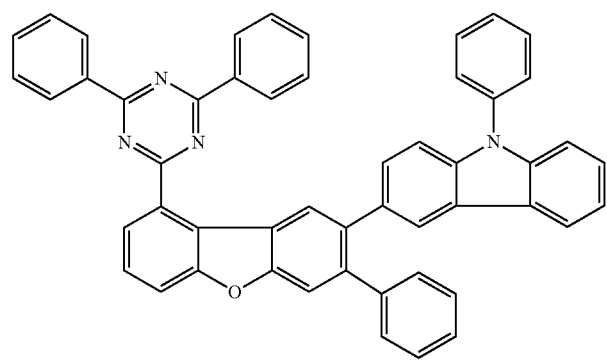 [SMILES: c1ccc(-c2nc(-c3ccccc3)nc(-c3cccc4oc5cc(-c6ccccc6)c(-c6ccc7c(c6)c6ccccc6n7-c6ccccc6)cc5c34)n2)cc1]
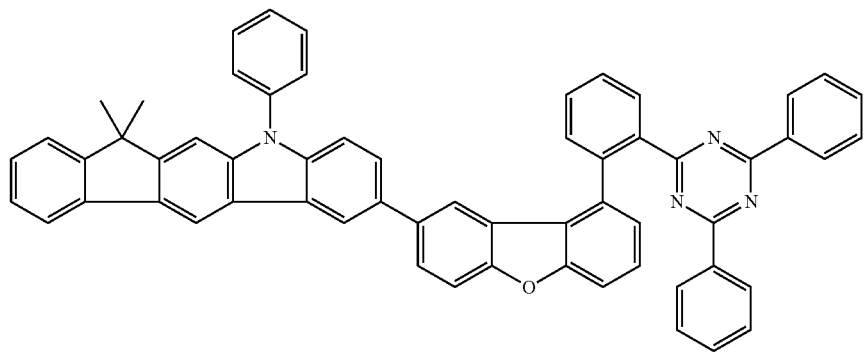 [SMILES: CC1(C)c2ccccc2-c2cc3c4cc(-c5ccc6oc7cccc(-c8ccccc8-c8nc(-c9ccccc9)nc(-c9ccccc9)n8)c7c6c5)ccc4n(-c4ccccc4)c3cc21]
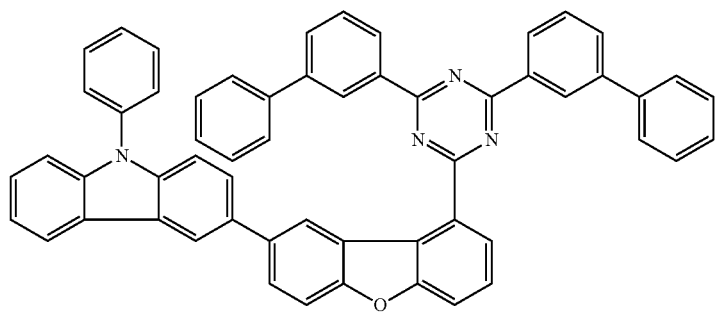 [SMILES: c1ccc(-c2cccc(-c3nc(-c4cccc(-c5ccccc5)c4)nc(-c4cccc5oc6ccc(-c7ccc8c(c7)c7ccccc7n8-c7ccccc7)cc6c45)n3)c2)cc1]

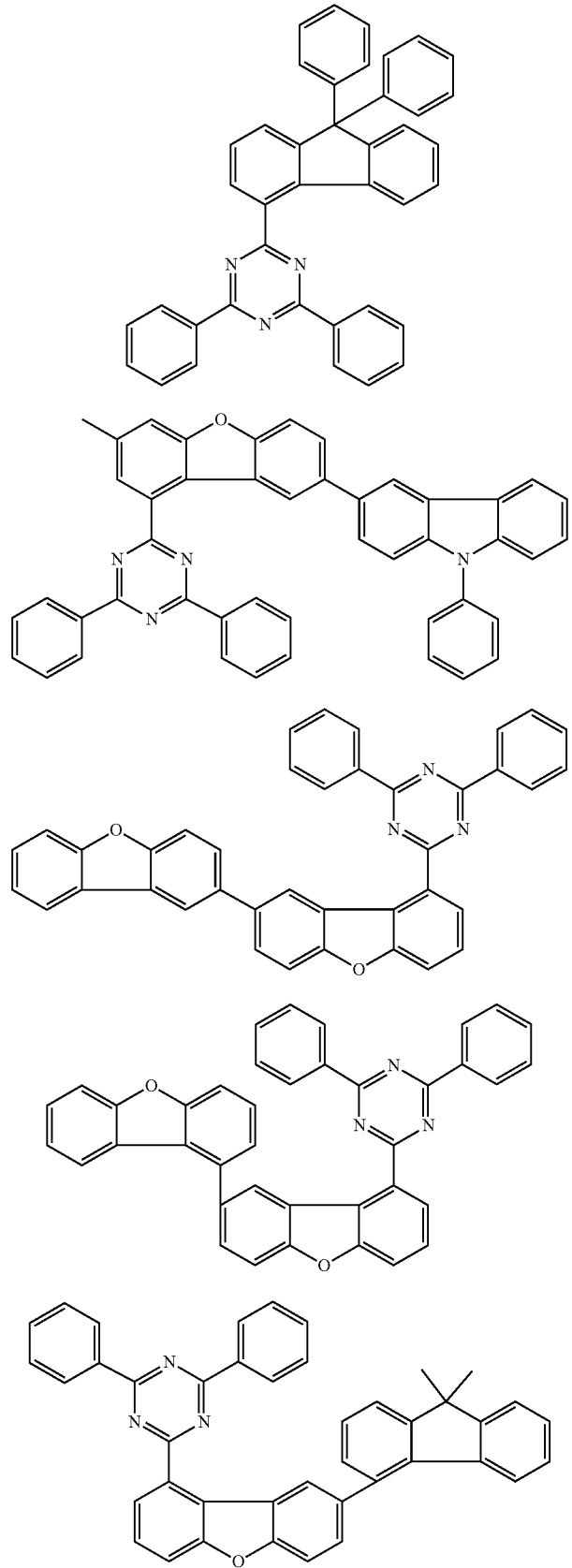

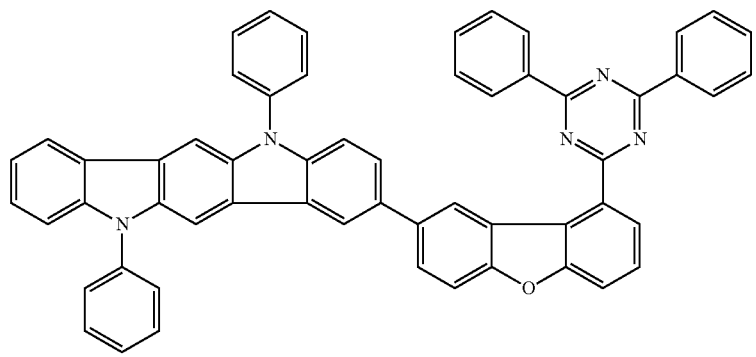 [SMILES: c1ccc(-c2nc(-c3ccccc3)nc(-c3cccc4oc5ccc(-c6ccc7c(c6)c6cc8c(cc6n7-c6ccccc6)c6ccccc6n8-c6ccccc6)cc5c34)n2)cc1]
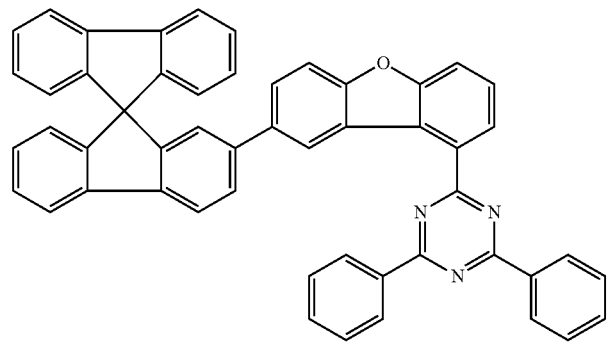 [SMILES: c1ccc(-c2nc(-c3ccccc3)nc(-c3cccc4c3Cc3cc(-c5ccc6c(c5)C5(c7ccccc7-c7ccccc75)c5ccccc5-6)ccc3O4)n2)cc1]
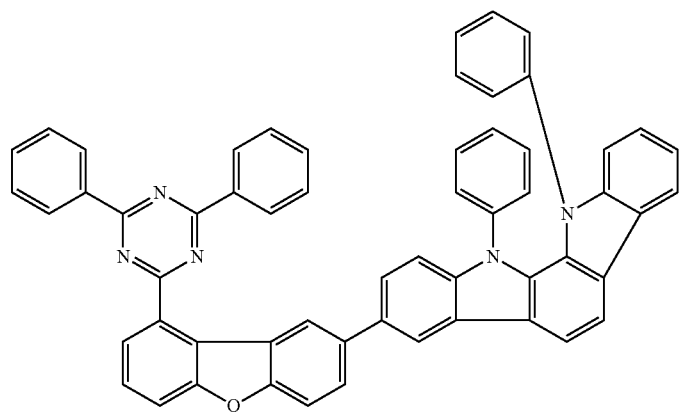 [SMILES: c1ccc(-c2nc(-c3ccccc3)nc(-c3cccc4oc5ccc(-c6ccc7c(c6)c6ccc8c9ccccc9n(-c9ccccc9)c8c6n7-c6ccccc6)cc5c34)n2)cc1]
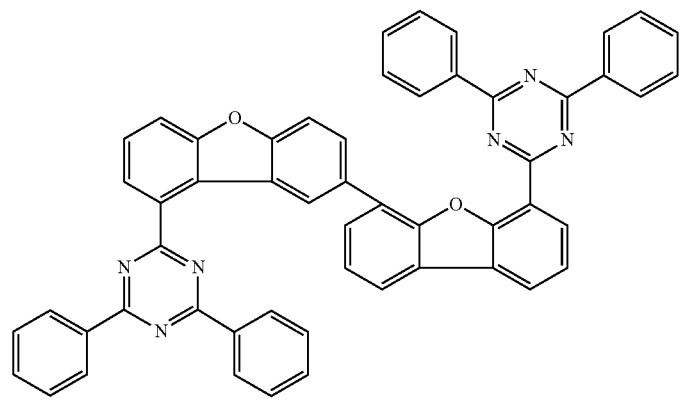 [SMILES: c1ccc(-c2nc(-c3ccccc3)nc(-c3cccc4c3oc3c(-c5ccc6oc7cccc(-c8nc(-c9ccccc9)nc(-c9ccccc9)n8)c7c6c5)cccc34)n2)cc1]

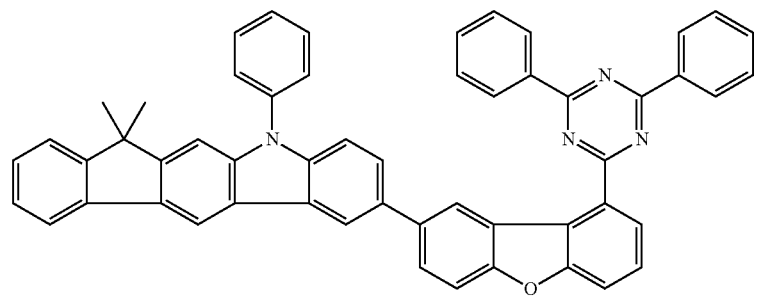 [SMILES: CC1(C)c2ccccc2-c2cc3c4cc(-c5ccc6oc7cccc(-c8nc(-c9ccccc9)nc(-c9ccccc9)n8)c7c6c5)ccc4n(-c4ccccc4)c3cc21]
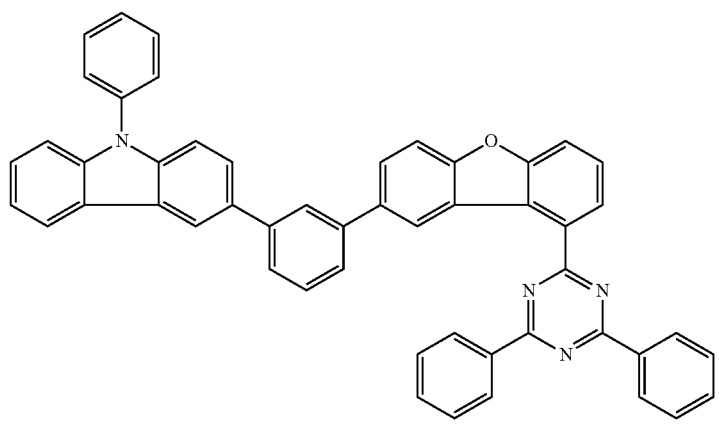 [SMILES: c1ccc(-c2nc(-c3ccccc3)nc(-c3cccc4oc5ccc(-c6cccc(-c7ccc8c(c7)c7ccccc7n8-c7ccccc7)c6)cc5c34)n2)cc1]
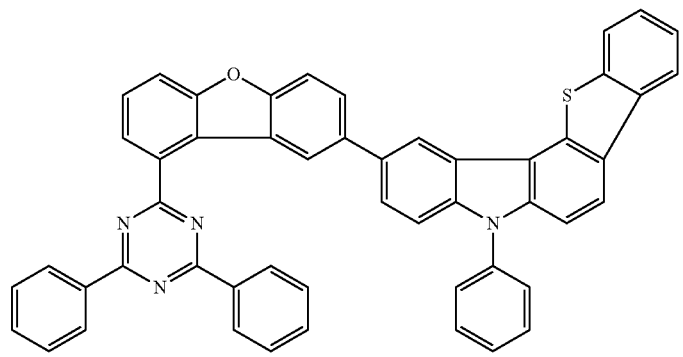 [SMILES: c1ccc(-c2nc(-c3ccccc3)nc(-c3cccc4oc5ccc(-c6ccc7c(c6)c6c8sc9ccccc9c8ccc6n7-c6ccccc6)cc5c34)n2)cc1]
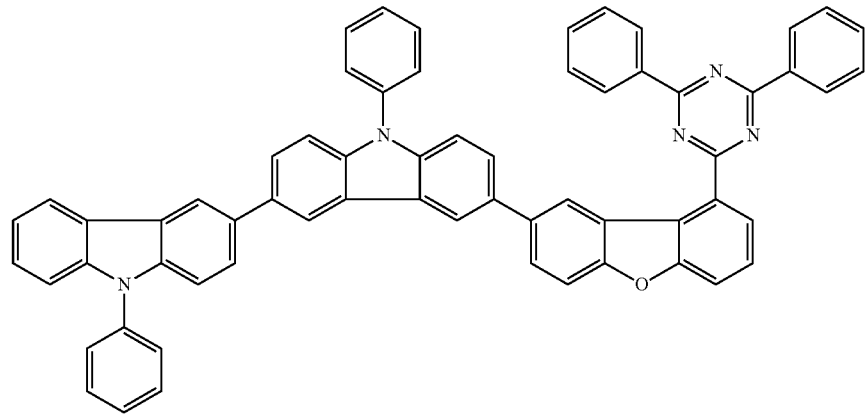 [SMILES: c1ccc(-c2nc(-c3ccccc3)nc(-c3cccc4oc5ccc(-c6ccc7c(c6)c6cc(-c8ccc9c(c8)c8ccccc8n9-c8ccccc8)ccc6n7-c6ccccc6)cc5c34)n2)cc1]

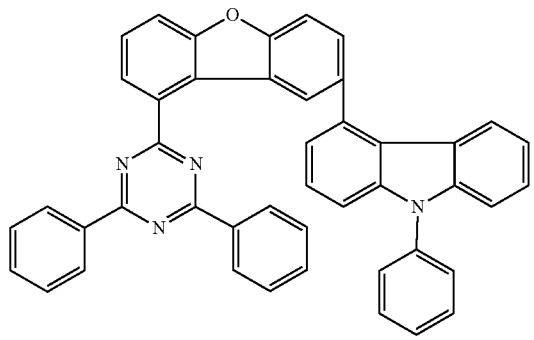 [SMILES: c1ccc(-c2nc(-c3ccccc3)nc(-c3cccc4oc5ccc(-c6cccc7c6c6ccccc6n7-c6ccccc6)cc5c34)n2)cc1]
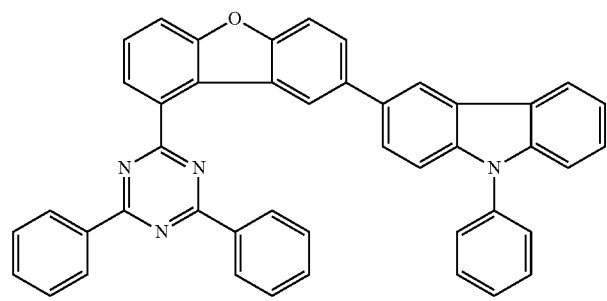 [SMILES: c1ccc(-c2nc(-c3ccccc3)nc(-c3cccc4oc5ccc(-c6ccc7c(c6)c6ccccc6n7-c6ccccc6)cc5c34)n2)cc1]
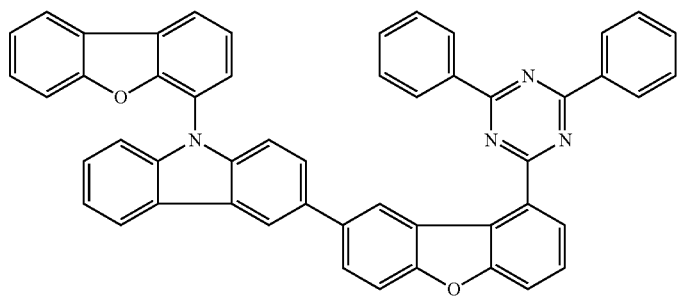 [SMILES: c1ccc(-c2nc(-c3ccccc3)nc(-c3cccc4oc5ccc(-c6ccc7c(c6)c6ccccc6n7-c6cccc7c6oc6ccccc67)cc5c34)n2)cc1]
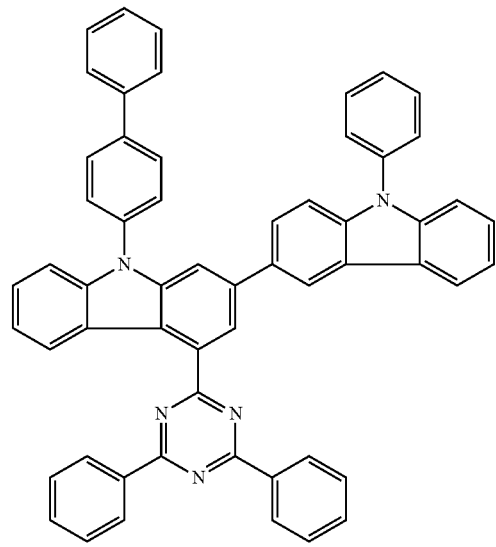 [SMILES: c1ccc(-c2ccc(-n3c4ccccc4c4c(-c5nc(-c6ccccc6)nc(-c6ccccc6)n5)cc(-c5ccc6c(c5)c5ccccc5n6-c5ccccc5)cc43)cc2)cc1]

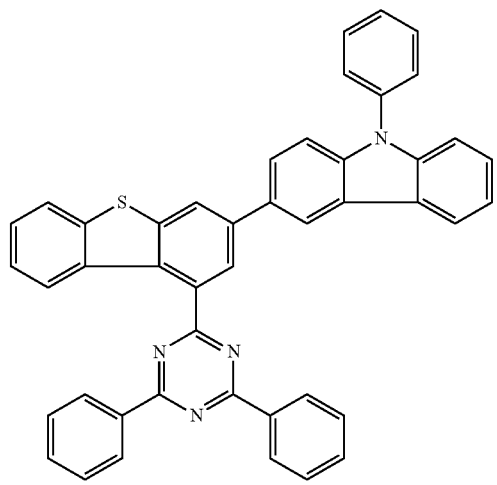 [SMILES: c1ccc(-c2nc(-c3ccccc3)nc(-c3cc(-c4ccc5c(c4)c4ccccc4n5-c4ccccc4)cc4sc5ccccc5c34)n2)cc1]
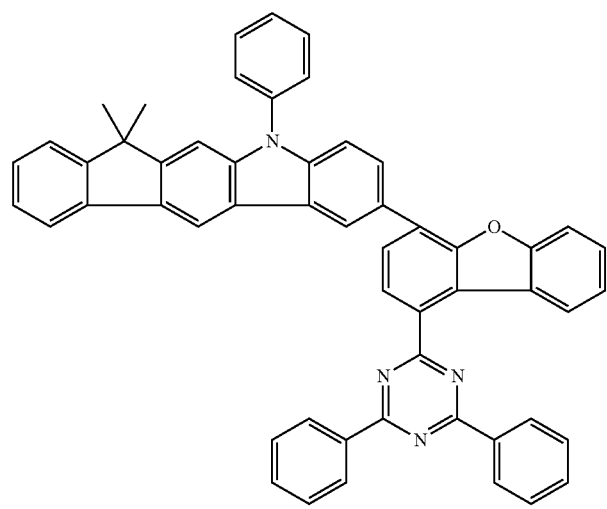 [SMILES: CC1(C)c2ccccc2-c2cc3c4cc(-c5ccc(-c6nc(-c7ccccc7)nc(-c7ccccc7)n6)c6c5oc5ccccc56)ccc4n(-c4ccccc4)c3cc21]
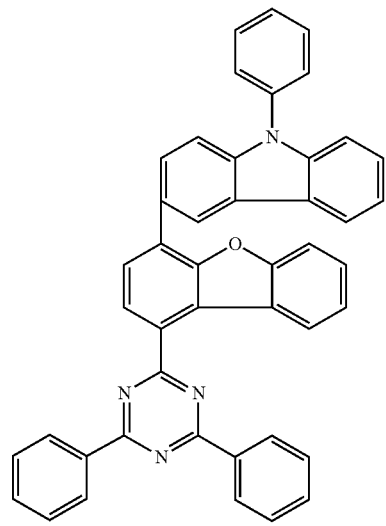 [SMILES: c1ccc(-c2nc(-c3ccccc3)nc(-c3ccc(-c4ccc5c(c4)c4ccccc4n5-c4ccccc4)c4oc5ccccc5c34)n2)cc1]

-continued
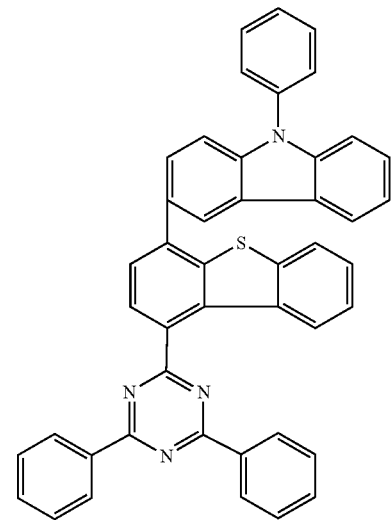 [SMILES: c1ccc(-c2nc(-c3ccccc3)nc(-c3ccc(-c4ccc5c(c4)c4ccccc4n5-c4ccccc4)c4sc5ccccc5c34)n2)cc1]
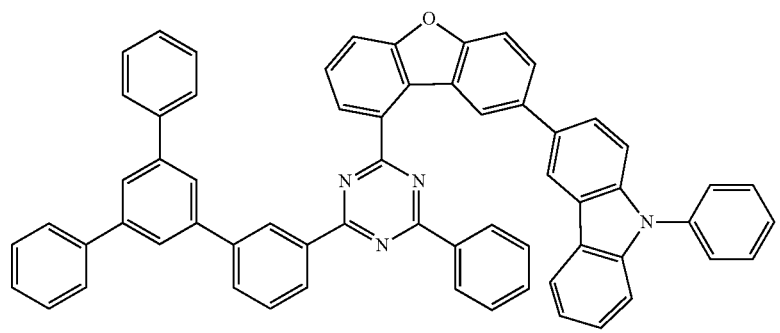 [SMILES: c1ccc(-c2cc(-c3ccccc3)cc(-c3cccc(-c4nc(-c5ccccc5)nc(-c5cccc6oc7ccc(-c8ccc9c(c8)c8ccccc8n9-c8ccccc8)cc7c56)n4)c3)c2)cc1]
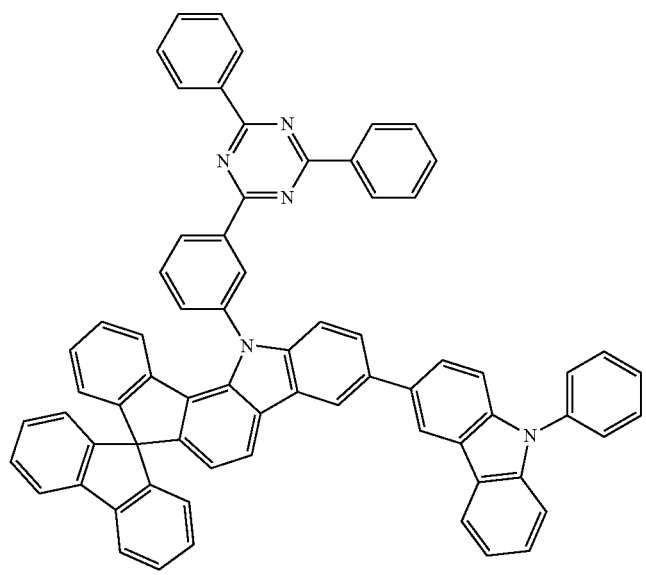 [SMILES: c1ccc(-c2nc(-c3ccccc3)nc(-c3cccc(-n4c5ccc(-c6ccc7c(c6)c6ccccc6n7-c6ccccc6)cc5c5ccc6c(c54)-c4ccccc4C64c5ccccc5-c5ccccc54)c3)n2)cc1]

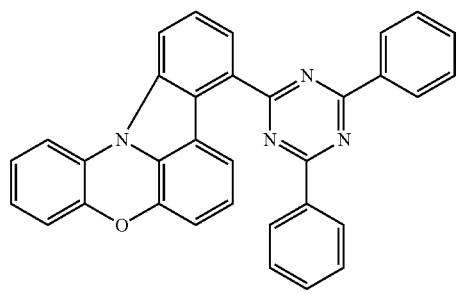 [SMILES: c1ccc(-c2nc(-c3ccccc3)nc(-c3cccc4c3c3cccc5c3n4-c3ccccc3O5)n2)cc1]
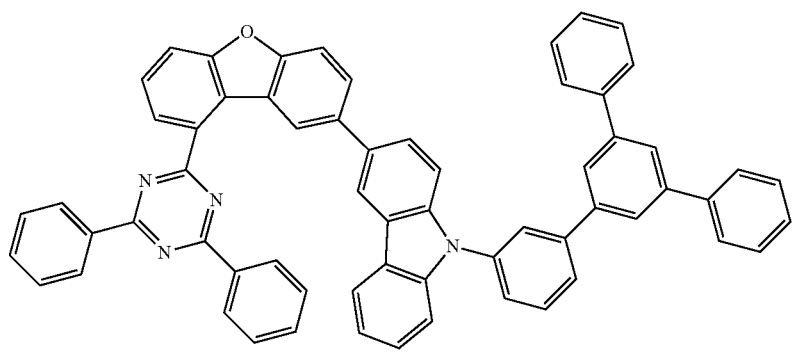 [SMILES: c1ccc(-c2cc(-c3ccccc3)cc(-c3cccc(-n4c5ccccc5c5cc(-c6ccc7oc8cccc(-c9nc(-c%10ccccc%10)nc(-c%10ccccc%10)n9)c8c7c6)ccc54)c3)c2)cc1]
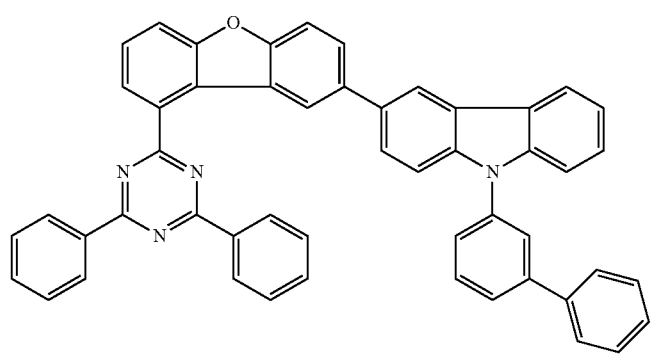 [SMILES: c1ccc(-c2cccc(-n3c4ccccc4c4cc(-c5ccc6oc7cccc(-c8nc(-c9ccccc9)nc(-c9ccccc9)n8)c7c6c5)ccc43)c2)cc1]
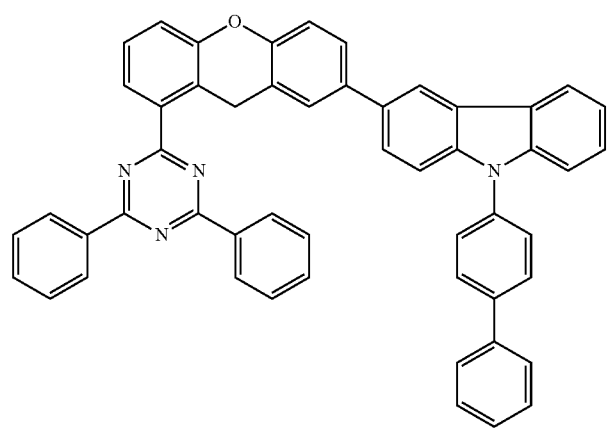 [SMILES: c1ccc(-c2ccc(-n3c4ccccc4c4cc(-c5ccc6c(c5)Cc5c(cccc5-c5nc(-c7ccccc7)nc(-c7ccccc7)n5)O6)ccc43)cc2)cc1]

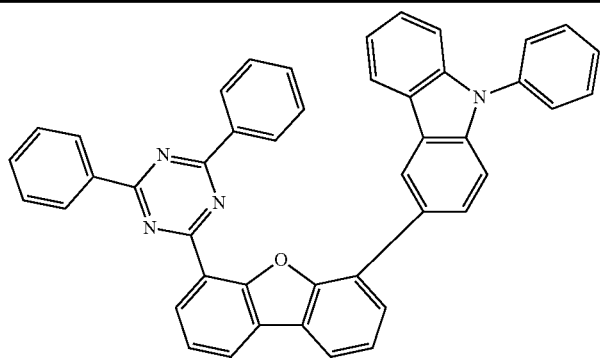
Examples of suitable quinazoline compounds are the compounds depicted in the following table:
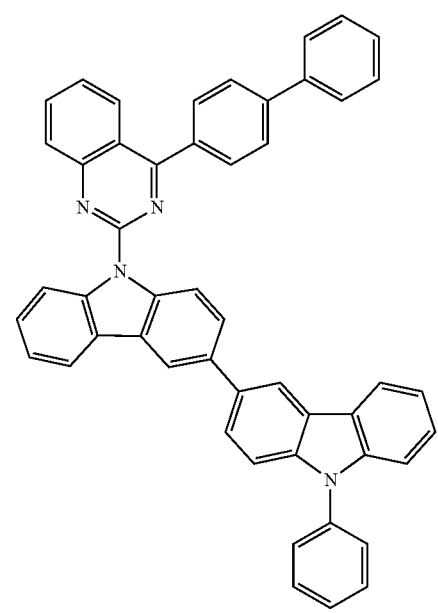 [SMILES: c1ccc(-c2ccc(-c3nc(-n4c5ccccc5c5cc(-c6ccc7c(c6)c6ccccc6n7-c6ccccc6)ccc54)nc4ccccc34)cc2)cc1]
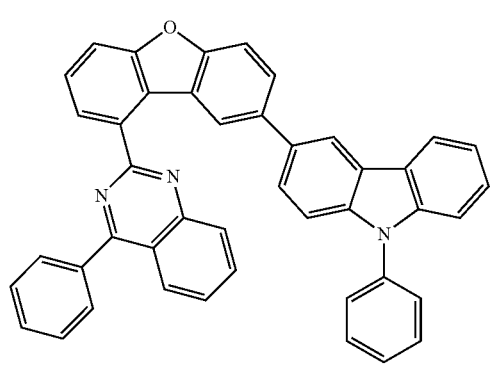 [SMILES: c1ccc(-c2nc(-c3cccc4oc5ccc(-c6ccc7c(c6)c6ccccc6n7-c6ccccc6)cc5c34)nc3ccccc23)cc1]
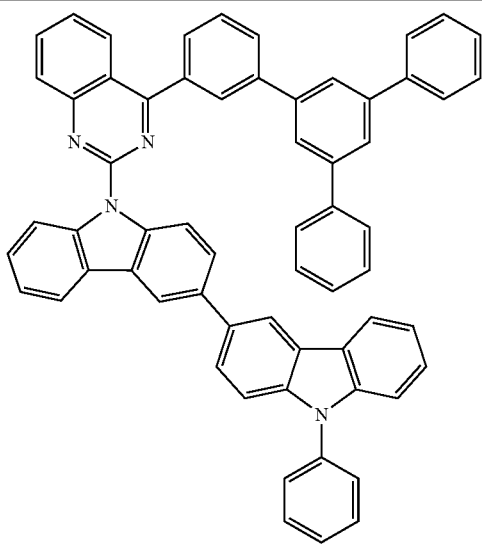 [SMILES: c1ccc(-c2cc(-c3ccccc3)cc(-c3cccc(-c4nc(-n5c6ccccc6c6cc(-c7ccc8c(c7)c7ccccc7n8-c7ccccc7)ccc65)nc5ccccc45)c3)c2)cc1]
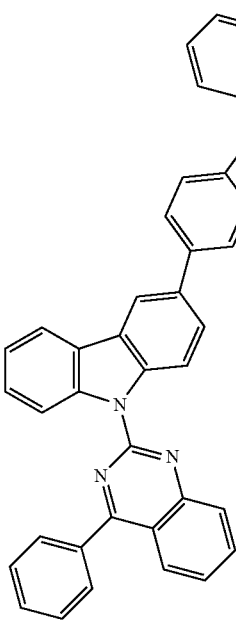
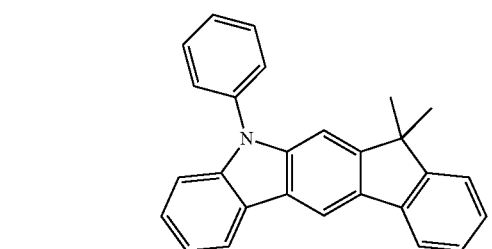

-continued

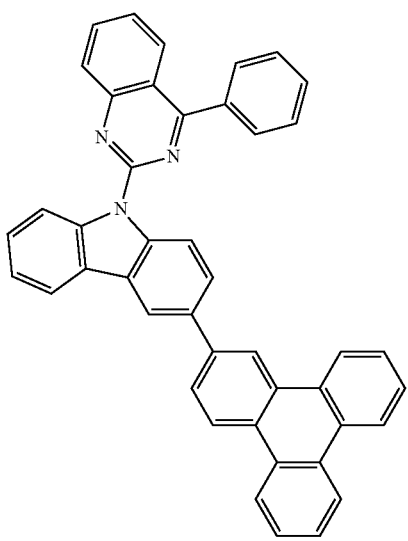 [SMILES: c1ccc(-c2nc(-n3c4ccccc4c4cc(-c5ccc6c7ccccc7c7ccccc7c6c5)ccc43)nc3ccccc23)cc1]

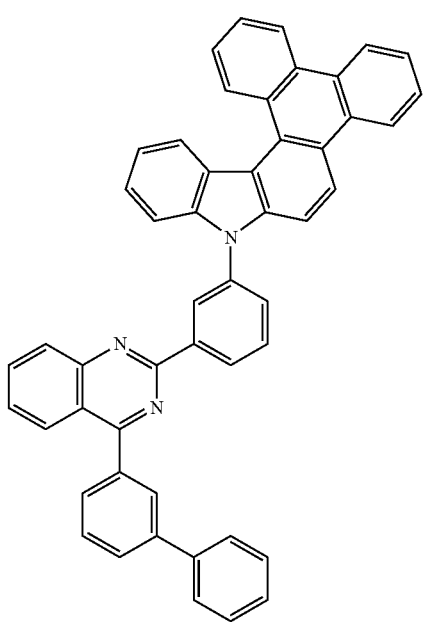 [SMILES: c1ccc(-c2cccc(-c3nc(-c4cccc(-n5c6ccccc6c6c7c8ccccc8c8ccccc8c7ccc65)c4)nc4ccccc34)c2)cc1]

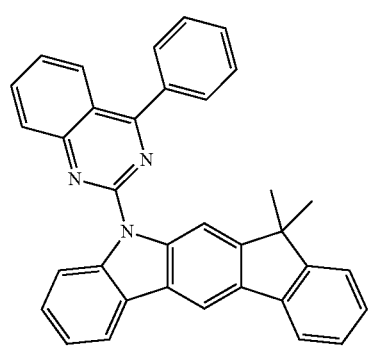 [SMILES: CC1(C)c2ccccc2-c2cc3c4ccccc4n(-c4nc(-c5ccccc5)c5ccccc5n4)c3cc21]

-continued

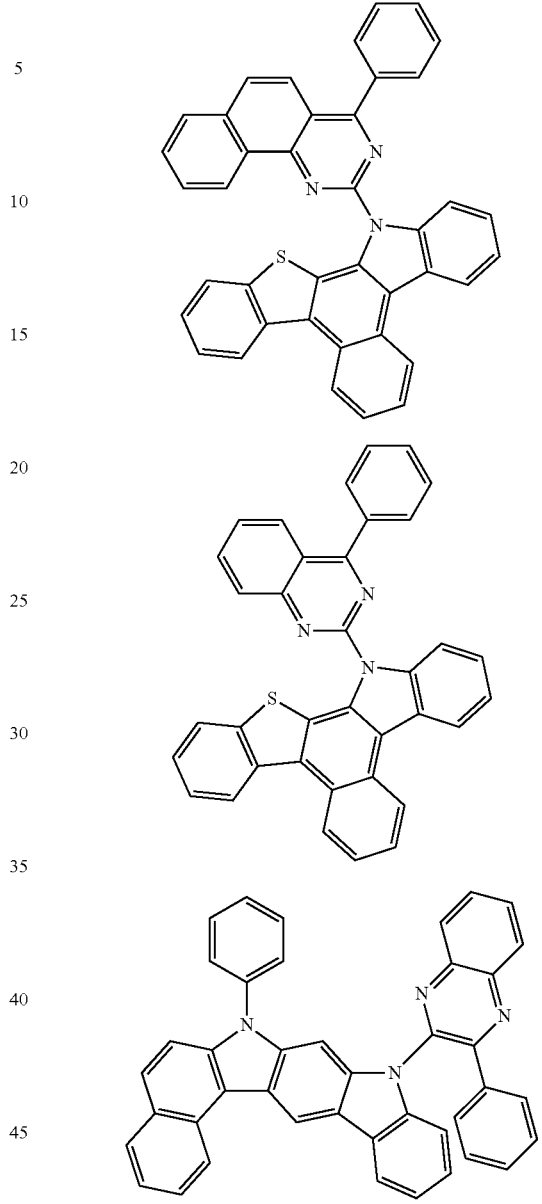

When the compound of formula (1) or according to the preferred embodiments is used as matrix material for an emitting compound in an emitting layer, it may be used in combination with one or more phosphorescent materials (triplet emitters), preference being given to materials that phosphoresce in the red, orange, yellow or green. Phosphorescence in the context of this invention is understood to mean luminescence from an excited state having higher spin multiplicity, i.e. a spin state >1, especially from an excited triplet state. In the context of this invention, all iridium, platinum and copper compounds, especially those that are luminescent, are referred to as phosphorescent materials. In that case, the mixture of the compound of formula (1) or according to the preferred embodiments and the emitting compound contains between 99% and 1% by weight, preferably between 98% and 10% by weight, more preferably between 97% and 60% by weight and most preferably between 95% and 70% by weight of the compound of formula (1) or according to the preferred embodiments, based on the overall mixture of emitter and matrix material. Correspondingly, the mixture contains between 1% and 99% by weight, preferably between 2% and 90% by weight, more preferably between 3% and 40% by weight and most preferably between 5% and 30% by weight of the emitter, based on the overall mixture of emitter and matrix material. In the case of use of a mixture of multiple emitters rather than just one emitter, these preferences apply correspondingly to the total proportion of emitters in the emitting layer.

Suitable phosphorescent compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum. It may also be preferable when the electroluminescent device comprises two or more phosphorescent dopants, in which case the dopant that emits at shorter wavelength is used as co-matrix for the dopant that emits at longer wavelength. In this embodiment, it is especially preferable when one of the dopants emits in the red and the other dopant emits in the yellow or green.

Examples of the emitters described above can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439, WO 2018/011186 and WO 2018/041769, WO 2019/020538, WO 2018/178001, WO 2019/115423 and WO 2019/158453. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Examples of phosphorescent dopants are adduced below.

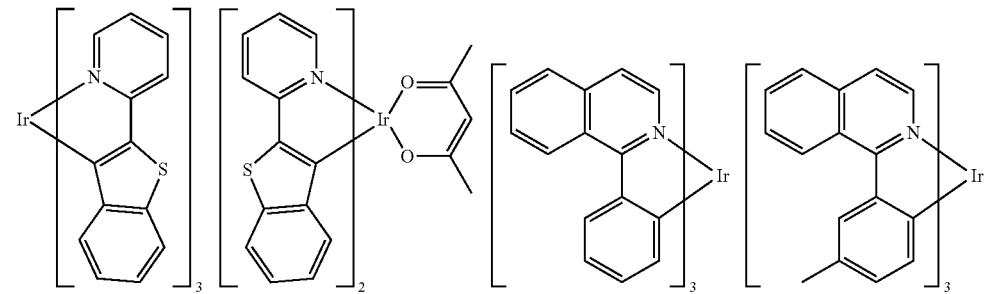

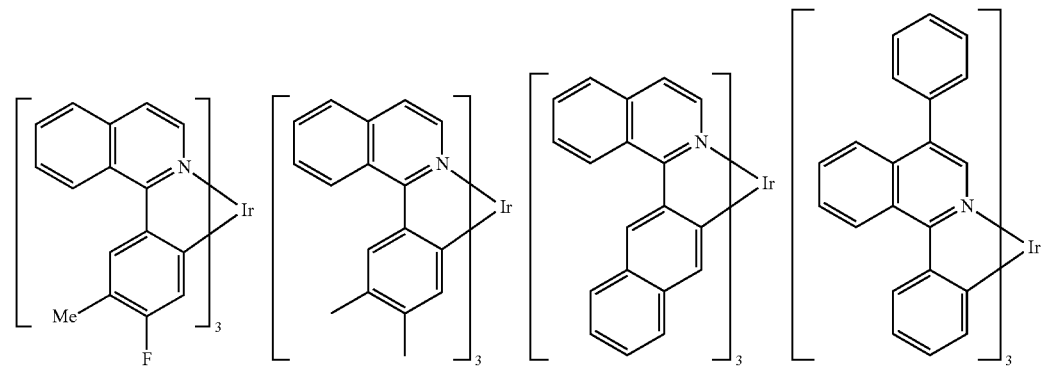

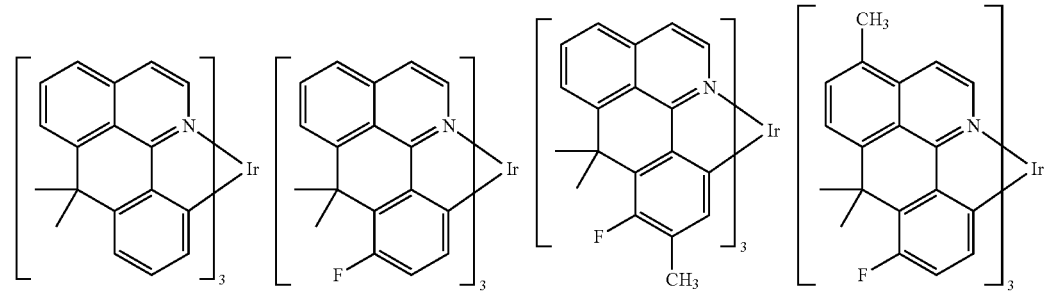

171
172
-continued
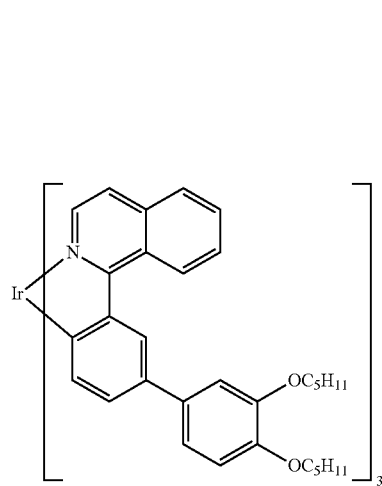
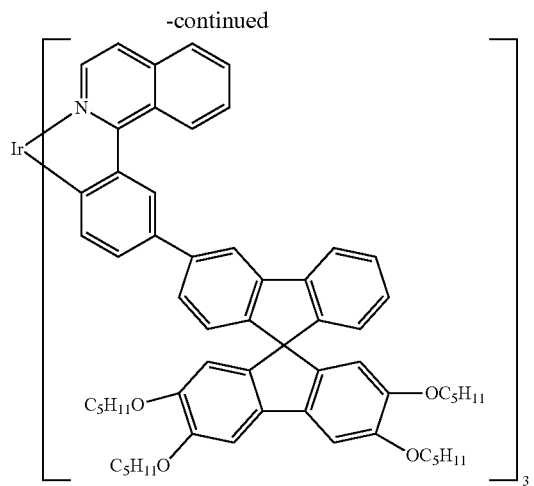
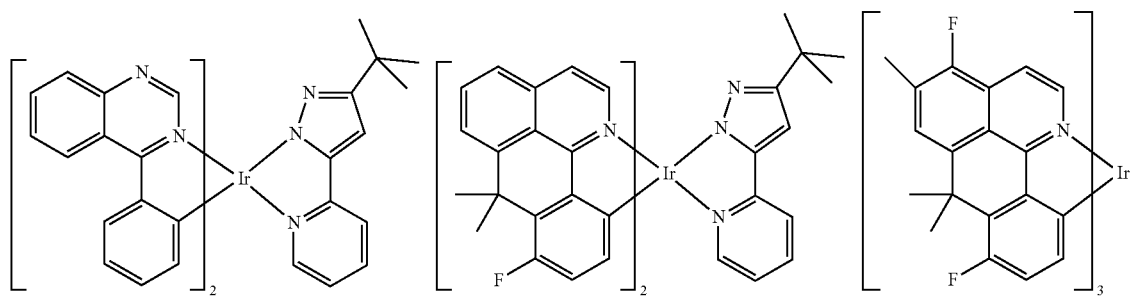
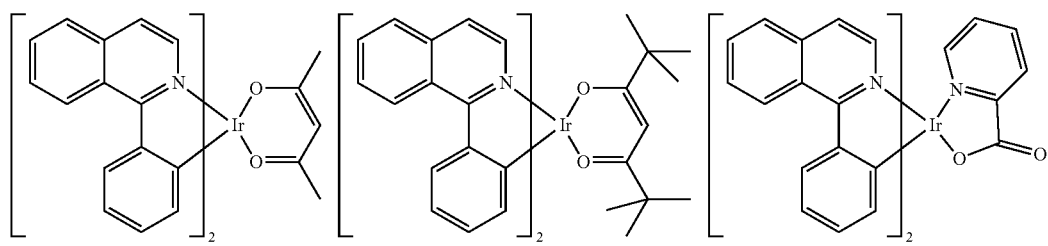
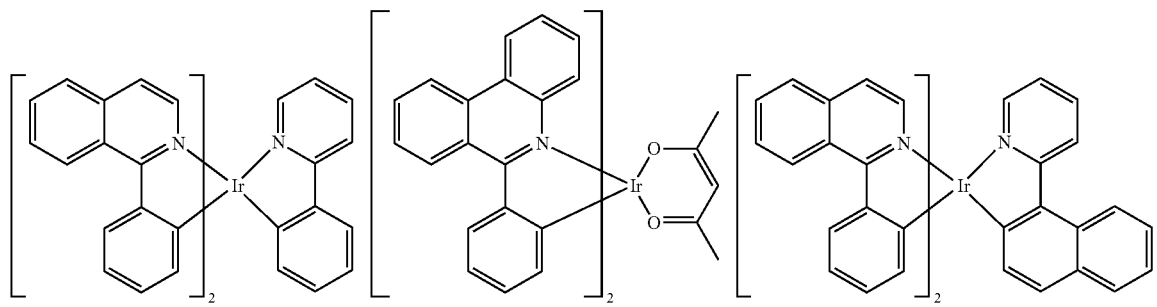
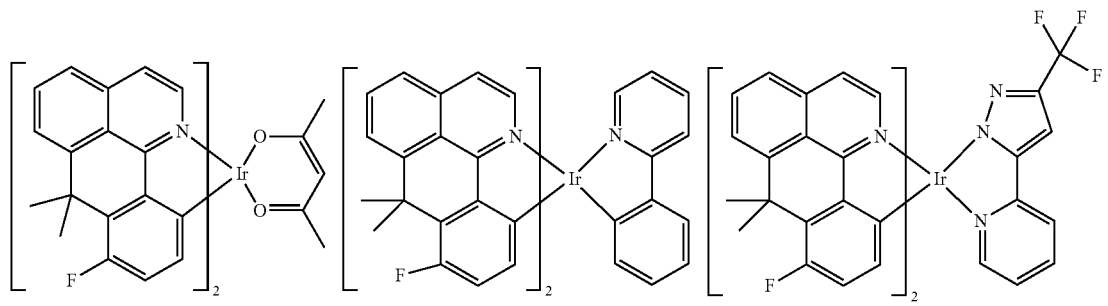

-continued
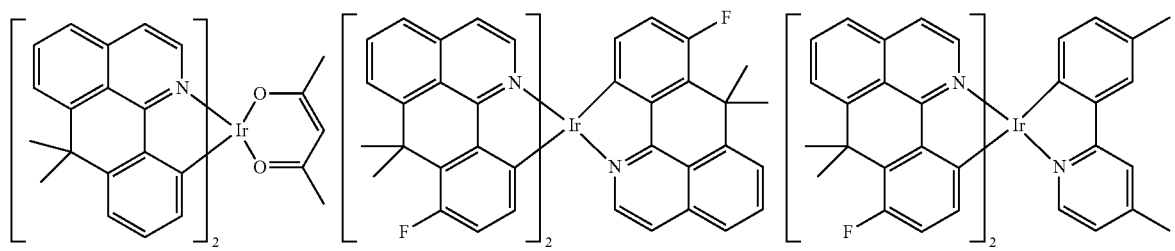
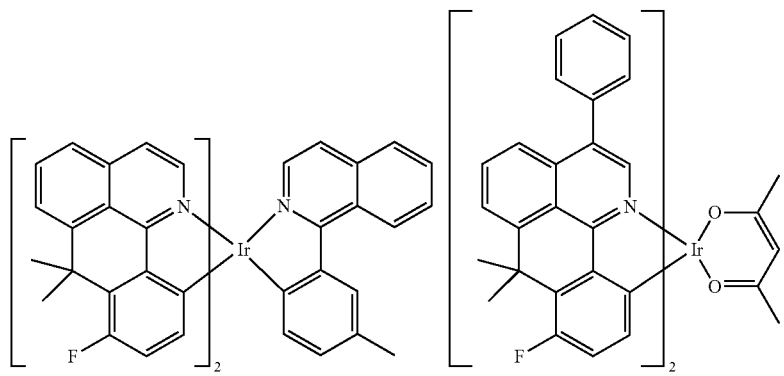
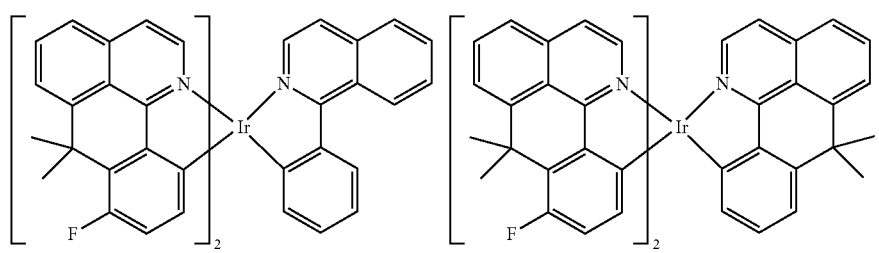
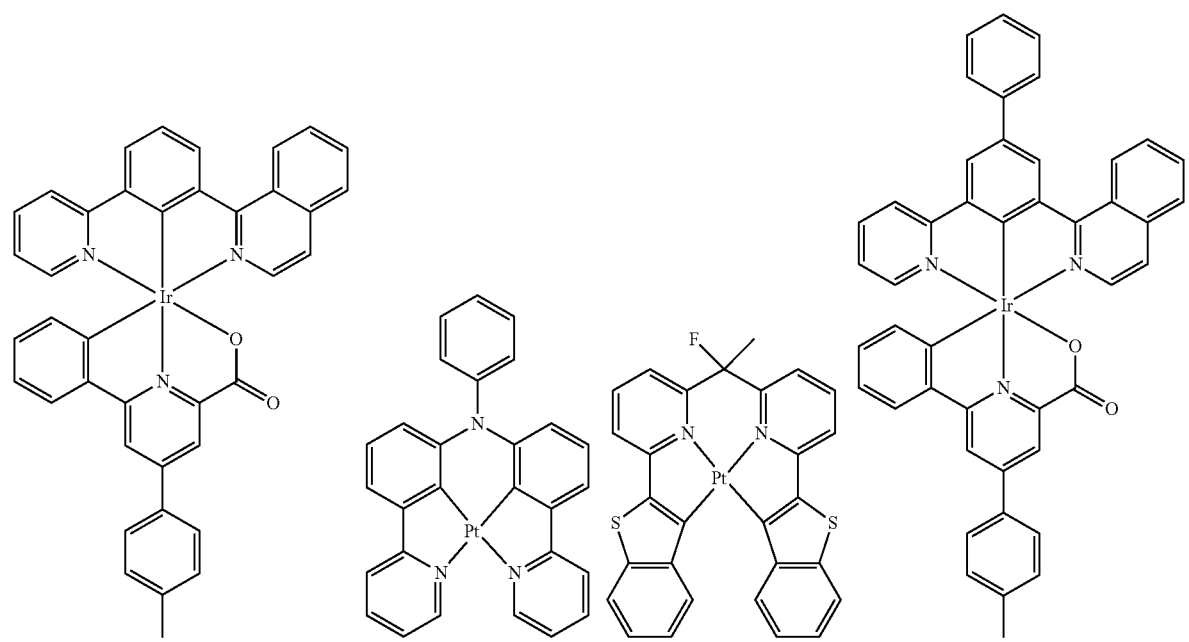

175 176
-continued
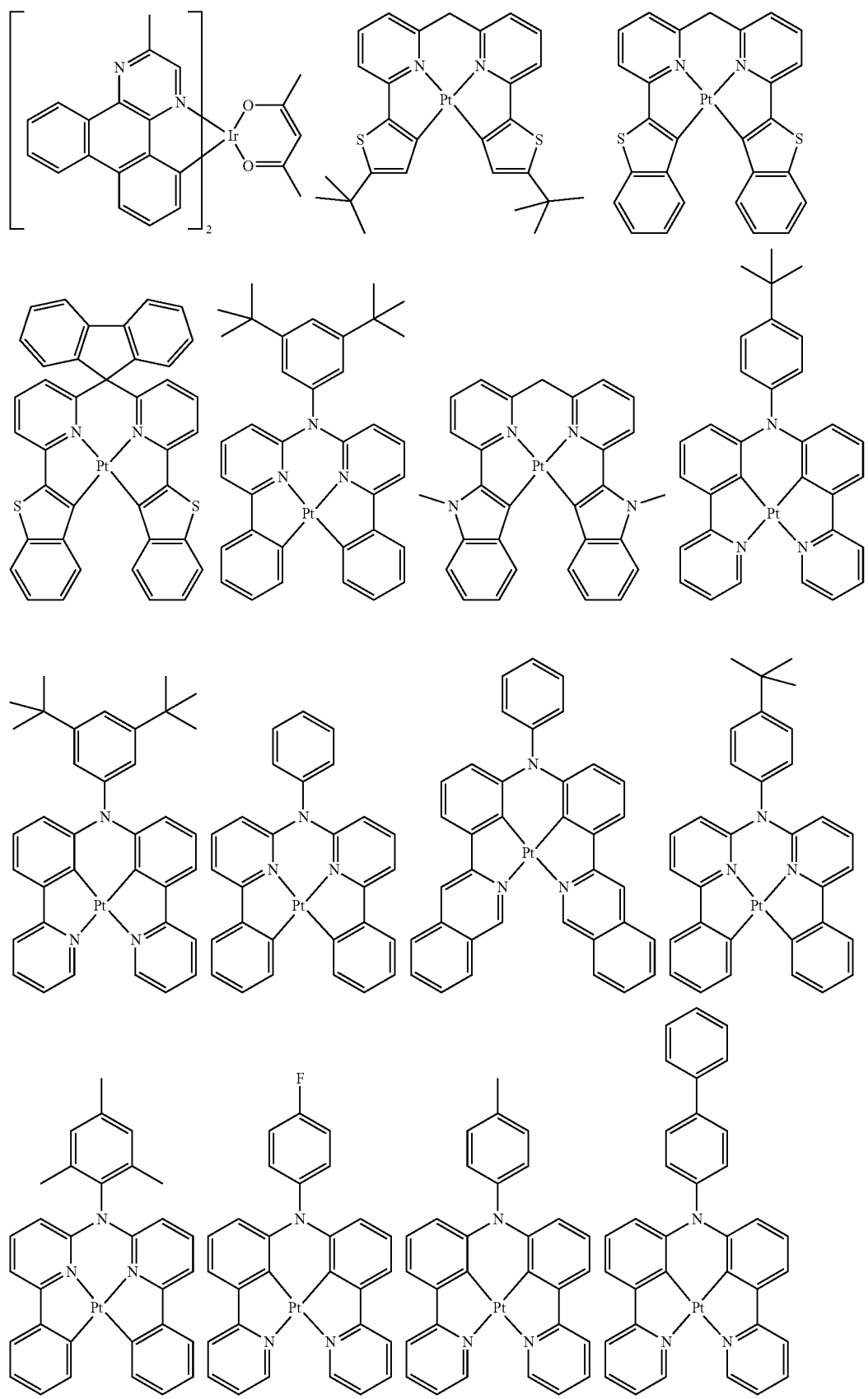

-continued
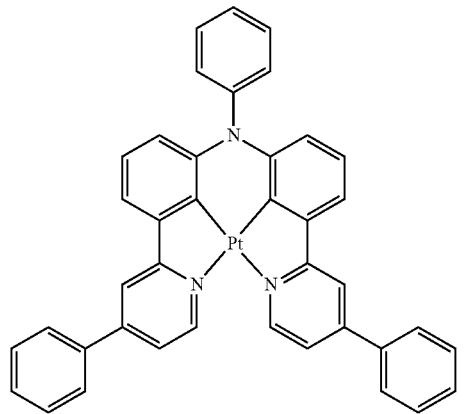
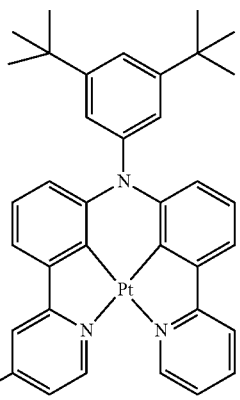
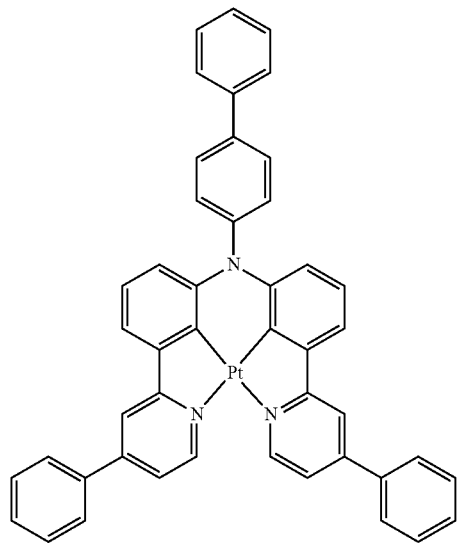
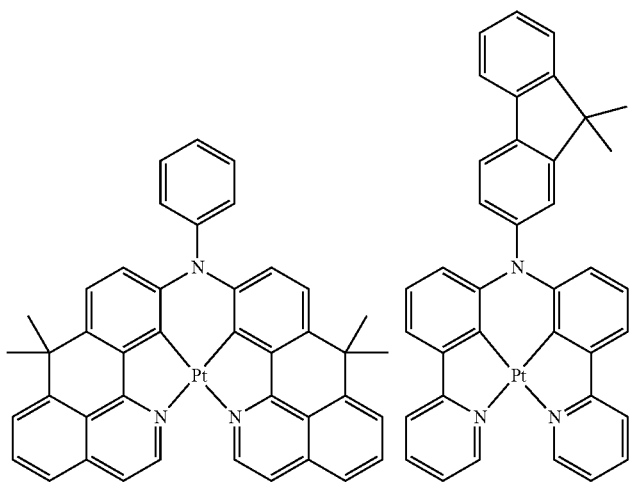
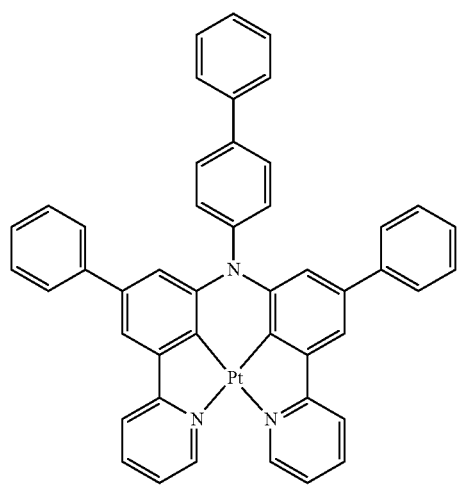
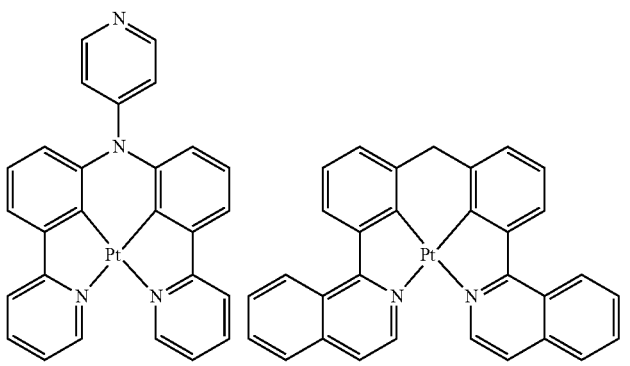

-continued
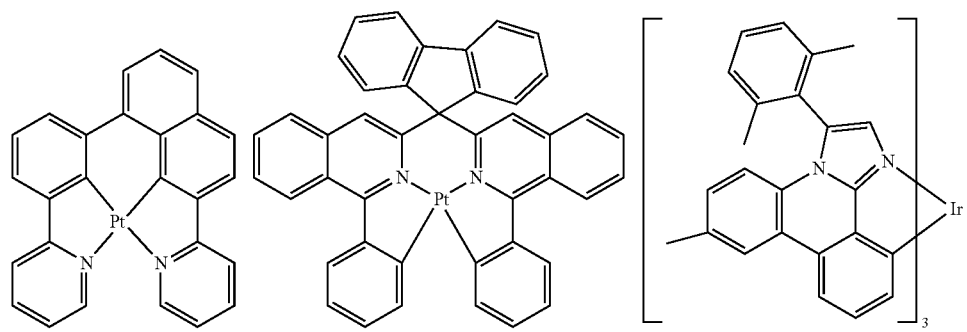
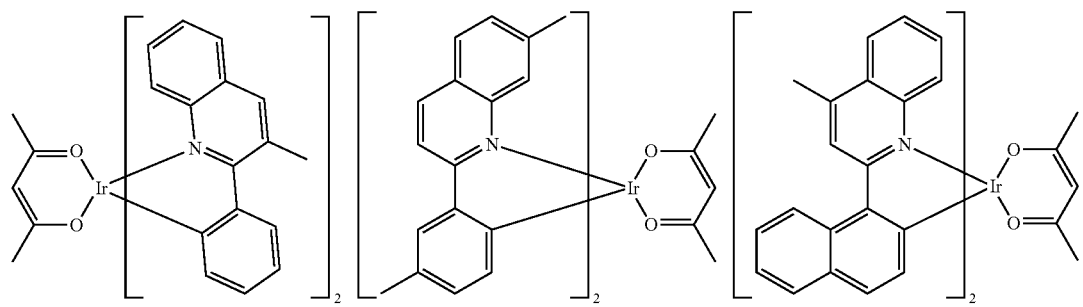
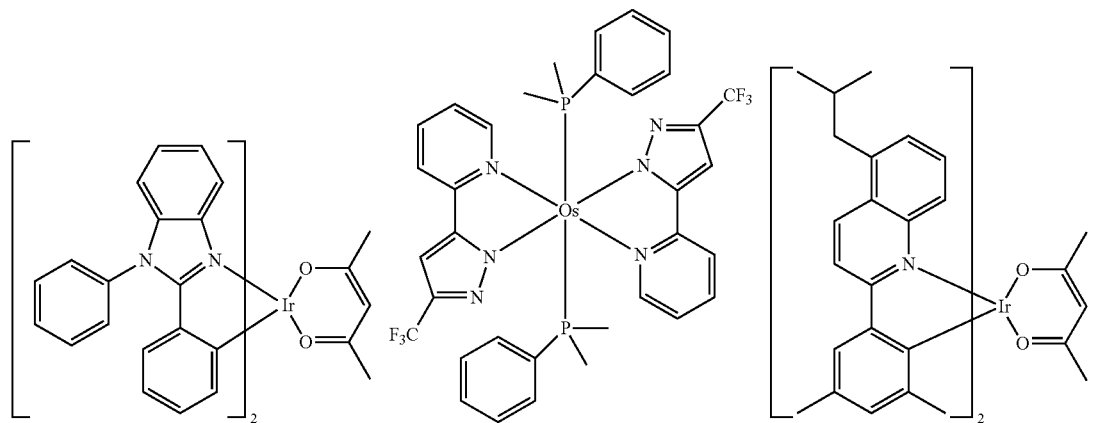
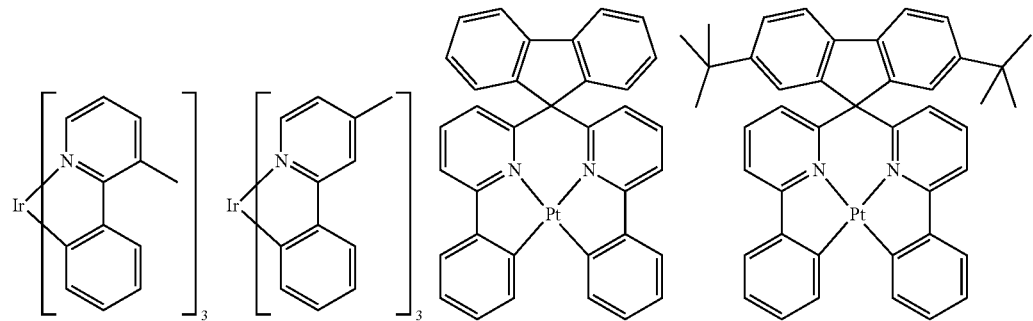

-continued
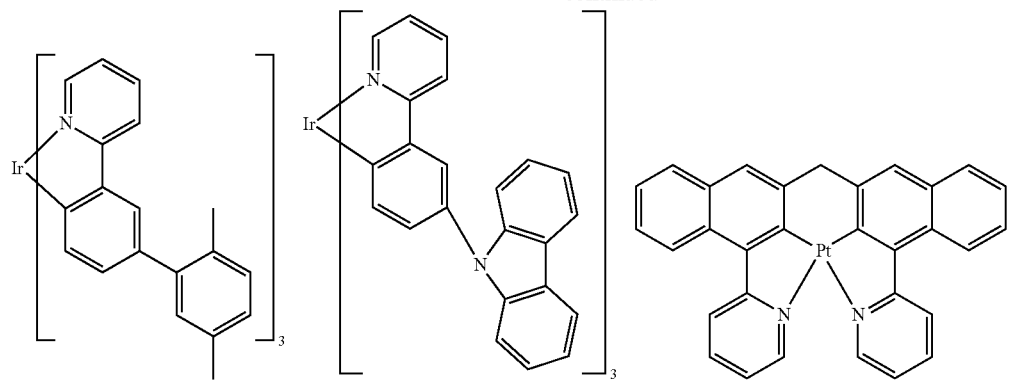
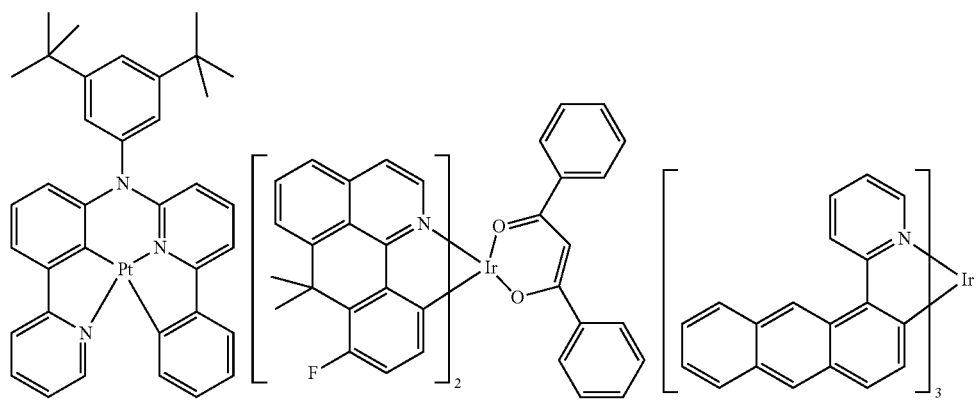
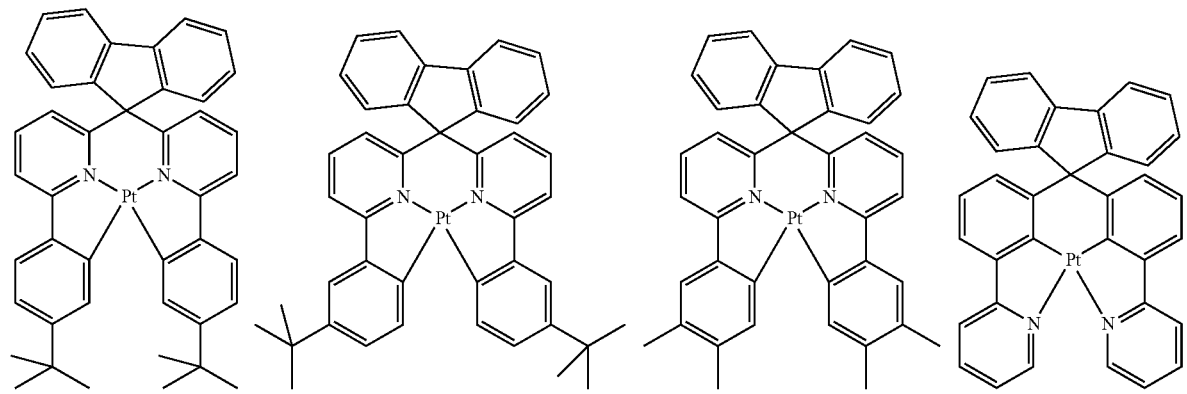
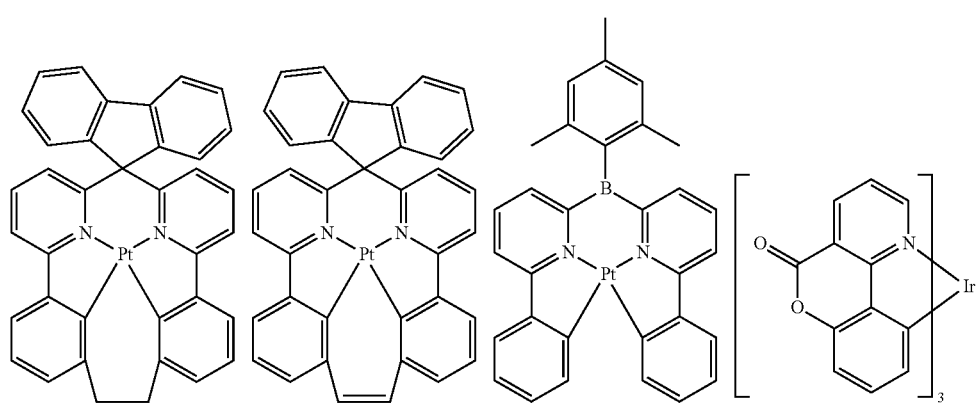

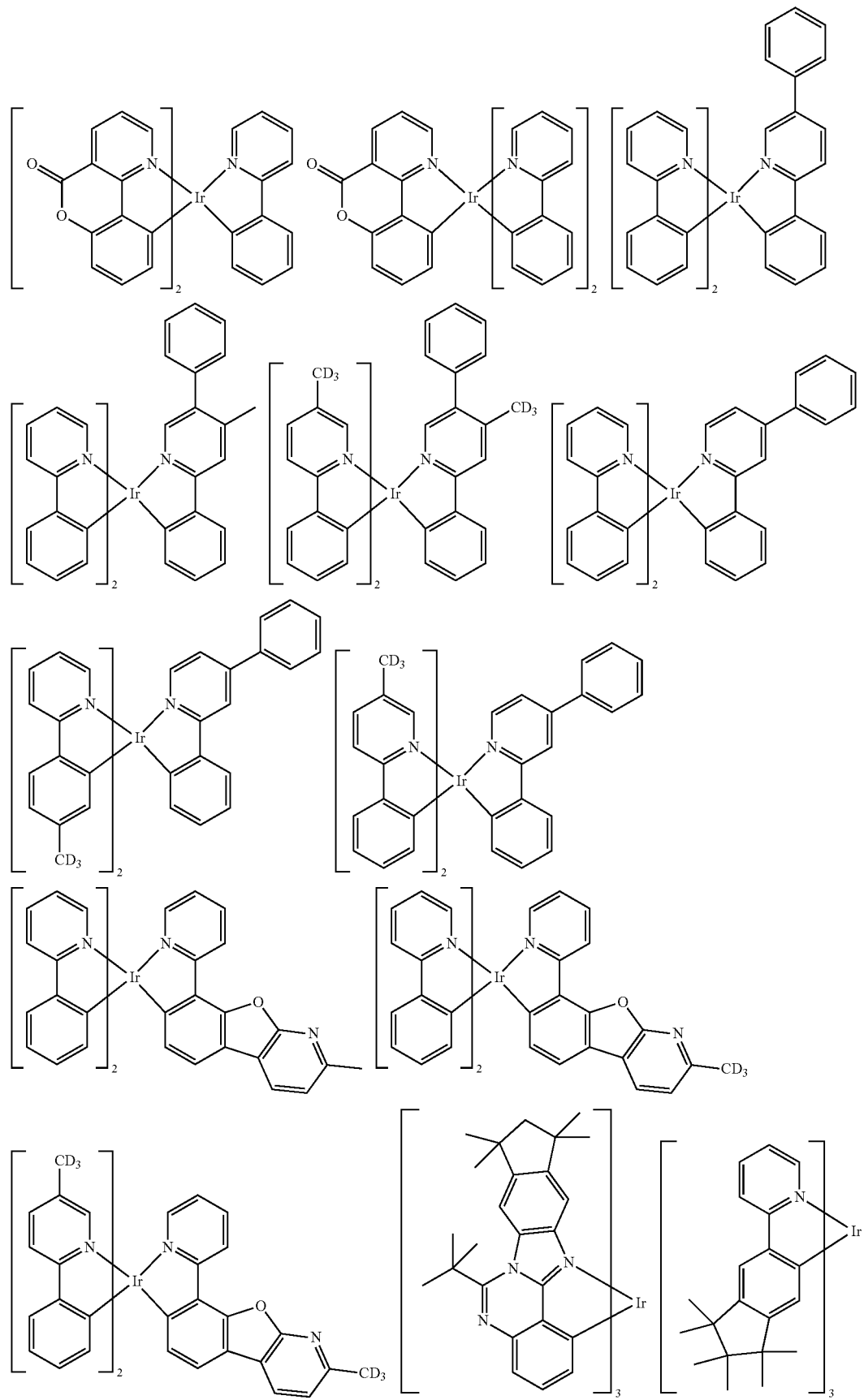

-continued
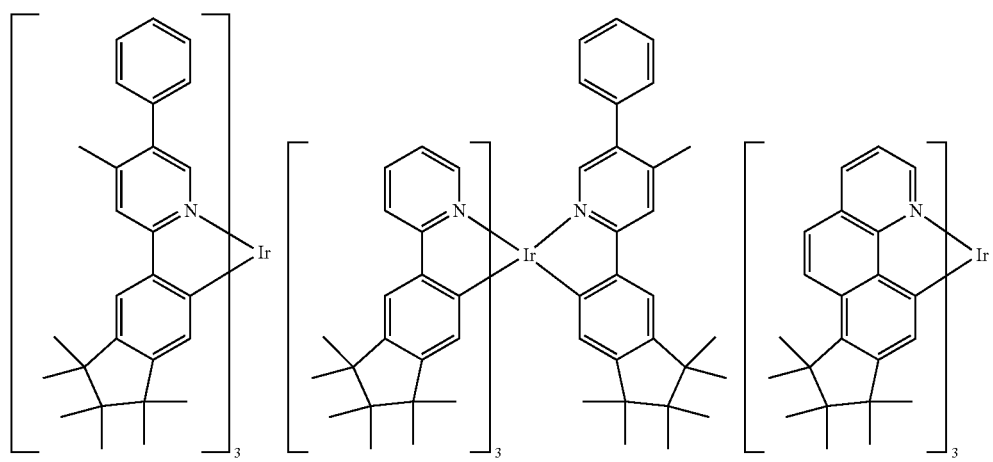
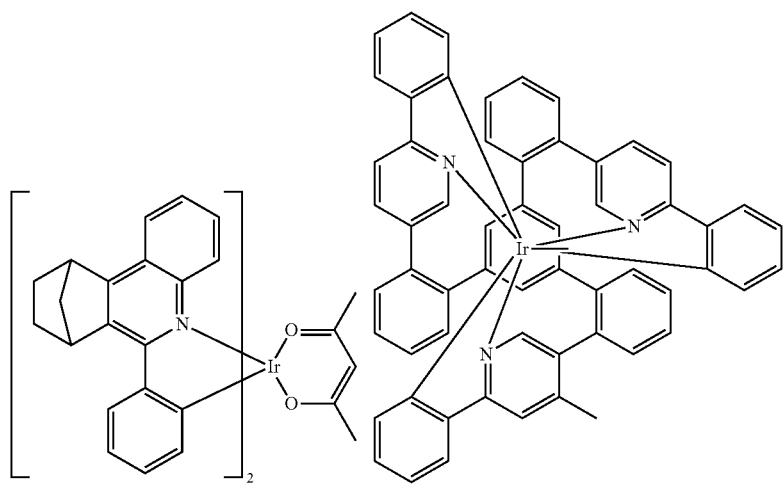
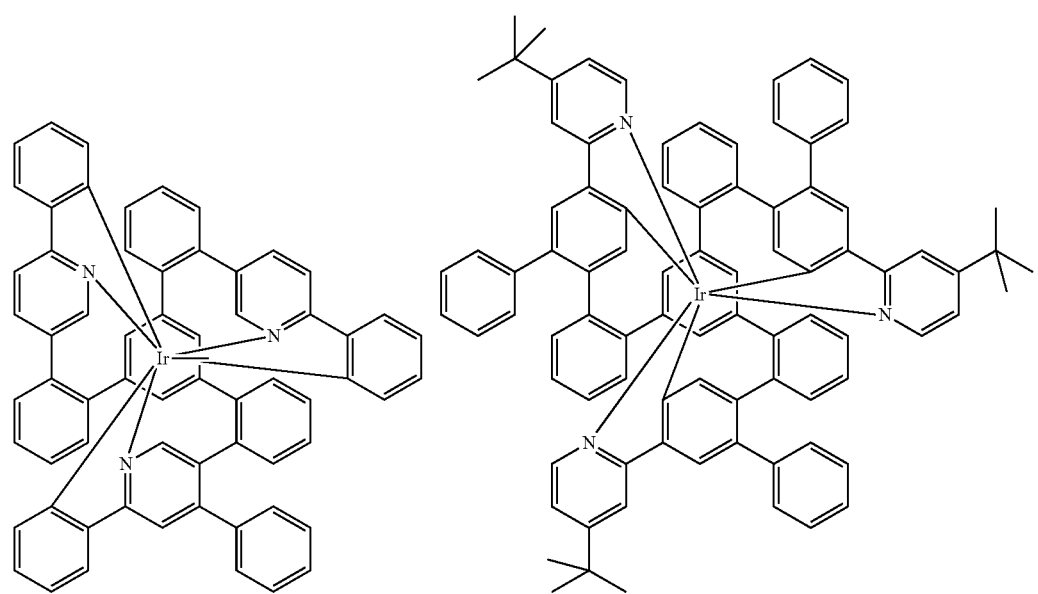

-continued
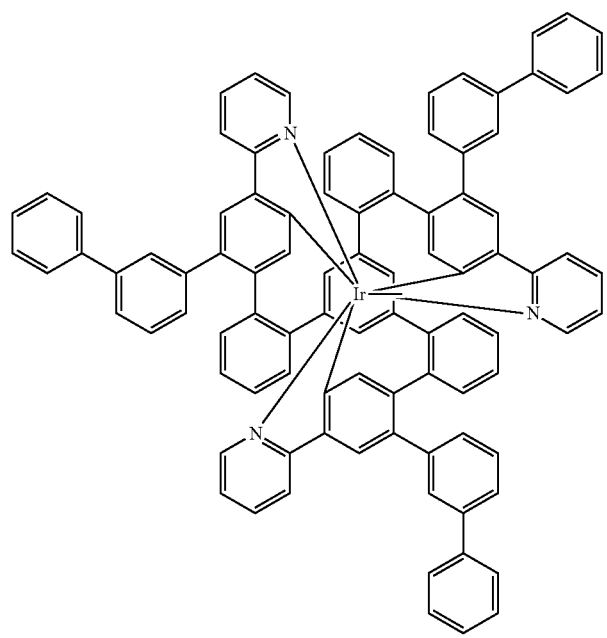
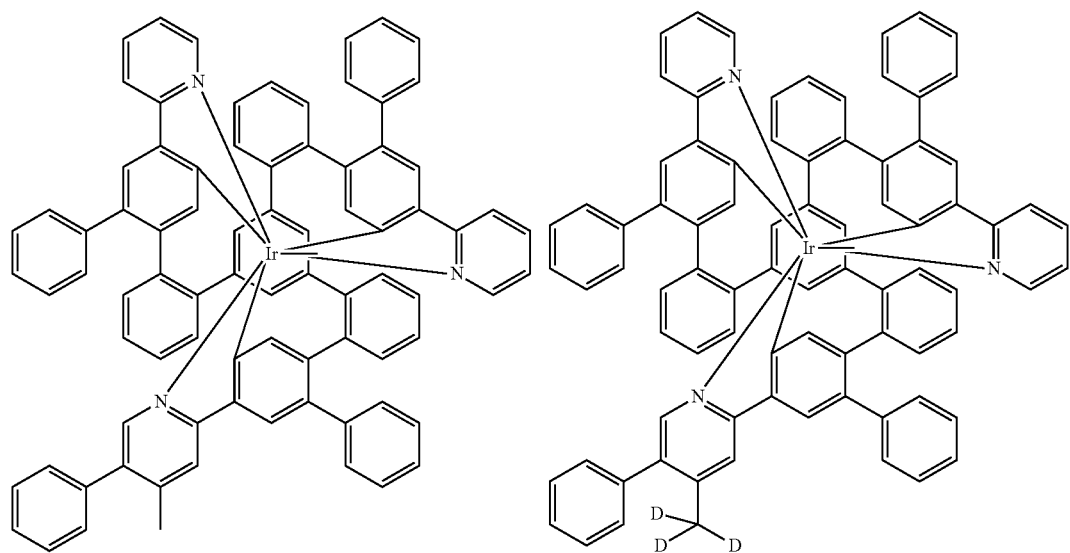

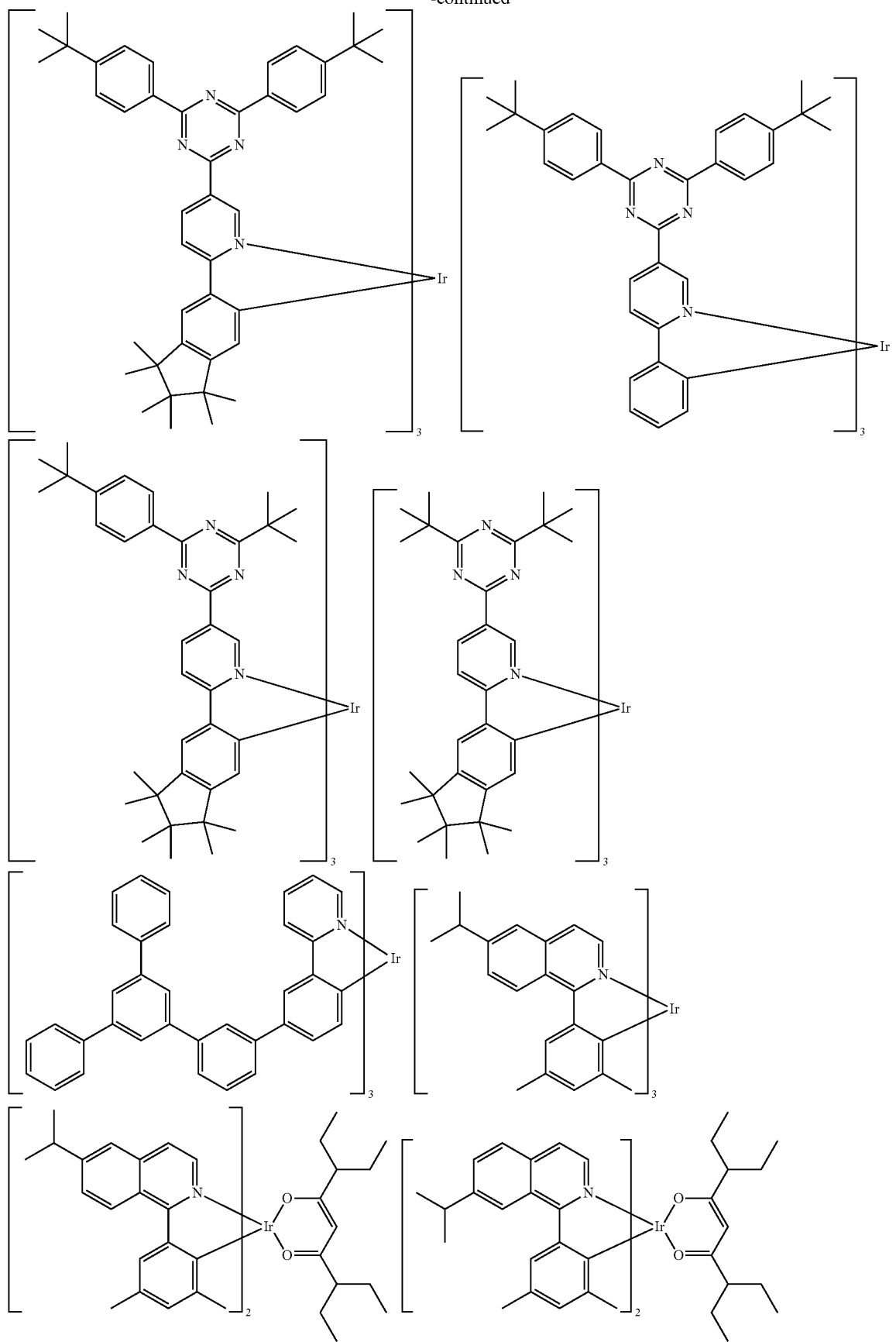

-continued

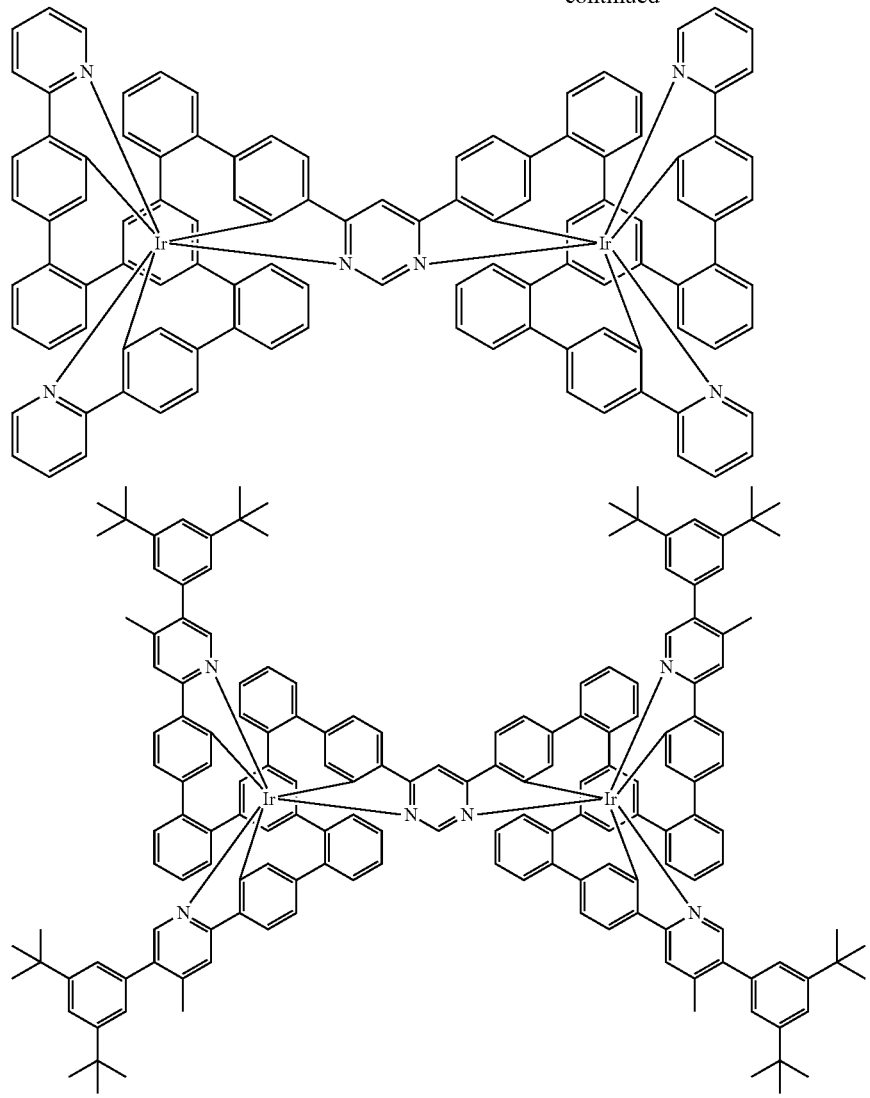

Additionally preferred is an organic electroluminescent device, characterized in that one or more layers are coated by a sublimation process. The materials are applied here by vapour deposition in vacuum sublimation systems at a pressure of less than $10^{-5}$ mbar, preferably less than $10^{-6}$ mbar, where the pressure may also be lower, for example less than $10^{-7}$ mbar.

Preference is likewise given to an organic electroluminescent device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example screen printing, flexographic printing or offset printing, but more preferably LITI (light-induced thermal imaging, thermal transfer printing) or inkjet printing. For this purpose, soluble compounds are needed. High solubility can be achieved by suitable substitution of the compounds.

The organic electroluminescent device can also be produced as a hybrid system by applying one or more layers from solution and applying one or more other layers by vapour deposition. For example, it is possible to apply an emitting layer comprising a compound of formula (1) and a phosphorescent dopant from solution, and to apply a hole blocker layer and/or an electron transport layer thereto by vapour deposition under reduced pressure. It is likewise possible to apply the emitting layer comprising a compound of formula (1) and a phosphorescent dopant by vapour deposition under reduced pressure, and to apply one or more other layers from solution.

The person skilled in the art is aware of these methods in general terms and is able to apply them without difficulty to organic electroluminescent devices comprising compounds of formula (1) or the preferred embodiments detailed above.

The compounds of the invention, when used in organic electroluminescent devices, have the following surprising advantages over the prior art:

1. The compounds of the invention have high thermal stability and a low tendency to crystallization. More particularly, they have a lower tendency to crystallization than corresponding fluorene derivatives that do not contain an Ar group on the fluorene base skeleton. This enables baking of the layer at a higher temperature after production from solution, which constitutes a significant technical advantage. A higher baking temperature can achieve better device performance, which is especially manifested in an improved lifetime. In the event of crystallization of the compounds, poorer efficiency is generally observed.

2. The compounds of the invention have high solubility in standard organic solvents, for example toluene, and very good film formation properties, and are therefore of particularly good suitability for processing from solution. More particularly, they show better solubility compared to corresponding fluorene derivatives that do not contain an Ar group on the fluorene base skeleton.

3. Solutions comprising the compounds of the invention have excellent long-term solution stability. More particularly, the solutions have improved long-term stability compared to solutions containing fluorene derivatives lacking an Ar group.

4. The OLEDs produced with the compounds of the invention generally have a long lifetime. More particularly, the OLEDs produced with the compounds of the invention have a better lifetime than the OLEDs comprising a comparable fluorene derivative in the emitting layer, but one in which the Ar group is bonded in the 2 position rather than 4 position on the fluorene base skeleton.

The invention is described in more detail by the examples which follow, without any intention of restricting it thereby. The person skilled in the art is able, without exercising inventive skill, to prepare further compounds of the invention and use them in organic electroluminescent devices.

EXAMPLES

The syntheses which follow, unless stated otherwise, are conducted under a protective gas atmosphere in dried solvents. The solvents and reagents can be purchased from ALDRICH or ABCR. The numbers given for the reactants that are not commercially available are the corresponding CAS numbers.

The following synthesis units can be used for synthesis of the materials of the invention:

Boronic Acids

BB-1

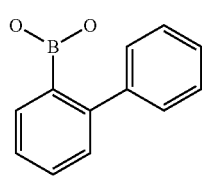

CAS-1817781-37-5

BB-2

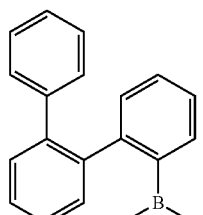

CAS-1310405-29-8

BB-3

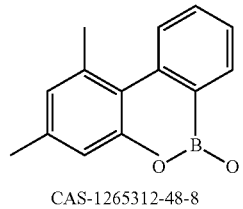

CAS-1265312-48-8

BB-4

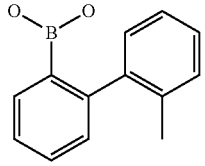

CAS-1228458-44-3

BB-5

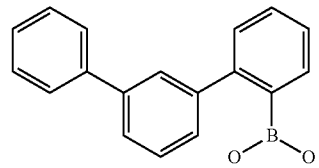

CAS-1133796-50-5

BB-6

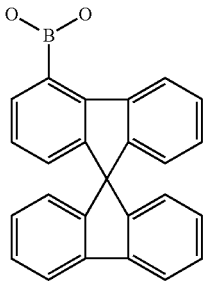

CAS-1421789-05-0

BB-7

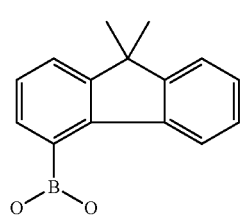

CAS-1246022-50-3

BB-8

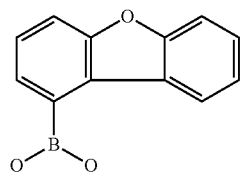

CAS-162607-19-4

Ortho-Bromomethyl Ester

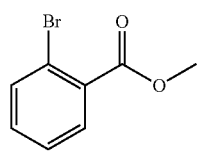

CAS-610-94-6    BB-9

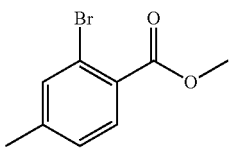

CAS-87808-49-9    BB-10

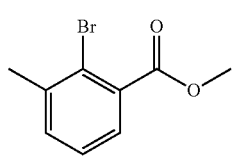

CAS-131001-86-0    BB-11

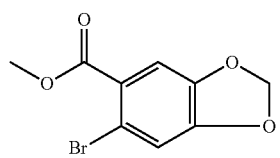

CAS-61441-09-6    BB-12

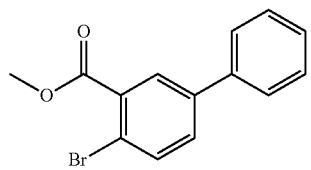

CAS-727408-92-6    BB-13

Syntheses of the Materials of the Invention

Example 1: Coupling of ortho-bromobenzoate and [1,1'-biphenyl]-2-boronic Acid

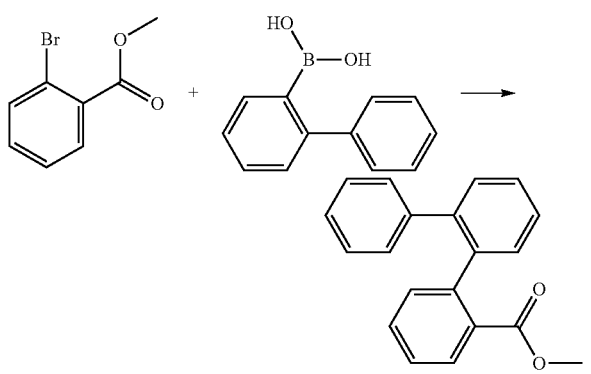

In a baked-out 1 l 4-neck flask with precision glass stirrer, reflux condenser, thermometer and protective gas connection, 30 g (139.5 mmol) of 2-bromobenzoate (BB-9), 33.2 g (167.4 mmol, 1.2 eq.) of biphenyl-2-boronic acid (BB-1), 32.5 g (306.9 mmol, 2.2 eq.) of sodium carbonate and 1.83 g (6.98 mmol, 0.05 eq.) of triphenylphosphine are dissolved in 450 ml of THF and 150 ml of water and degassed. 0.78 g (3.49 mmol, 0.025 eq.) of palladium(II) acetate is added to the reaction mixture, which is stirred under reflux for 24 h. After cooling to room temperature, 300 ml of ethyl acetate are added, the organic phase is separated off and the solvent is removed under reduced pressure. The residue is taken up in ethyl acetate, filtered through silica gel and dried under reduced pressure. 33.5 g (116.2 mmol, 83% yield) of the colourless solid BB-50 is obtained.

Analogously to this method, the boronic acids specified can be coupled to methyl ortho-bromobenzoates with similar yields:

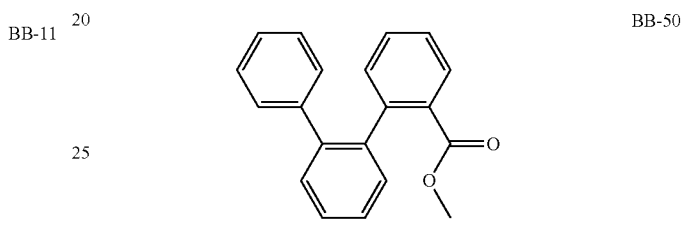

Reactants: BB-1 / BB-9    BB-50

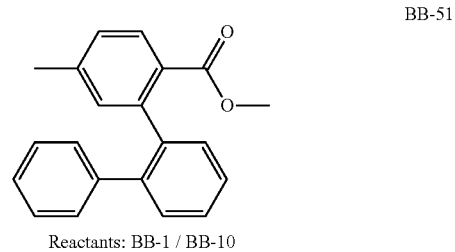

Reactants: BB-1 / BB-10    BB-51

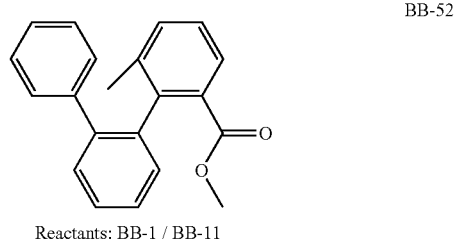

Reactants: BB-1 / BB-11    BB-52

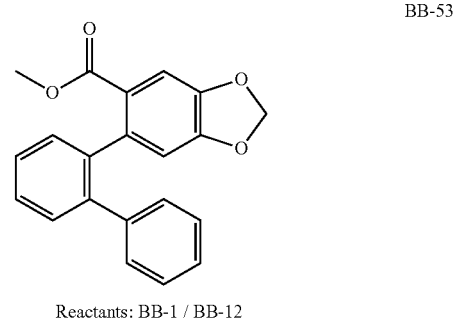

Reactants: BB-1 / BB-12    BB-53

BB-54
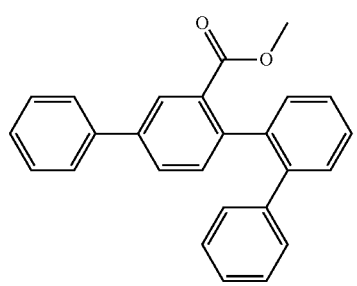
Reactants: BB-1 / BB-13
BB-55
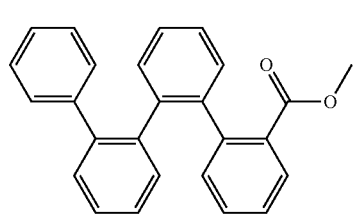
Reactants: BB-2 / BB-9
BB-56
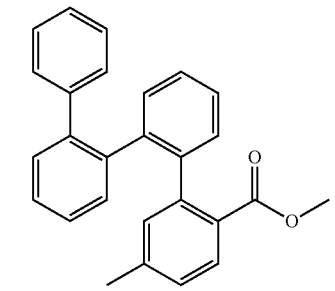
Reactants: BB-2 / BB-10
BB-57
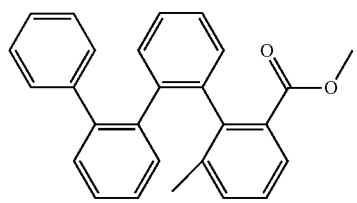
Reactants: BB-2 / BB-11
BB-58
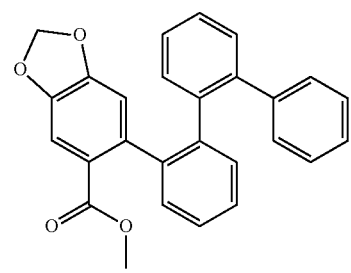
Reactants: BB-2 / BB-12
BB-59
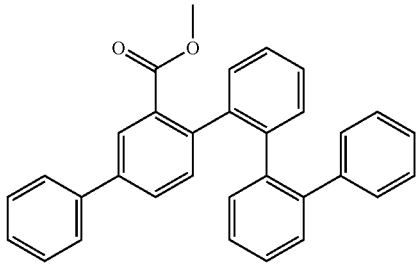
Reactants: BB-2 / BB-13
BB-60
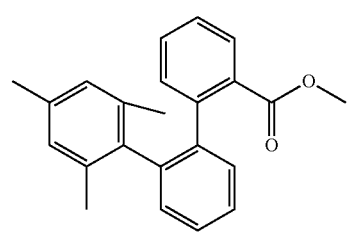
Reactants: BB-3 / BB-9
BB-61
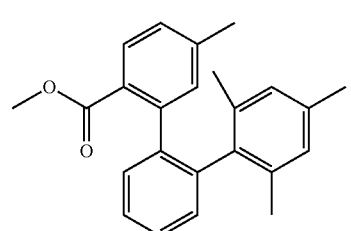
Reactants: BB-3 / BB-10
BB-62
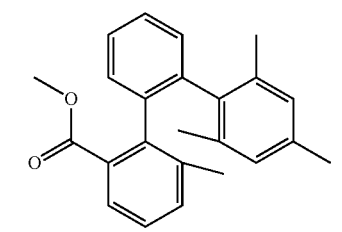
Reactants: BB-3 / BB-103
BB-63
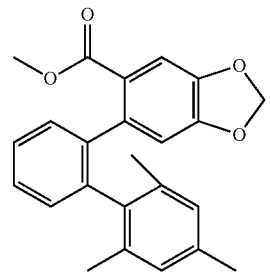
Reactants: BB-3 / BB-12

BB-64
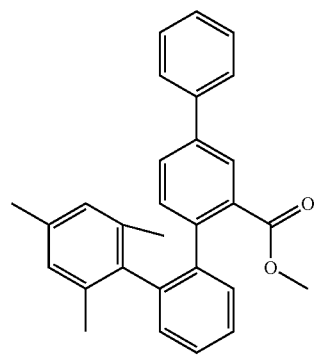
Reactants: BB-3 / BB-13
BB-65
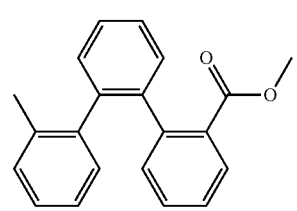
Reactants: BB-4 / BB-9
BB-66
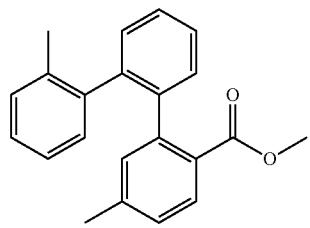
Reactants: BB-4 / BB-10
BB-67
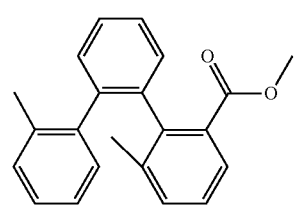
Reactants: BB-4 / BB-11
BB-68
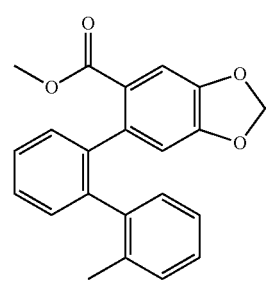
Reactants: BB-4 / BB-12
BB-69
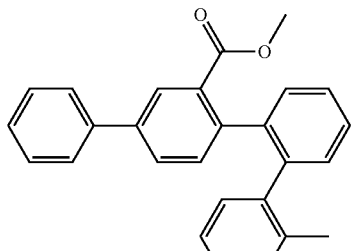
Reactants: BB-4 / BB-13
BB-70
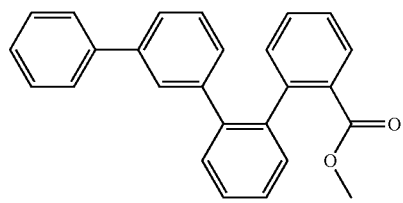
Reactants: BB-4 / BB-13
BB-71
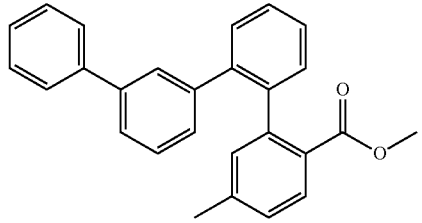
Reactants: BB-5 / BB-10
BB-72
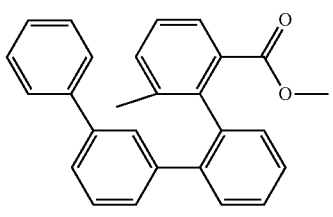
Reactants: BB-5 / BB-11
BB-73
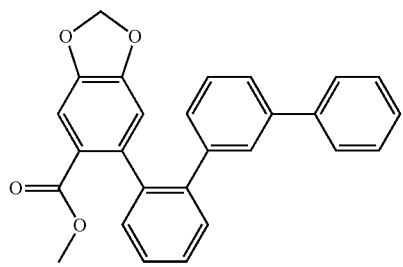
Reactants: BB-5 / BB-12

BB-74
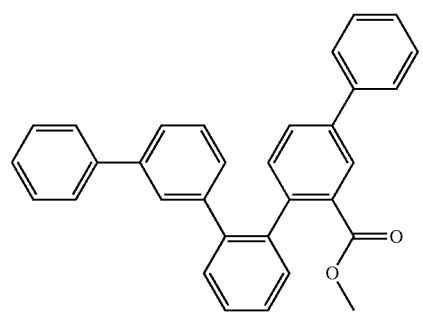
Reactants: BB-5 / BB-13
BB-75
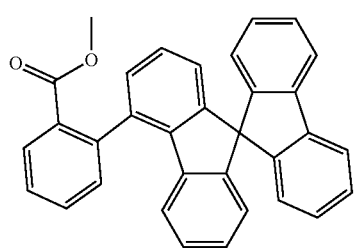
Reactants: BB-6 / BB-9
BB-76
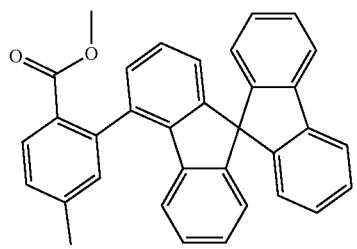
Reactants: BB-6 / BB-10
BB-77
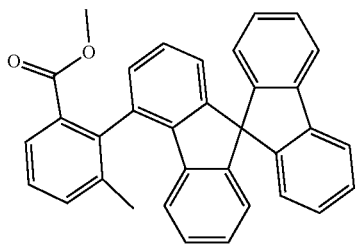
Reactants: BB-6 / BB-11
BB-78
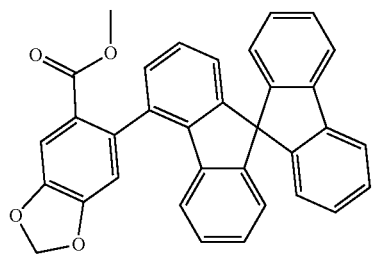
Reactants: BB-6 / BB-12
BB-79
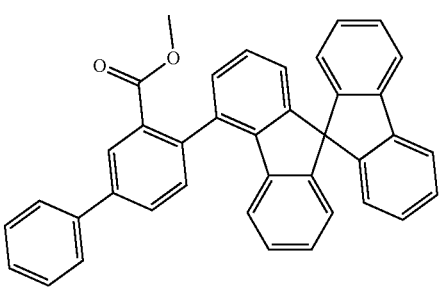
Reactants: BB-6 / BB-13
BB-80
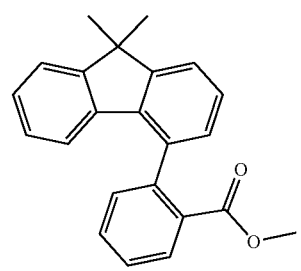
Reactants: BB-7 / BB-9
BB-81
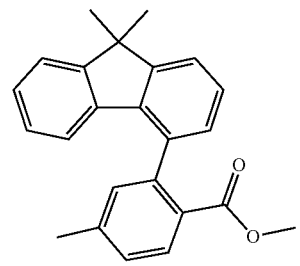
Reactants: BB-7 / BB-10
BB-82
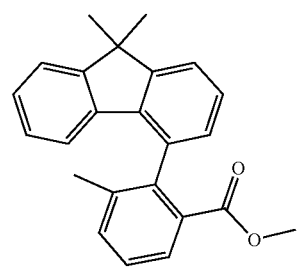
Reactants: BB-7 / BB-11
BB-83
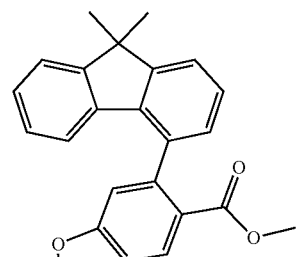
Reactants: BB-7 / BB-12

BB-84
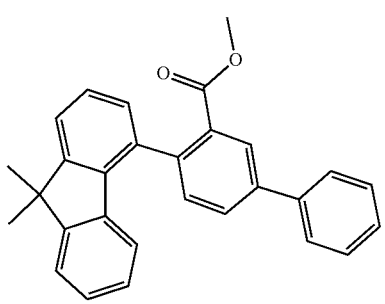
Reactants: BB-7 / BB-13
BB-85
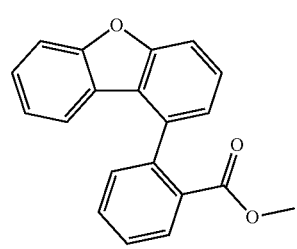
Reactants: BB-8 / BB-9
BB-86
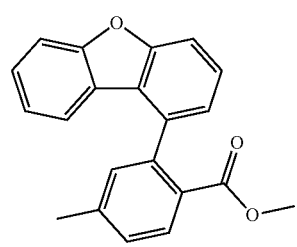
Reactants: BB-8 / BB-10
BB-87
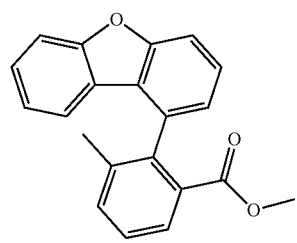
Reactants: BB-8 / BB-103
BB-88
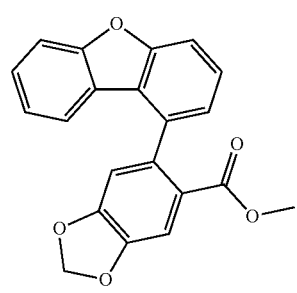
Reactants: BB-8 / BB-12
BB-89
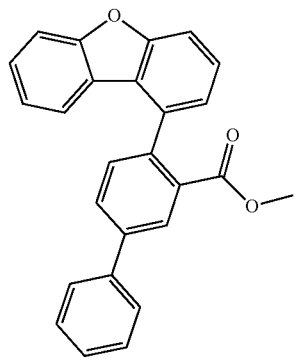
Reactants: BB-8 / BB-13
Example 2: Conversion of the Methyl Esters to 9,9'-diarylfluorenes
Synthesis Units:
BB-90
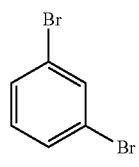
CAS: 108-36-1
BB-91
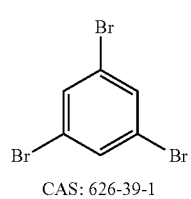
CAS: 626-39-1
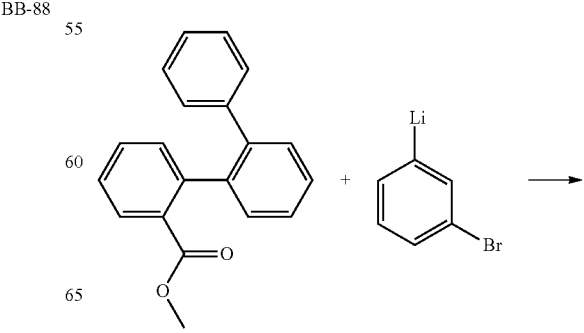

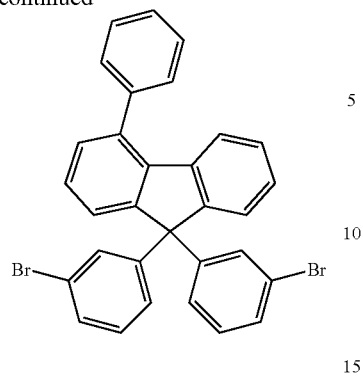

In a baked-out 1 l 4-neck flask with precision glass stirrer, reflux condenser, thermometer and protective gas connection, 27.65 ml (228.9 mmol) of 1,3-dibromobenzene BB-90 (CAS: 108-36-1) is dissolved in 450 ml of anhydrous 2-methoxy-2-methylpropane, inertized with argon and cooled down to −70° C. 143.7 ml (228.9 mmol, 1 eq.) of a 15% n-butyllithium solution in n-hexane is gradually added dropwise at such a rate that the internal temperature does not exceed −65° C. The solution is stirred at −70° C. for a further 90 minutes. This gives rise to a white suspension. 30 g (132.9 mmol) of methyl [1,1',2',1"]terphenyl-2-carboxylate (BB-50) is dissolved in 18.3 ml of anhydrous 2-methoxy-2-methylpropane, inertized with argon and gradually added dropwise to the white suspension at such a rate that the internal temperature does not rise above −65° C. The mixture is thawed gradually to room temperature overnight. 200 ml of water is rapidly metered in and the mixture is stirred for 60 minutes. The aqueous phase is separated off and the organic phase is freed of sufficient solvent for it to turn cloudy. 300 ml of heptane is added, such that a solid precipitates out of the solution. The solid is filtered off with suction, washed with heptane and dried.

The dried solid is transferred to a 4 l 4-neck flask with reflux condenser, precision glass stirrer, thermometer and protective gas connection, and admixed with 950 ml of 100% acetic acid and 22 ml of 25% hydrochloric acid. The mixture is heated under reflux for 72 h, giving rise to a brown solution. After cooling to room temperature, 1000 ml of water are added, such that the solution turns cloudy. The product is extracted with toluene. 30.5 g (55.24 mmol, 53% yield) of the colourless solid BB-100 is obtained.

It is possible to prepare the following intermediates with similar yields and identical reaction conditions:

BB-100

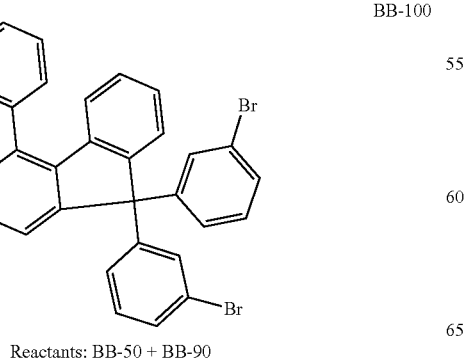

Reactants: BB-50 + BB-90

BB-101

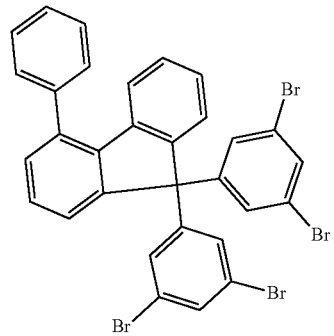

Reactants: BB-50 + BB-91

BB-102

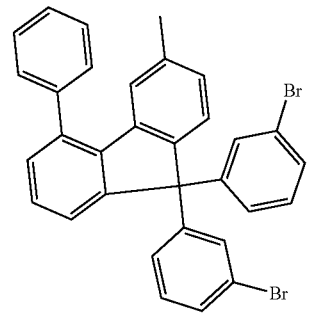

Reactants: BB-51 + BB-90

BB-103

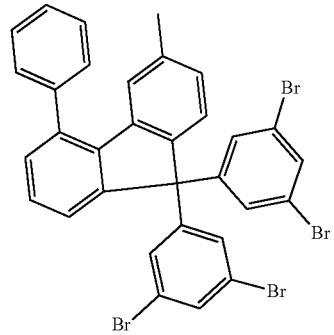

Reactants: BB-51 + BB-91

BB-104

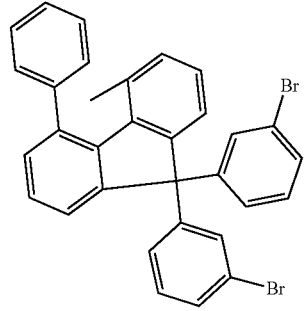

Reactants: BB-52 + BB-90

-continued
BB-105
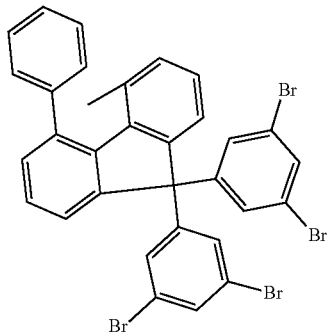
Reactants: BB-52 + BB-91
BB-106
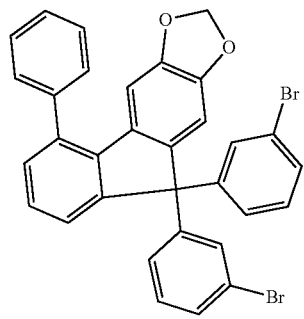
Reactants: BB-53 + BB-90
lp;1p
BB-107
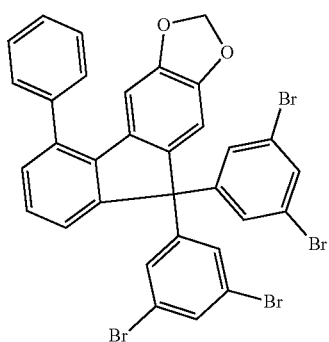
Reactants: BB-53 + BB-91
BB-108
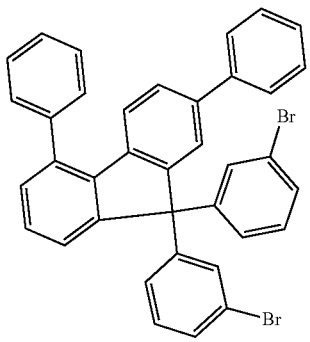
Reactants: BB-54 + BB-90
-continued
BB-109
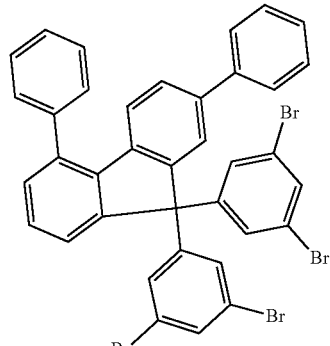
Reactants: BB-54 + BB-91
BB-110
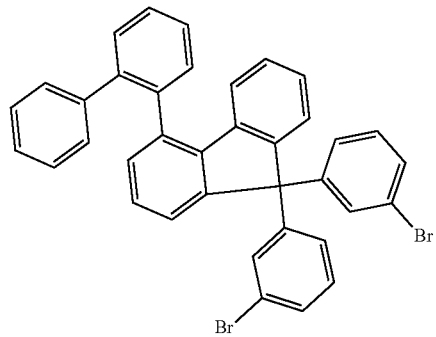
Reactants: BB-55 + BB-90
BB-111
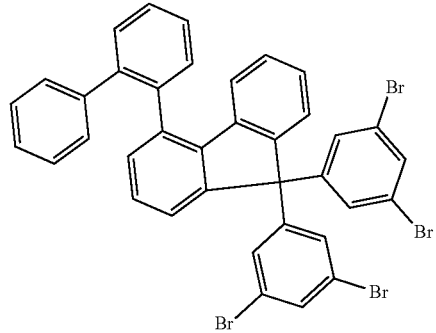
Reactants: BB-55 + BB-91
BB-112
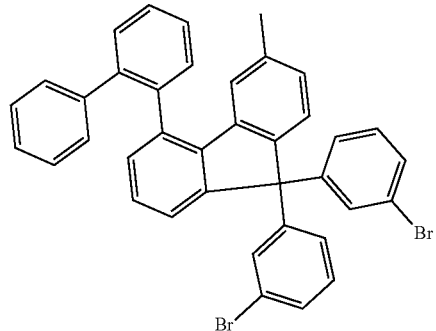
Reactants: BB-56 + BB-90

BB-113
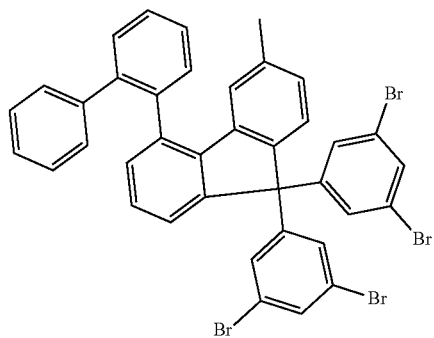
Reactants: BB-56 + BB-91
BB-114
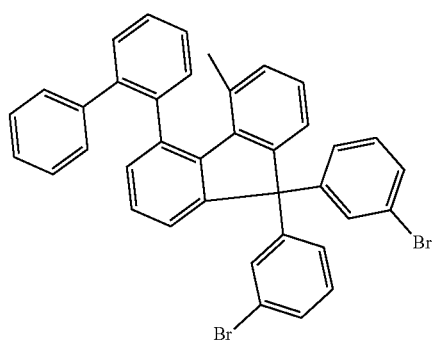
Reactants: BB-57 + BB-90
BB-115
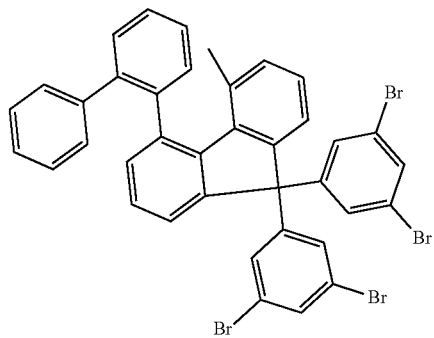
Reactants: BB-57 + BB-91
BB-116
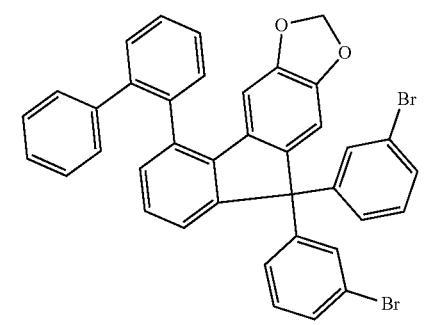
Reactants: BB-58 + BB-90
BB-117
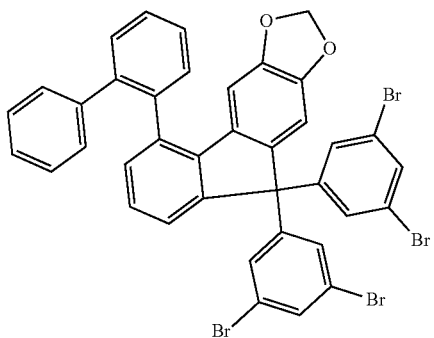
Reactants: BB-58 + BB-91
BB-118
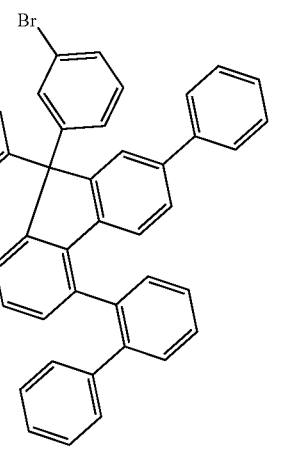
Reactants: BB-59 + BB-90
BB-119
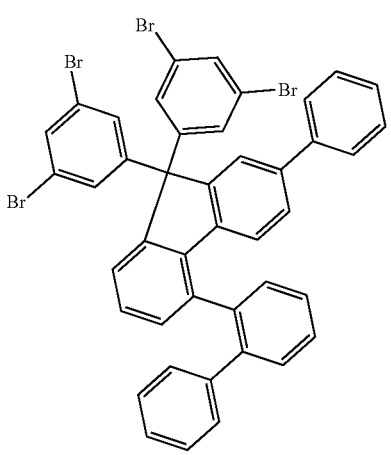
Reactants: BB-59 + BB-91

BB-120
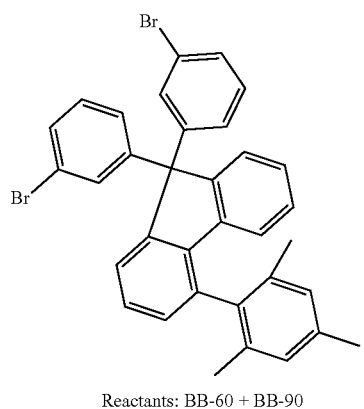
Reactants: BB-60 + BB-90
BB-121
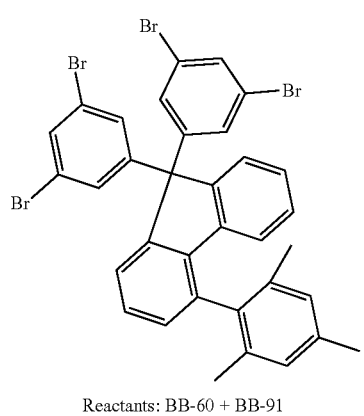
Reactants: BB-60 + BB-91
BB-122
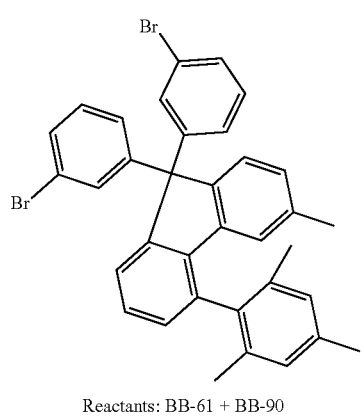
Reactants: BB-61 + BB-90
BB-123
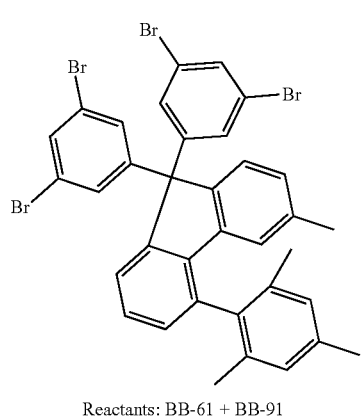
Reactants: BB-61 + BB-91
BB-124
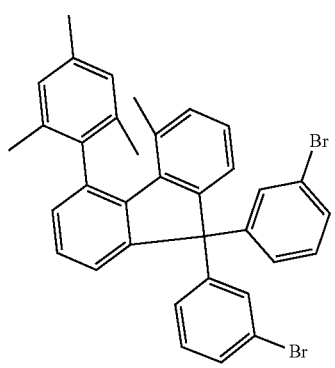
Reactants: BB-62 + BB-90
BB-125
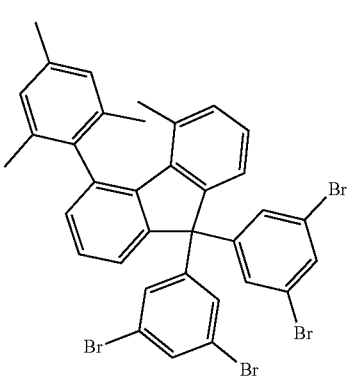
Reactants: BB-62 + BB-91
BB-126
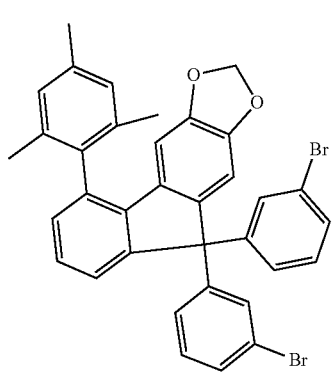
Reactants: BB-63 + BB-90
BB-127
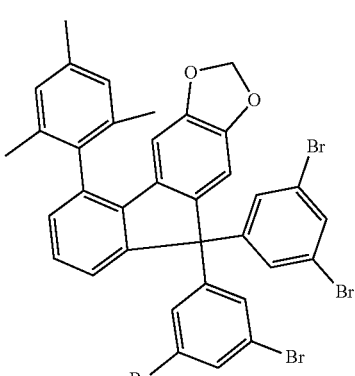
Reactants: BB-63 + BB-91

BB-128
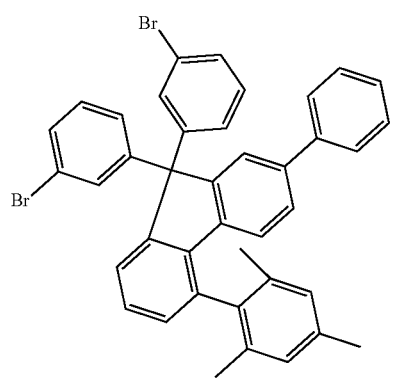
Reactants: BB-64 + BB-90
BB-129
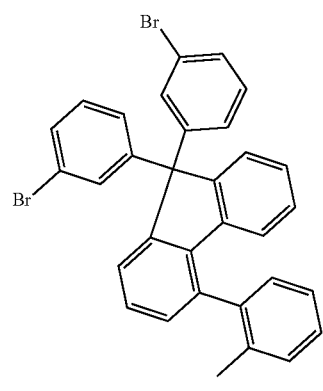
Reactants: BB-64 + BB-91
BB-130
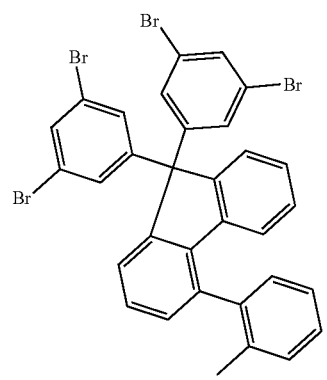
Reactants: BB-65 + BB-90
BB-131
Reactants: BB-65 + BB-91
BB-132
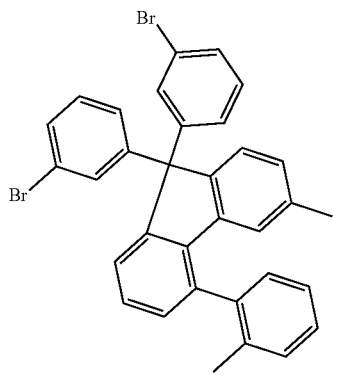
Reactants: BB-66 + BB-90
BB-133
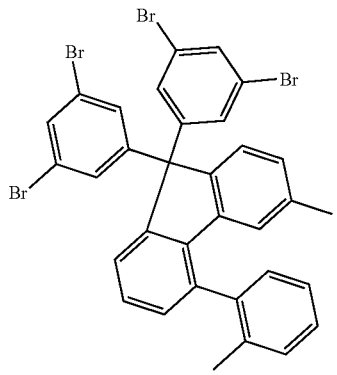
Reactants: BB-66 + BB-91
BB-134
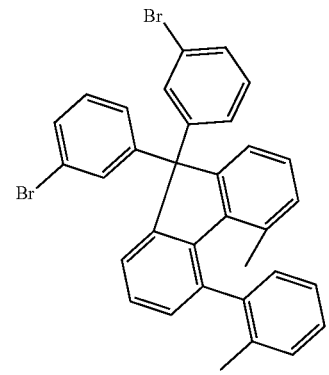
Reactants: BB-67 + BB-90
BB-135
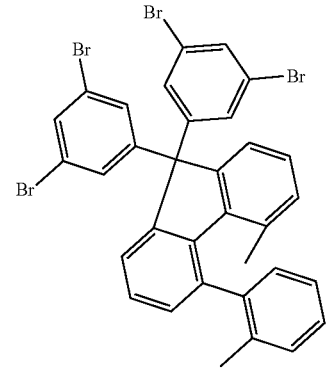
Reactants: BB-67 + BB-91

BB-135
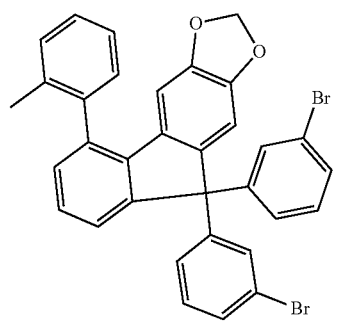
Reactants: BB-68 + BB-90
BB-136
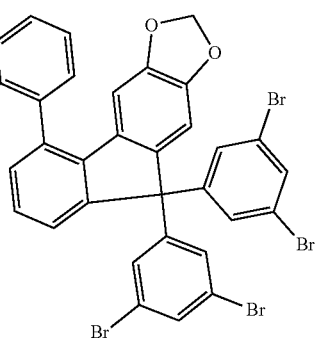
Reactants: BB-68 + BB-91
BB-137
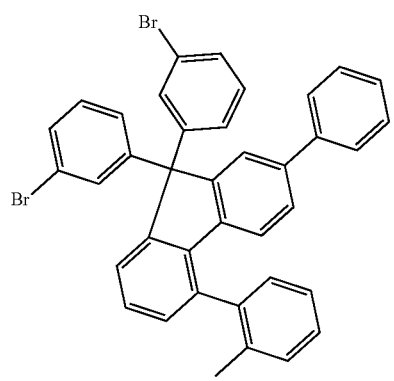
Reactants: BB-69 + BB-90
BB-138
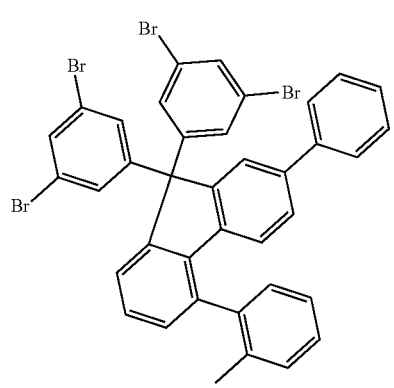
Reactants: BB-69 + BB-91
BB-139
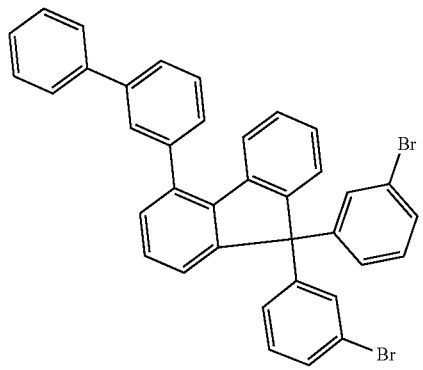
Reactants: BB-70 + BB-90
BB-140
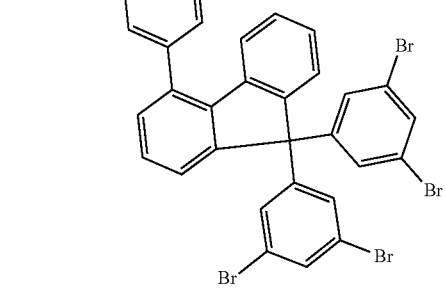
Reactants: BB-70 + BB-91
BB-141
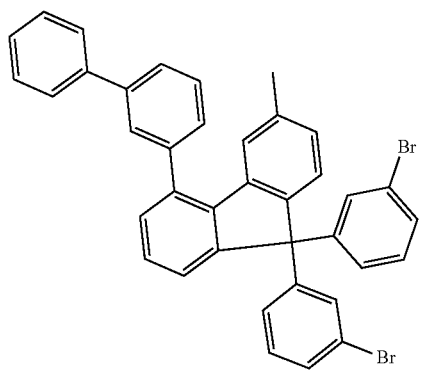
Reactants: BB-71 + BB-90

BB-142
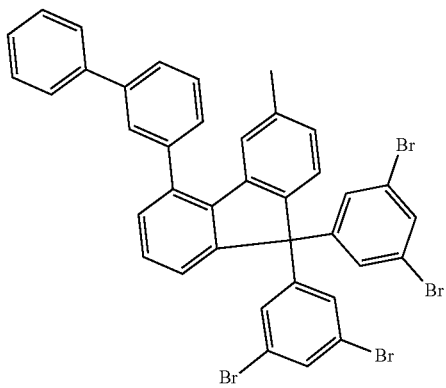
Reactants: BB-71 + BB-91
BB-143
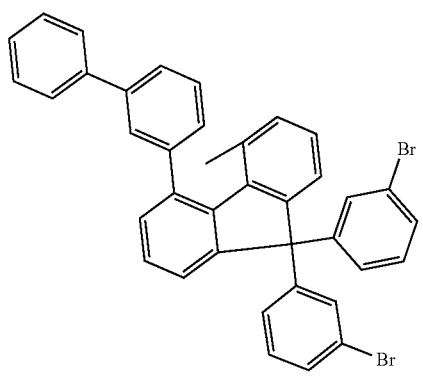
Reactants: BB-72 + BB-90
BB-144
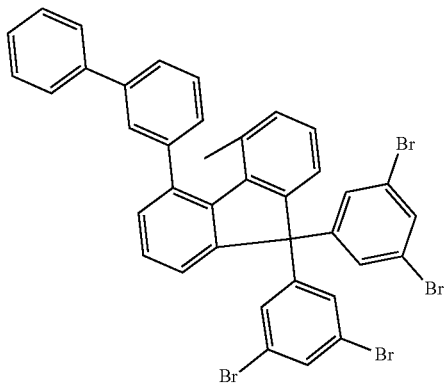
Reactants: BB-72 + BB-90
BB-145
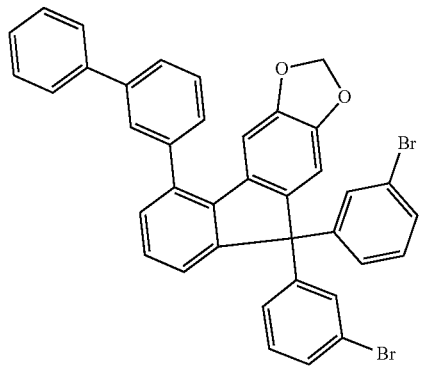
Reactants: BB-73 + BB-90
BB-146
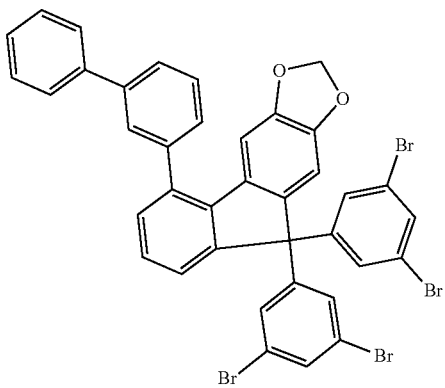
Reactants: BB-73 + BB-91
BB-147
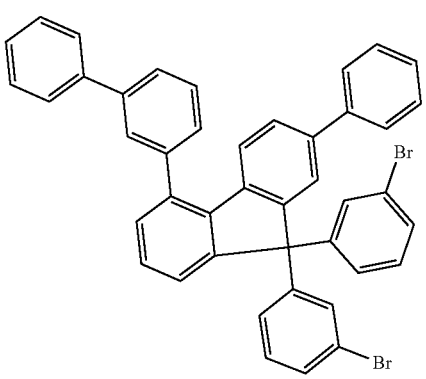
Reactants: BB-74 + BB-90

BB-148
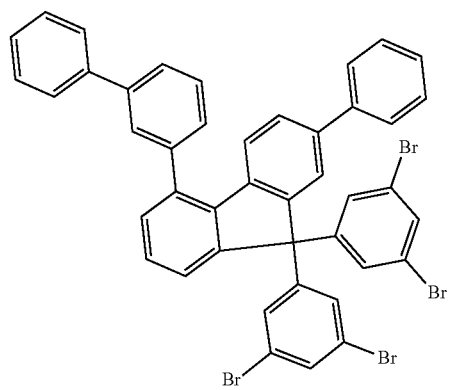
Reactants: BB-74 + BB-90
BB-149
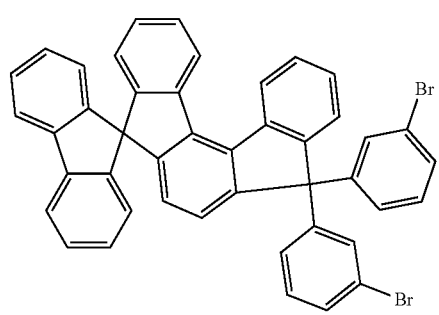
Reactants: BB-75 + BB-90
BB-150
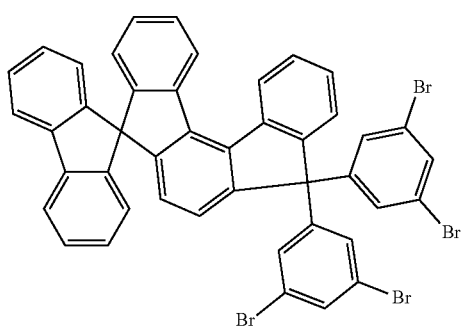
Reactants: BB-75 + BB-91
BB-151
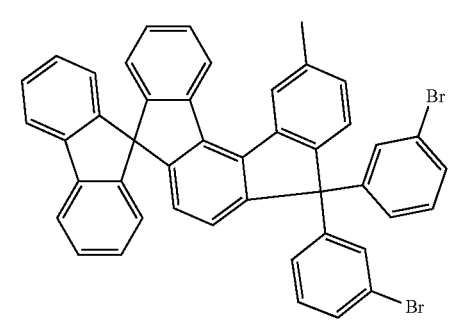
Reactants: BB-76 + BB-90
BB-152
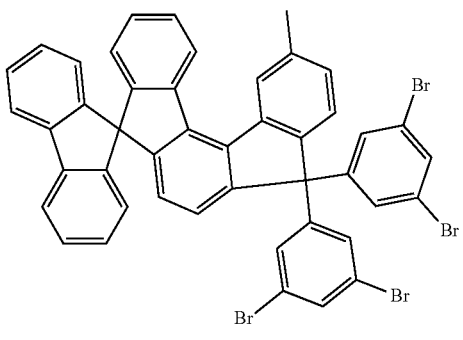
Reactants: BB-76 + BB-91
BB-153
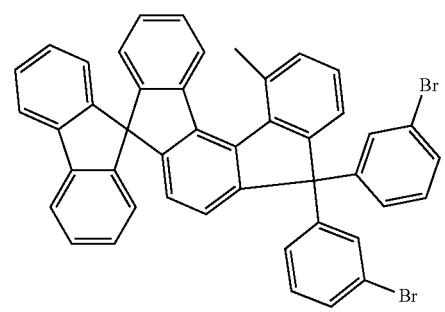
Reactants: BB-77 + BB-90
BB-154
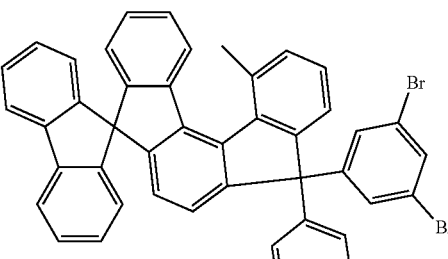
Reactants: BB-77 + BB-91
BB-155
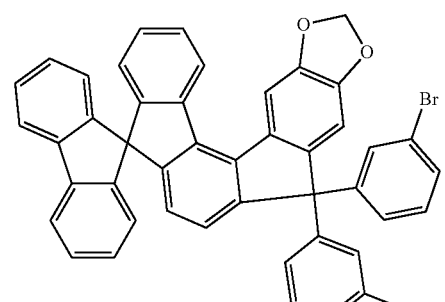
Reactants: BB-78 + BB-90

BB-156
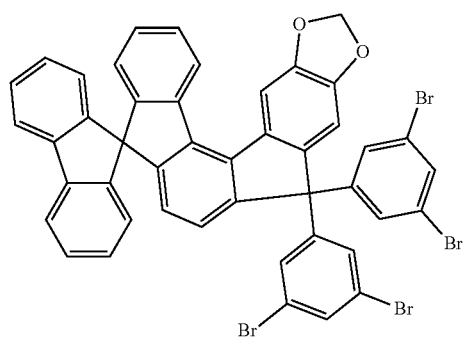
Reactants: BB-78 + BB-91
BB-157
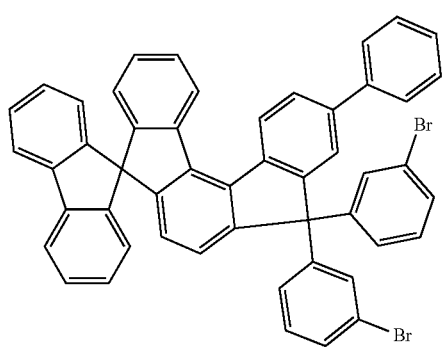
Reactants: BB-79 + BB-90
BB-158
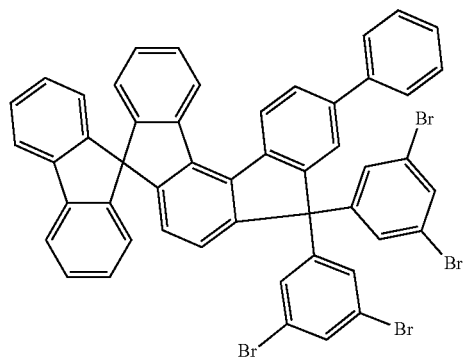
Reactants: BB-79 + BB-91
BB-159
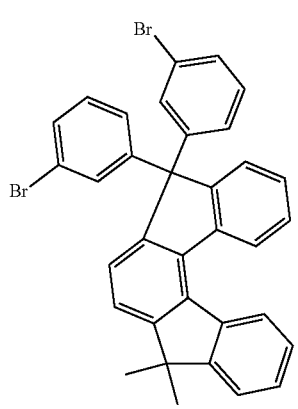
Reactants: BB-80 + BB-90
BB-160
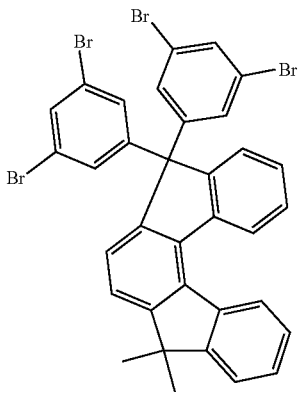
Reactants: BB-80 + BB-91
BB-161
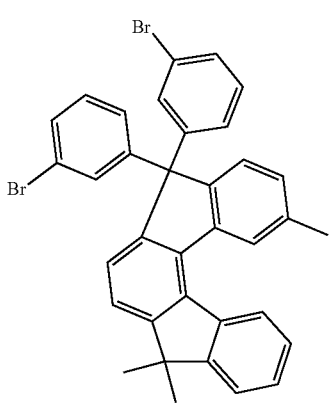
Reactants: BB-81 + BB-90
BB-162
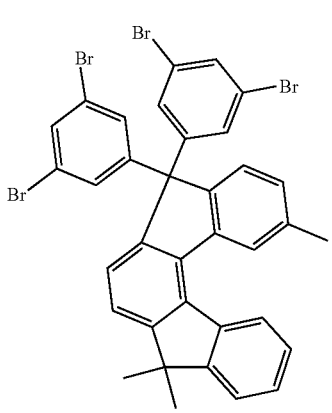
Reactants: BB-81 + BB-91

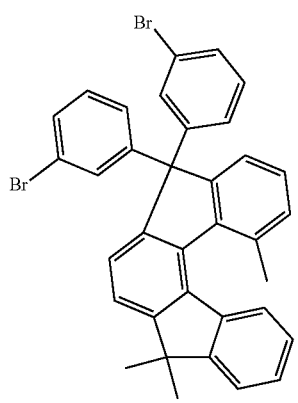
BB-163
Reactants: BB-82 + BB-90
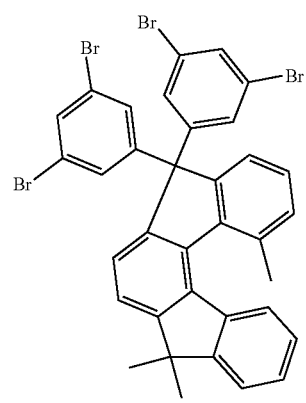
BB-164
Reactants: BB-82 + BB-91
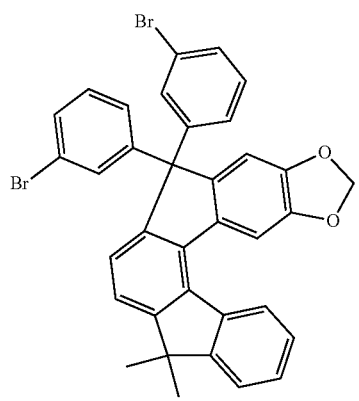
BB-165
Reactants: BB-83 + BB-90
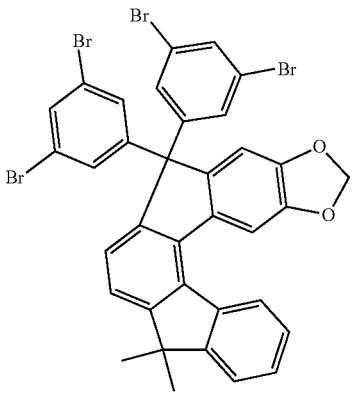
BB-166
Reactants: BB-83 + BB-91
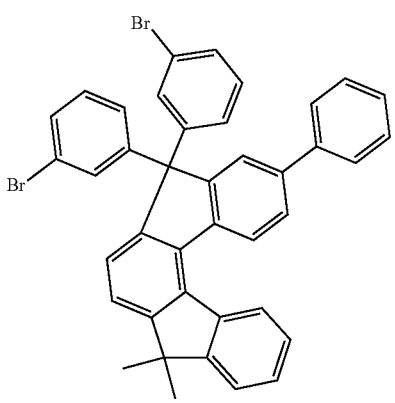
BB-167
Reactants: BB-84 + BB-90
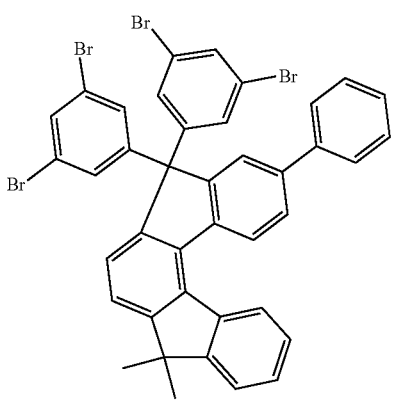
BB-168
Reactants: BB-84 + BB-91

BB-169
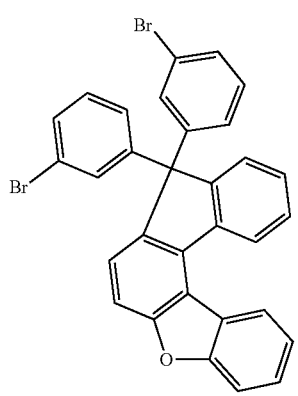
Reactants: BB-85 + BB-90
BB-170
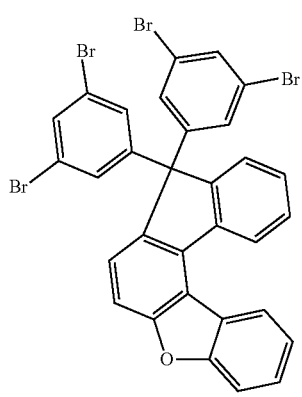
Reactants: BB-85 + BB-91
BB-171
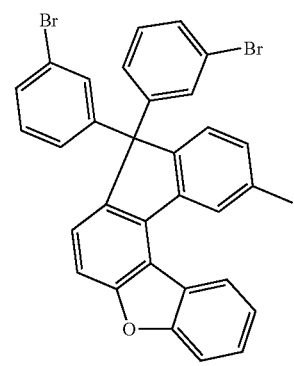
Reactants: BB-86 + BB-90
BB-172
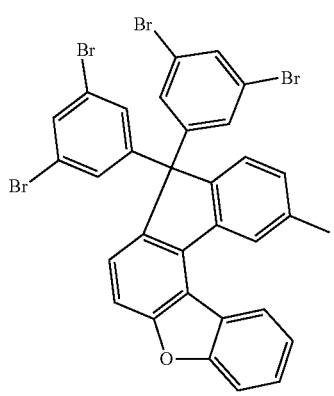
Reactants: BB-86 + BB-91
BB-173
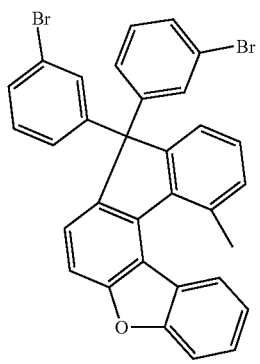
Reactants: BB-87 + BB-90
BB-174
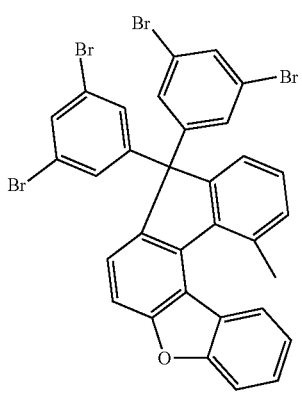
Reactants: BB-87 + BB-91
BB-175
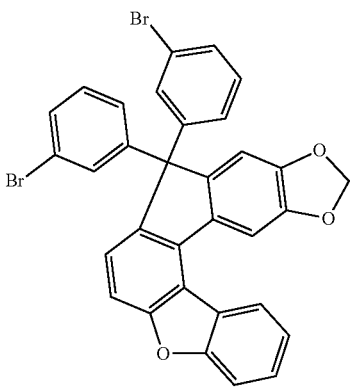
Reactants: BB-88 + BB-90

Example 3: Synthesis of the Materials of the Invention
The following are among the synthesis units that can be utilized for synthesis of the materials of the invention:
BB-176
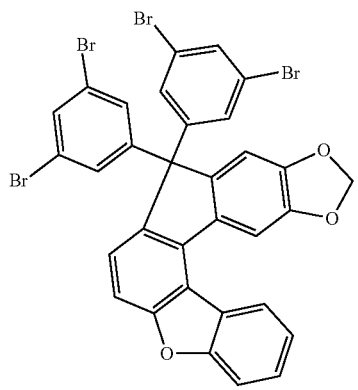
Reactants: BB-88 + BB-91
BB-177
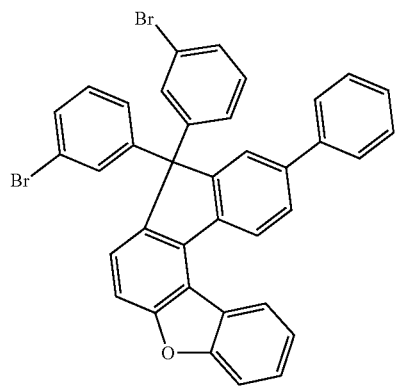
Reactants: BB-89 + BB-90
BB-178
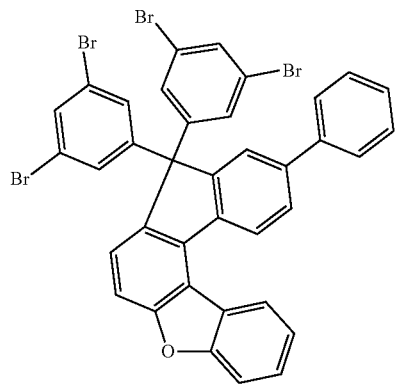
Reactants: BB-89 + BB-91
BB-179
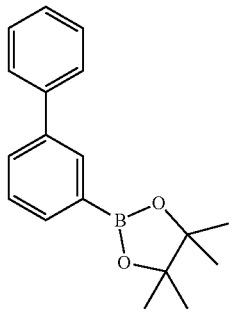
CAS-912844-88-3
BB-180
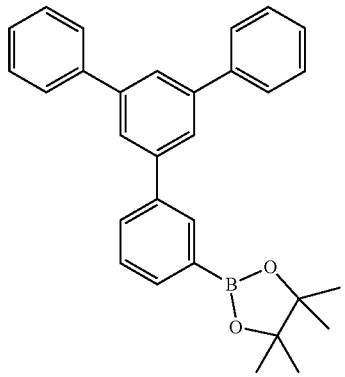
CAS-1257248-43-3
BB-181
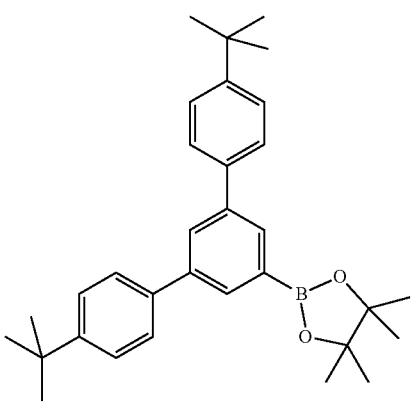
CAS-848437-85-4

-continued

BB-182

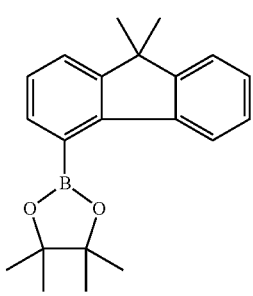

CAS-1365692-79-0

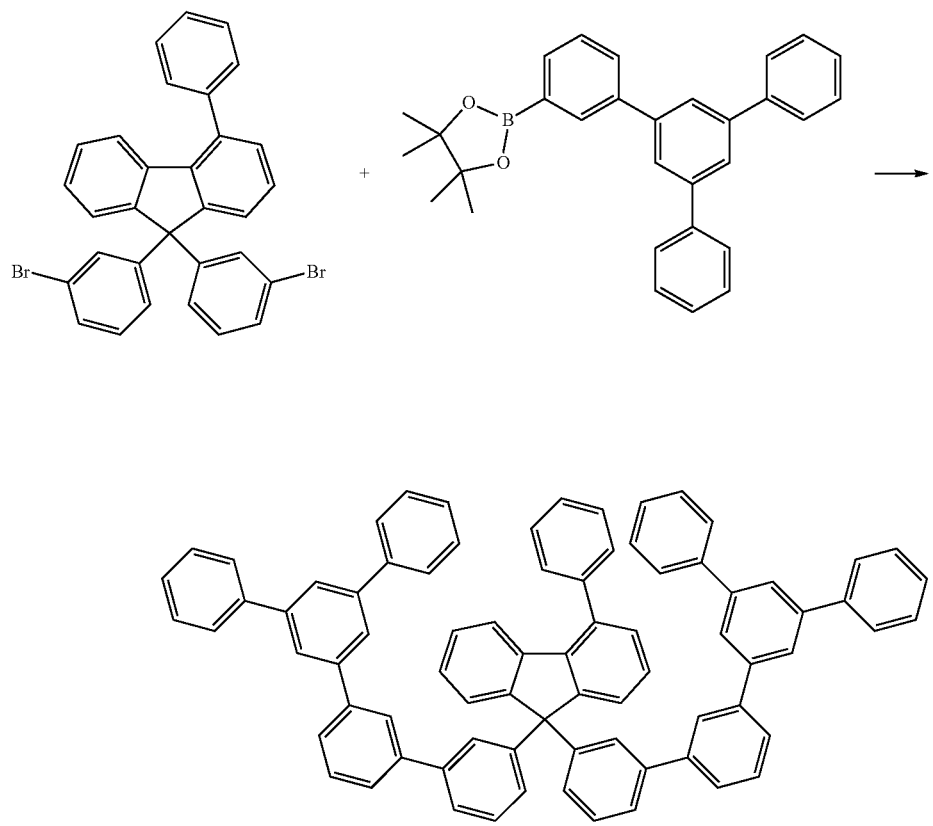

The following are weighed into a 2 l multineck flask with reflux condenser, argon connection and precision glass stirrer: 15 g (27.16 mmol) of BB-100, 24.07 g (55.68 mmol, 2.05 eq.) BB-180, 3.14 g (2.72 mmol, 0.1 eq.) of tetrakis(triphenylphosphine)palladium(0) (CAS: 14221-01-3), followed by inertization. 400 ml of tetrahydrofuran and 85 ml of a 20% tetraethylammonium hydroxide solution in water are added, followed by inertization again. The reaction mixture is heated under reflux for 24 h, cooled down and admixed with water. The phases are separated, and the organic phase is extracted with water and dried over sodium sulfate. The solvent is removed under reduced pressure, and the residue is taken up in toluene and filtered through silica gel. The solvent is removed under reduced pressure and the residue is dried in a drying cabinet. The solid is repeatedly recrystallized from ethyl acetate. 3.1 g of a colourless solid M-0002 (11% yield, 3.09 mmol) are obtained.

Further materials of the invention can be obtained in similar yields by identical reaction conditions:
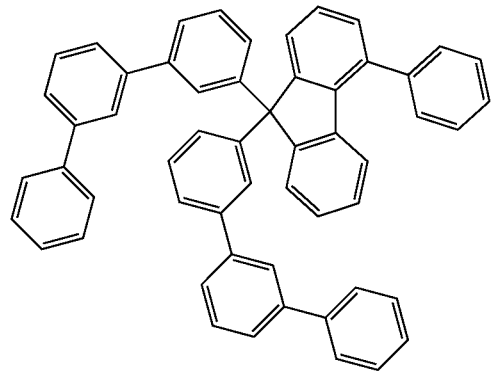
BB-100+BB-179
M-0001
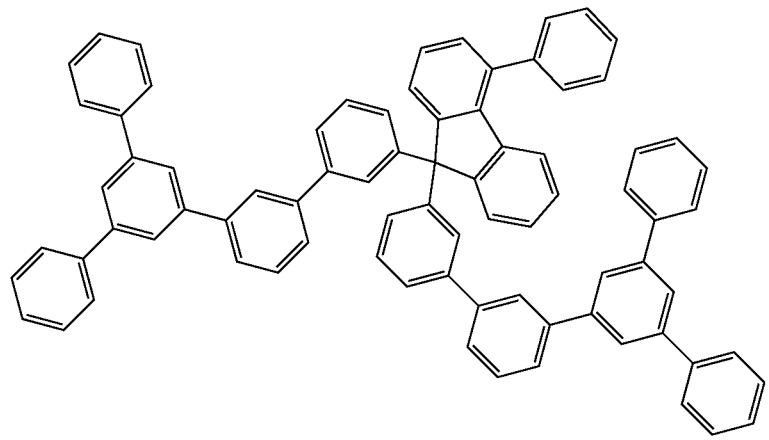
BB-100+BB-180
M-0002
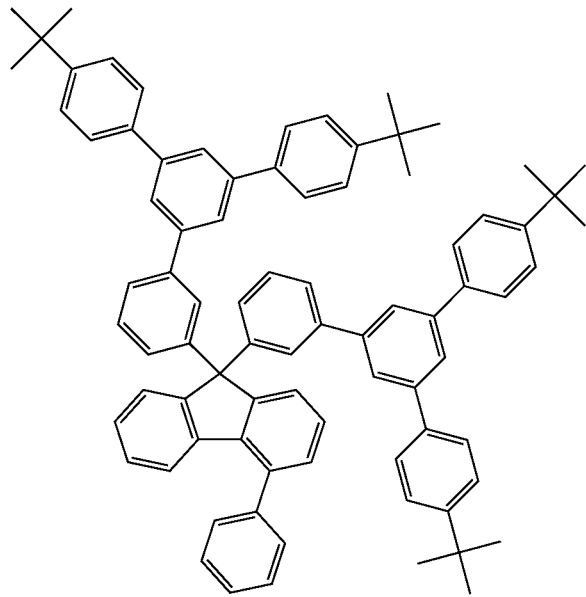
BB-100+BB-181
M-0003

-continued
M-0004
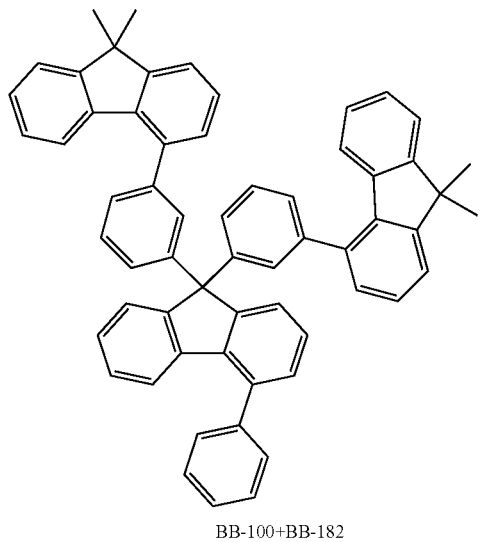
BB-100+BB-182
M-0005
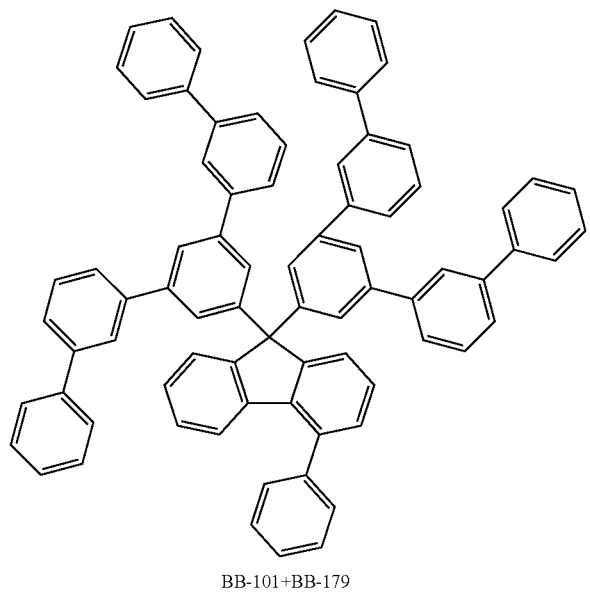
BB-101+BB-179
M-0006
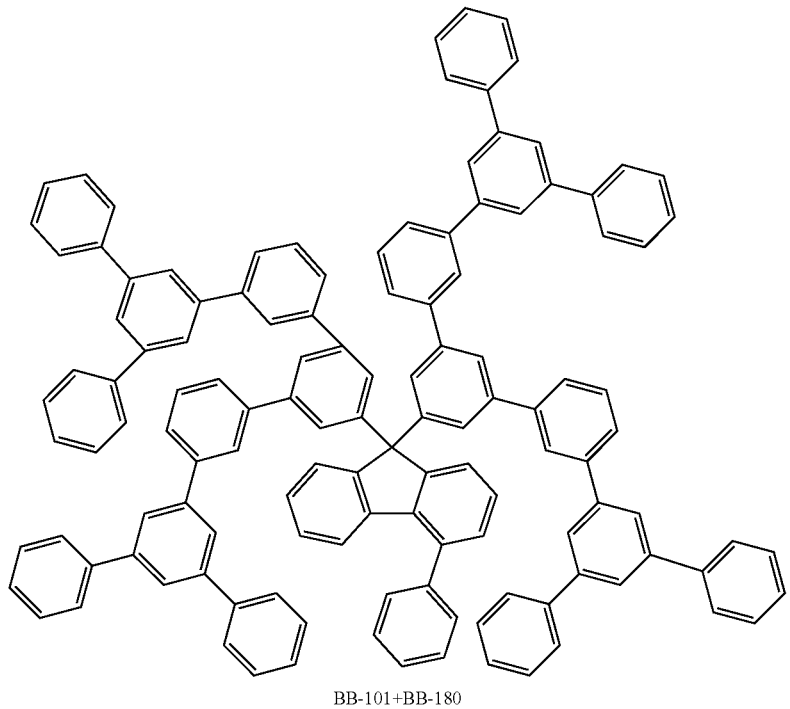
BB-101+BB-180

-continued
M-0007
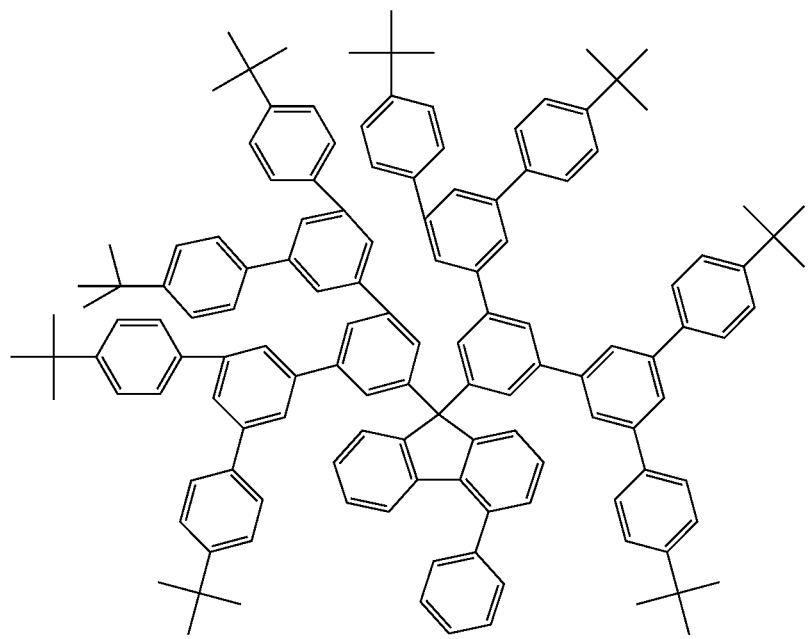
BB-101+BB-18
M-0008
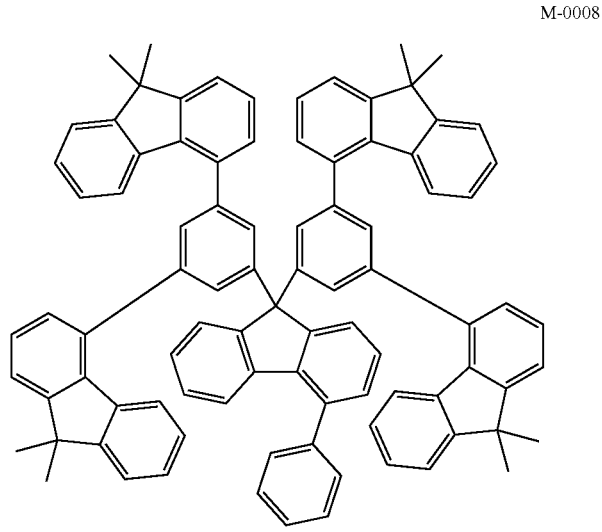
BB-101+BB-182
M-0009
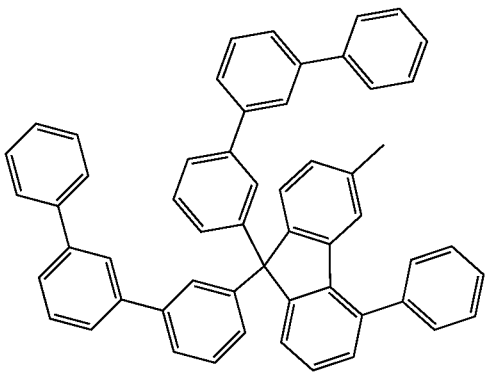
BB-102+BB-179

M-0010
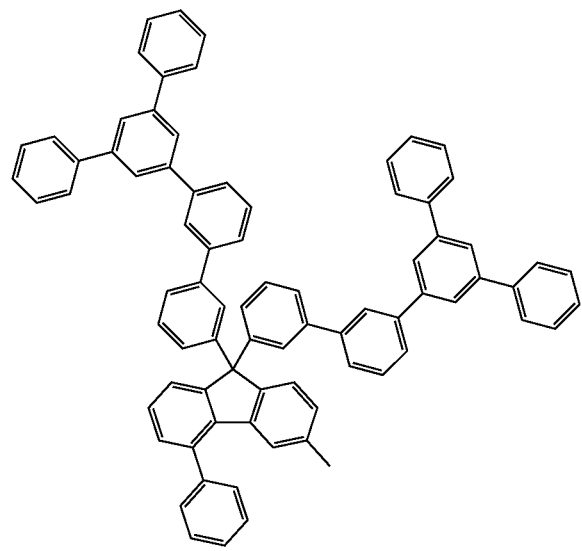
BB-102+BB-180
M-0011
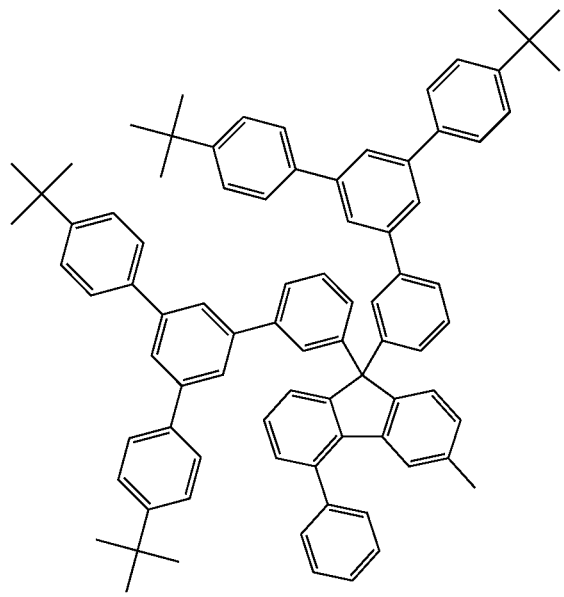
BB-102+BB-181
M-0012
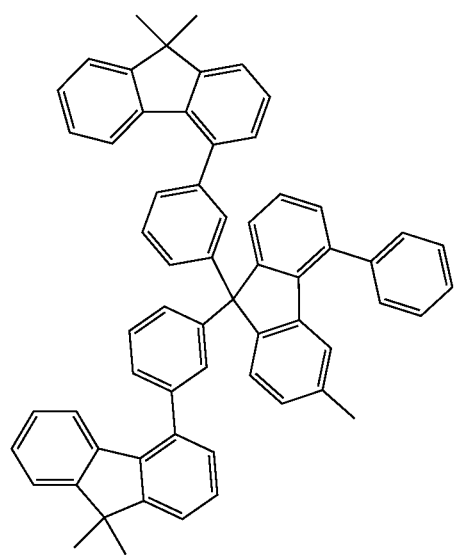
BB-102+BB-182
M-0013
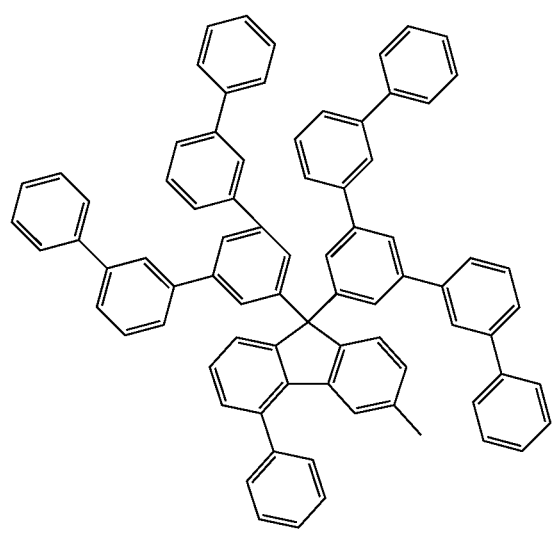
BB-103+BB-179

M-0014
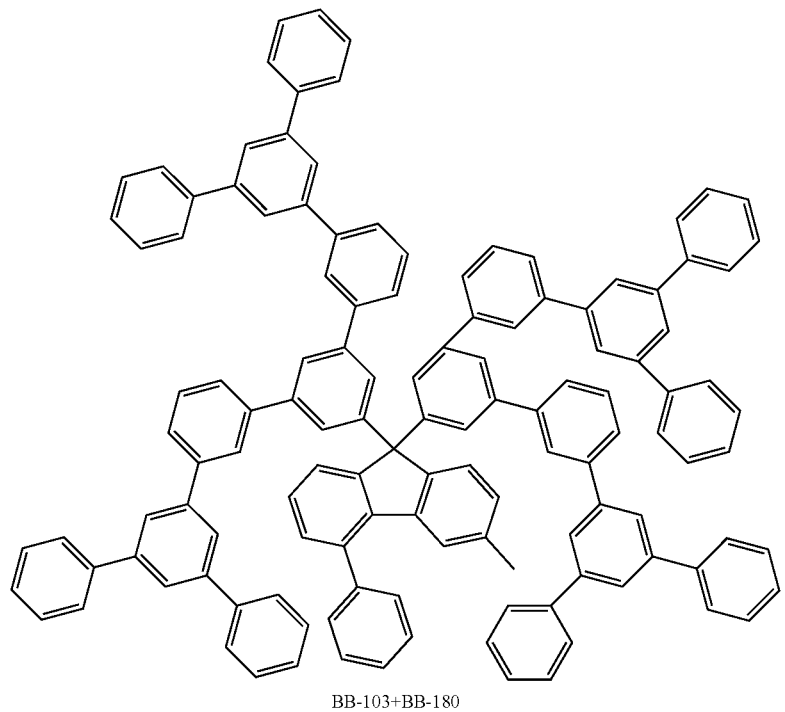
BB-103+BB-180
M-0015
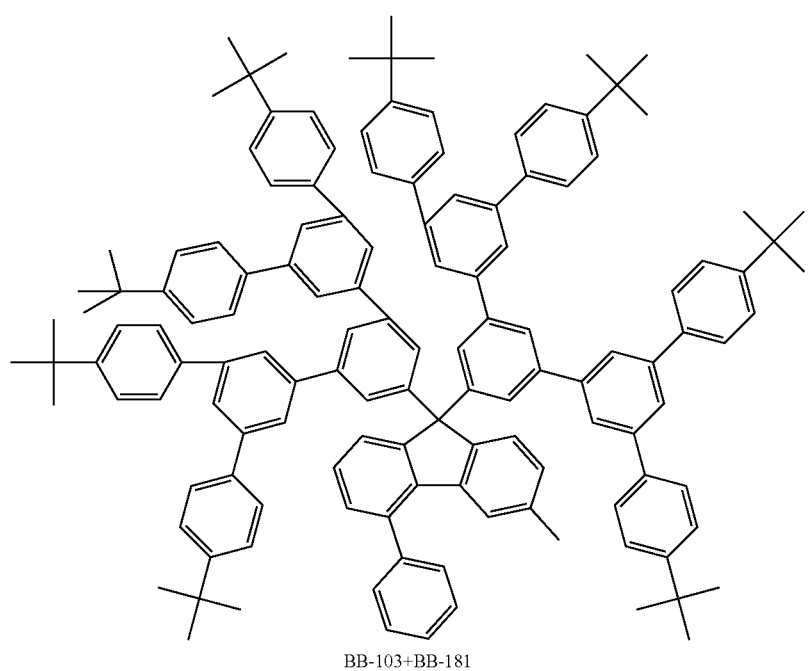
BB-103+BB-181

-continued
M-0016
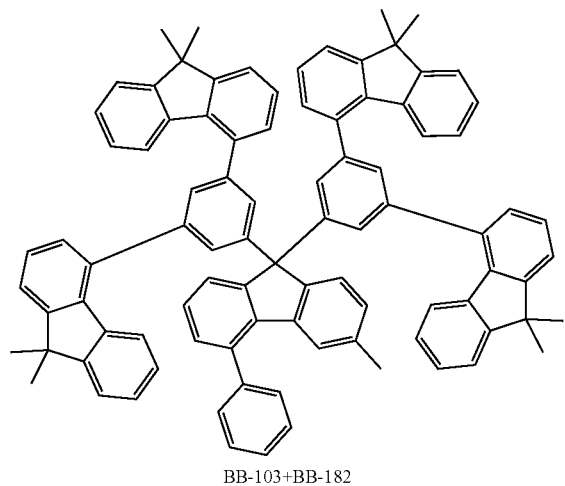
BB-103+BB-182
M-0017
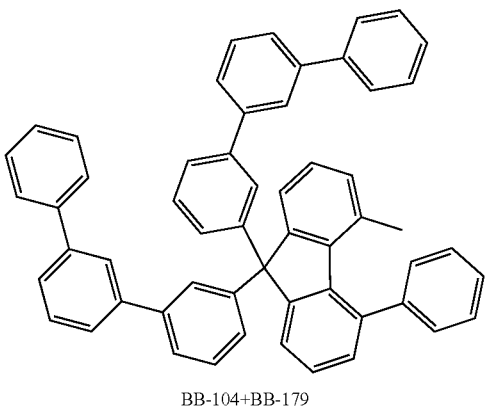
BB-104+BB-179
M-0018
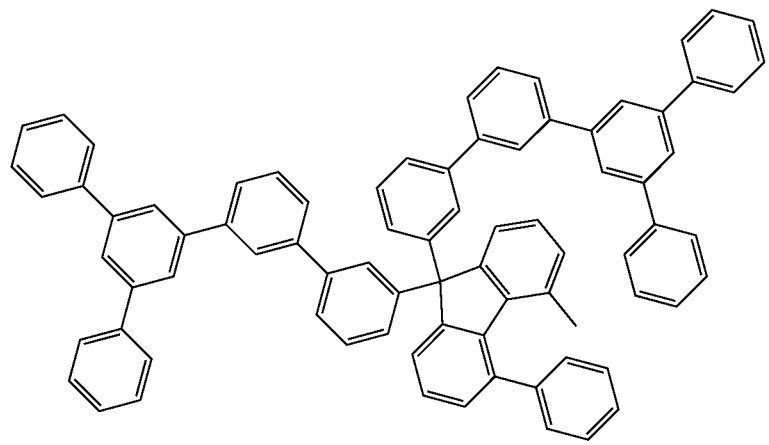
BB-104+BB-180
M-0019
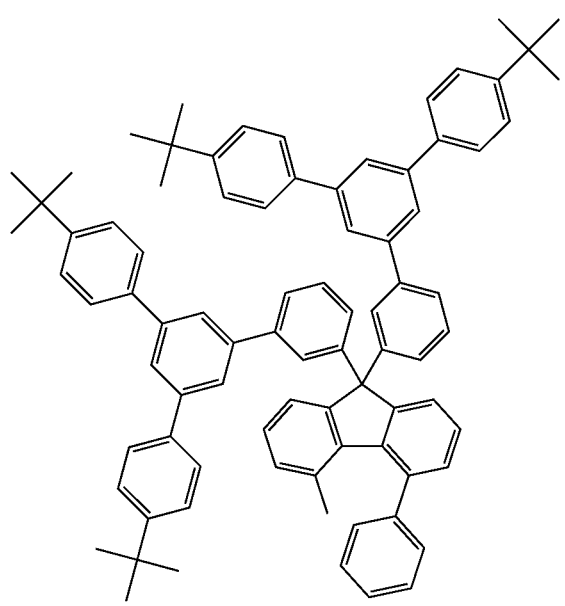
BB-104+BB-181
M-0020
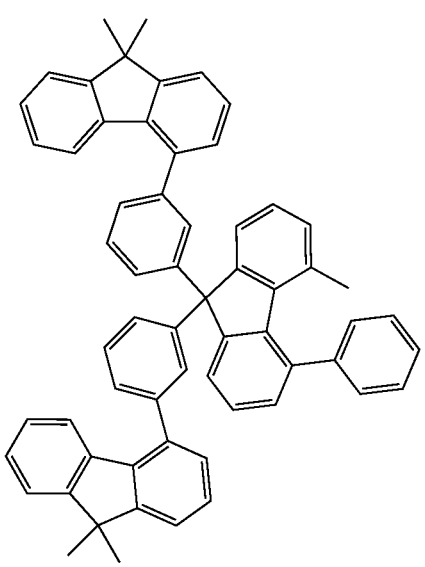
BB-104+BB-182

M-0021
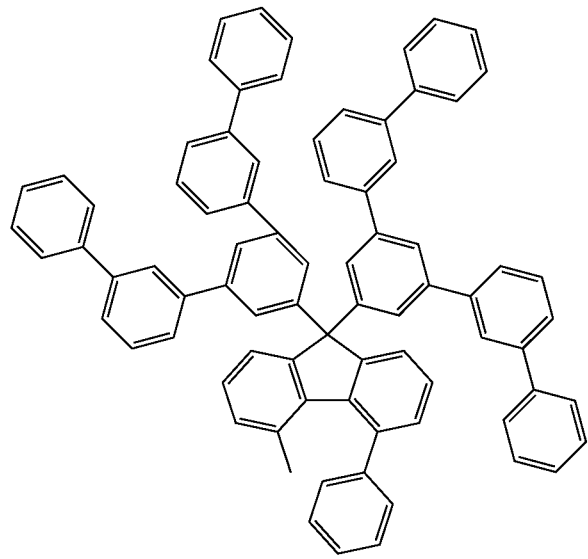
BB-105+BB-179
M-0022
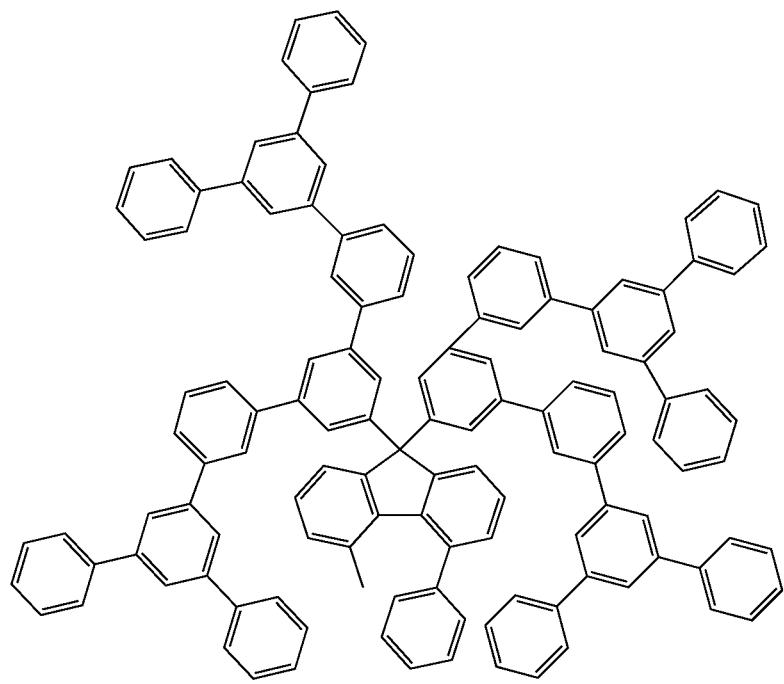
BB-105+BB-180

-continued
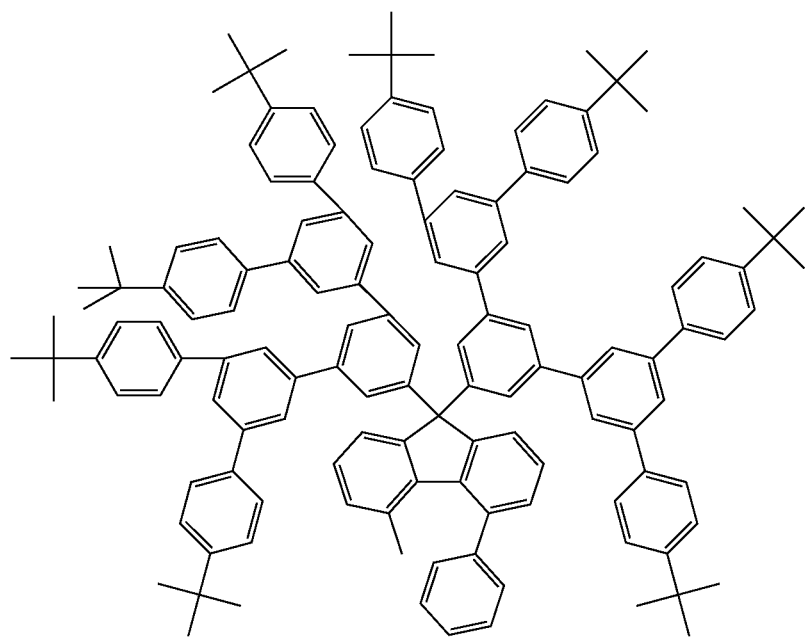
BB-105+BB-181
M-0023
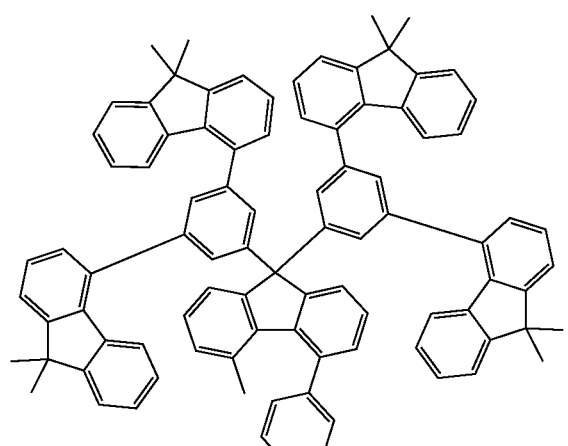
BB-105+BB-182
M-0024
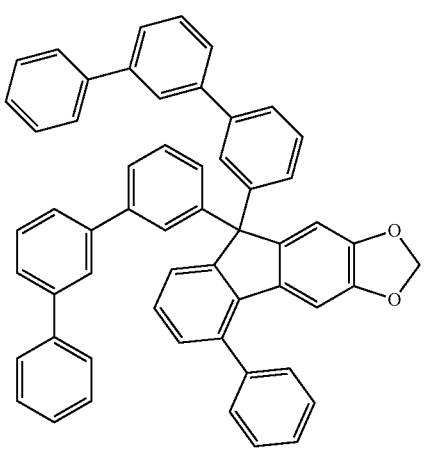
BB-106+BB-179
M-0025

-continued
M-0026
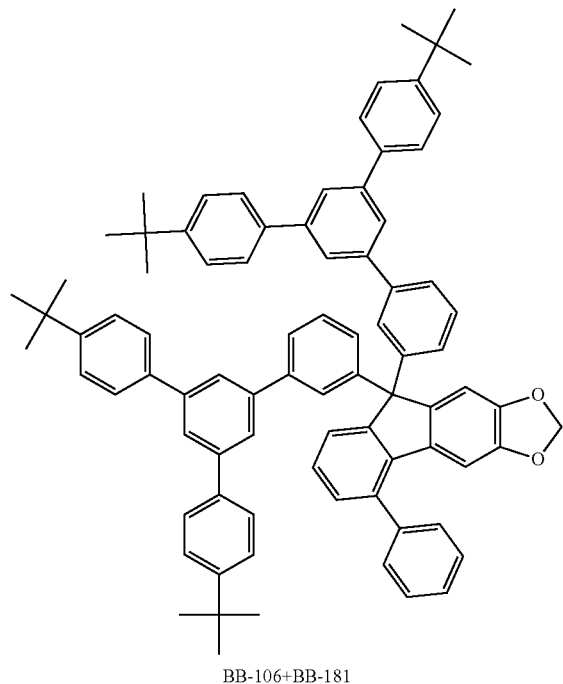
BB-106+BB-181
M-0027
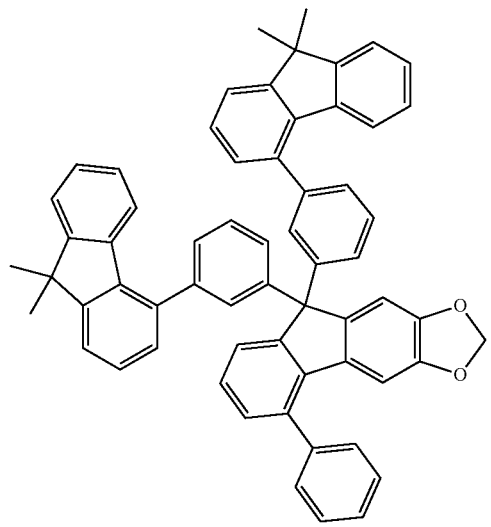
BB-106+BB-182
M-0028
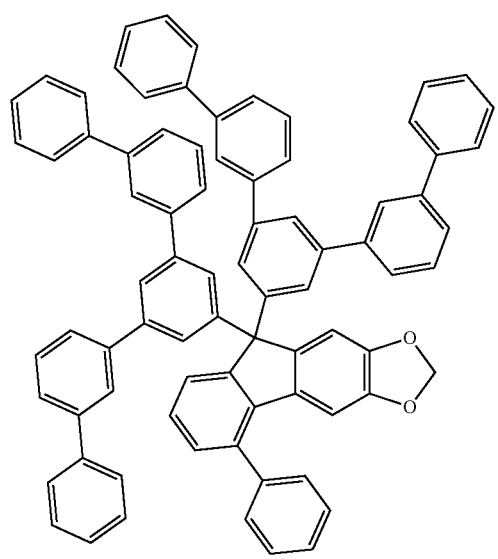
BB-107+BB-179
M-0029
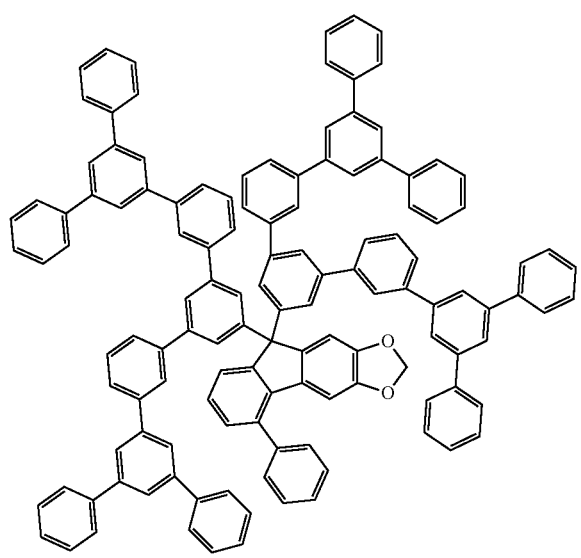
BB-107+BB-180

-continued
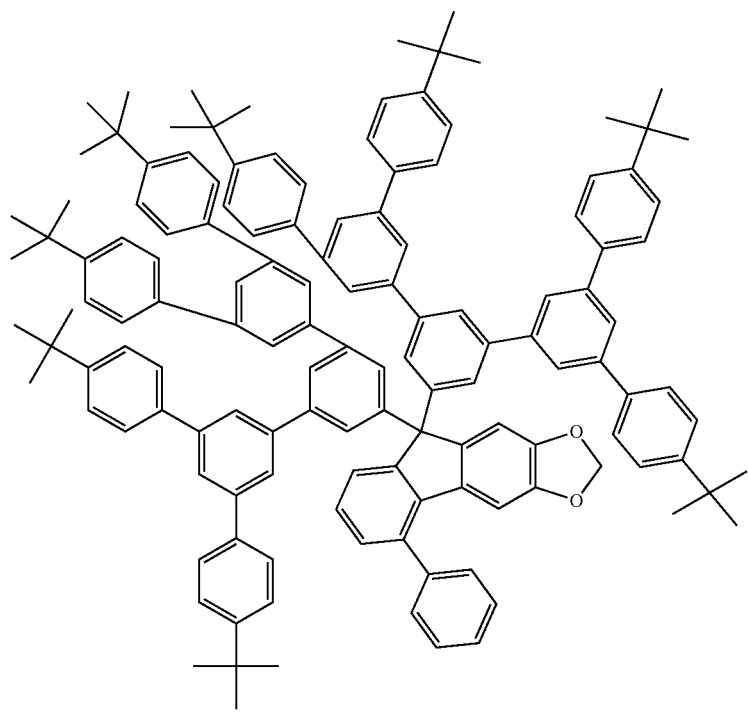
BB-107+BB-181
M-0030
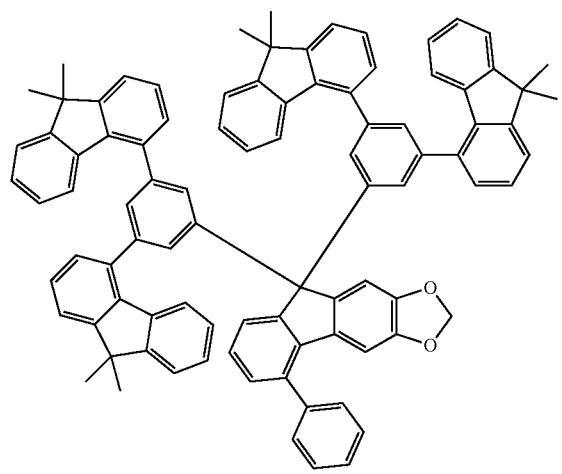
BB-107+BB-182
M-0031
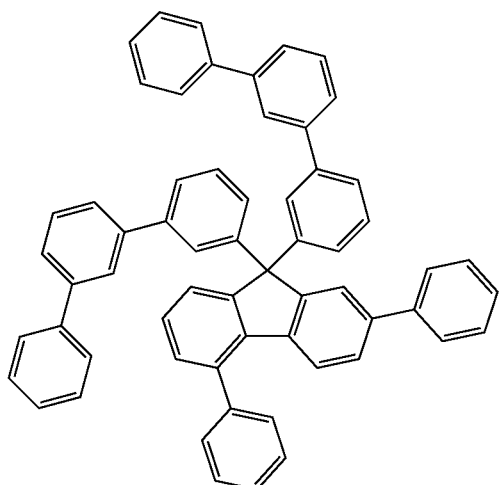
BB-108+BB-179
M-0032

-continued
M-0033
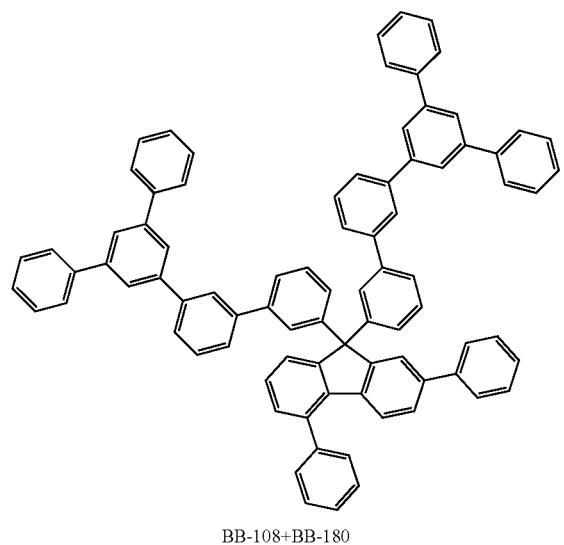
BB-108+BB-180
M-0034
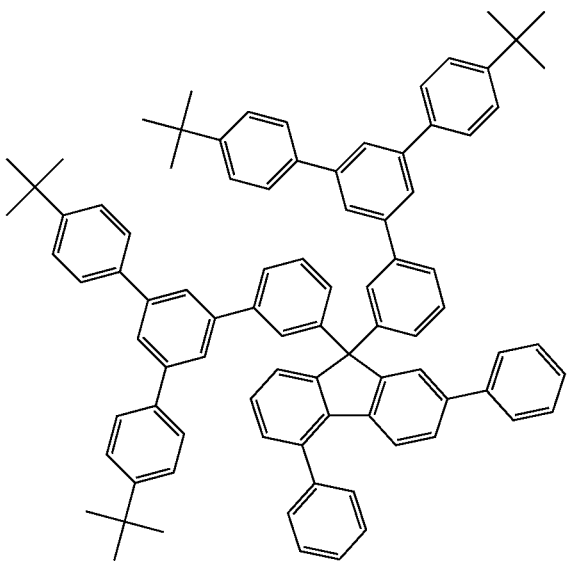
BB-108+BB-181
M-0035
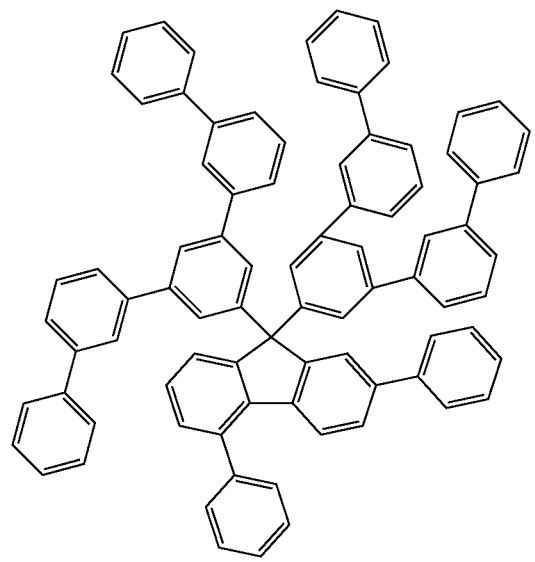
BB-109+BB-179

-continued
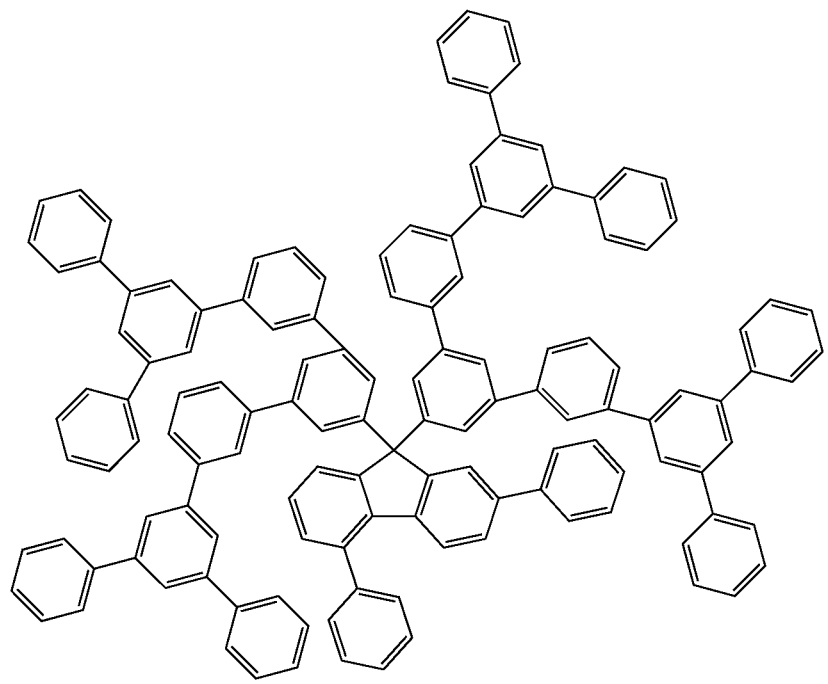
BB-109+BB-180
M-0036
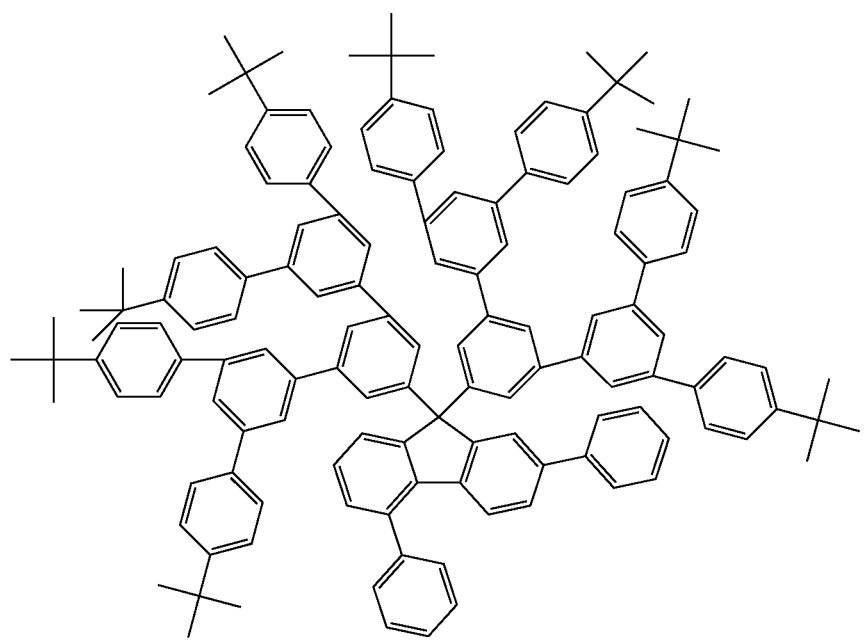
BB-109+BB-181
M-0037

-continued
M-0038
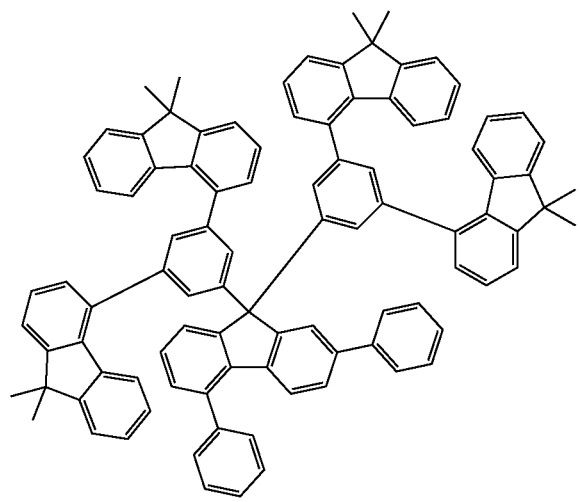
BB-109+BB-182
M-0039
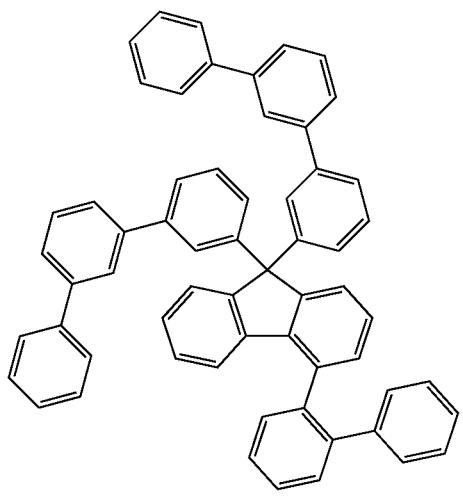
BB-110+BB-179
M-0040
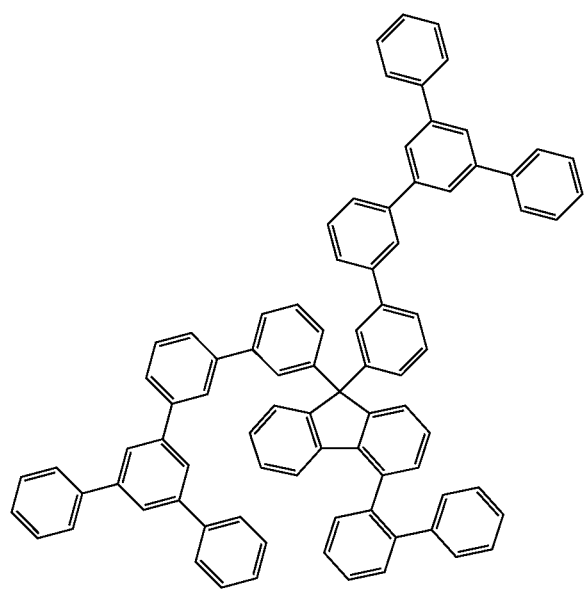
BB-110+BB-180
M-0041
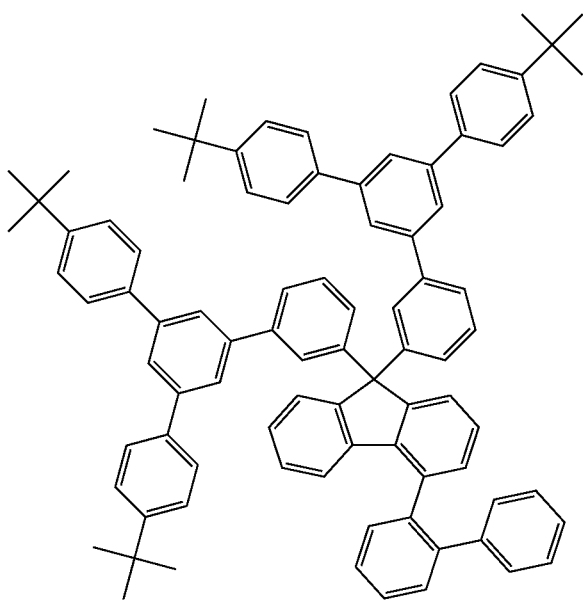
BB-110+BB-181

-continued
M-0042
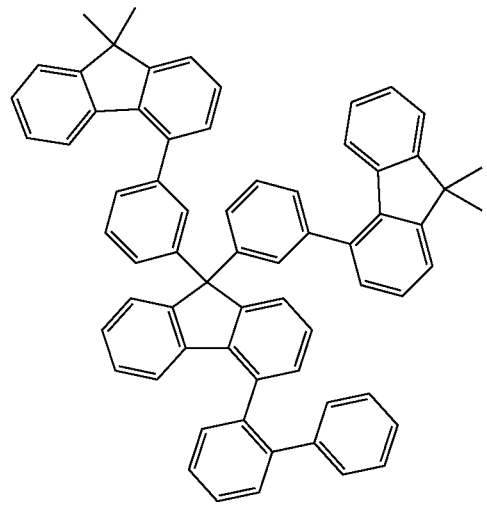
BB-110+BB-182
M-0043
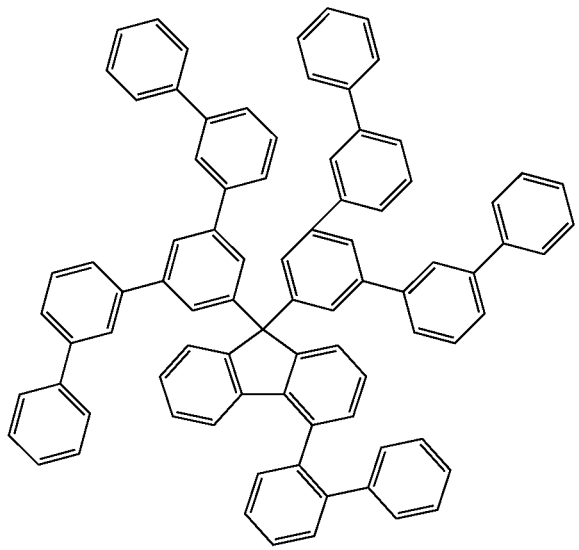
BB-110+BB-179
M-0044
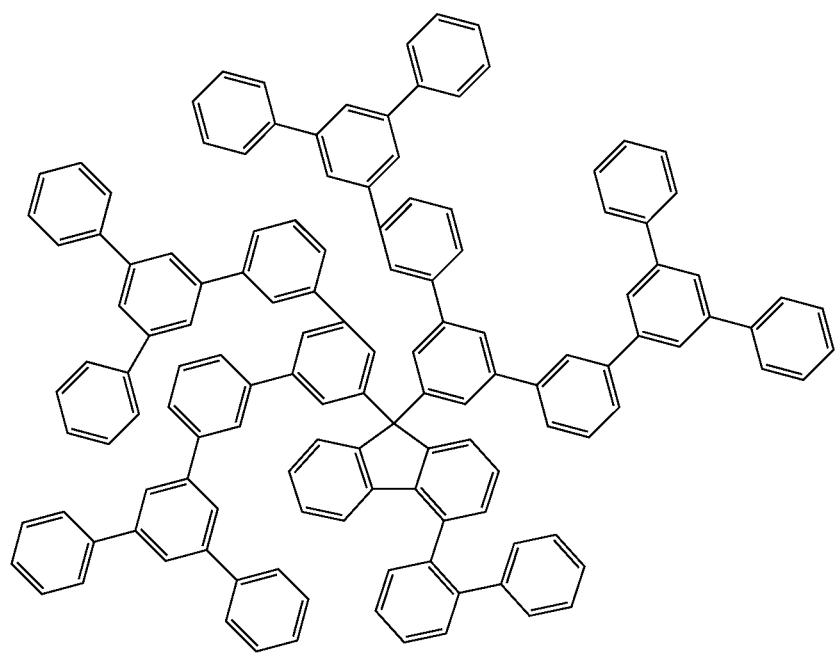
BB-111+BB-180

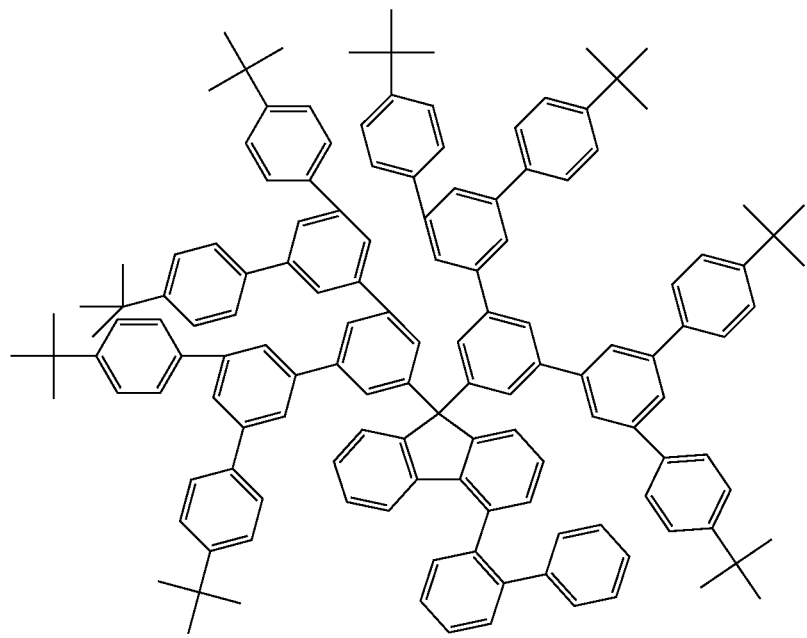
BB-111+BB-181
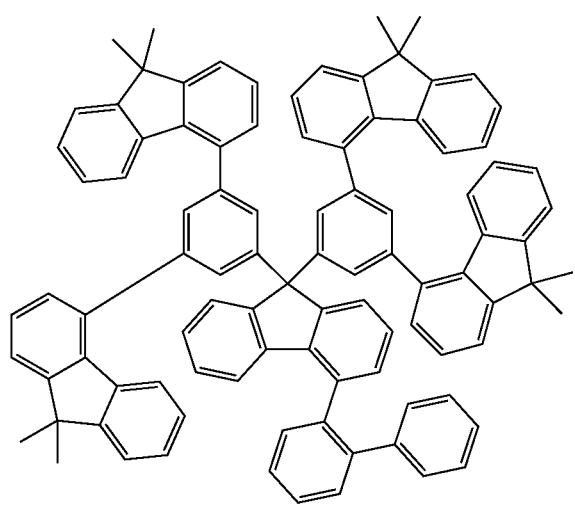
BB-111+BB-182
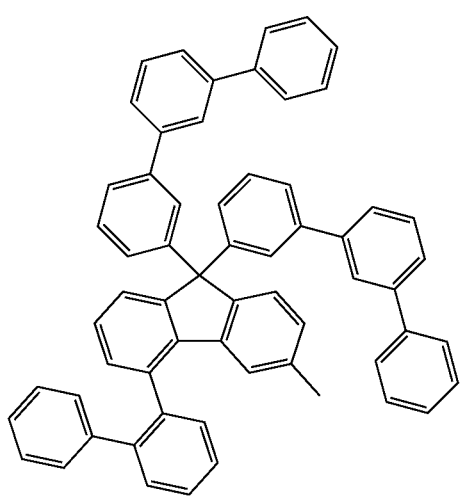
BB-112+BB-179
M-0045
M-0046
M-0047

M-0048
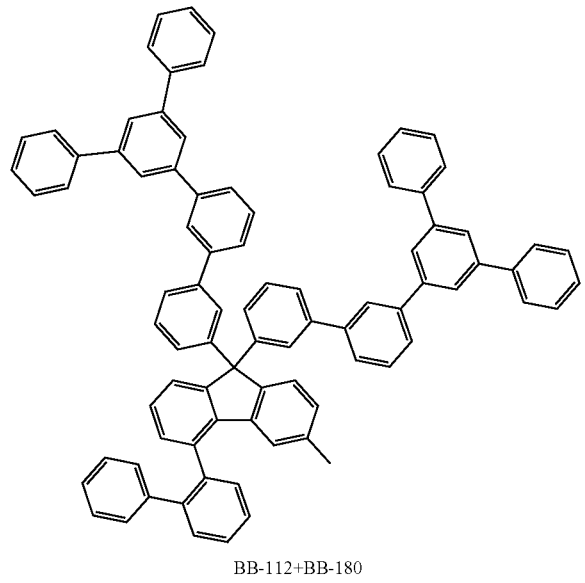
BB-112+BB-180
M-0049
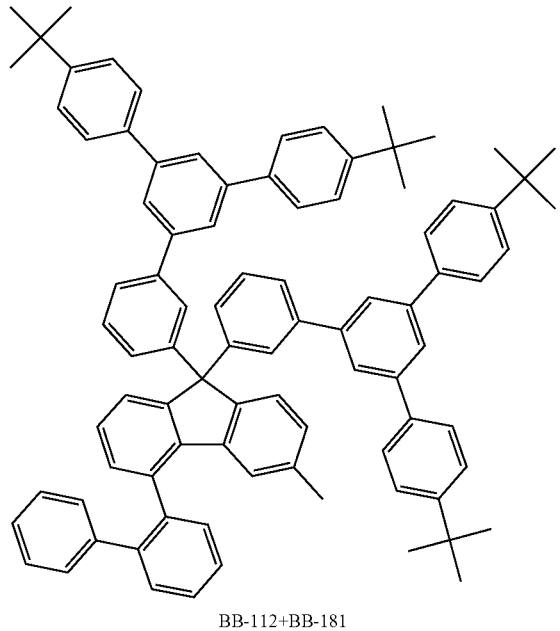
BB-112+BB-181
M-00050
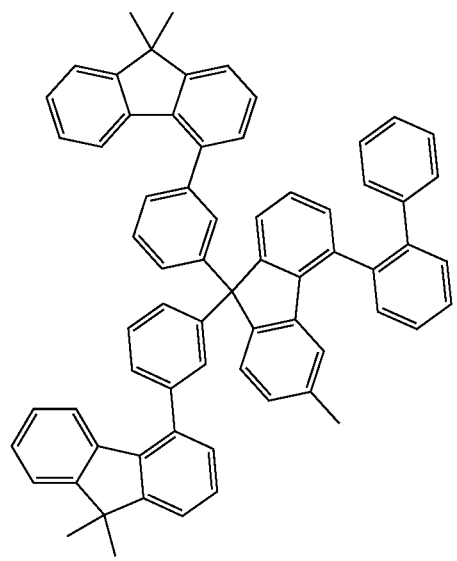
BB-112+BB-182
M-0051
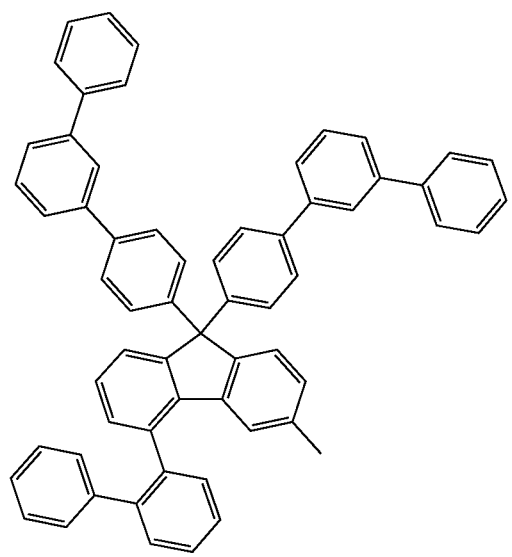
BB-2038+BB-179

M-0052
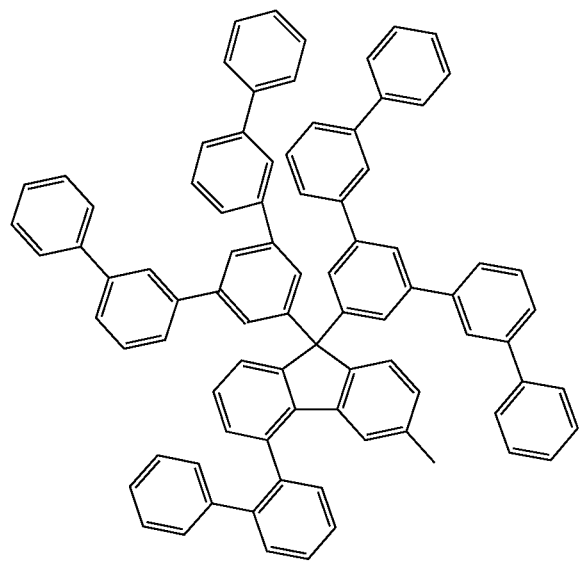
BB-113+BB-179
M-0053
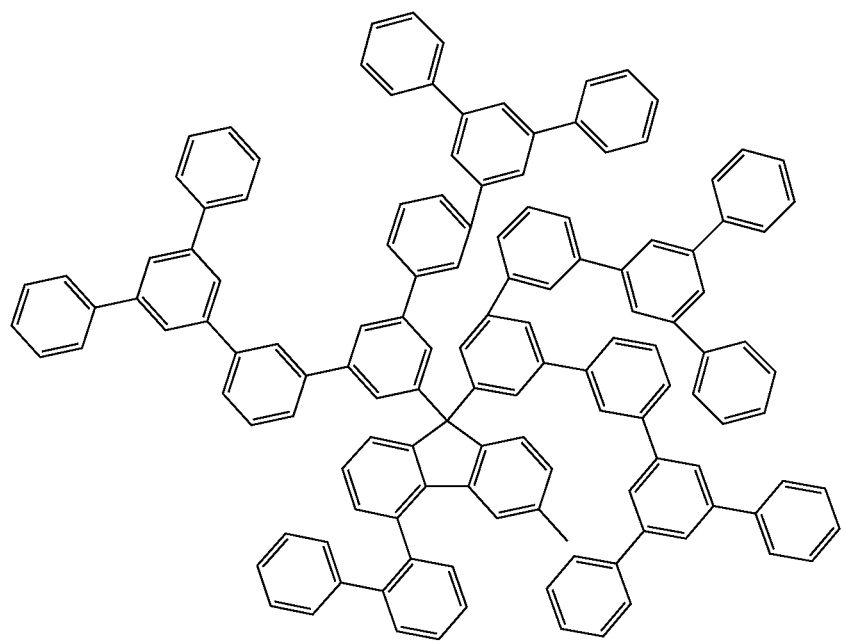
BB-113+BB-180

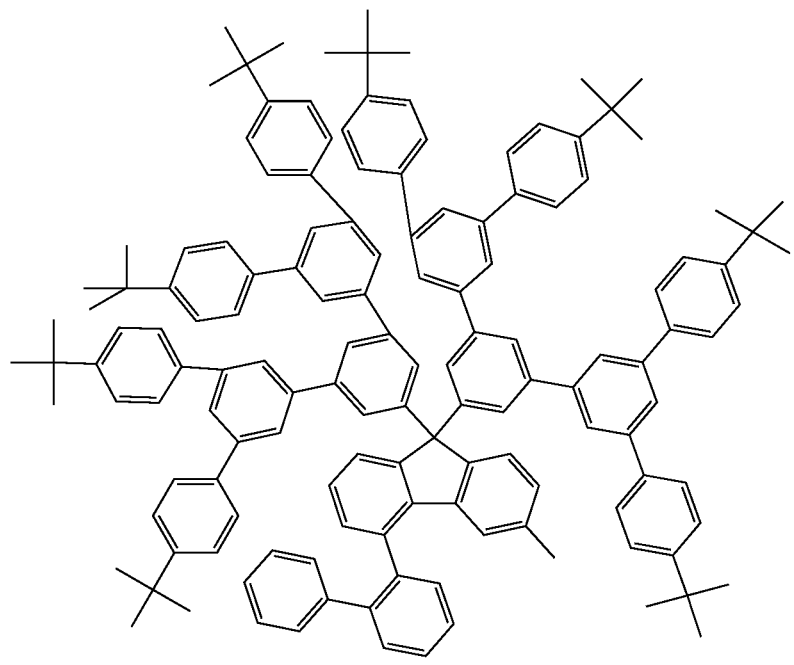
BB-113+BB-181
M-0054
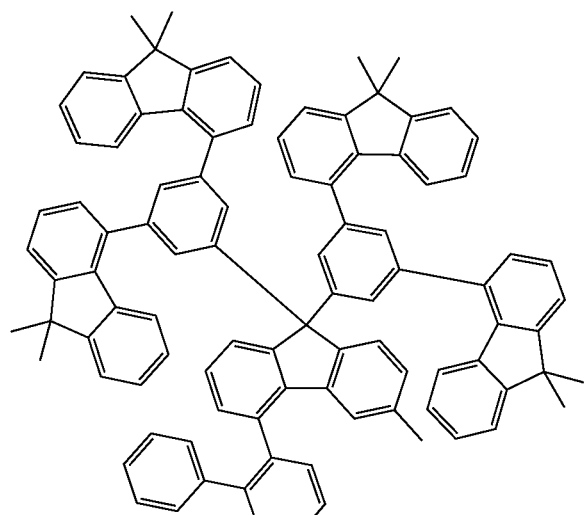
BB-113+BB-182
M-0055
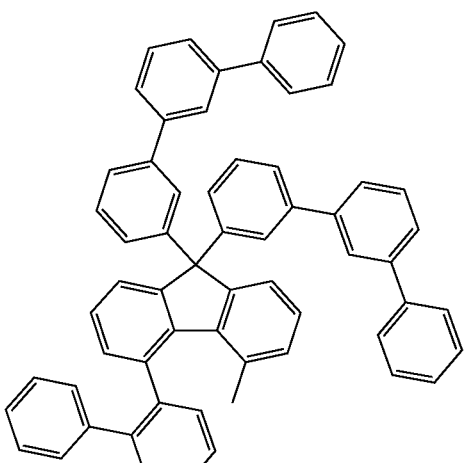
BB-114+BB-179
M-0056

-continued
M-0057
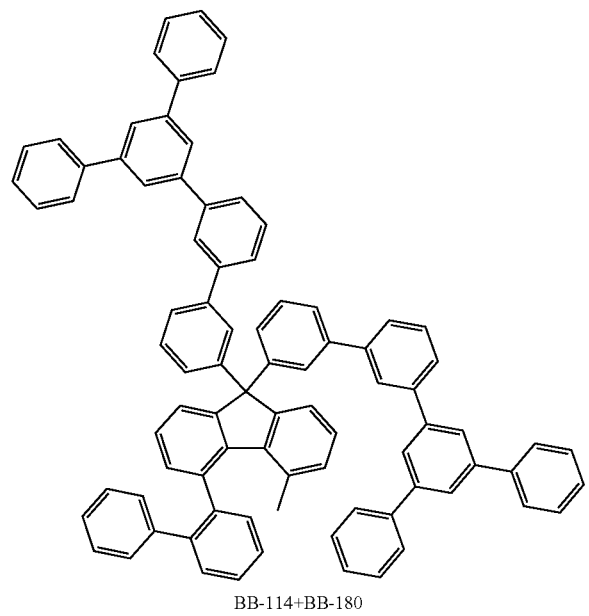
BB-114+BB-180
M-0058
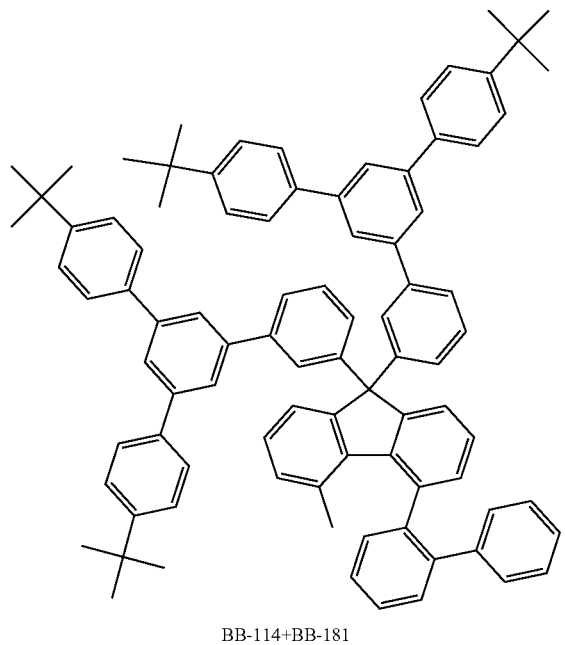
BB-114+BB-181
M-0059
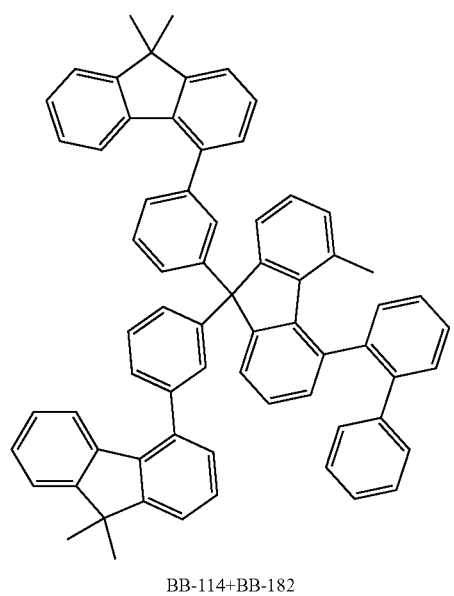
BB-114+BB-182
M-0060
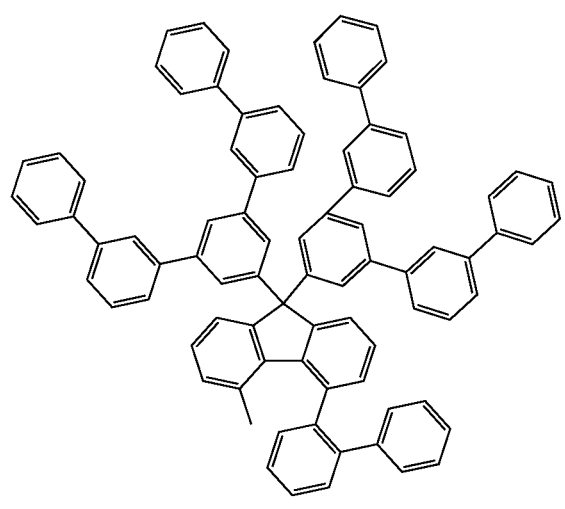
BB-115+BB-179

M-0061
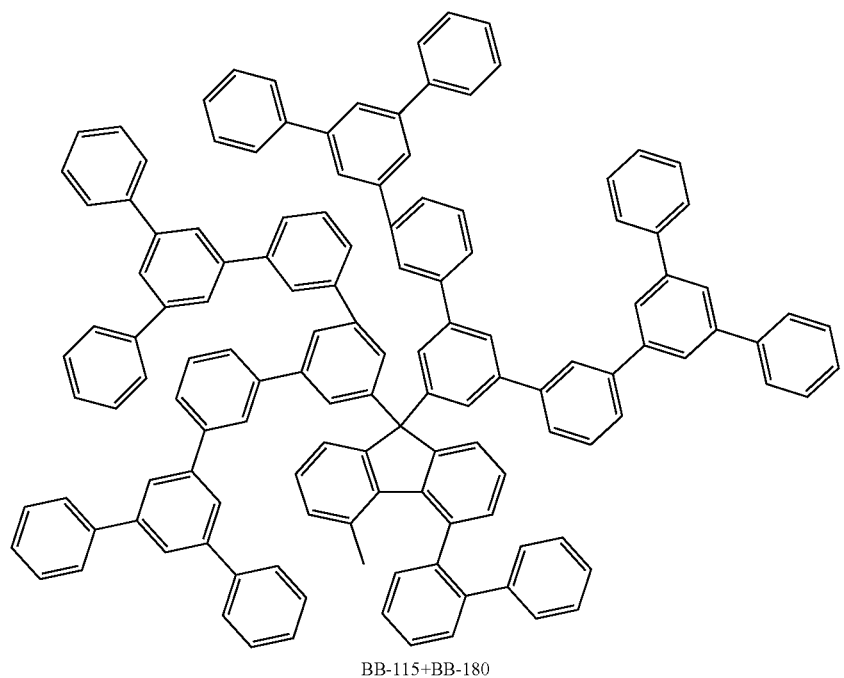
BB-115+BB-180
M-0062
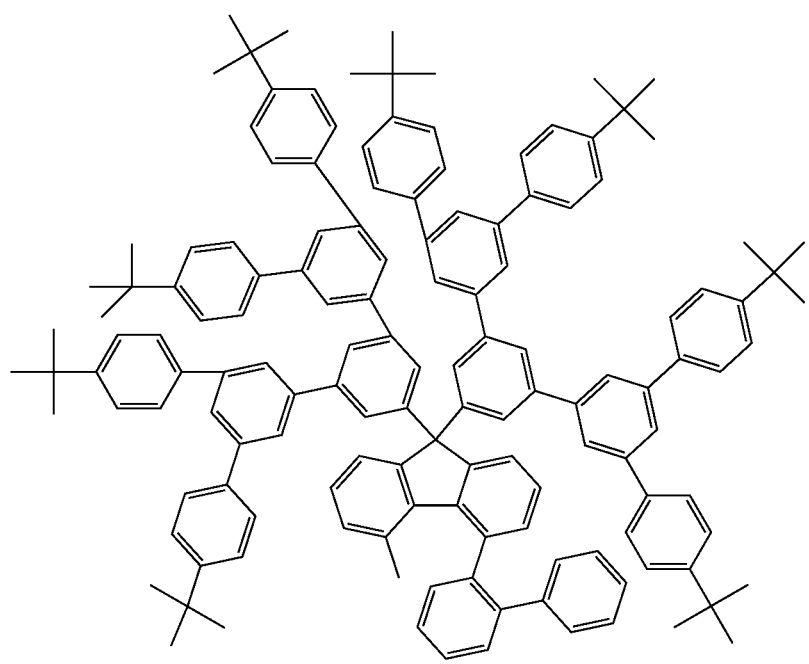
BB-115+BB-181

M-0063
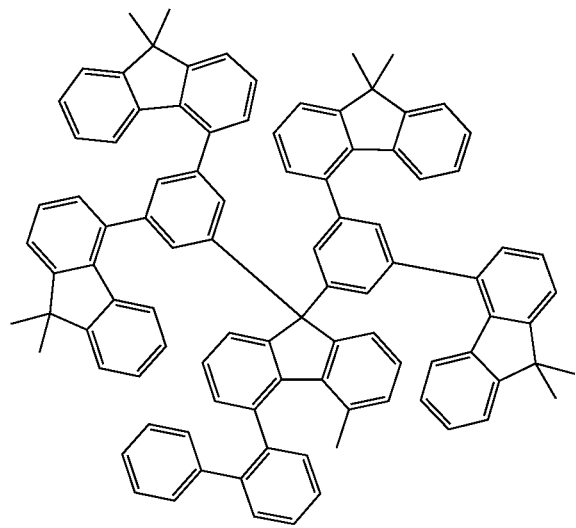
BB-115+BB-182
M-0064
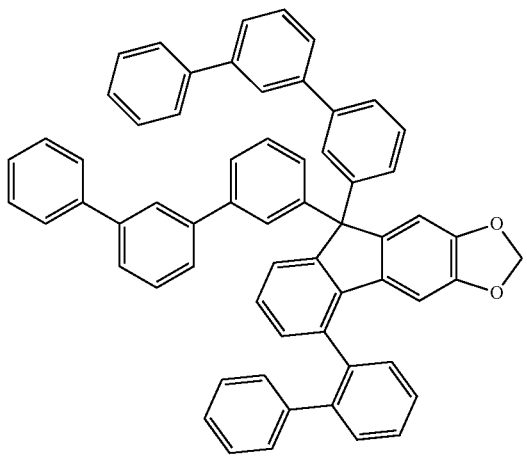
BB-116+BB-179
M-0065
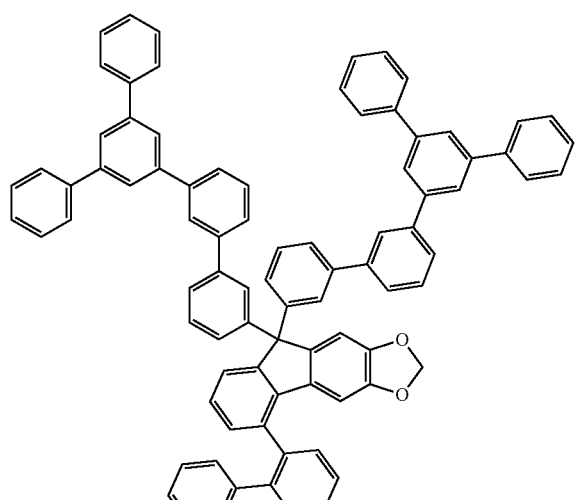
BB-116+BB-180
M-0066
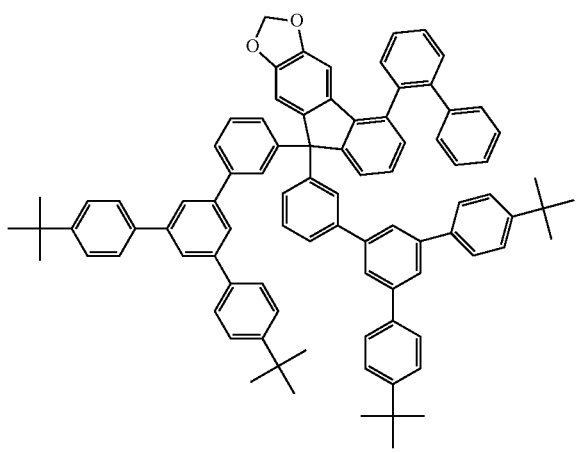
BB-116+BB-181

-continued
M-0067
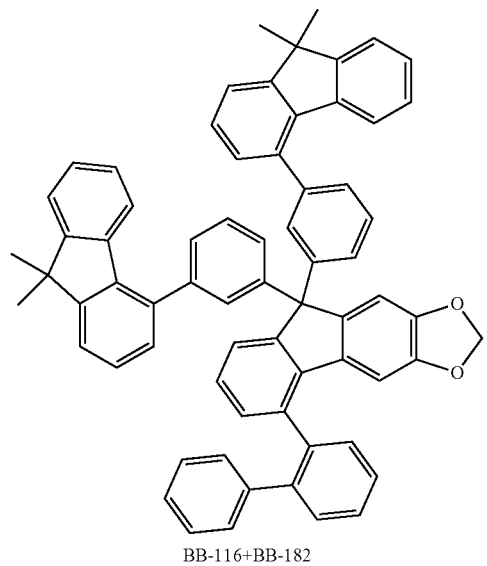
BB-116+BB-182
M-0068
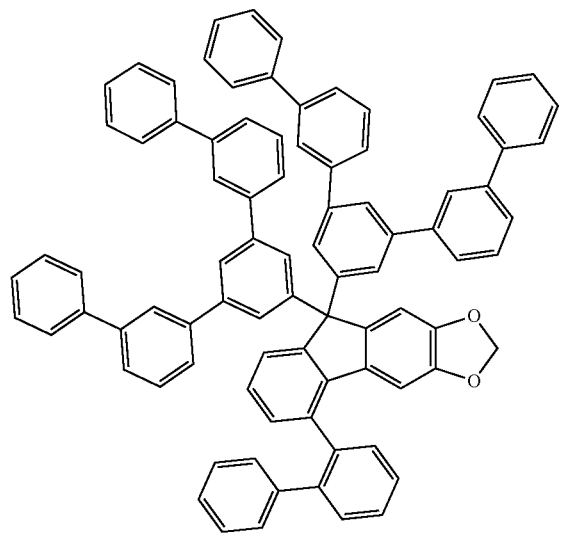
BB-117+BB-179
M-0069
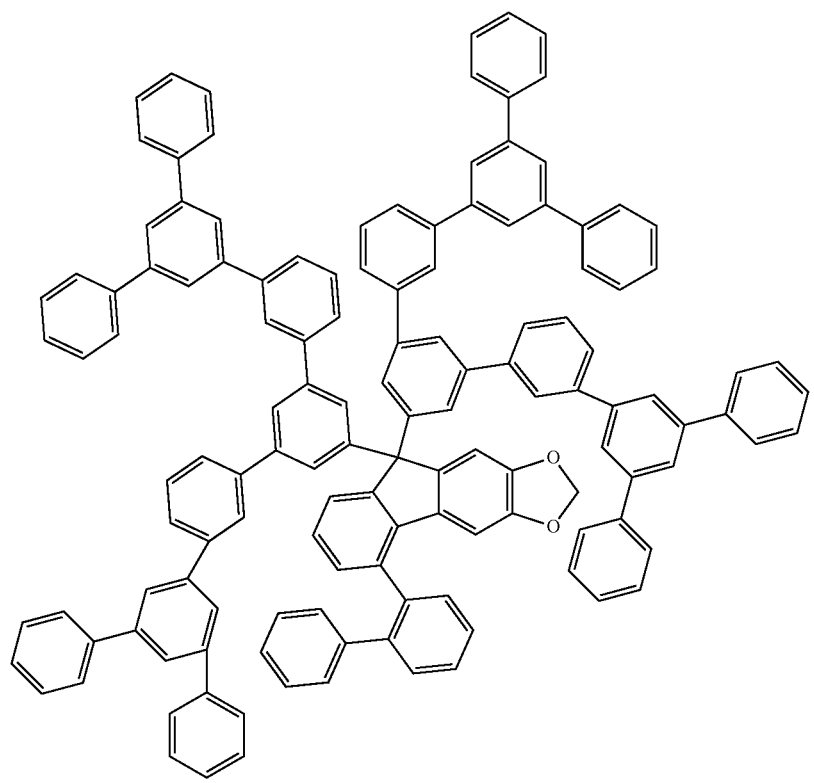
BB-117+BB-180

-continued
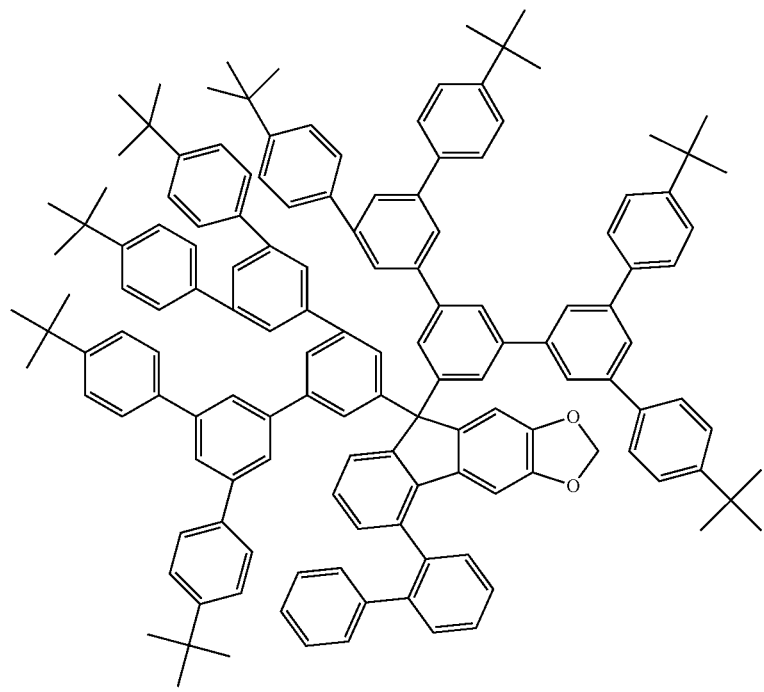
BB-117+BB-181
M-0070
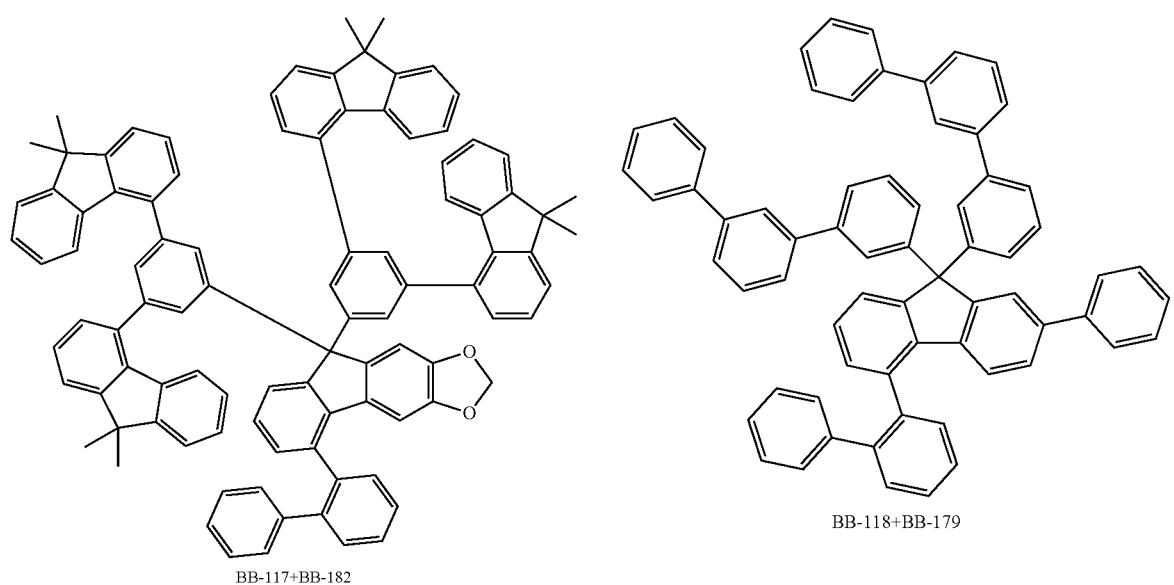
M-0071
BB-117+BB-182
M-0072
BB-118+BB-179

M-0073
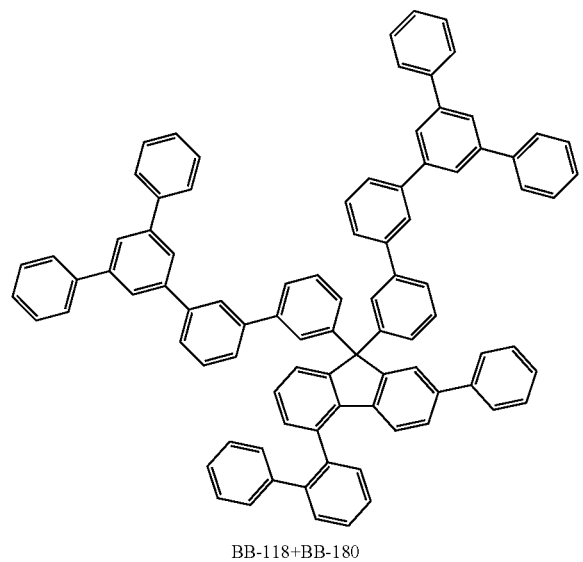
BB-118+BB-180
M-0074
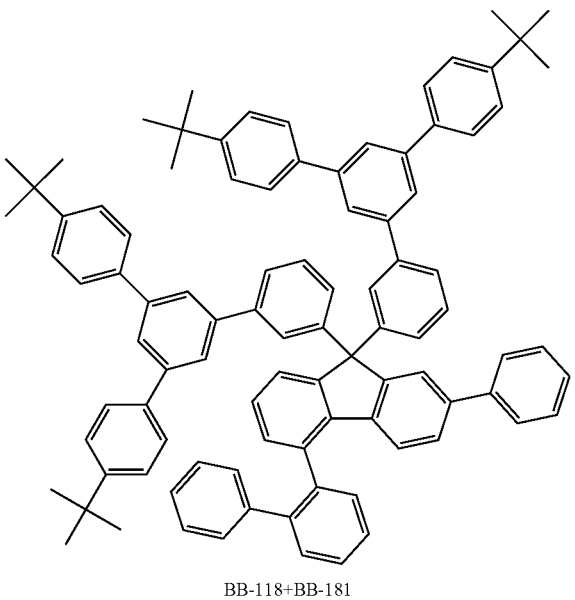
BB-118+BB-181
M-0075
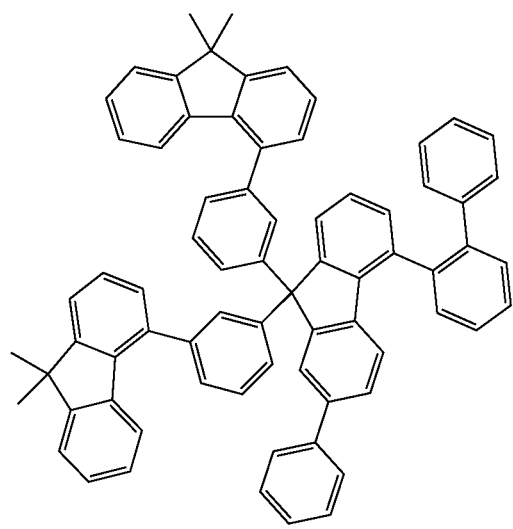
BB-118+BB-182
M-0076
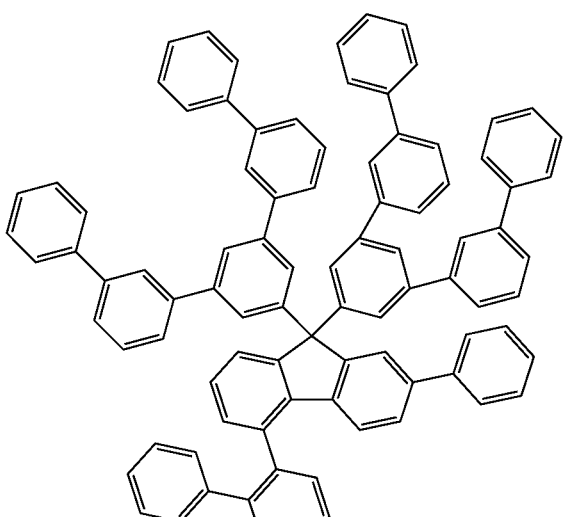
BB-119+BB-179

-continued
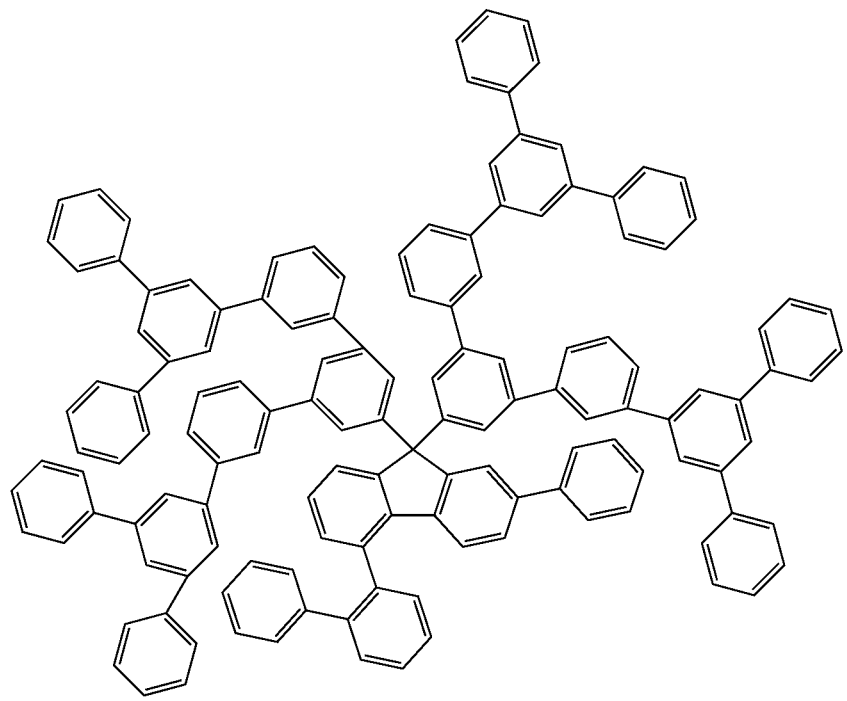
BB-119+BB-180
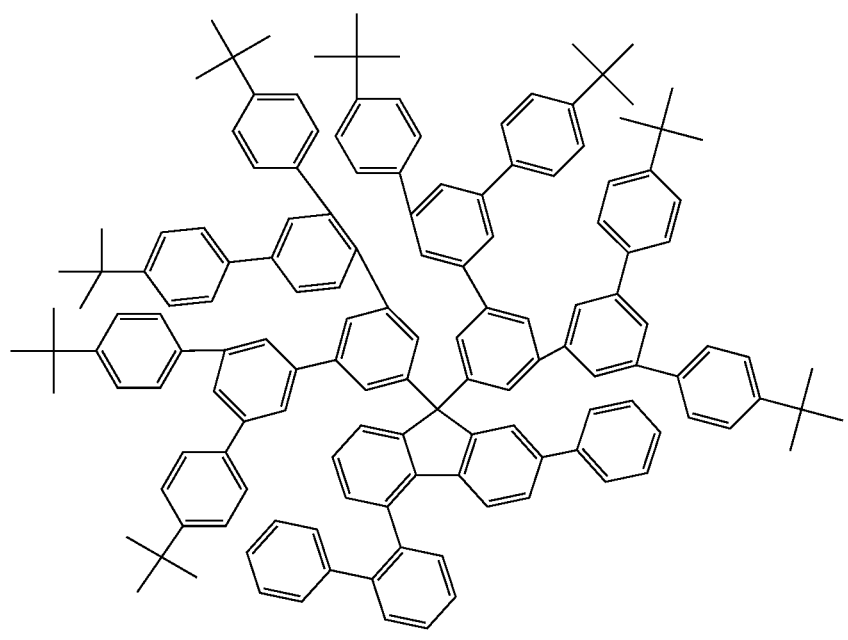
BB-119+BB-181
M-0077
M-0078

-continued
M-0079
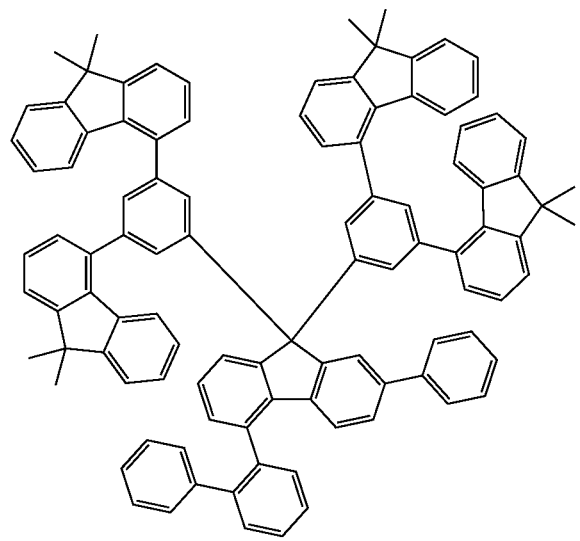
BB-119+BB-182
M-0080
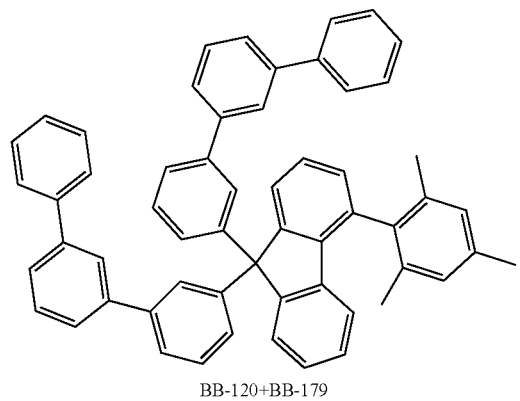
BB-120+BB-179
M-0081
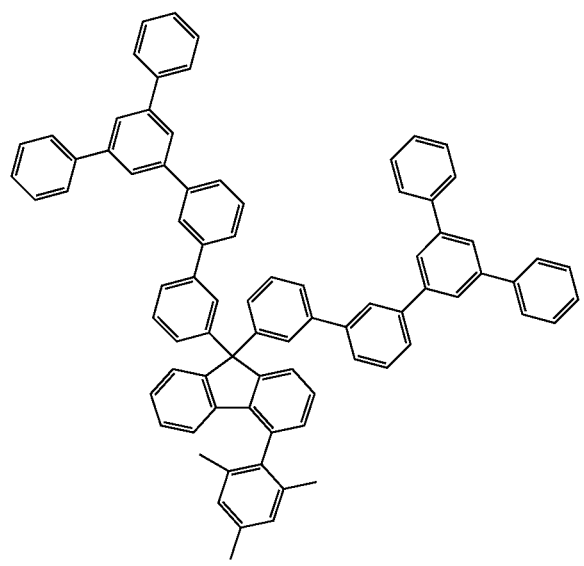
BB-120+BB-180
M-0082
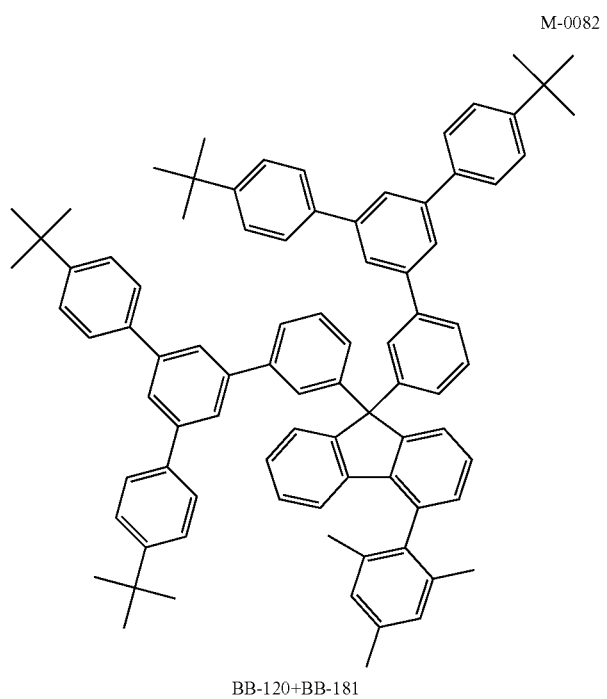
BB-120+BB-181

M-0083
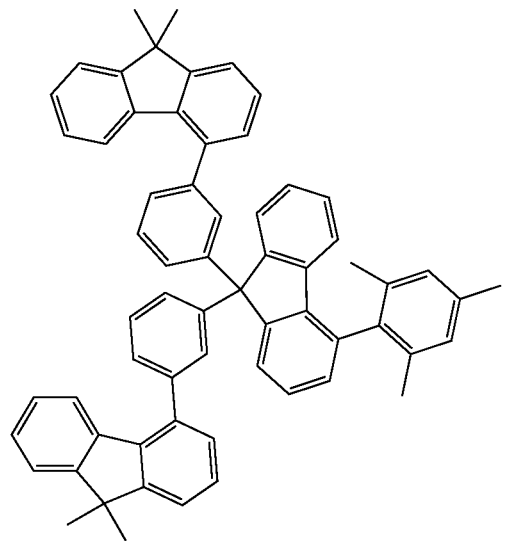
BB-120+BB-182
M-0084
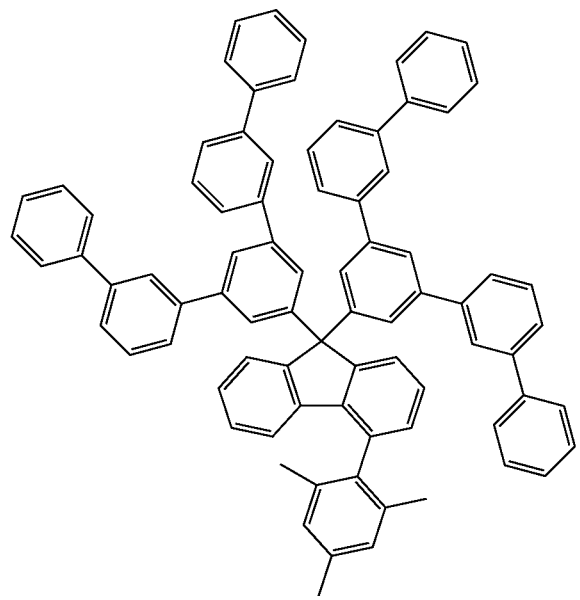
BB-121+BB-179
M-0085
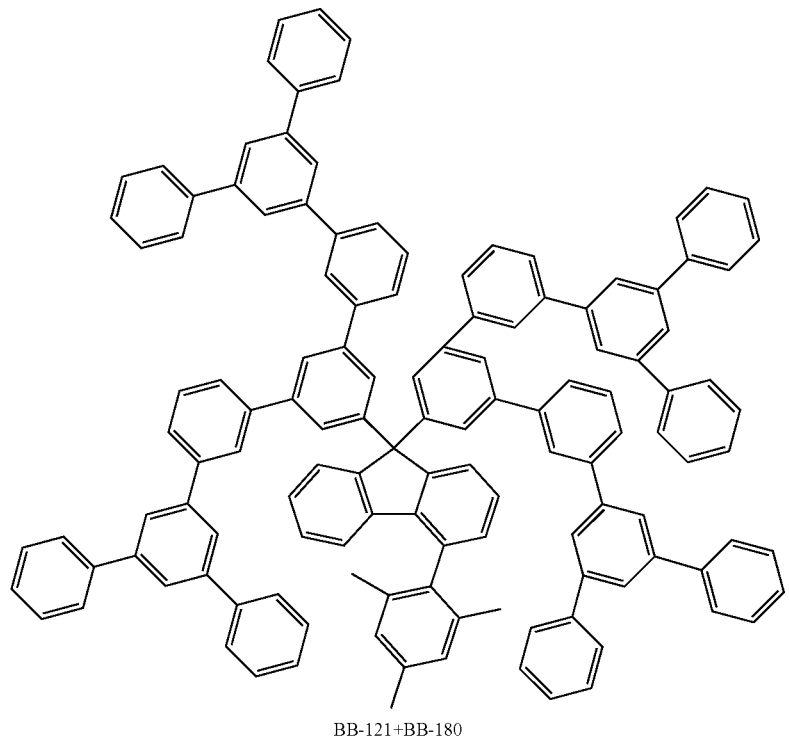
BB-121+BB-180

-continued
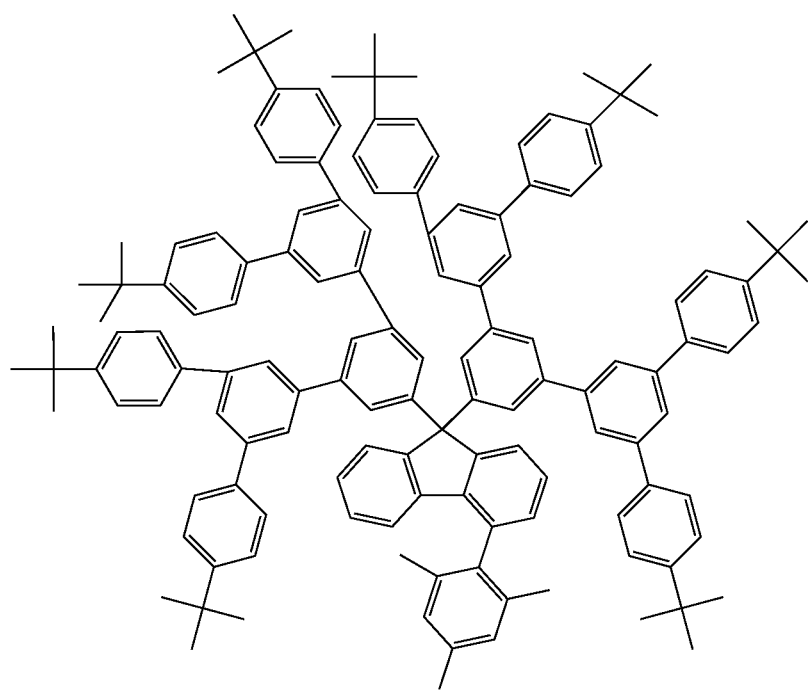
BB-121+BB-181
M-0086
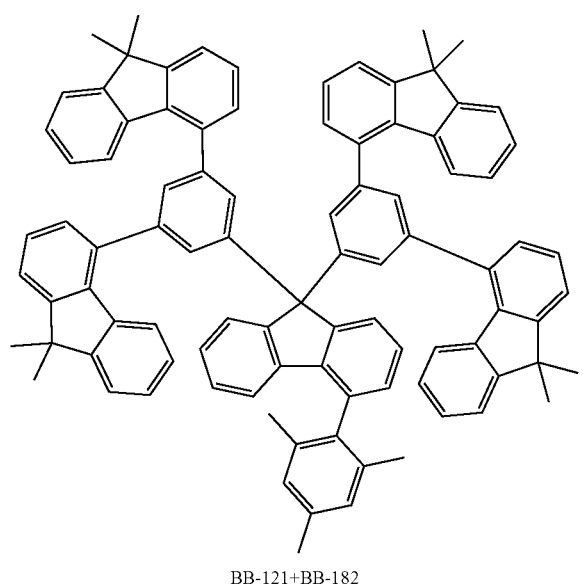
BB-121+BB-182
M-0087
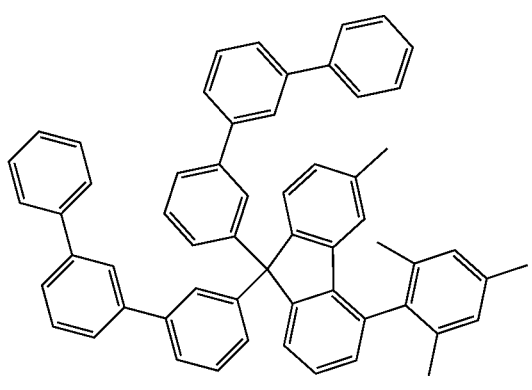
BB-123+BB-179
M-0088

-continued
M-0089
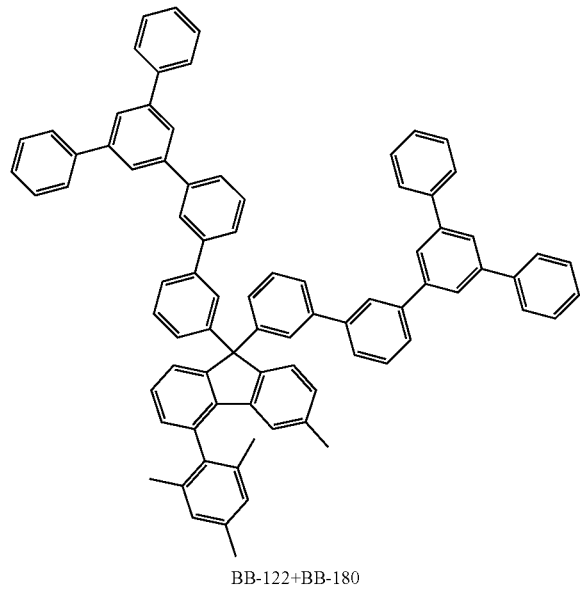
BB-122+BB-180
M-0090
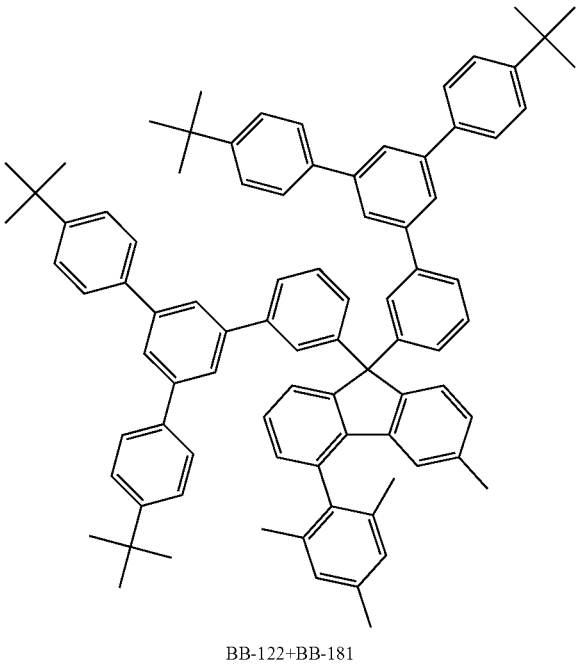
BB-122+BB-181
M-0091
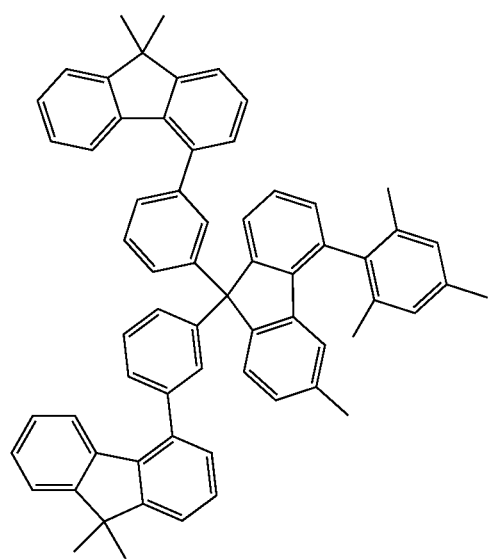
BB-122+BB-182
M-0092
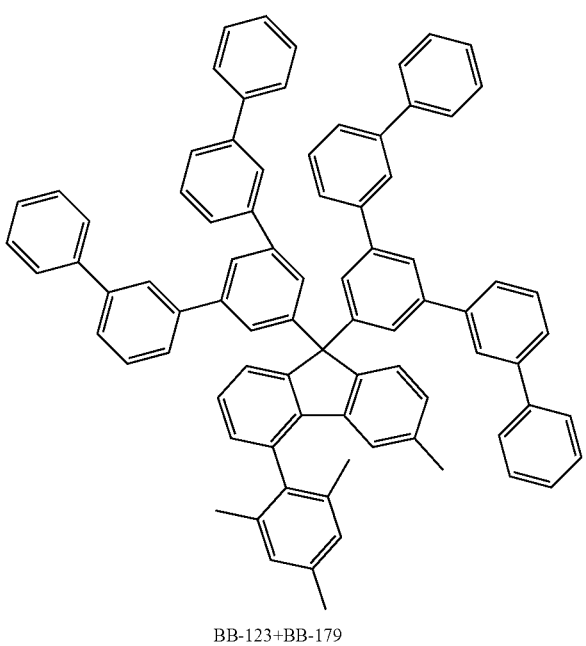
BB-123+BB-179

M-0093
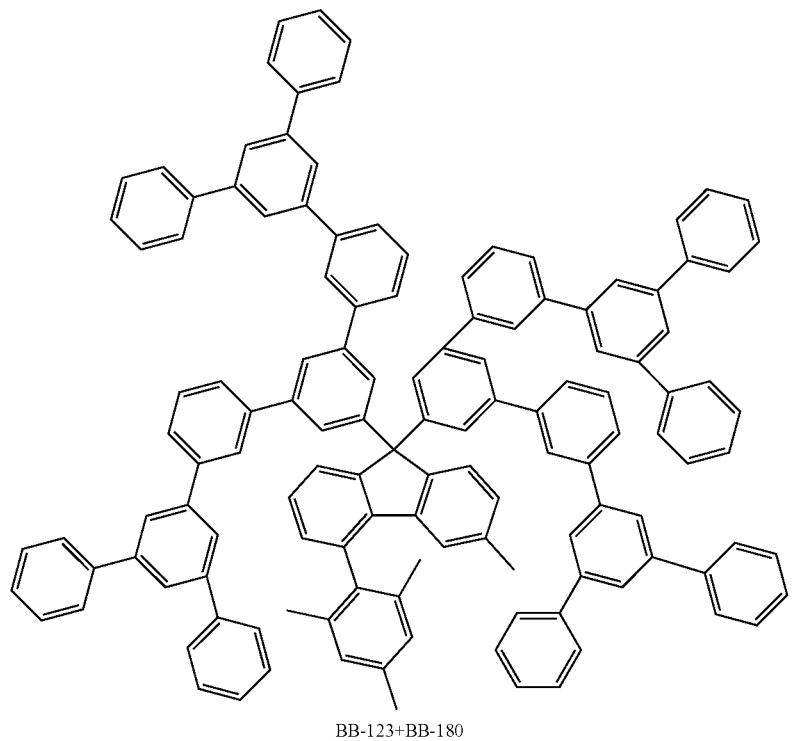
BB-123+BB-180
M-0094
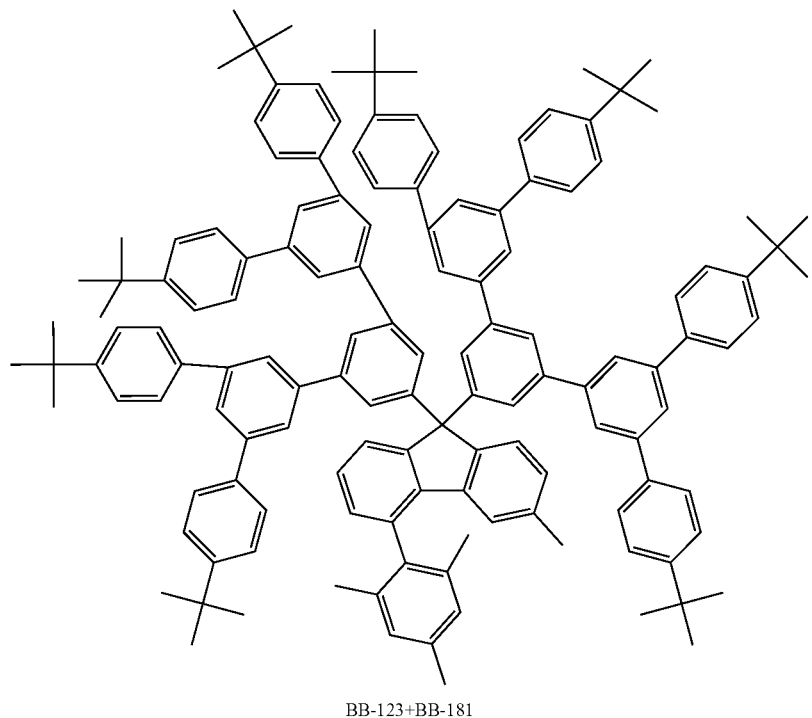
BB-123+BB-181

M-0095
M-0096
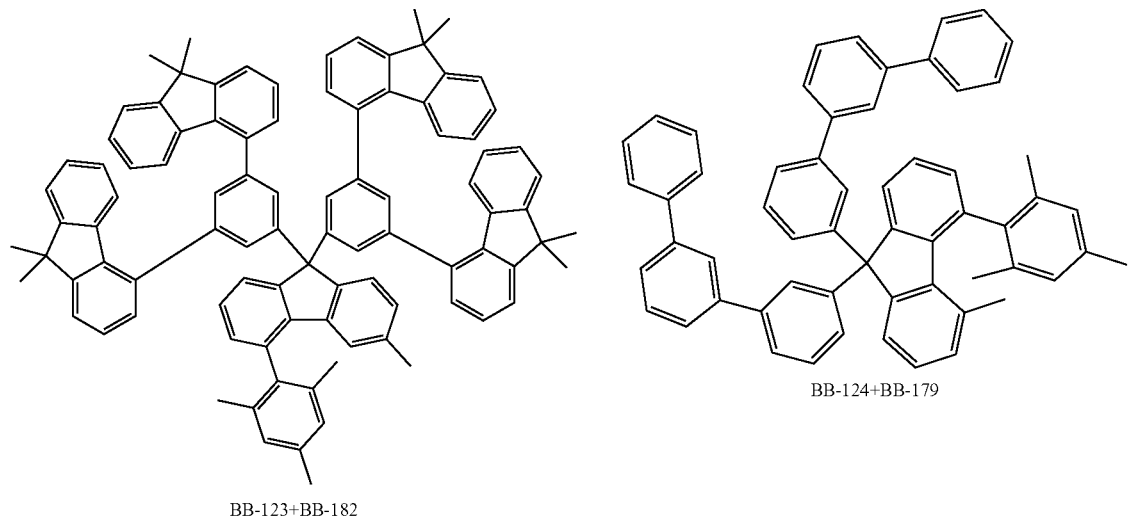
BB-123+BB-182
BB-124+BB-179
M-0097
M-0098
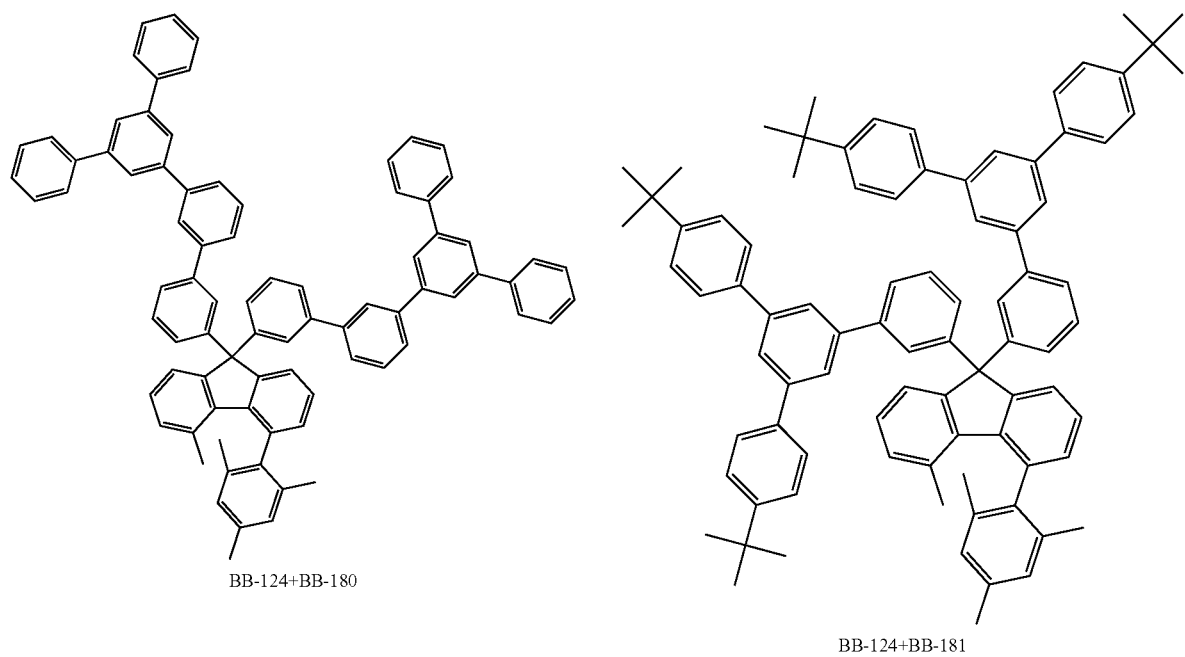
BB-124+BB-180
BB-124+BB-181

M-0099
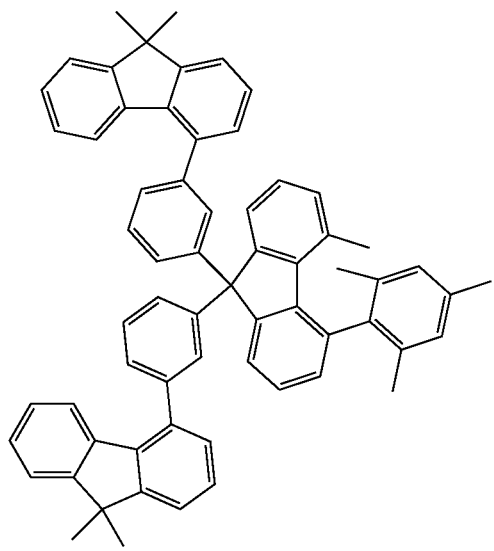
BB-124+BB-182
M-0100
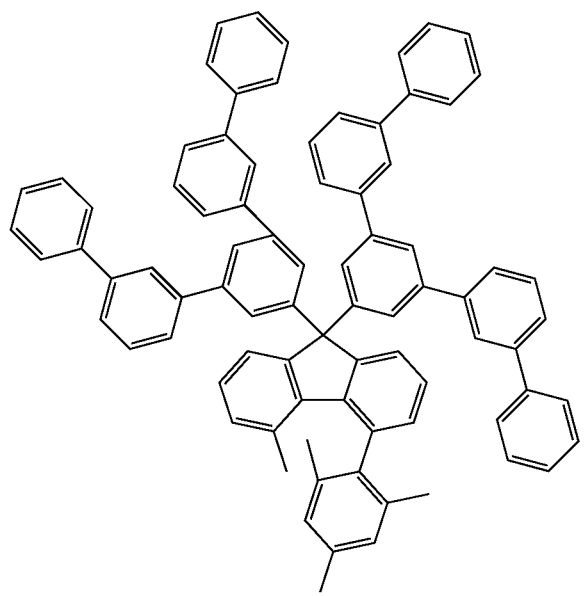
BB-125+BB-179
M-0101
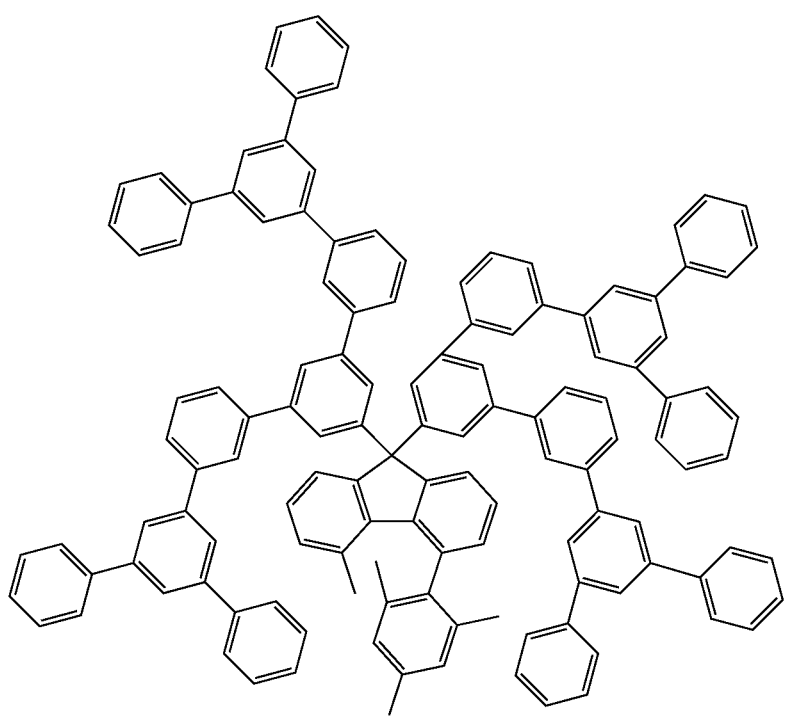
BB-125+BB-180

-continued
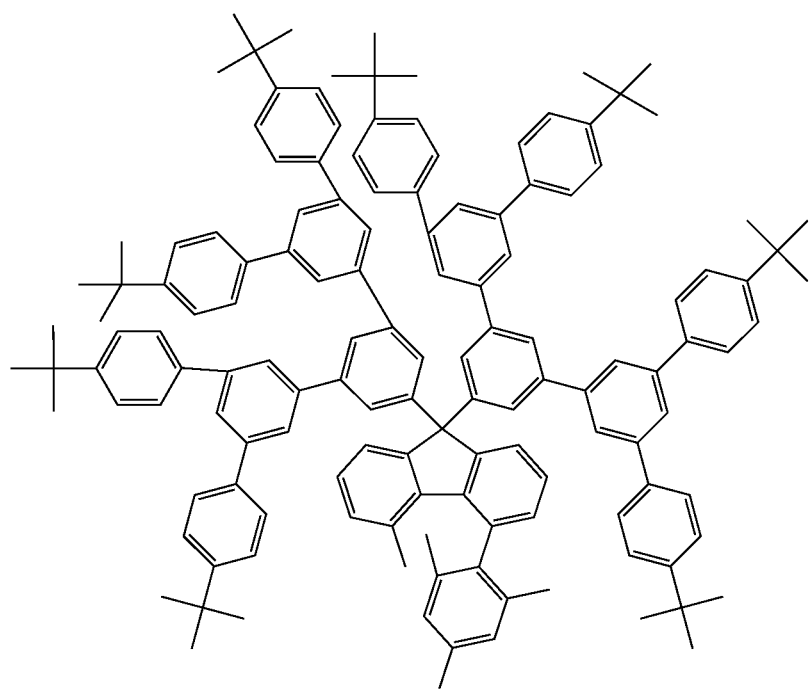
BB-125+BB-181
M-0102
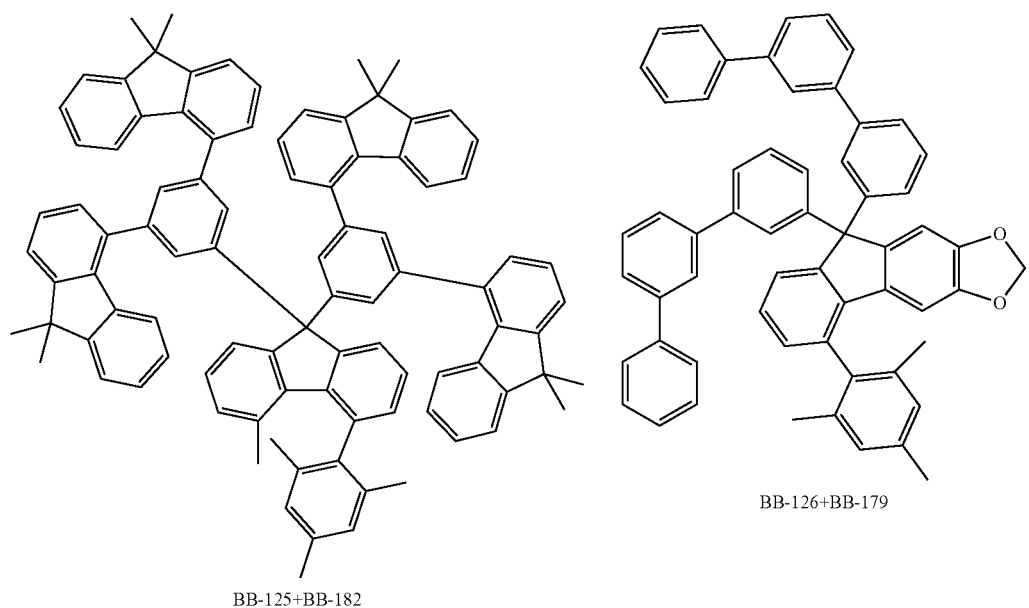
BB-125+BB-182
M-0103
BB-126+BB-179
M-0104

-continued
M-0105
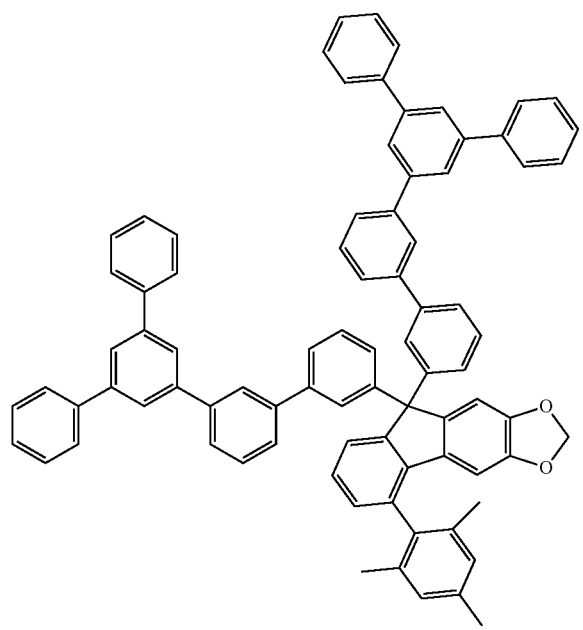
BB-126+BB-180
M-0106
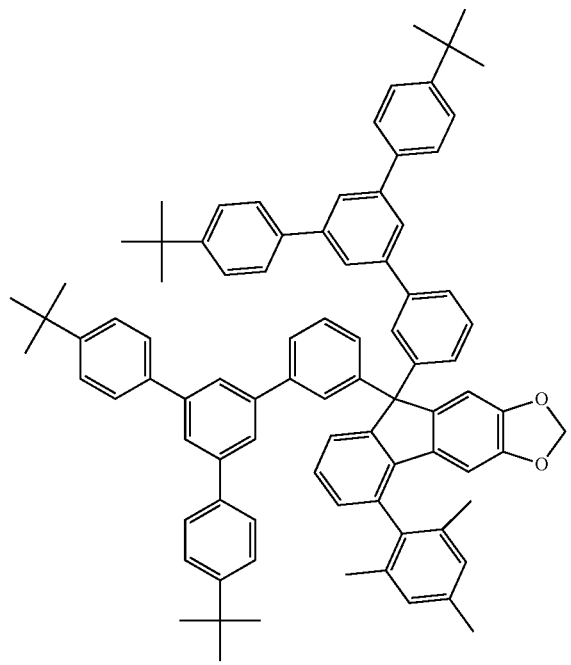
BB-126+BB-181
M-0107
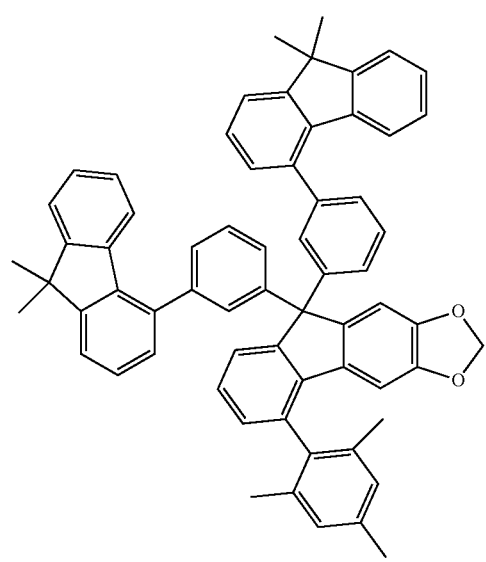
BB-126+BB-182
M-0108
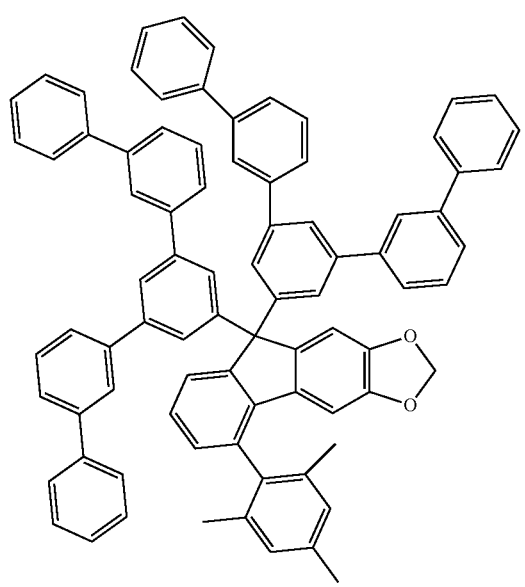
BB-127+BB-179

M-0109
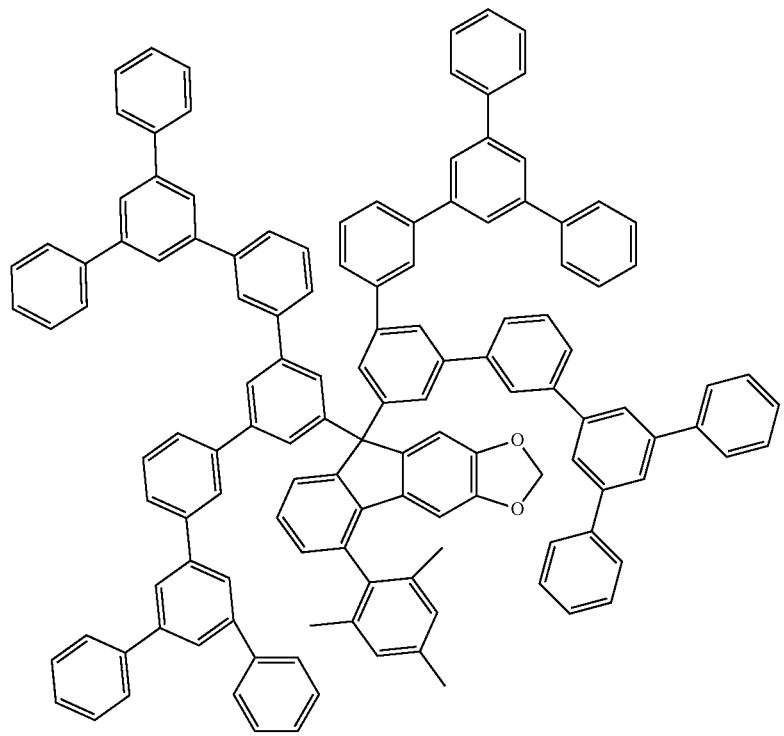
BB-127+BB-180
M-0110
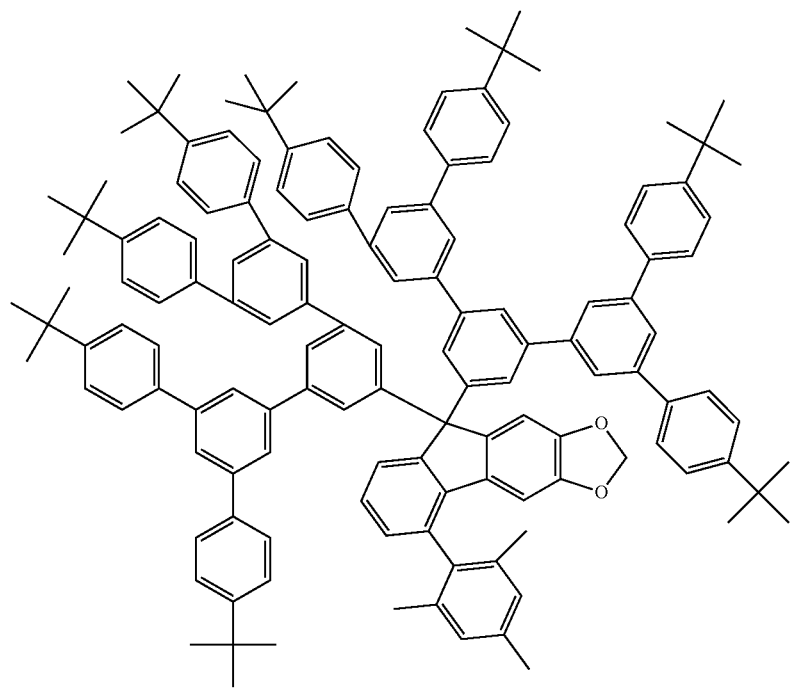
BB-127+BB-181

-continued
M-0111
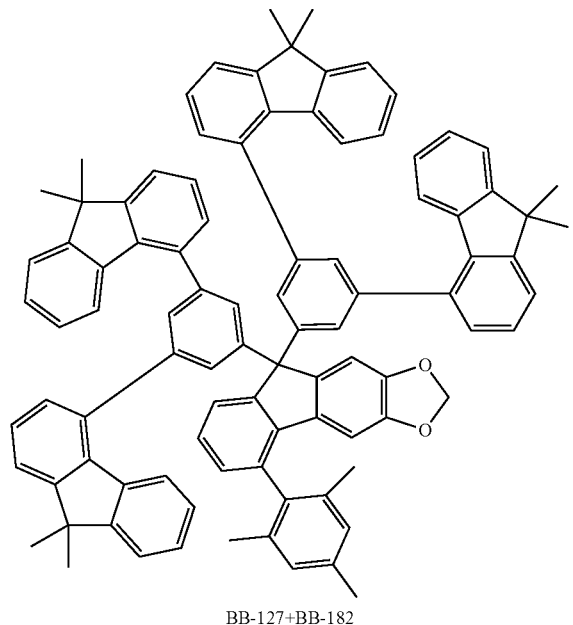
BB-127+BB-182
M-0112
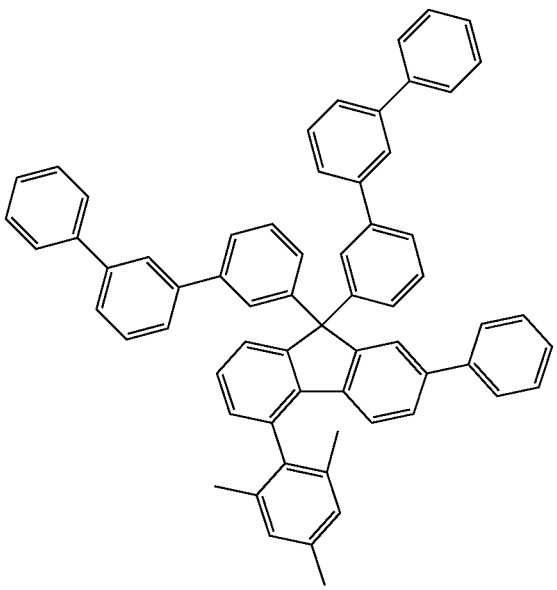
BB-128+BB-179
M-0113
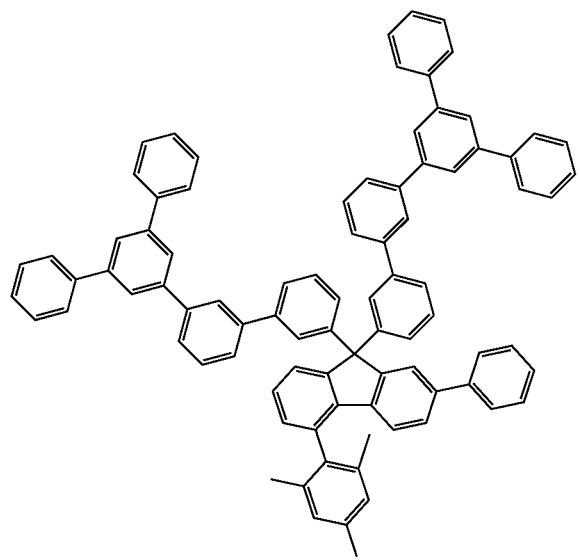
BB-128+BB-180
M-0114
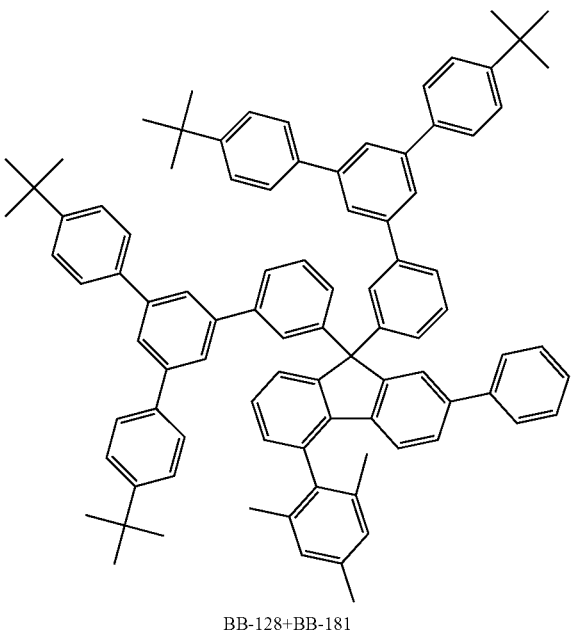
BB-128+BB-181

-continued
M-0115
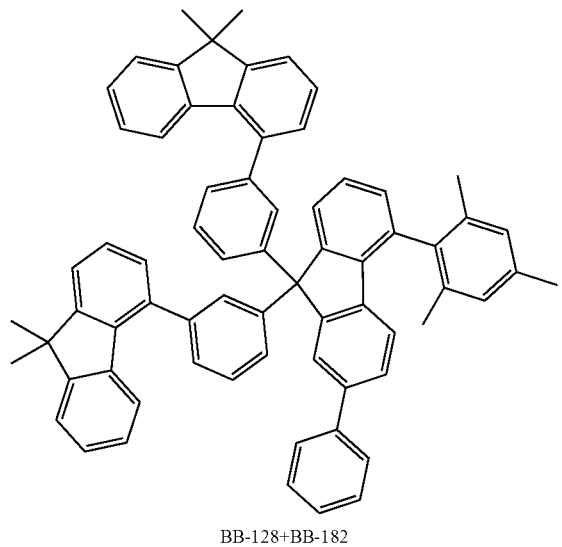
BB-128+BB-182
M-0116
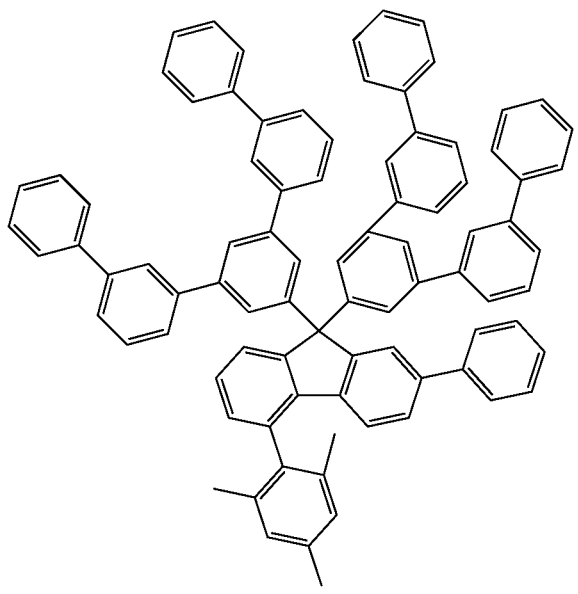
BB-129+BB-179
M-0117
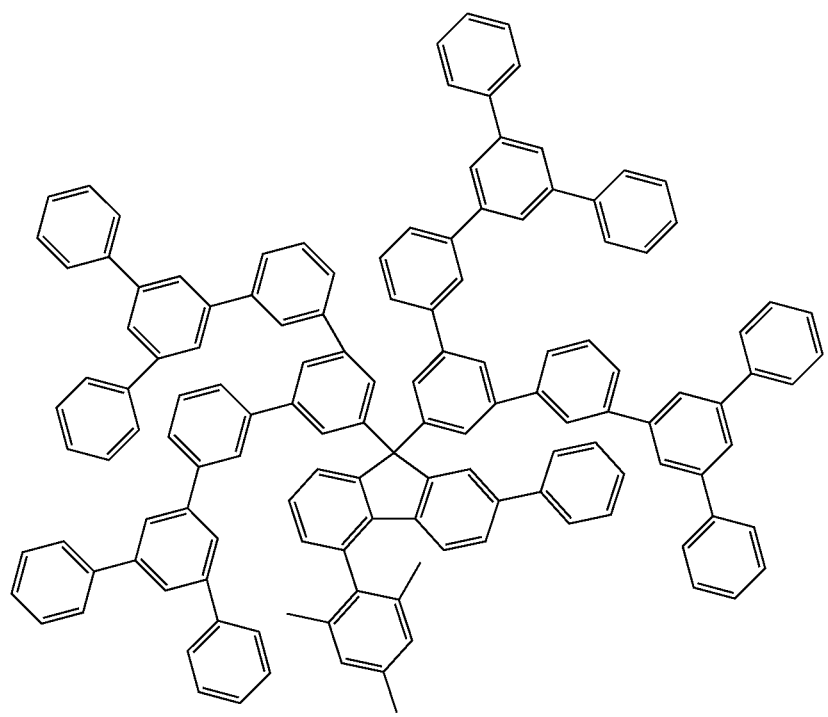
BB-129+BB-180

-continued
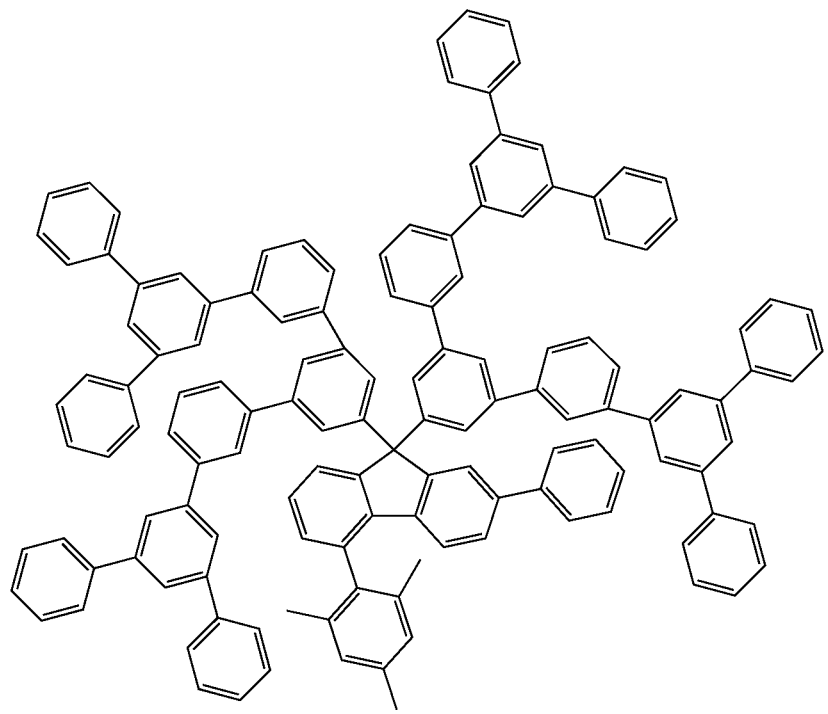
BB-129+BB-180
M-0118
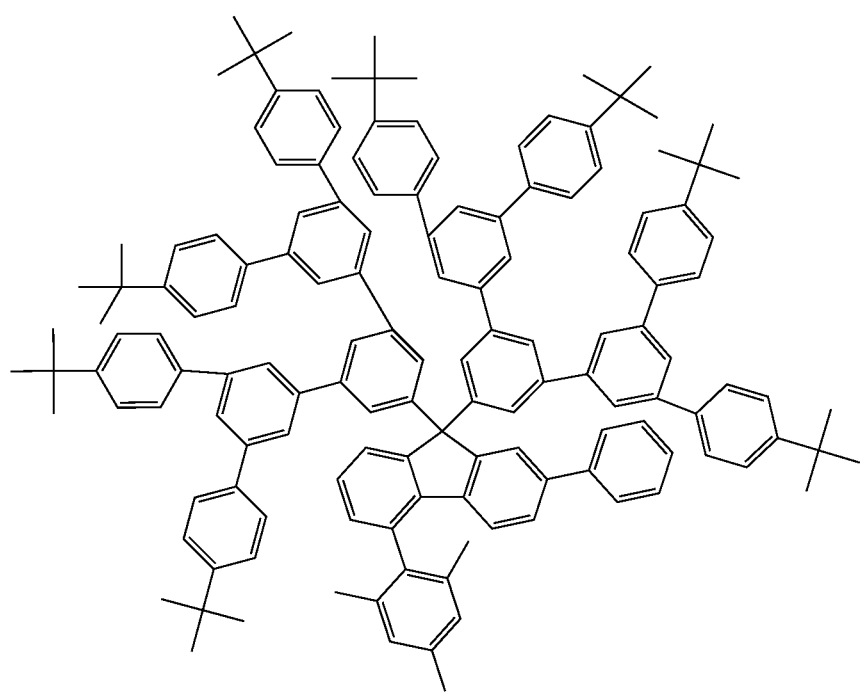
BB-129+BB-181
M-0119

-continued
M-120
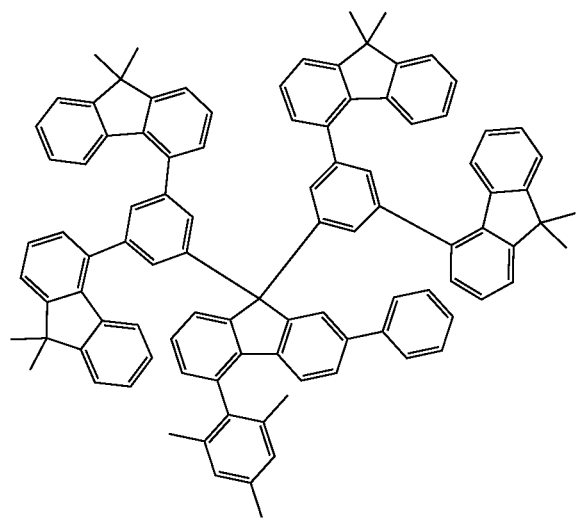
BB-129+BB-182
M-0121
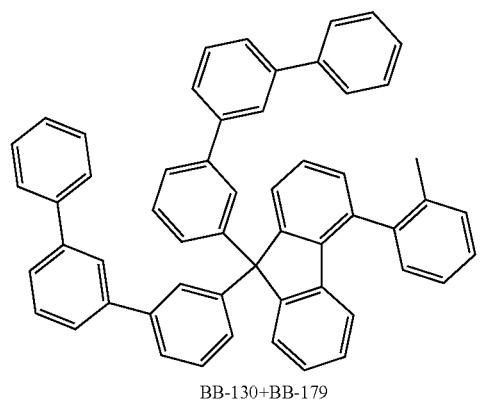
BB-130+BB-179
M-0122
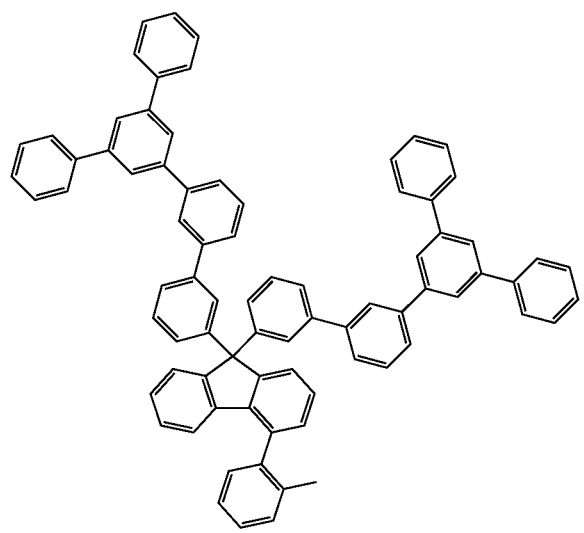
BB-130+BB-180
M-0123
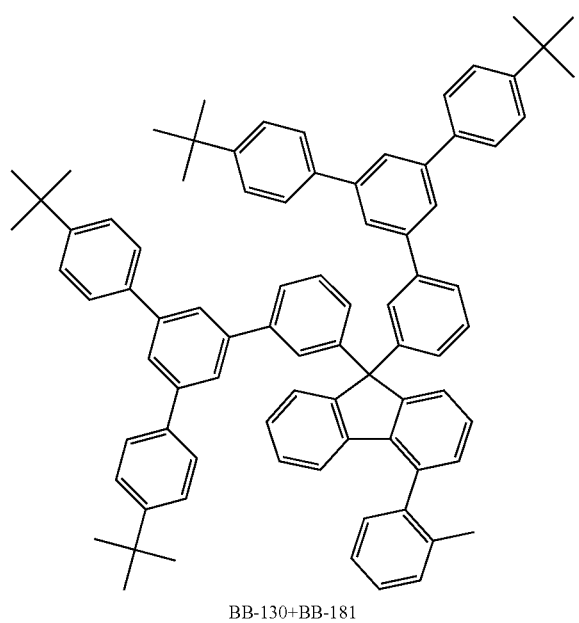
BB-130+BB-181

-continued
M-0124
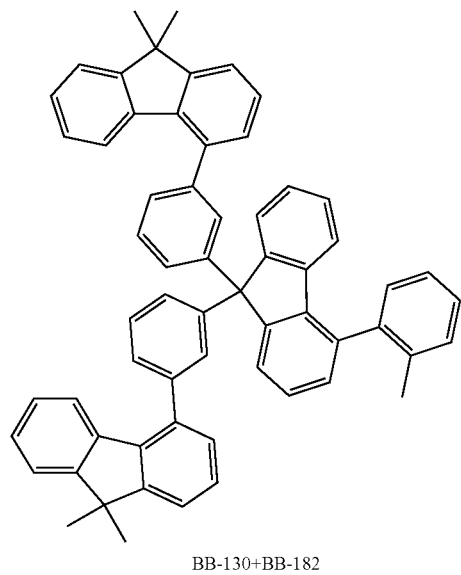
BB-130+BB-182
M-0125
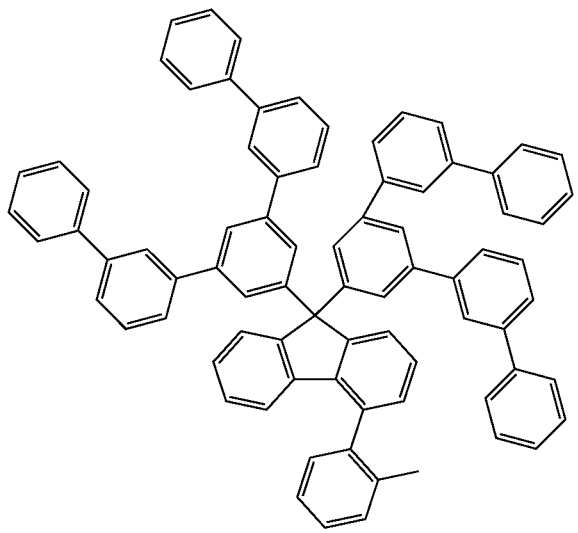
BB-131+BB-179
M-0126
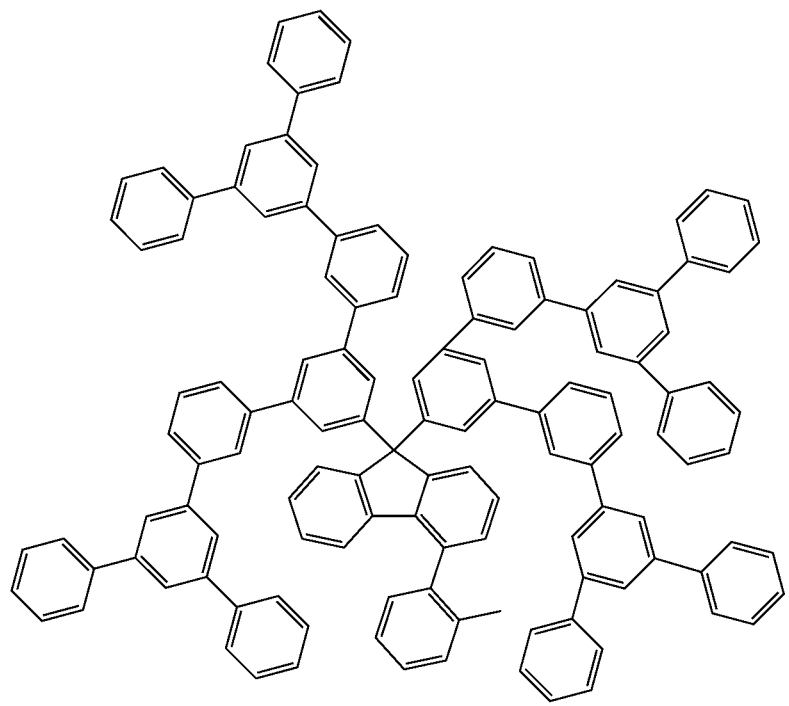
BB-131+BB-180

M-0127
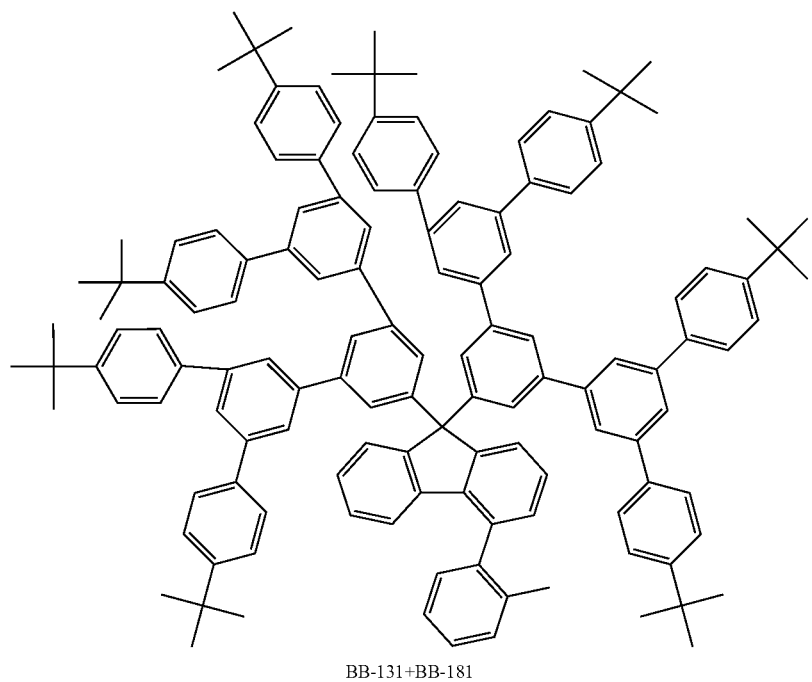
BB-131+BB-181
M-0128 M-0129
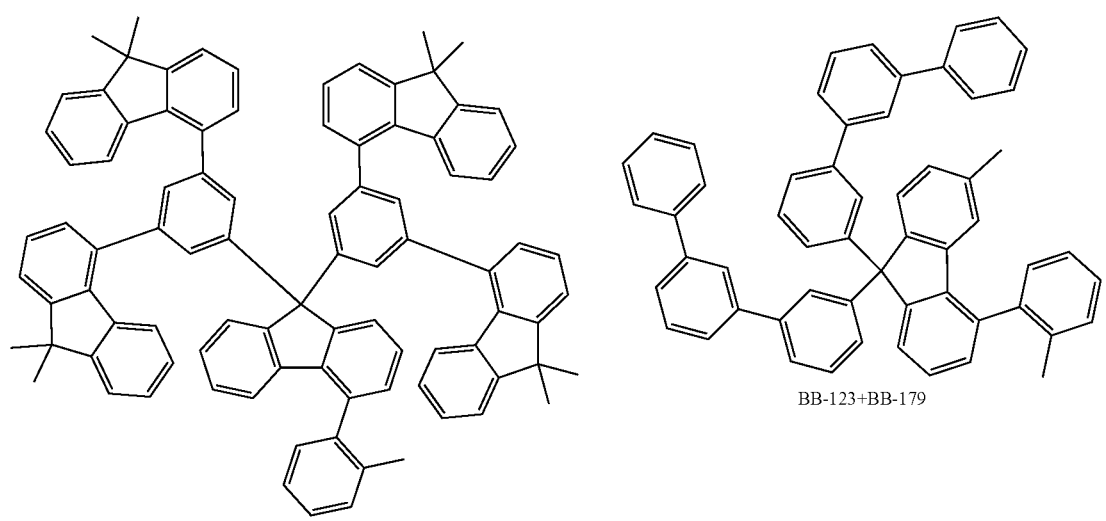
BB-131+BB-182
BB-123+BB-179

-continued
M-0130
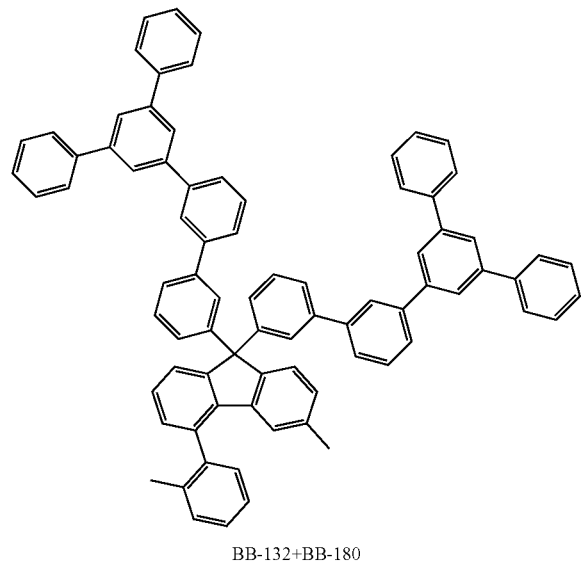
BB-132+BB-180
M-0131
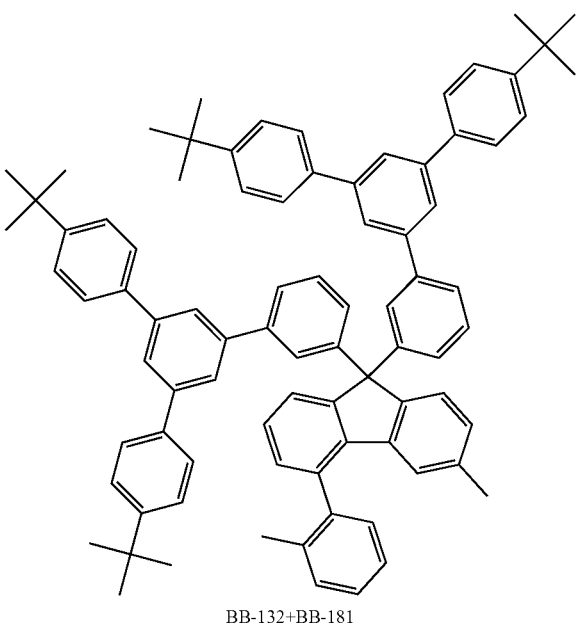
BB-132+BB-181
M-0132
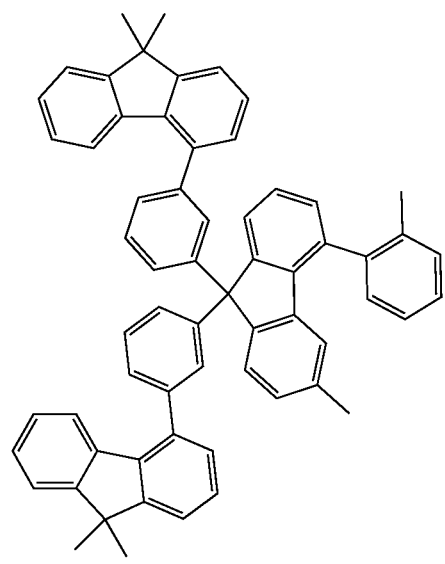
BB-132+BB-182
M-0133
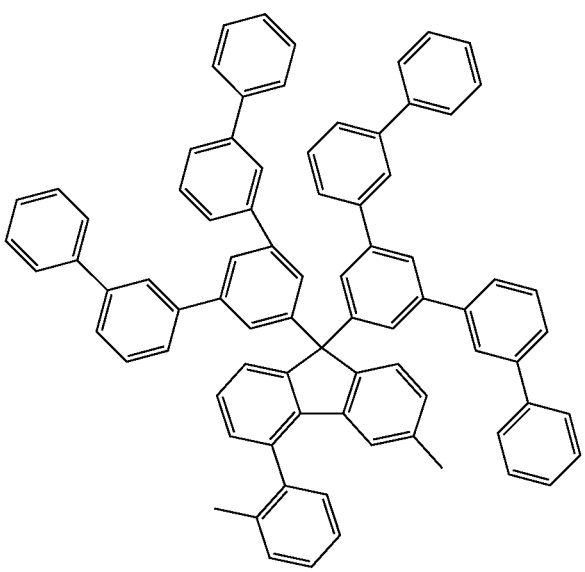
BB-133+BB-179

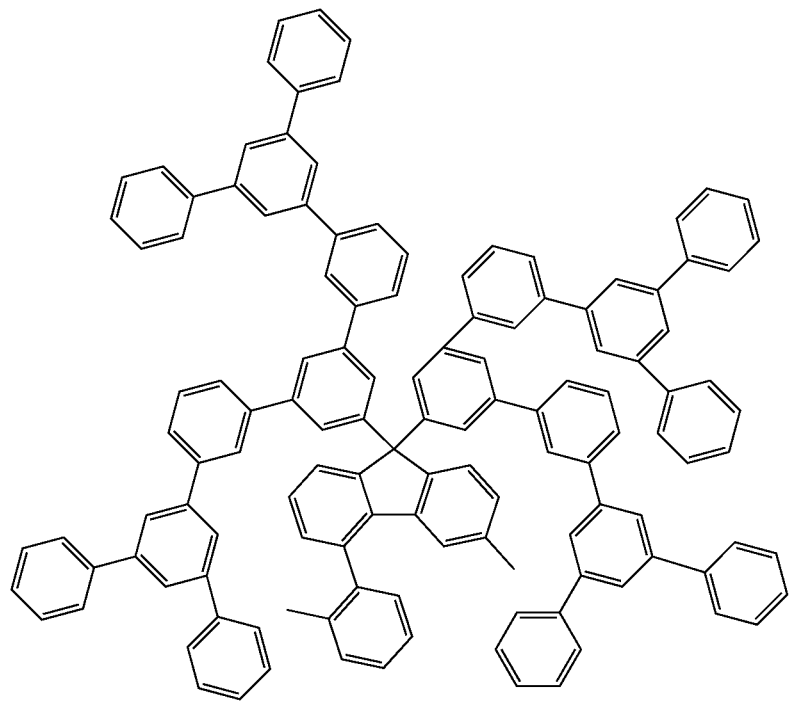
BB-133+BB-180
M-0134
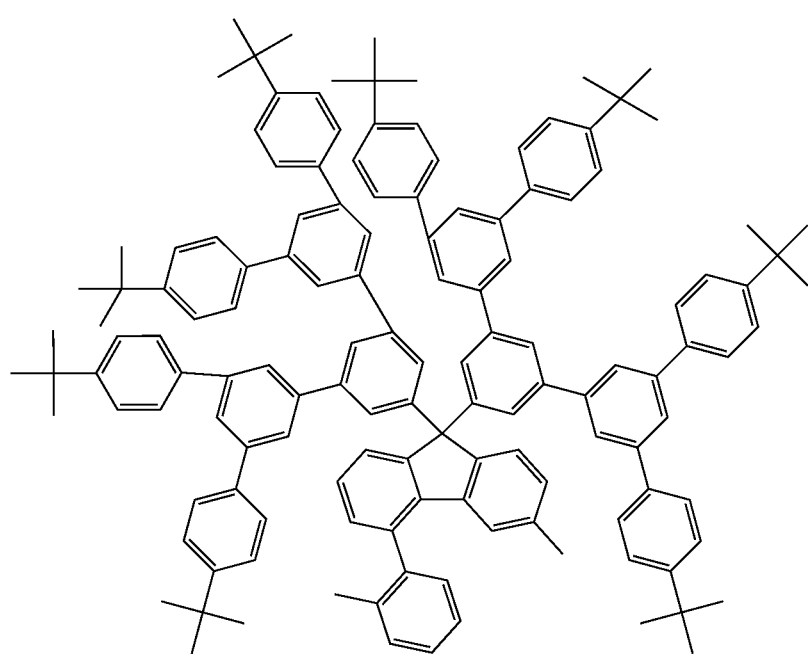
BB-133+BB-181
M-0135

-continued
M-0136
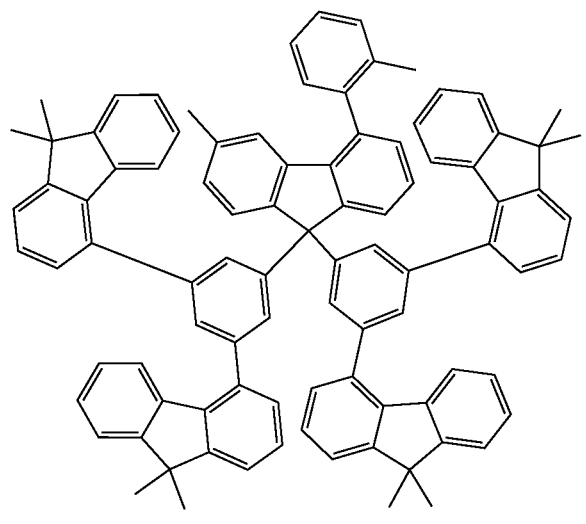
BB-133+BB-182
M-0137
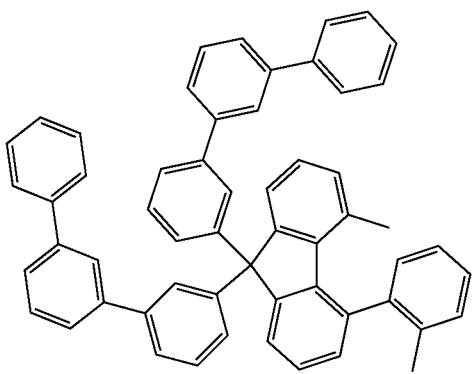
BB-134+BB-179
M-0138
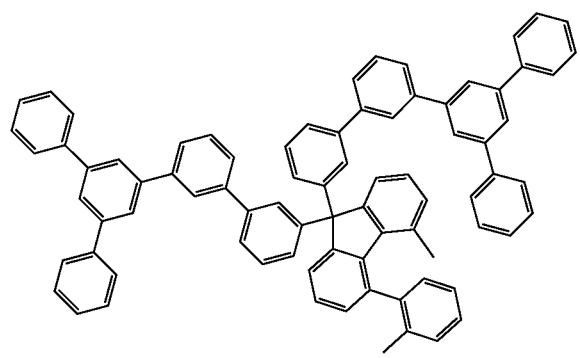
BB-134+BB-180
M-0139
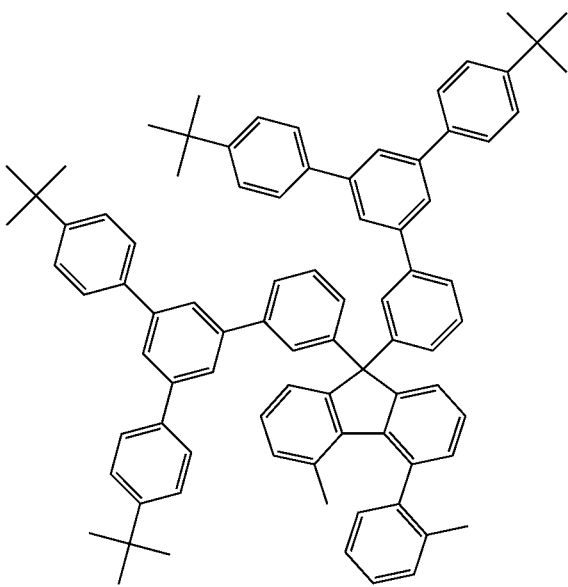
BB-134+BB-181

-continued
M-0140
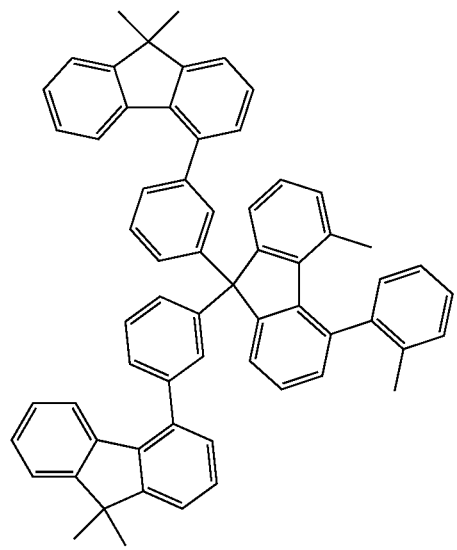
BB-134+BB-182
M-0141
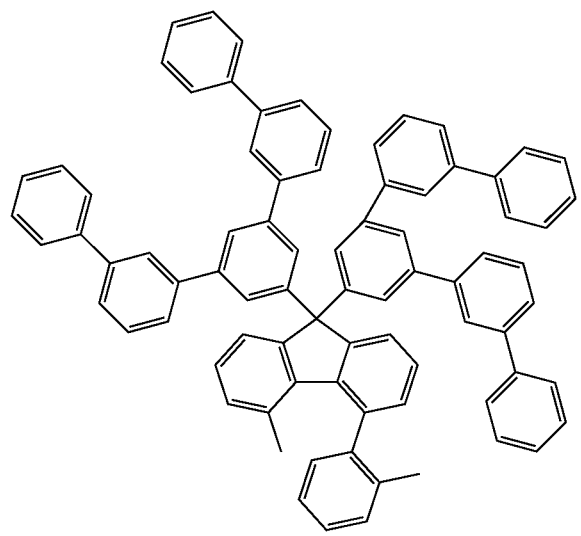
BB-135+BB-179
M-0142
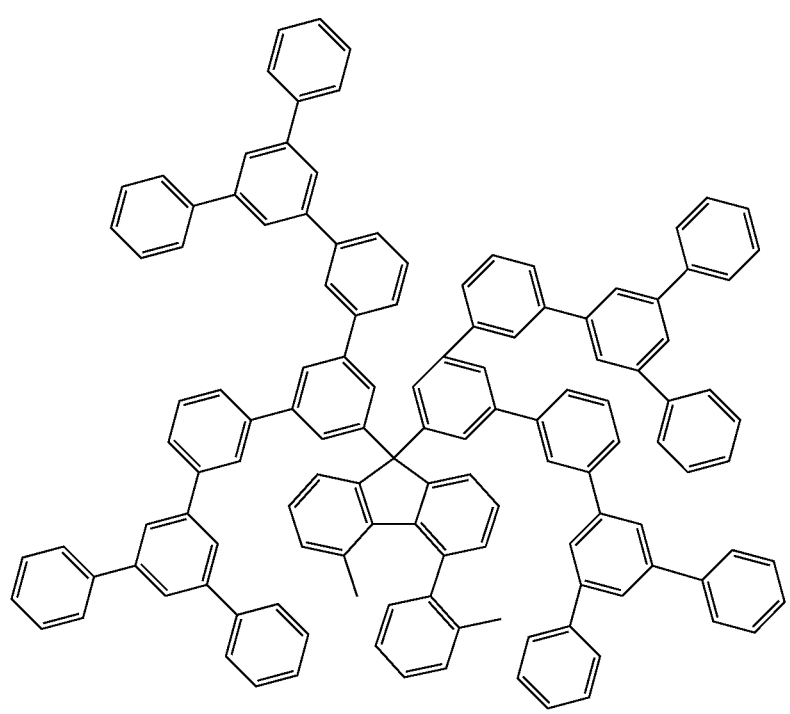
BB-135+BB-180

-continued
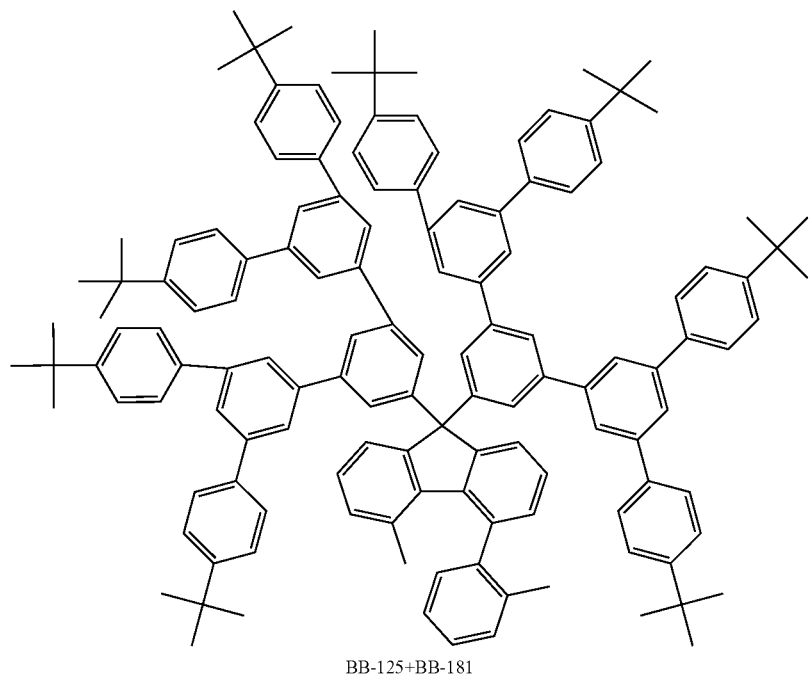
BB-125+BB-181
M-0143
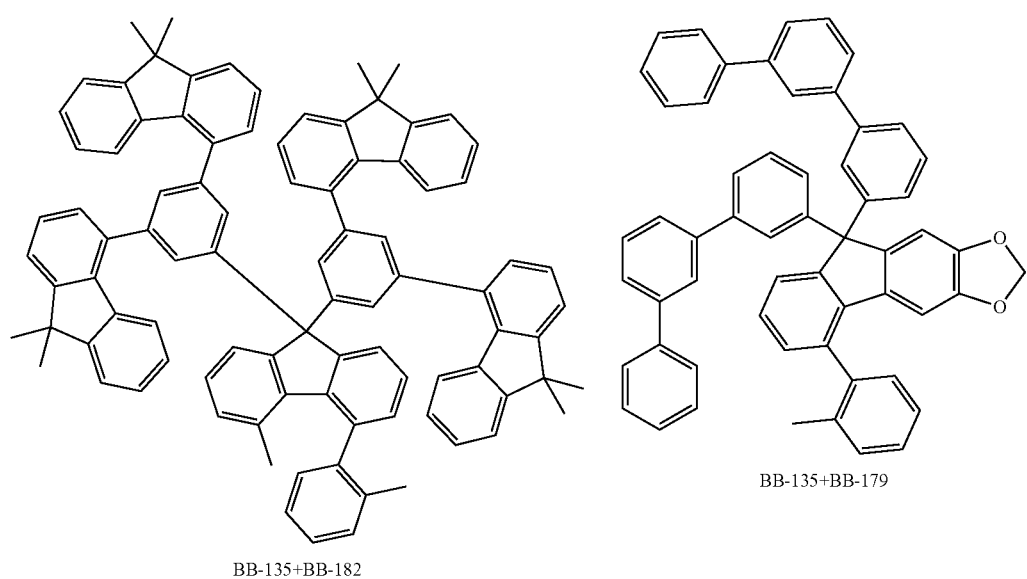
BB-135+BB-182
M-0144
BB-135+BB-179
M-0145

M-0146
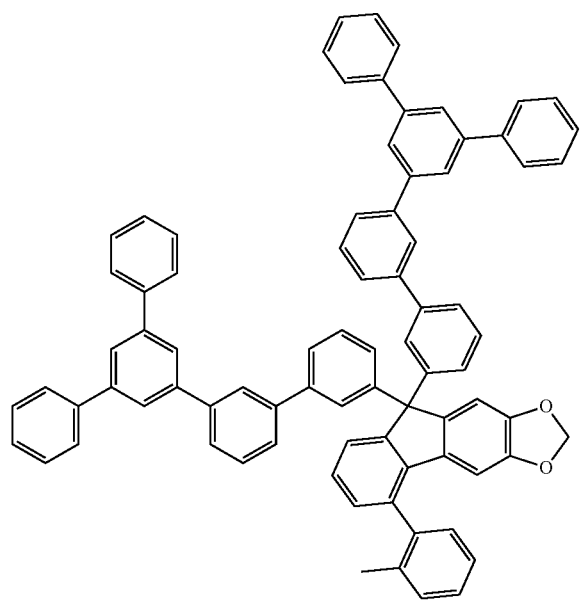
BB-135+BB-180
M-0147
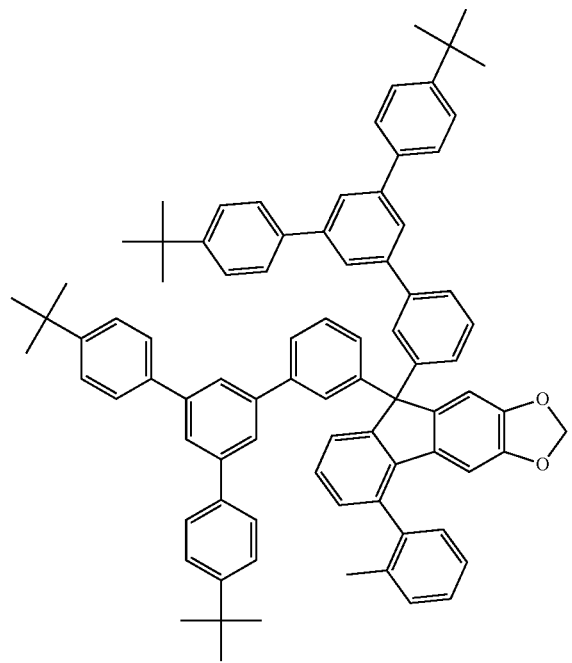
BB-135+BB-181
M-0148
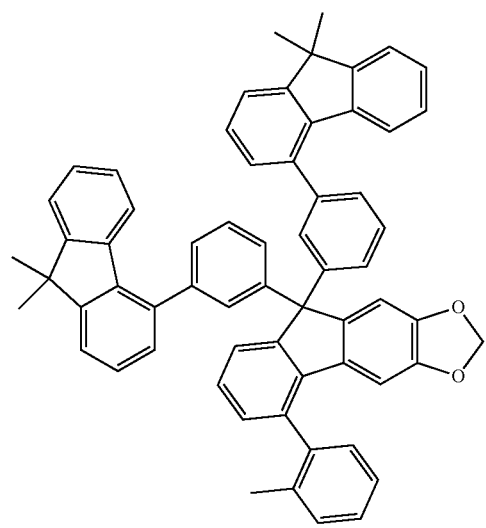
BB-135+BB-182
M-0149
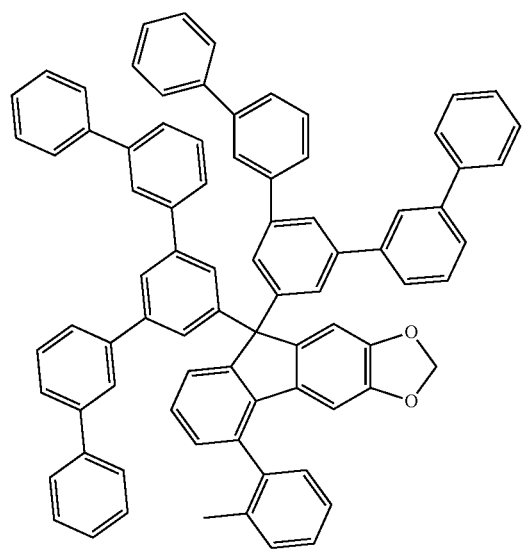
BB-136+BB-179

M-0150
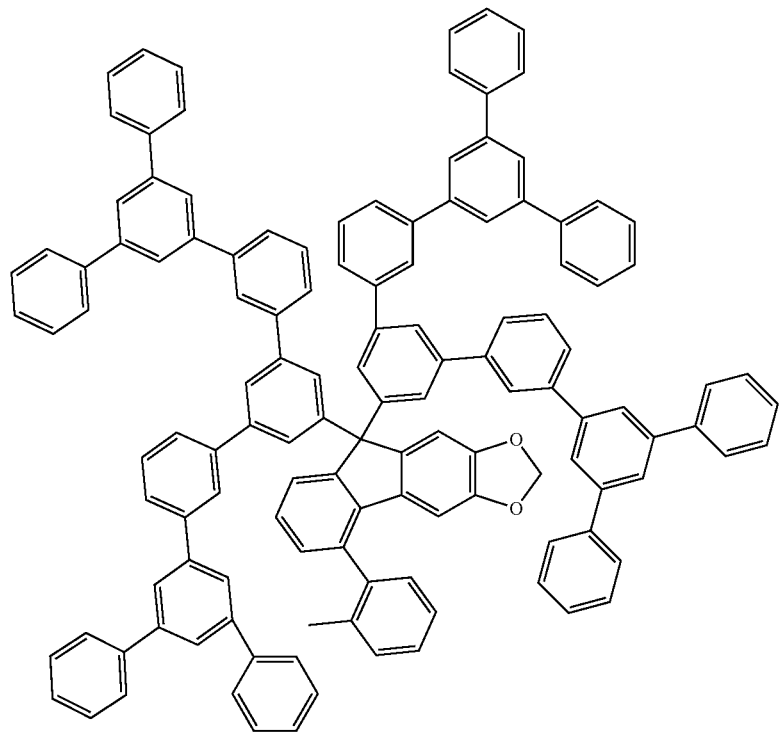
BB-136+BB-180
M-0151
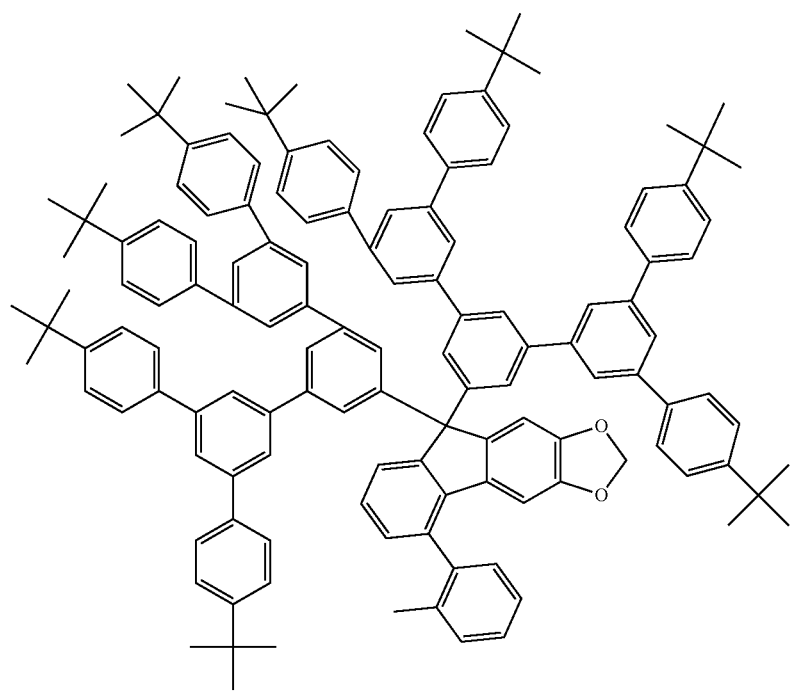
BB-136+BB-181

M-0152
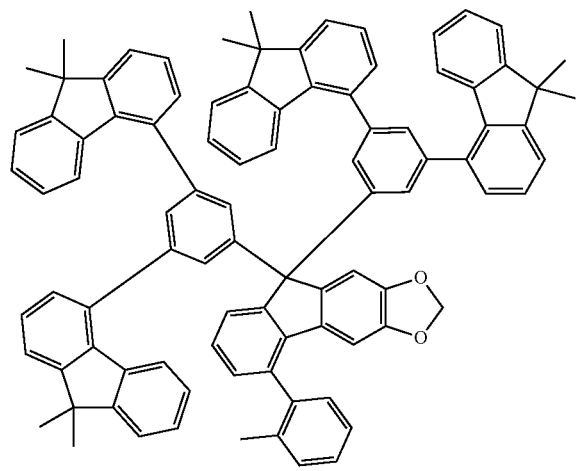
BB-136+BB-182
M-0153
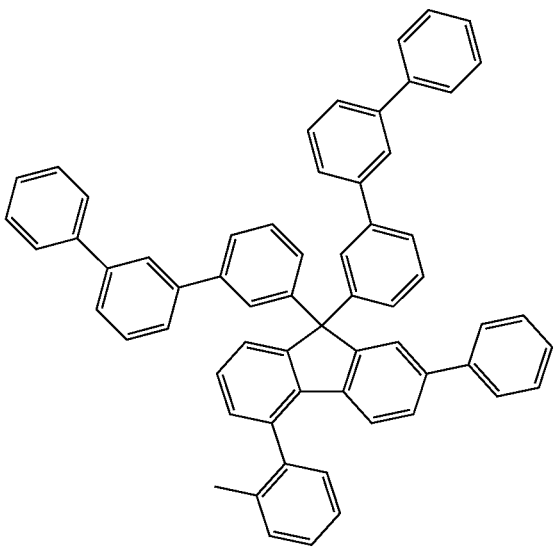
BB-137+BB-179
M-0154
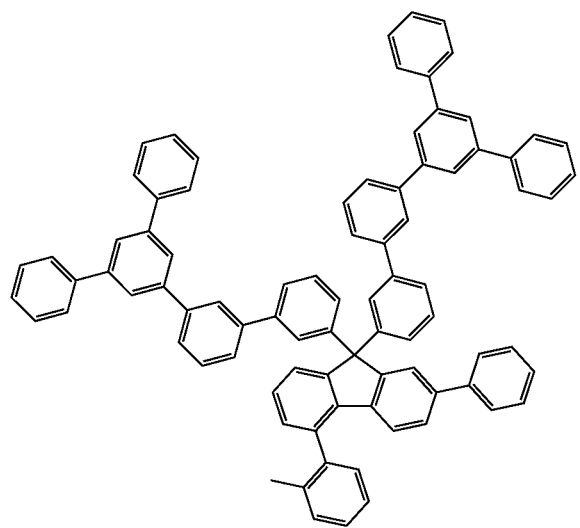
BB-137+BB-180
M-0155
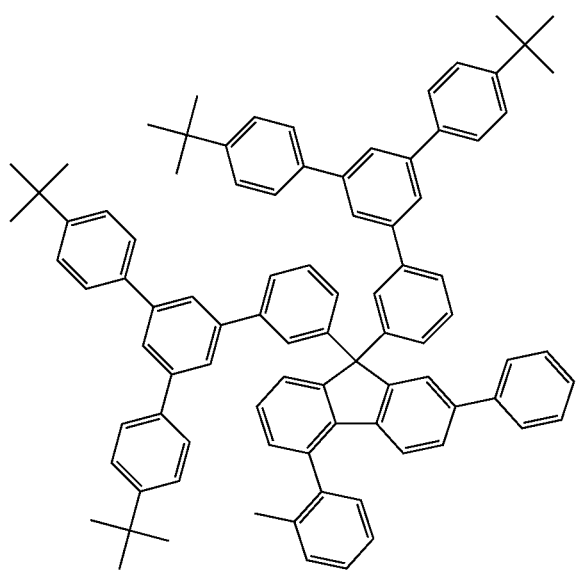
BB-137+BB-181

-continued
M-0156
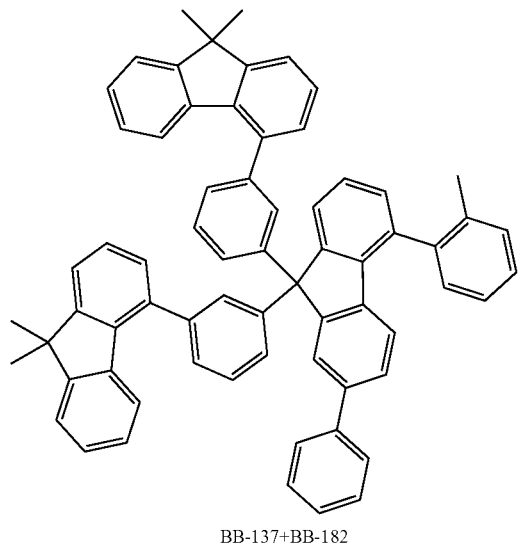
BB-137+BB-182
M-0157
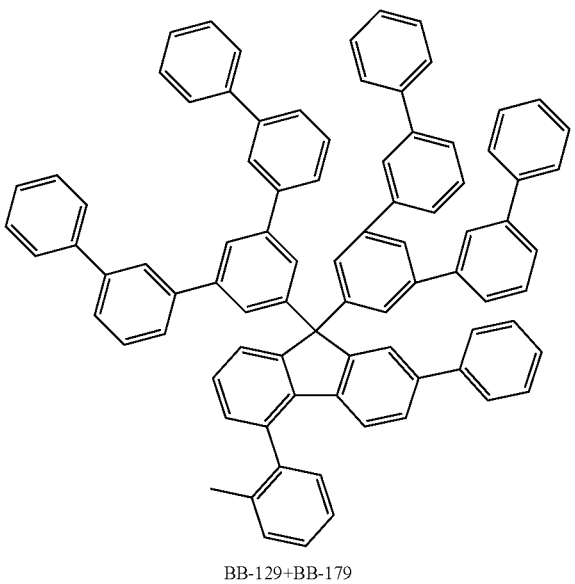
BB-129+BB-179
M-0158
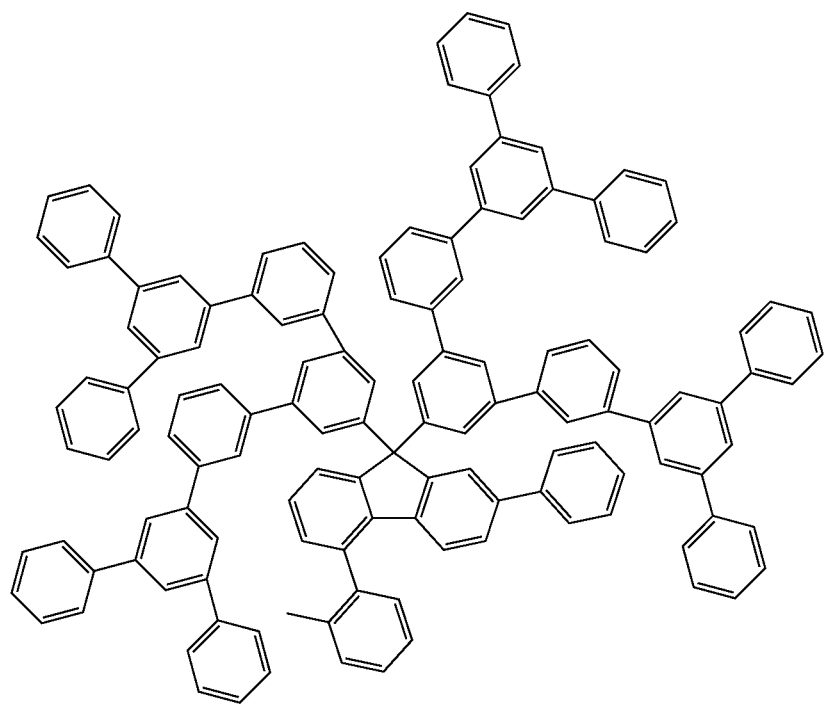
BB-138+BB-180

M-0159
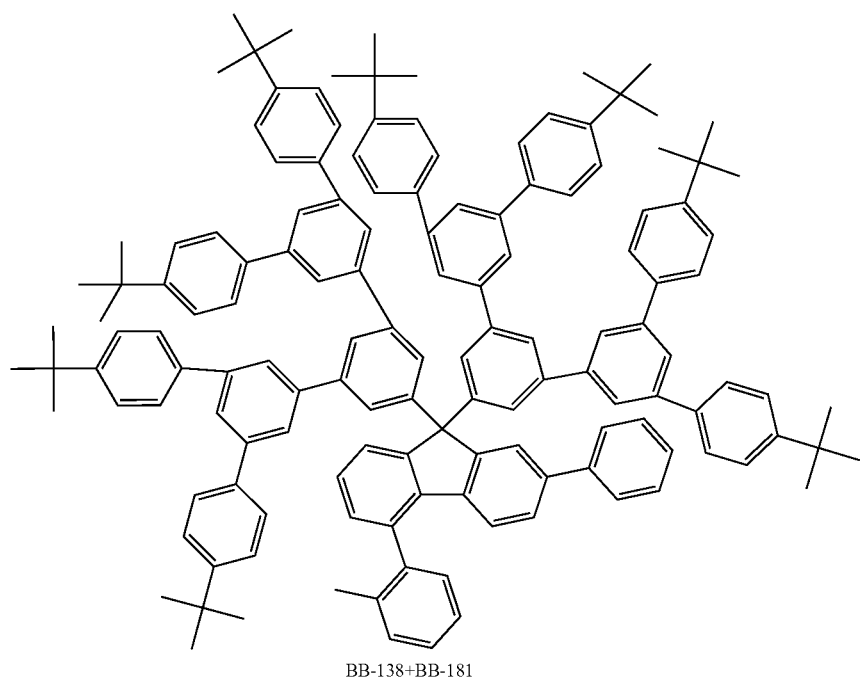
BB-138+BB-181
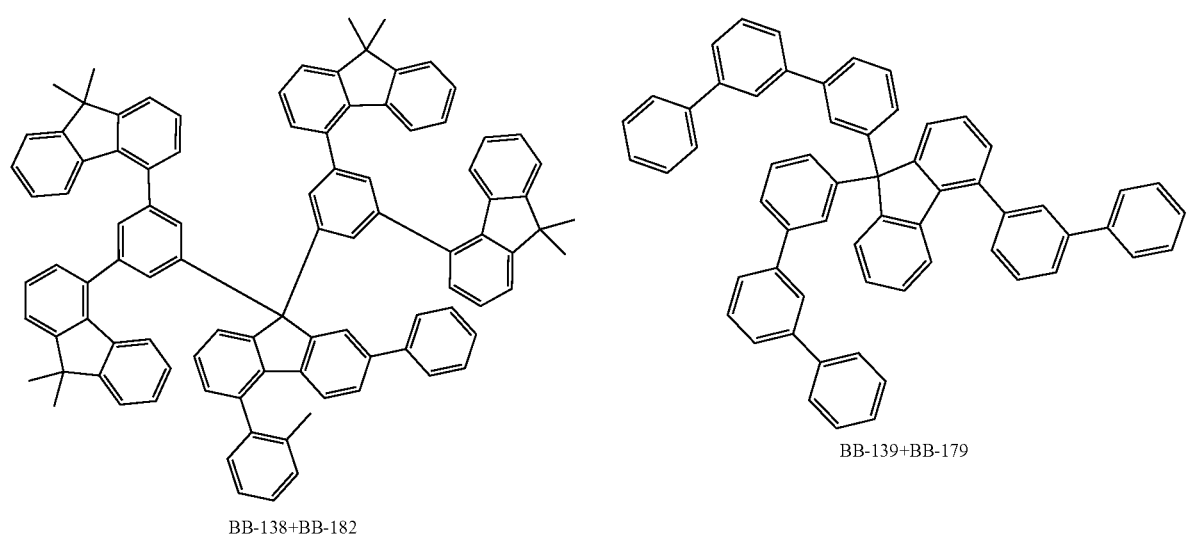
M-0160
BB-138+BB-182
M-0161
BB-139+BB-179

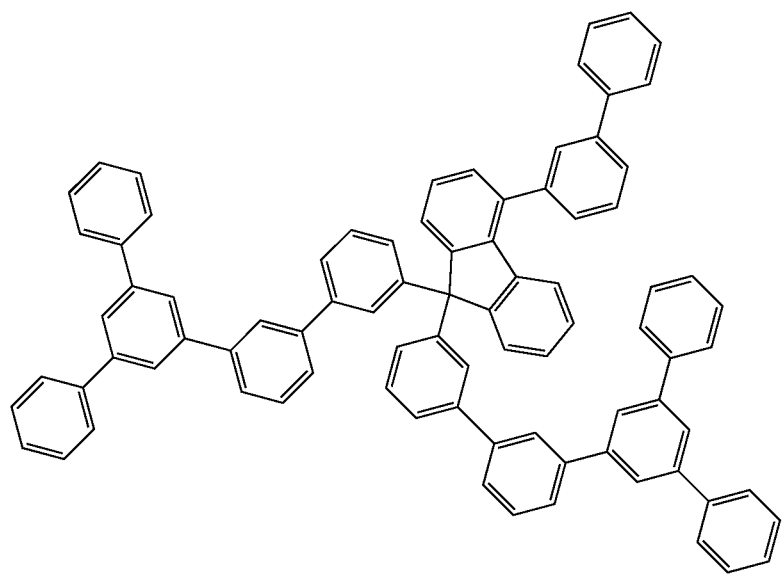
M-0162
BB-139 + BB-180
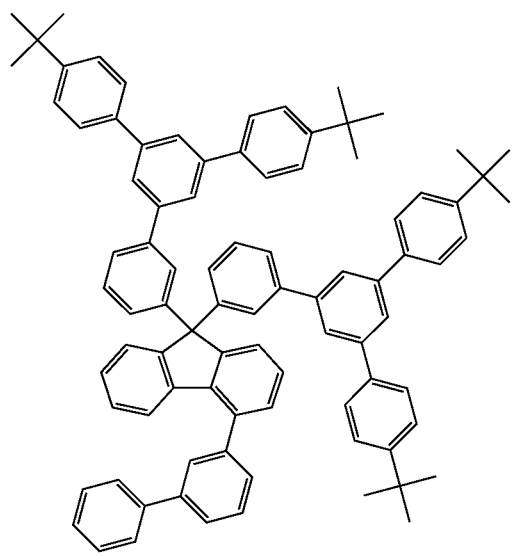
M-0163
BB-139 + BB-181
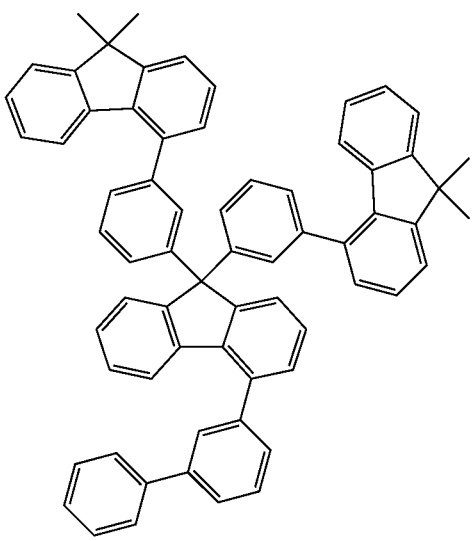
M-0164
BB-139 + BB-182

M-0165
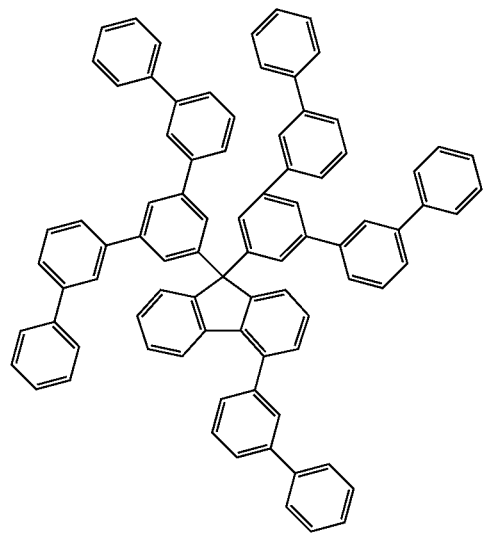
BB-140 + BB-179
M-0166
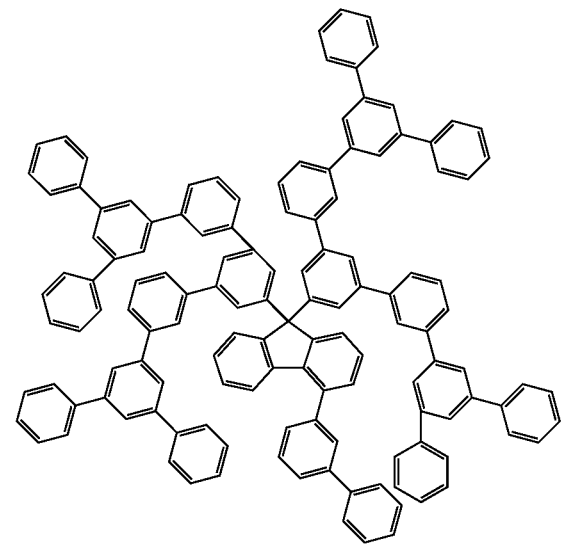
BB-140 + BB-180
M-0167
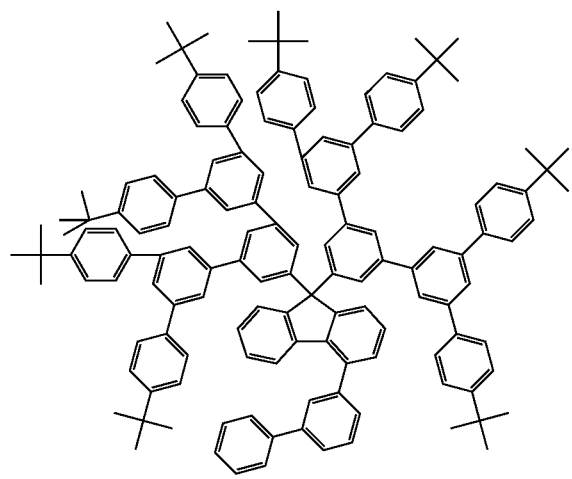
BB-140 + BB-181
M-0168
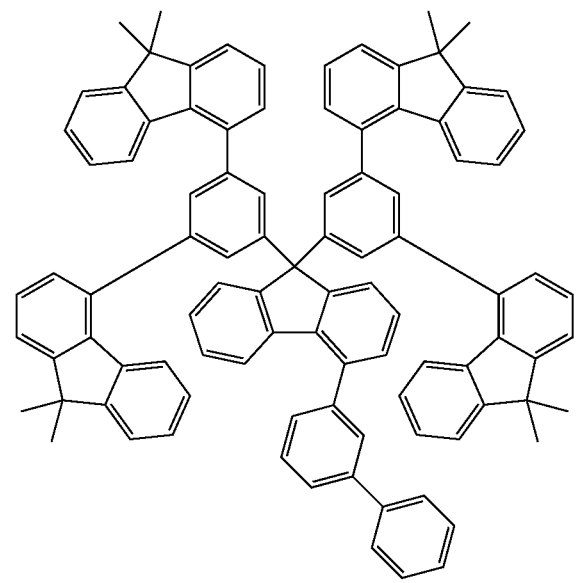
BB-140 + BB-182

M-0169
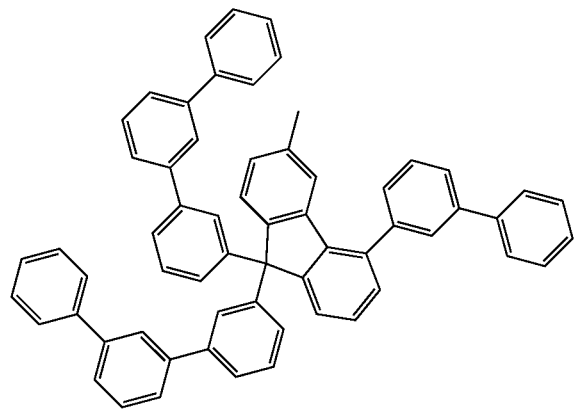
BB-141 + BB-179
M-0170
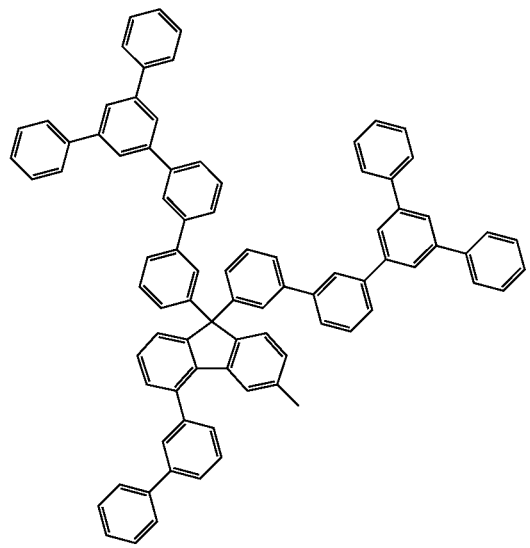
BB-141 + BB-180
M-0171
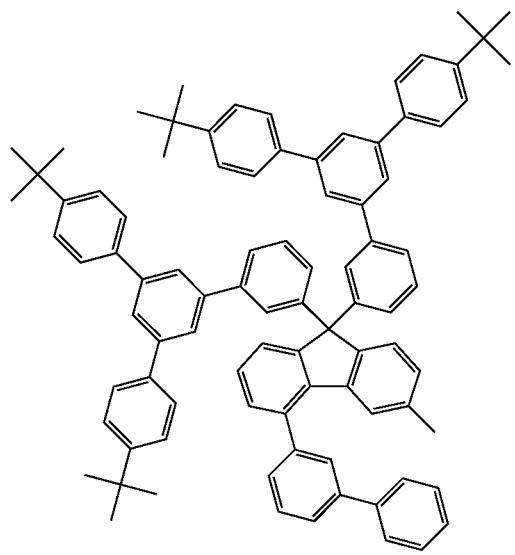
BB-141 + BB-181
M-0172
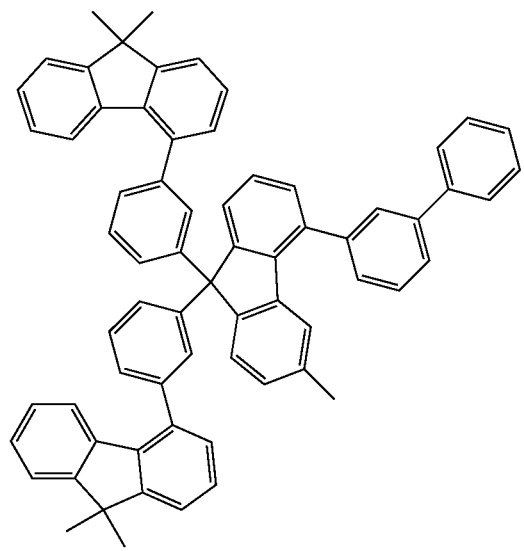
BB-141 + BB-182

-continued
M-0173
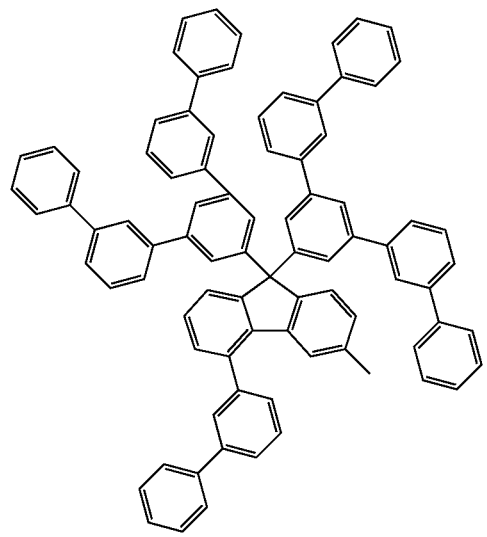
BB-142 + BB-179
M-0174
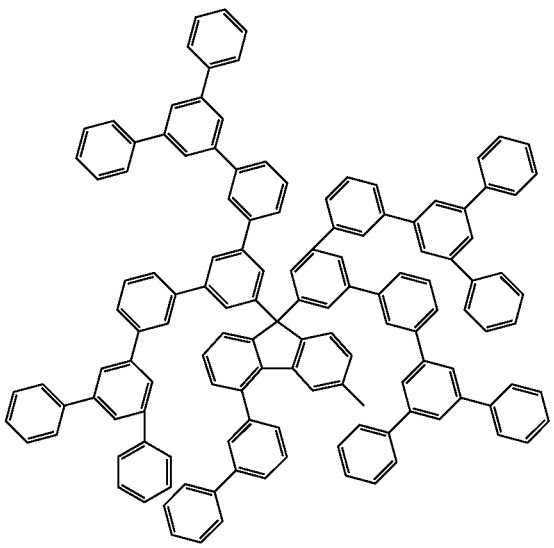
BB-142 + BB-180
M-0175
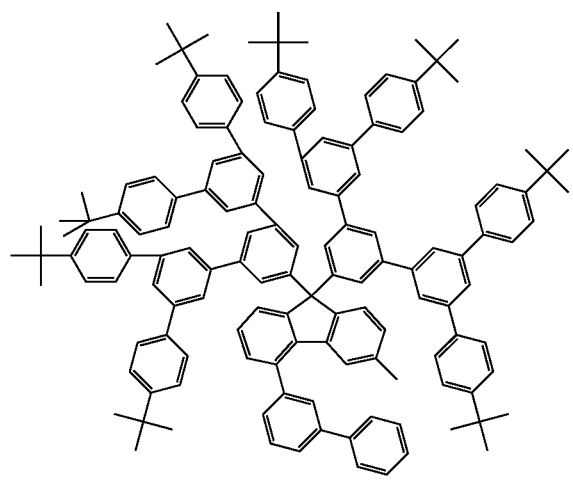
BB-142 + BB-181
M-0176
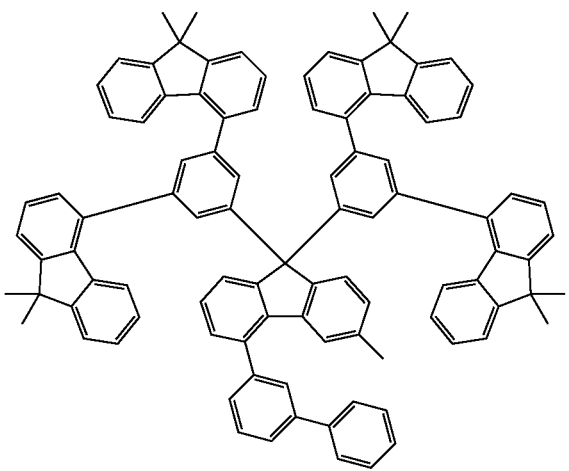
BB-142 + BB-182
M-0177
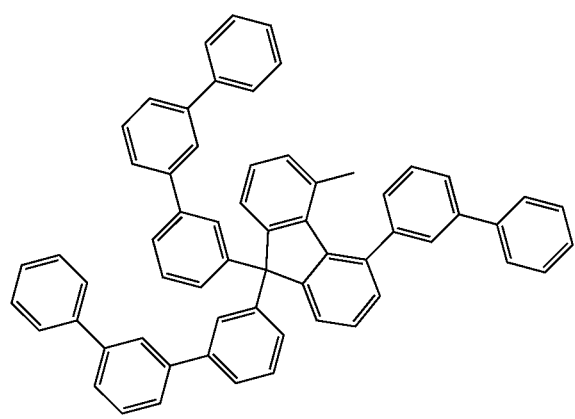
BB-143 + BB-179
M-0178
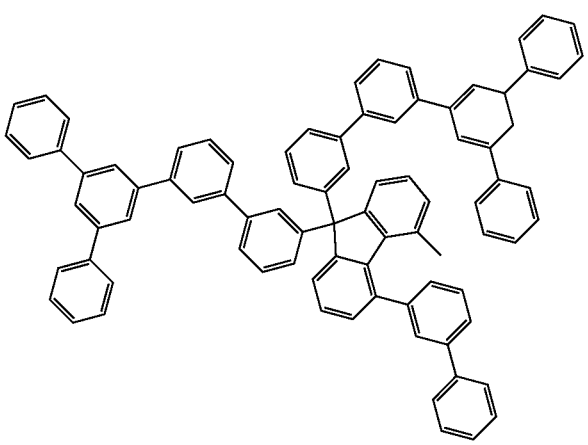
BB-143 + BB-180

M-0179
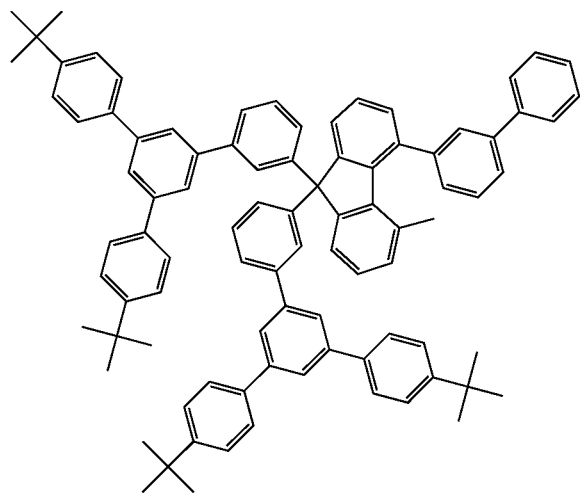
BB-143 + BB-181
M-0180
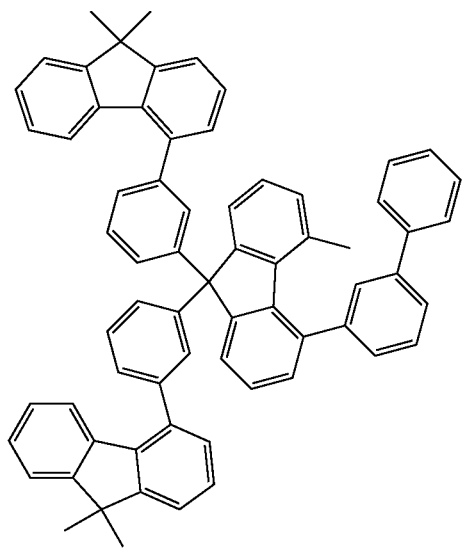
BB-143 + BB-182
M-0181
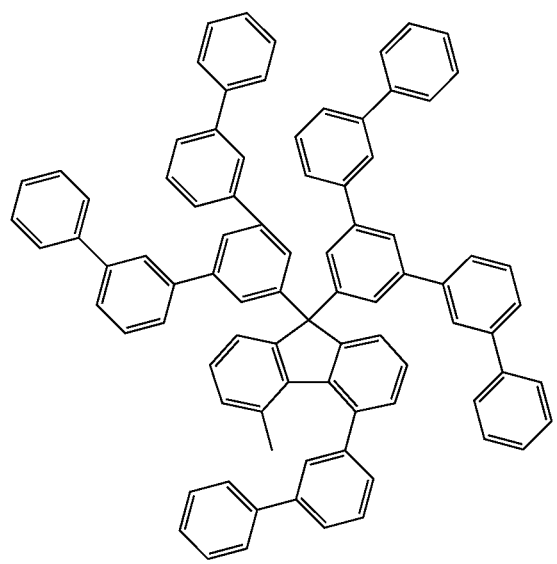
BB-144 + BB-179
M-0182
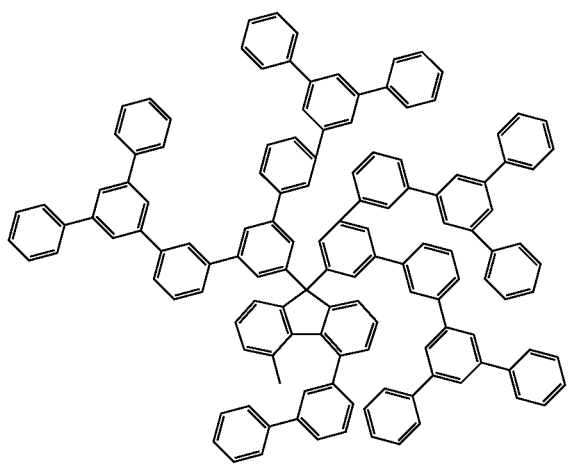
BB-144 + BB-180

M-0183
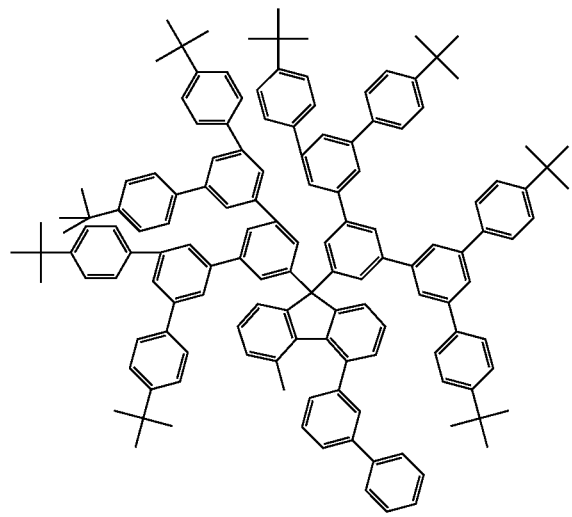
BB-144 + BB-181
M-0184
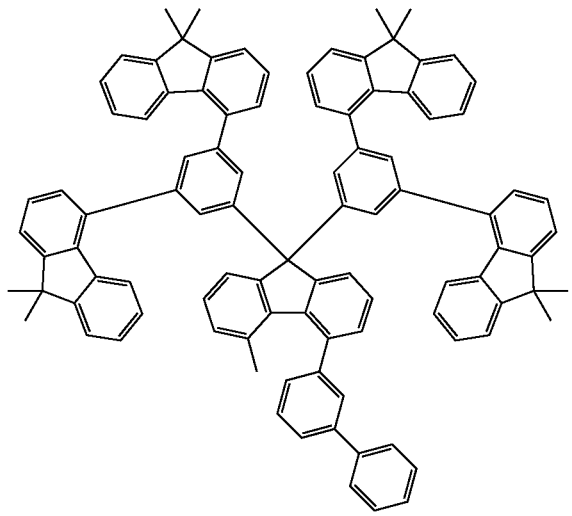
BB-144 + BB-182
M-0185
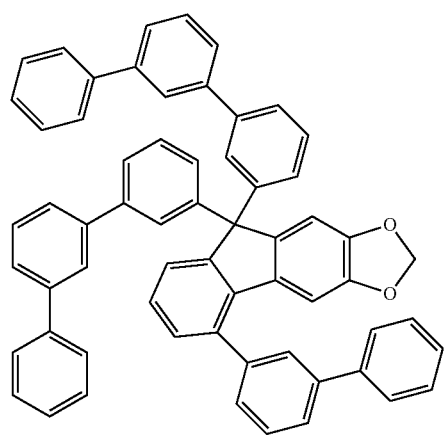
BB-145 + BB-179
M-0186
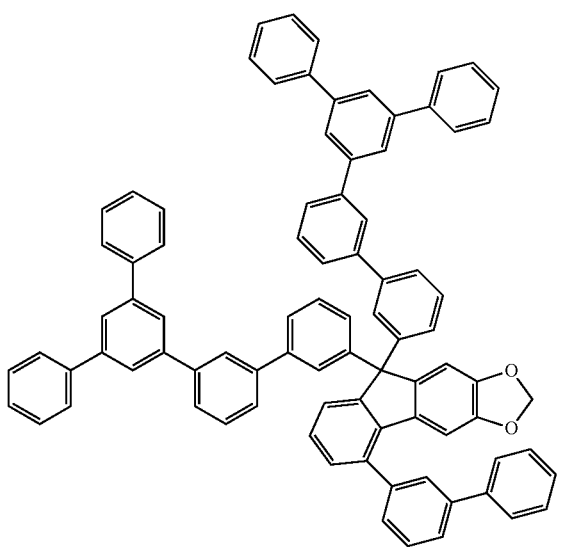
BB-145 + BB-180

-continued
M-0187
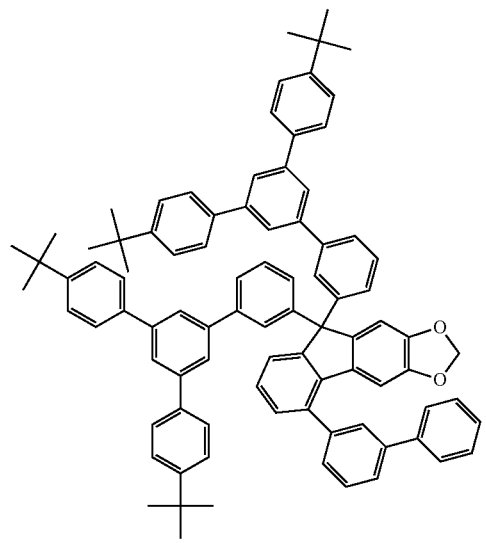
BB-145 + BB-181
M-0188
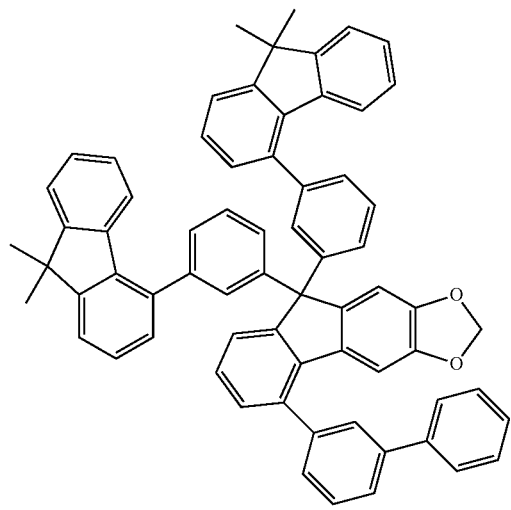
BB-145 + BB-182
M-0189
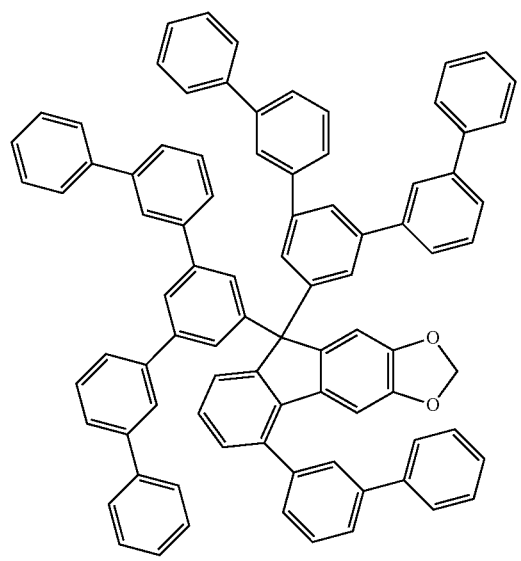
BB-146 + BB-179
M-0190
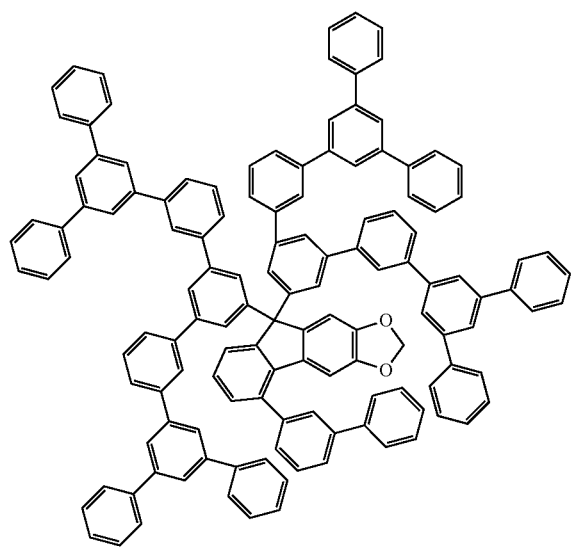
BB-146 + BB-180

-continued
M-0191
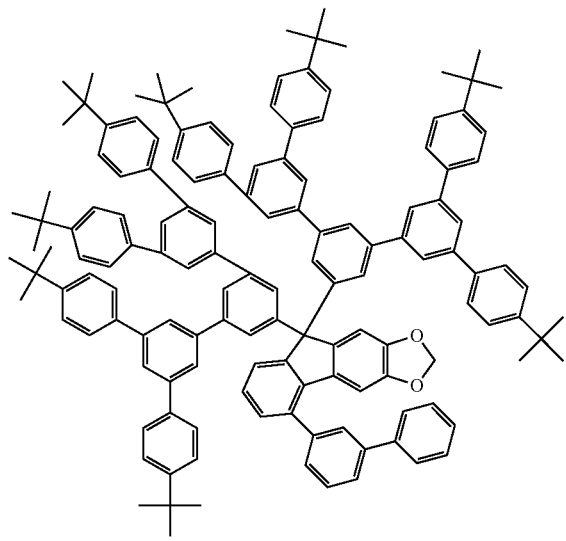
BB-146 + BB-181
M-0192
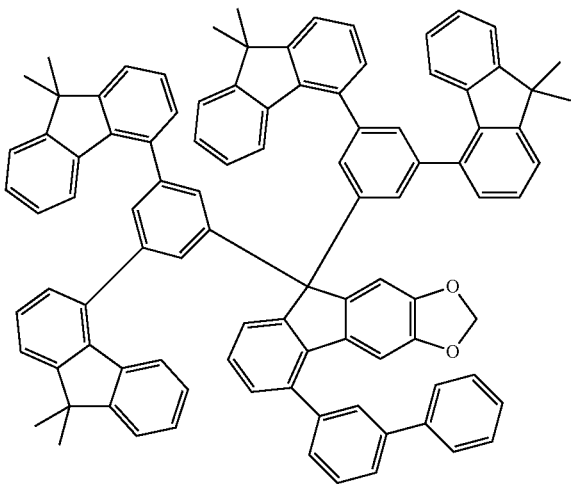
BB-146 + BB-182
M-0193
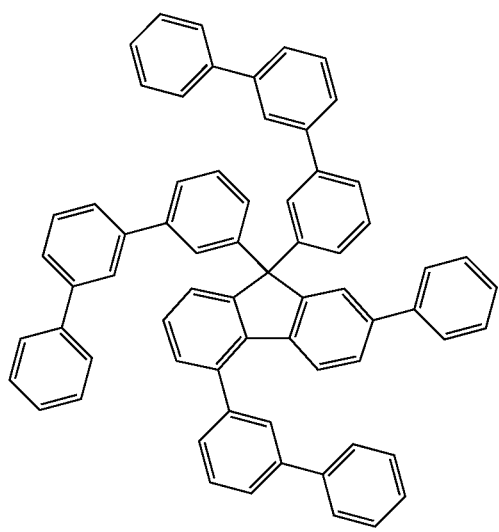
BB-147 + BB-179
M-0194
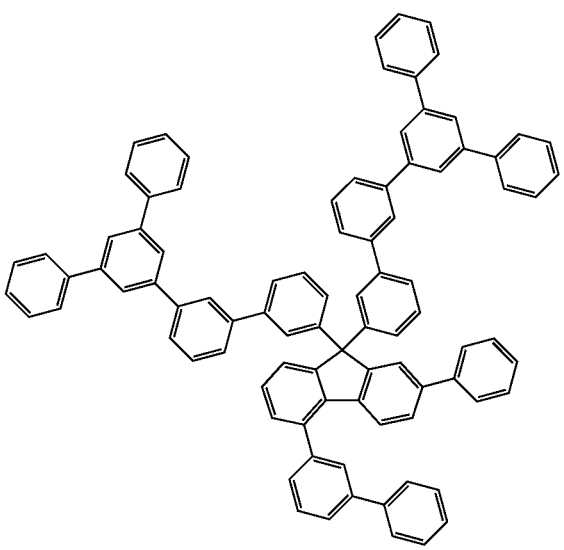
BB-147 + BB-180

-continued
M-0195
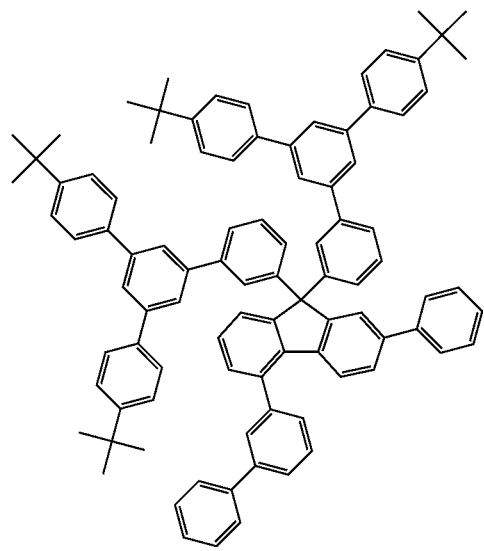
BB-147 + BB-181
M-0196
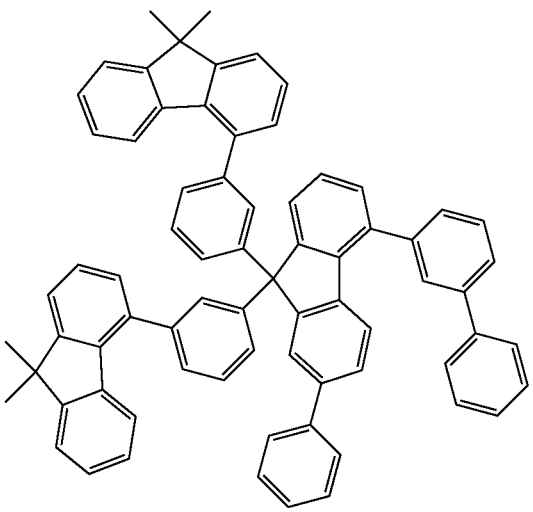
BB-147 + BB-182
M-0197
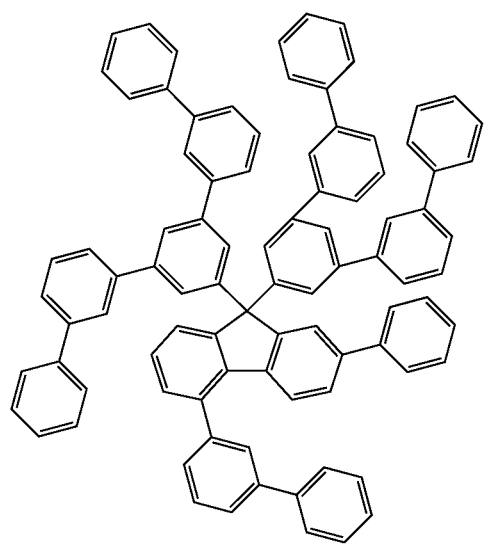
BB-148 + BB-179
M-0198
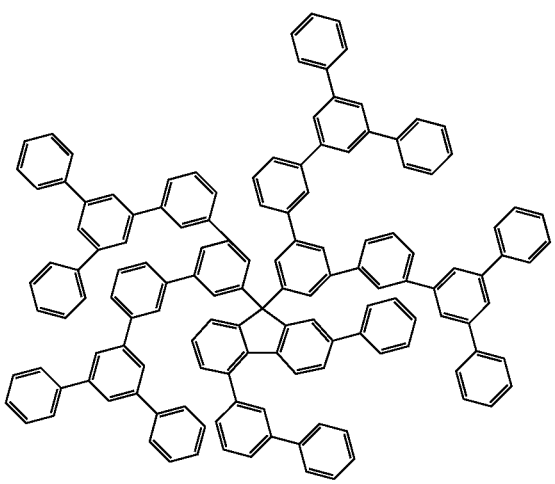
BB-148 + BB-180

-continued
M-0199
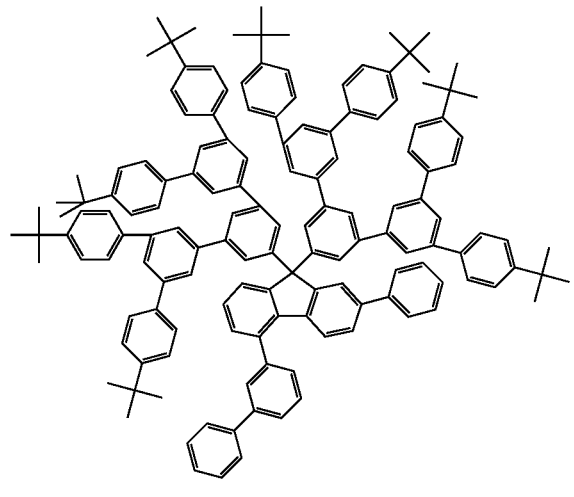
BB-148 + BB-181
M-0200
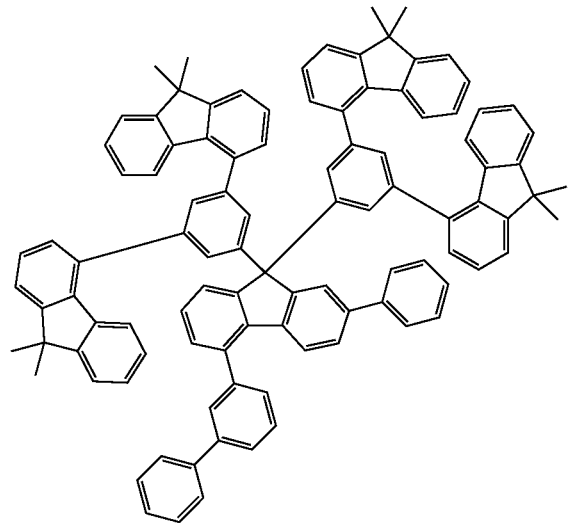
BB-148 + BB-182
M-0201
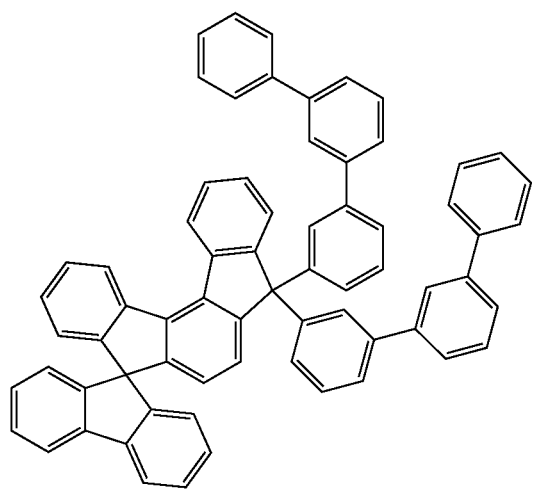
BB-149 + BB-179
M-0202
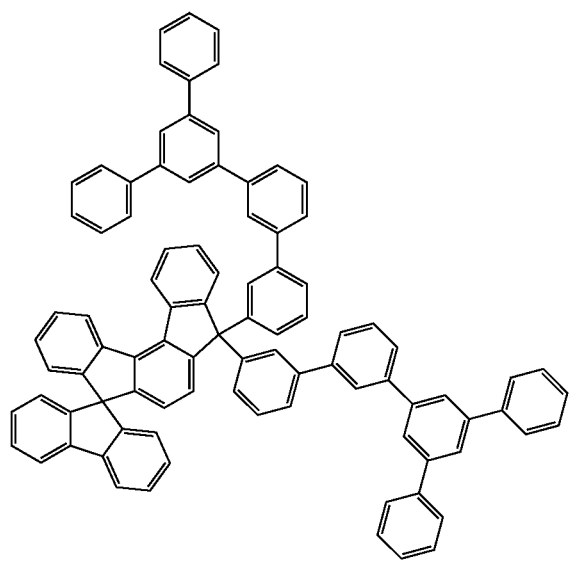
BB-149 + BB-180

-continued
M-0203
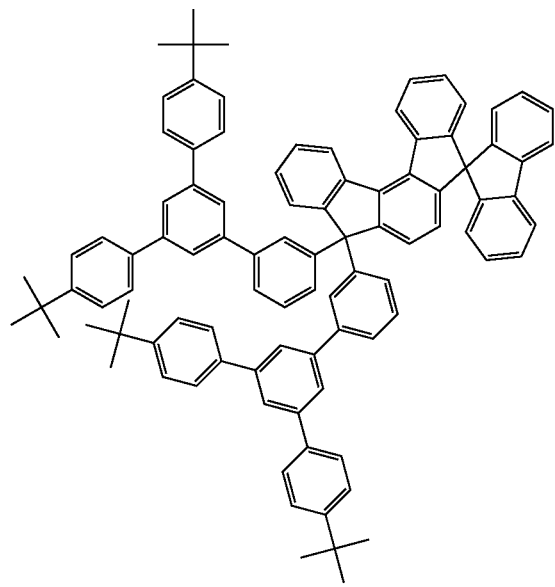
BB-149 + BB-181
M-0204
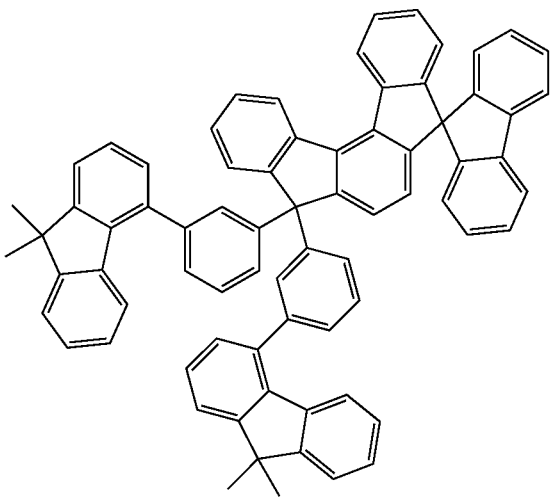
BB-149 + BB-182
M-0205
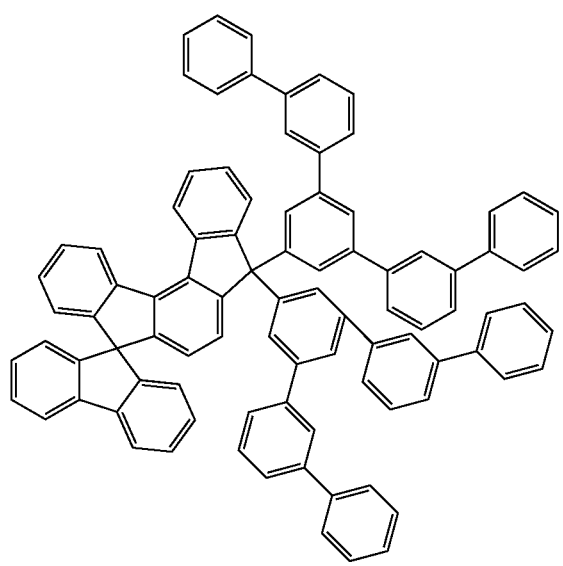
BB-150 + BB-179
M-0206
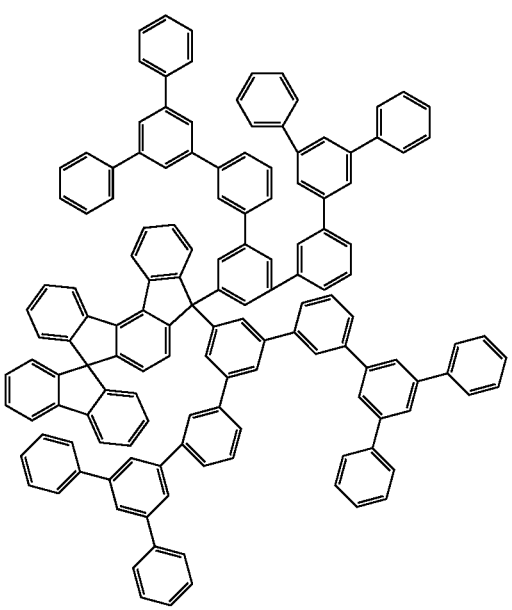
BB-150 + BB-180

-continued
M-0207
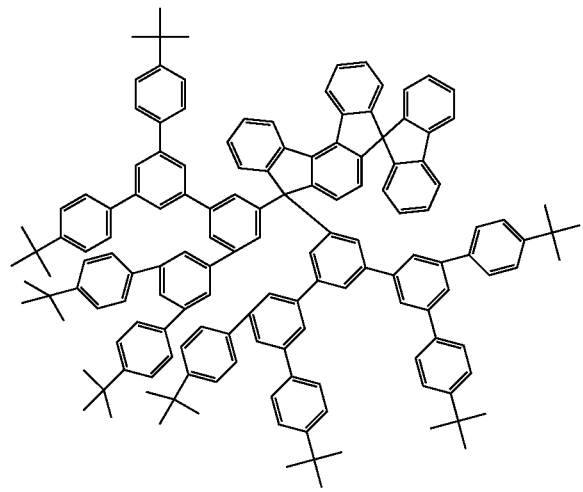
BB-150 + BB-181
M-0208
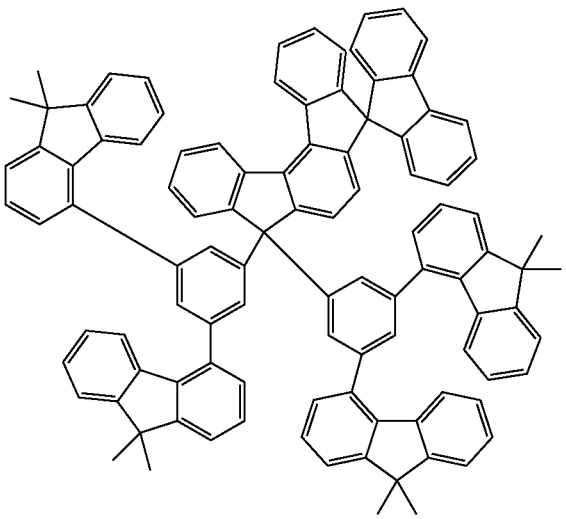
BB-150 + BB-182
M-0209
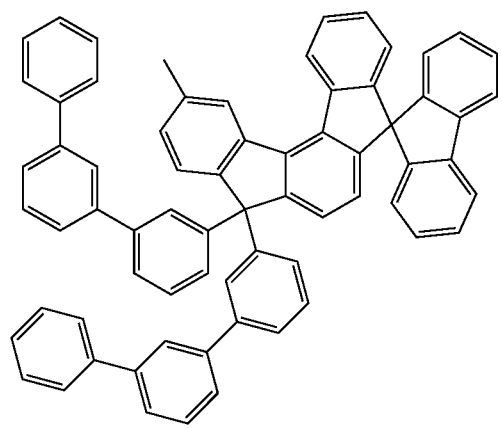
BB-151 + BB-179
M-0210
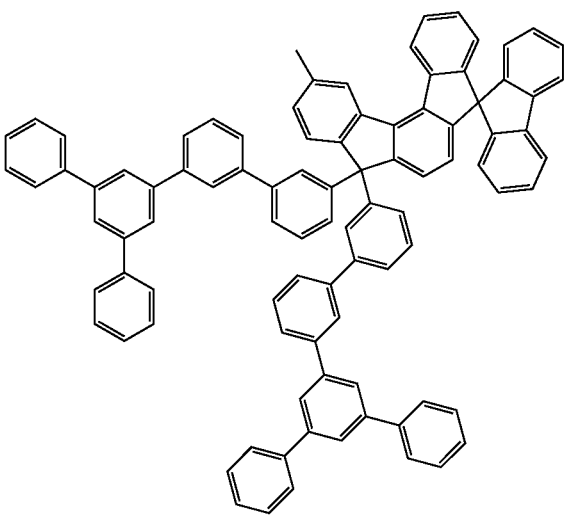
BB-151 + BB-180

-continued
M-0211
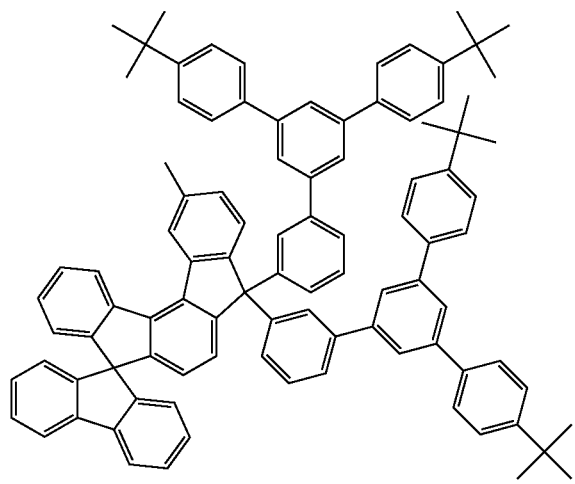
BB-151 + BB-181
M-0212
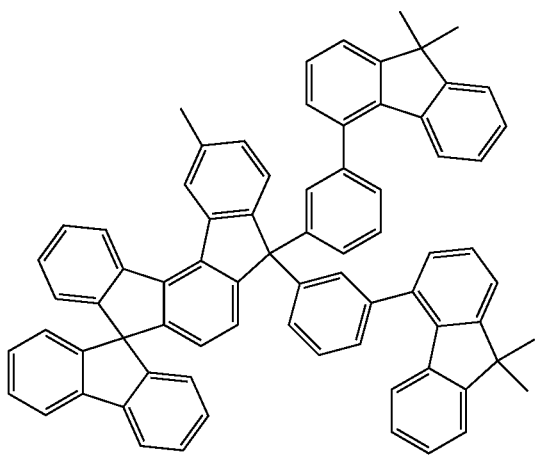
BB-151 + BB-182
M-0213
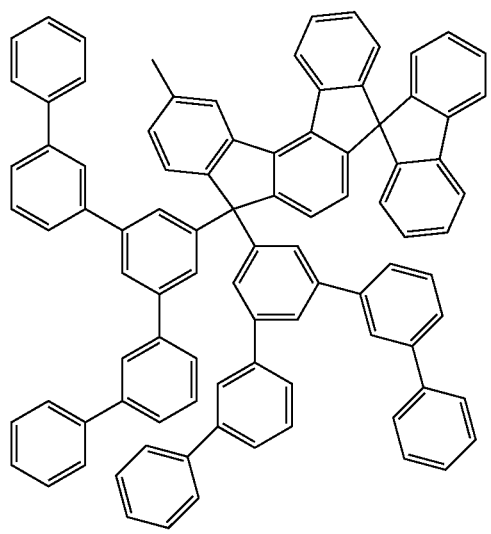
BB-152 + BB-179
M-0214
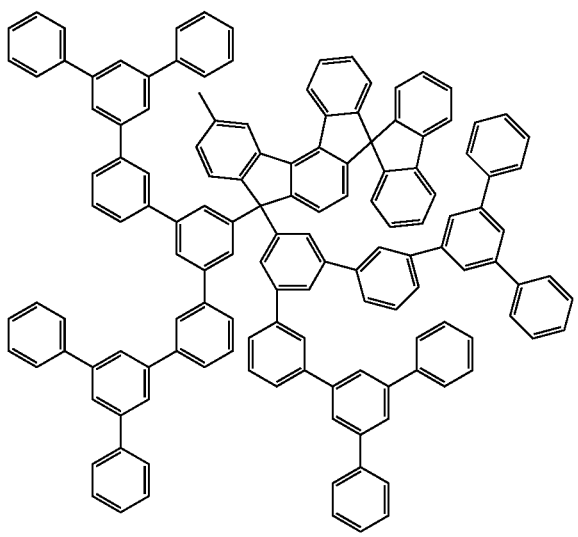
BB-152 + BB-180

-continued
M-0215
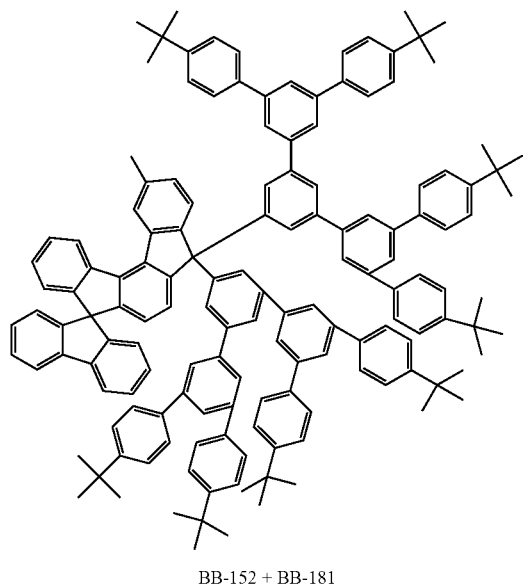
BB-152 + BB-181
M-0216
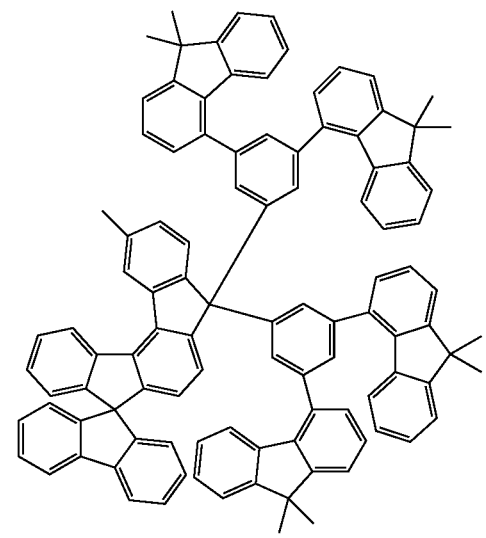
BB-152 + BB-182
M-0217
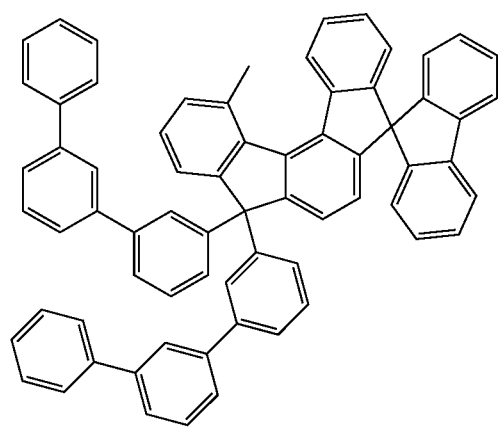
BB-153 + BB-179
M-0218
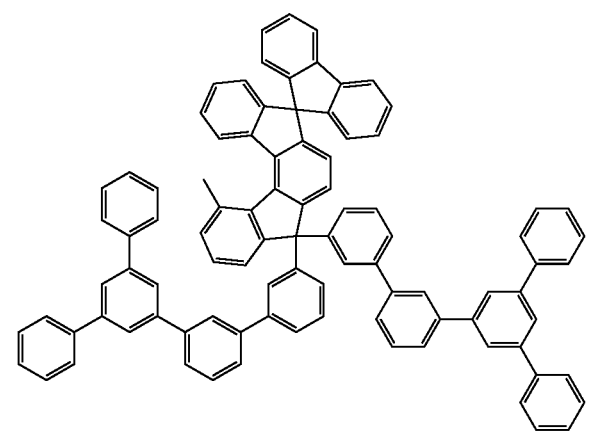
BB-153 + BB-180
M-0219
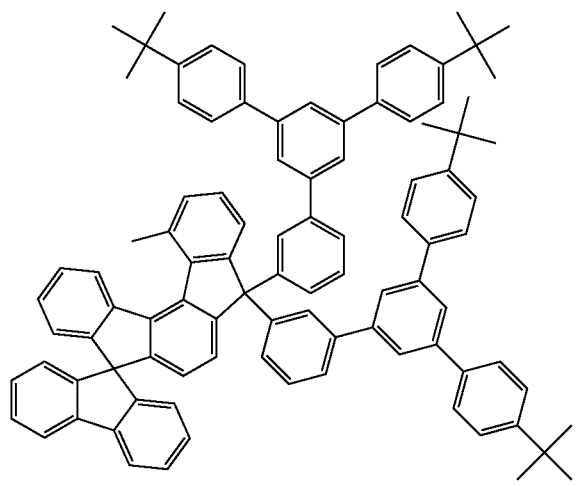
BB-153 + BB-181
M-0220
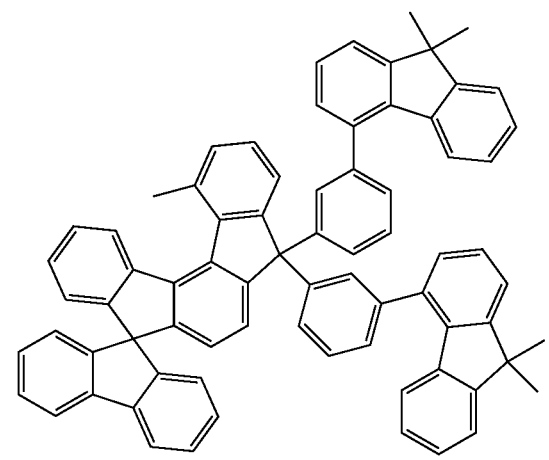
BB-153 + BB-182

-continued
M-0221
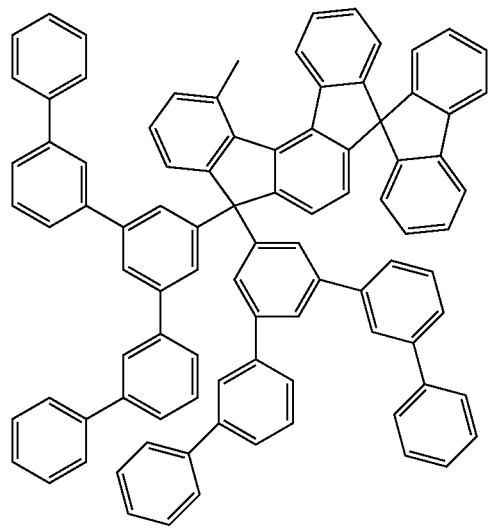
BB-154 + BB-179
M-0222
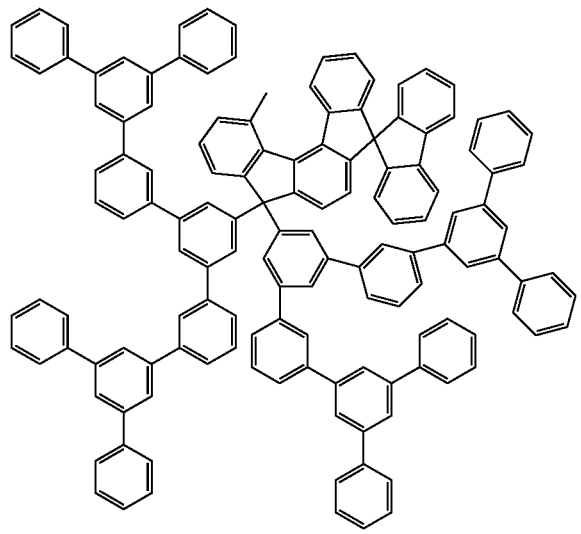
BB-154 + BB-180
M-0223
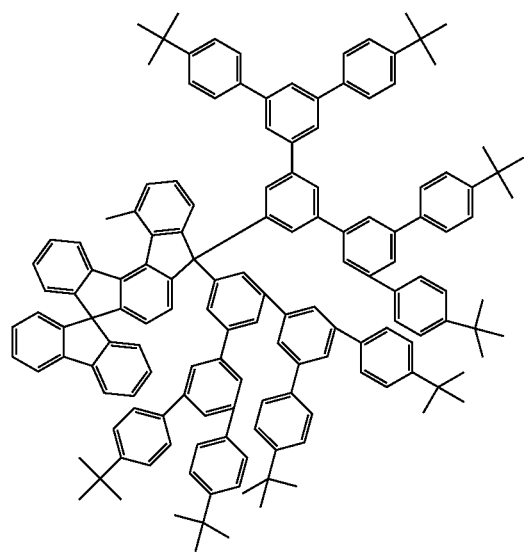
BB-154 + BB-181
M-0224
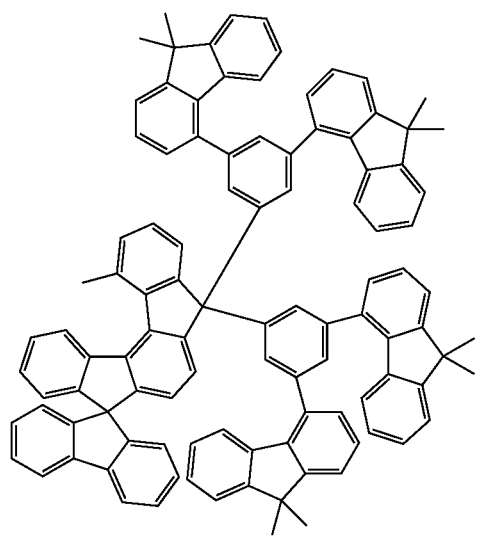
BB-154 + BB-182

-continued
M-0225
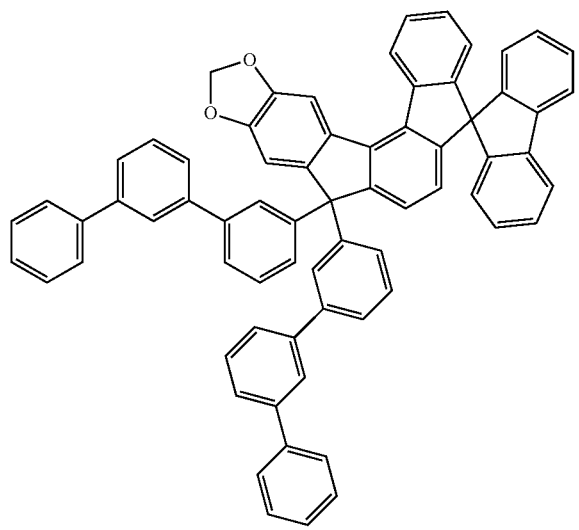
BB-155 + BB-179
M-0226
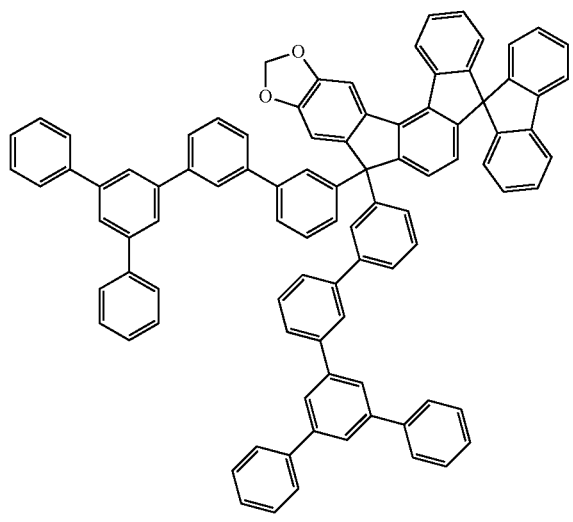
BB-155 + BB-180
M-0227
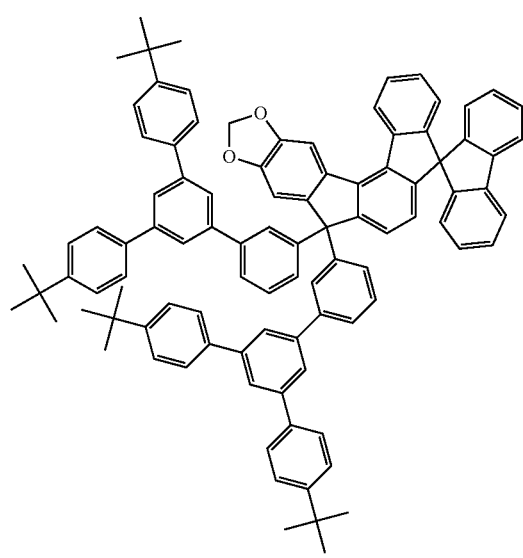
BB-155 + BB-181
M-0228
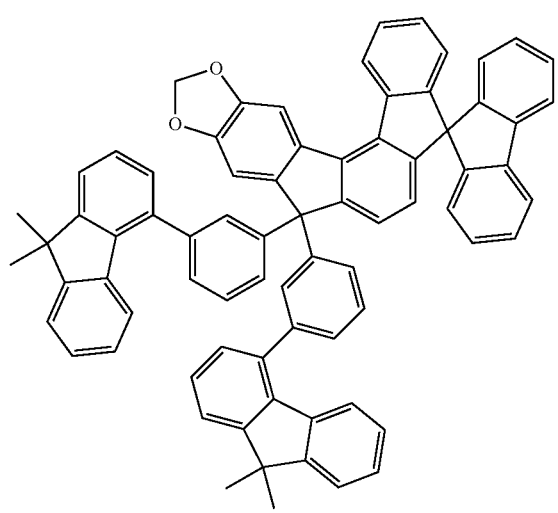
BB-155 + BB-182

-continued
M-0229
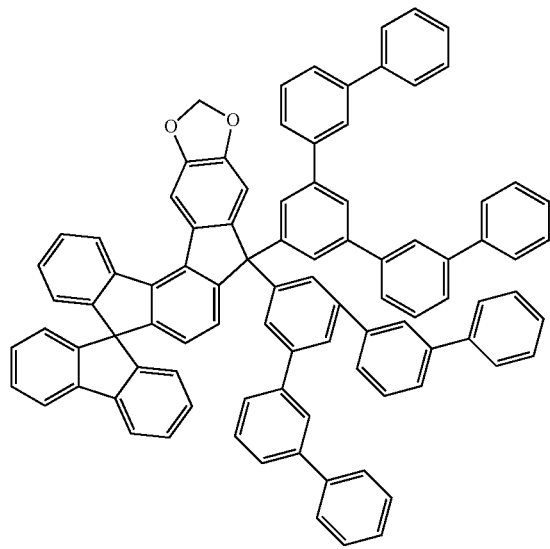
BB-156 + BB-179
M-0230
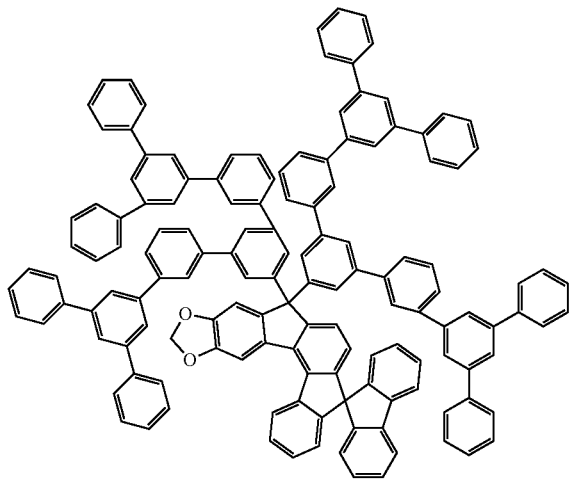
BB-156 + BB-180
M-0231
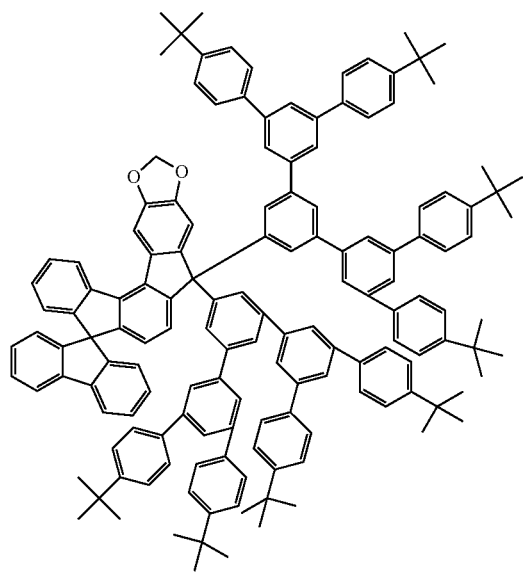
BB-156 + BB-181
M-0232
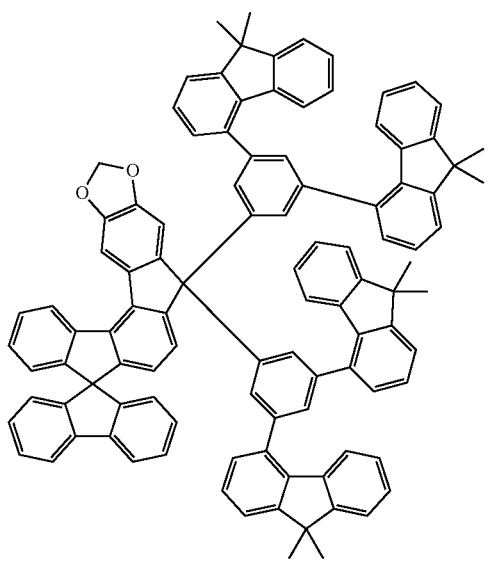
BB-156 + BB-182

-continued
M-0233
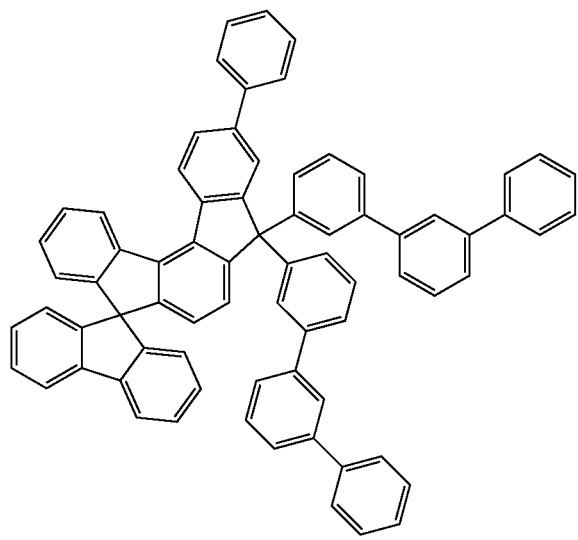
BB-157 + BB-179
M-0234
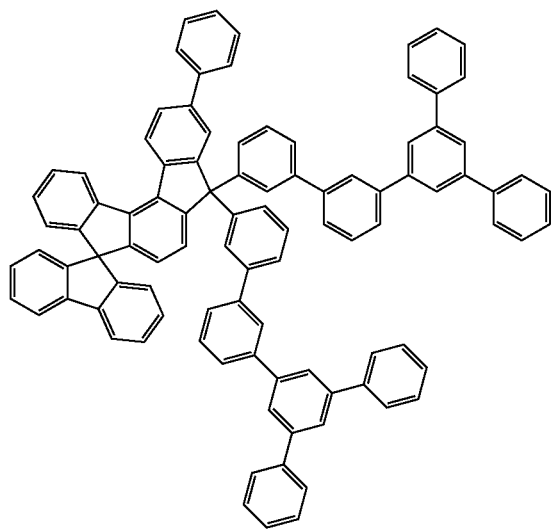
BB-157 + BB-180
M-0235
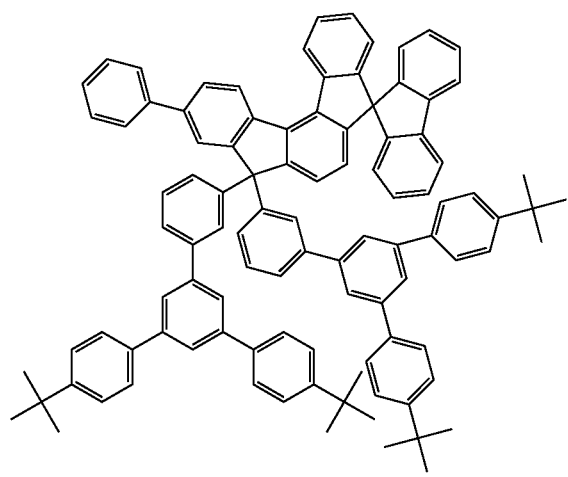
BB-157 + BB-181
M-0236
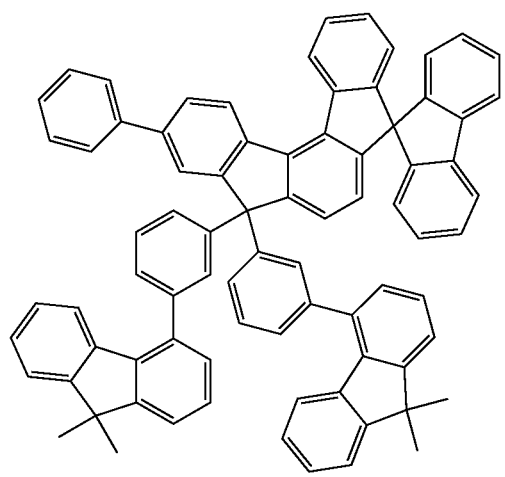
BB-157 + BB-182

-continued
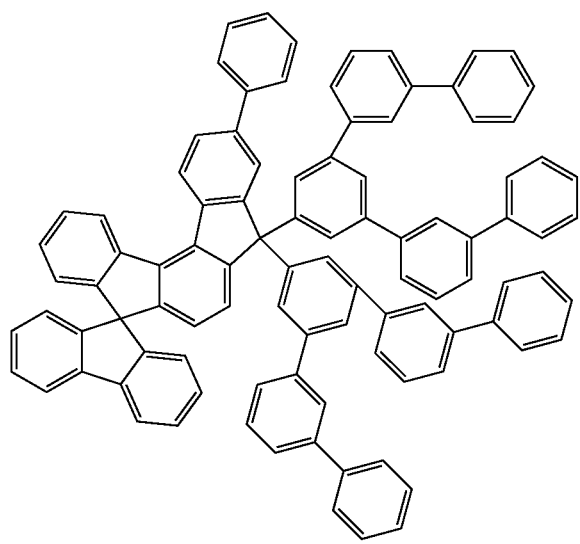
BB-158 + BB-179
M-0237
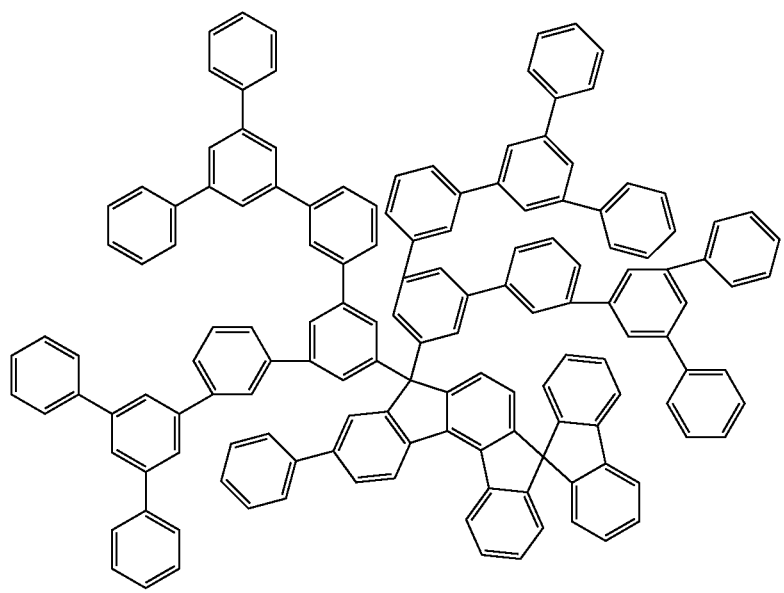
BB-158 + BB-180
M-0238

-continued
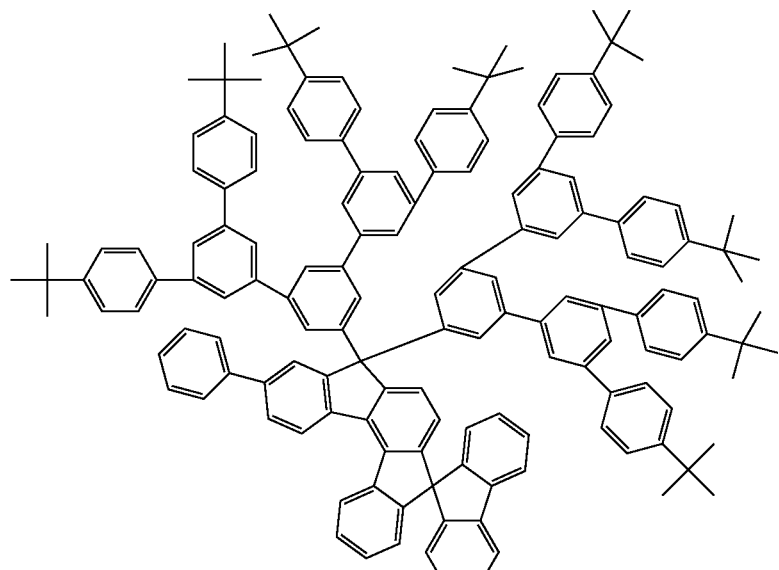
BB-158 + BB-181
M-0239
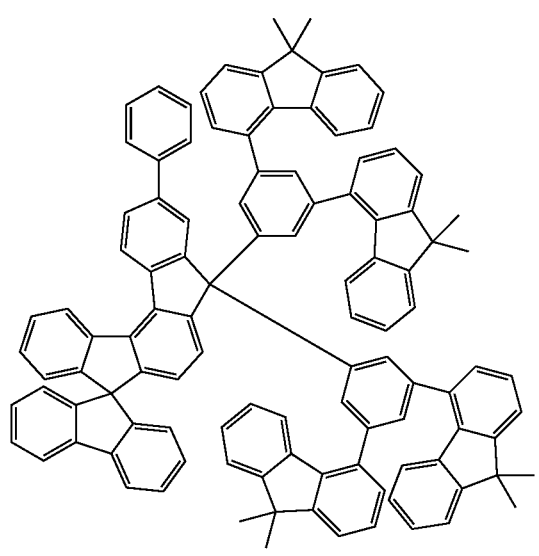
BB-158 + BB-182
M-0240
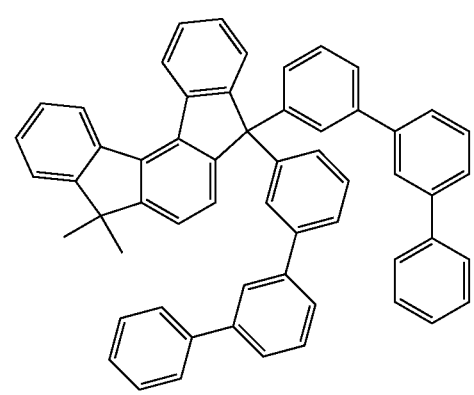
BB-159 + BB-179
M-0241

-continued
M-0242
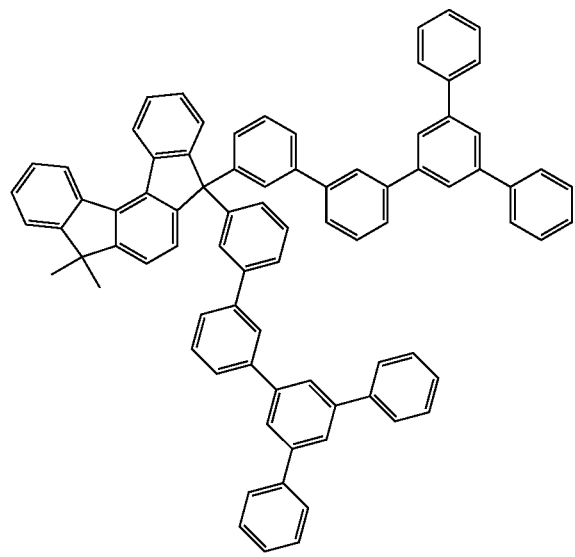
BB-159 + BB-180
M-0243
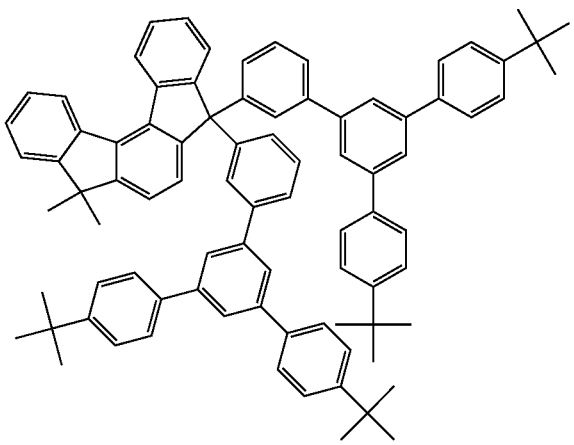
BB-159 + BB-181
M-0244
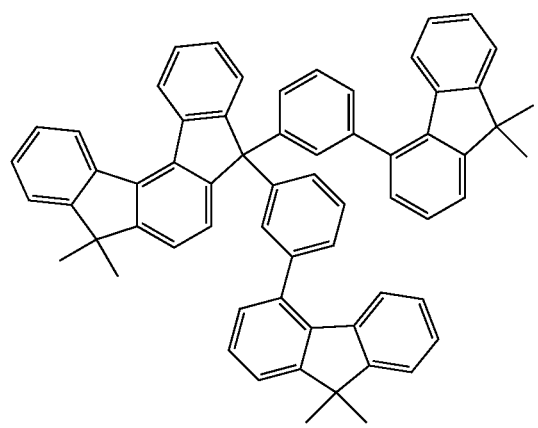
BB-159 + BB-182
M-0245
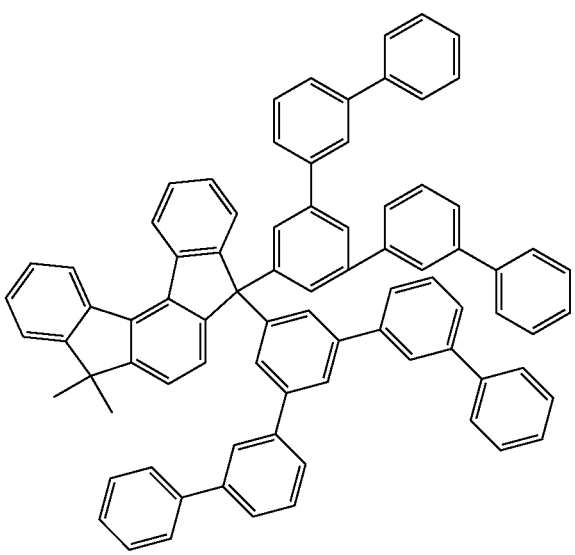
BB-160 + BB-179

-continued
M-0246
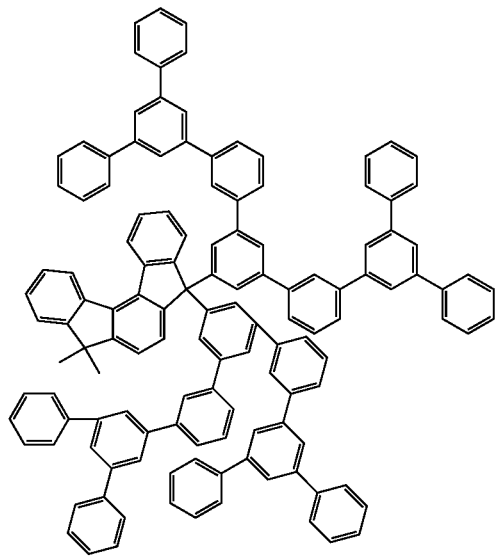
BB-160 + BB-180
M-0247
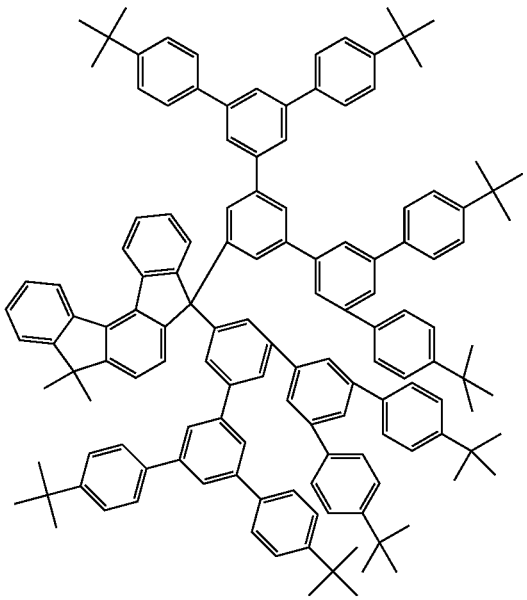
BB-160 + BB-181
M-0248
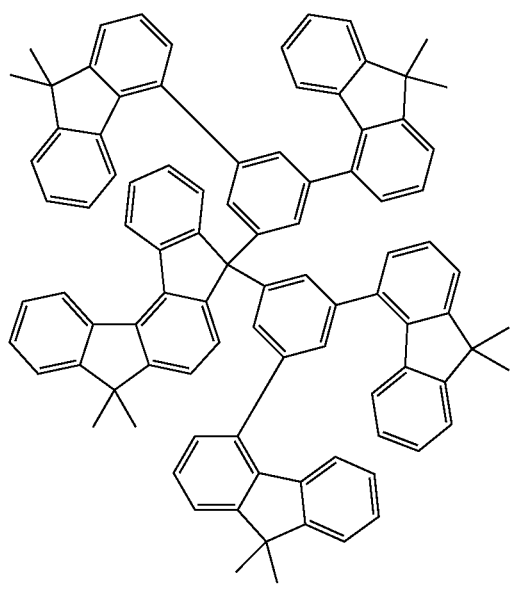
BB-160 + BB-182
M-0249
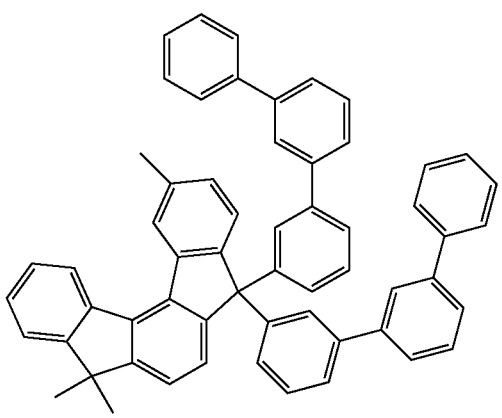
BB-161 + BB-179

-continued
M-0250
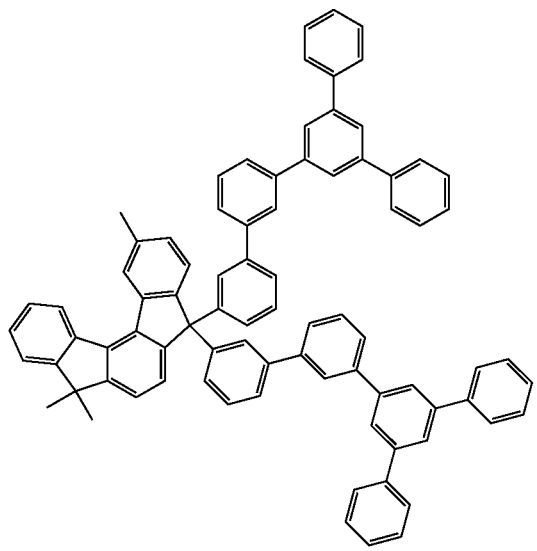
BB-161 + BB-180
M-0251
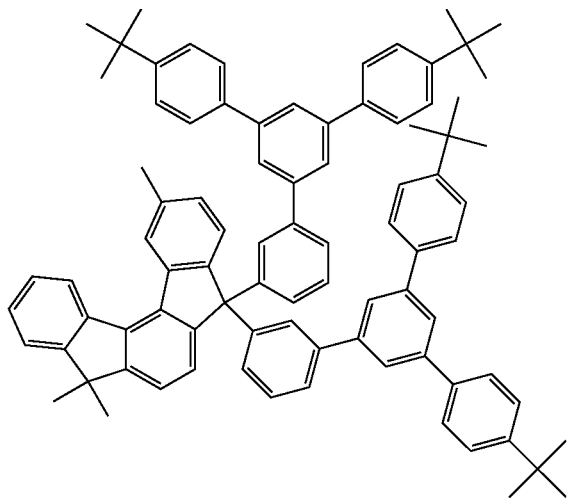
BB-161 + BB-181
M-0252
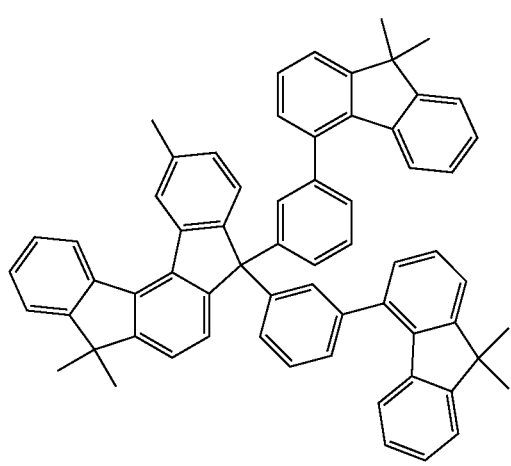
BB-161 + BB-182
M-0253
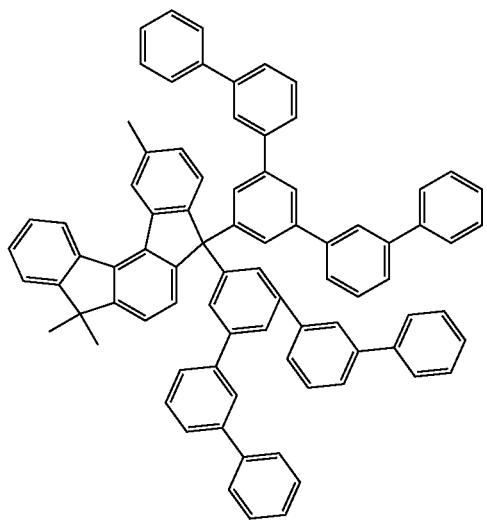
BB-162 + BB-179

-continued
M-0254
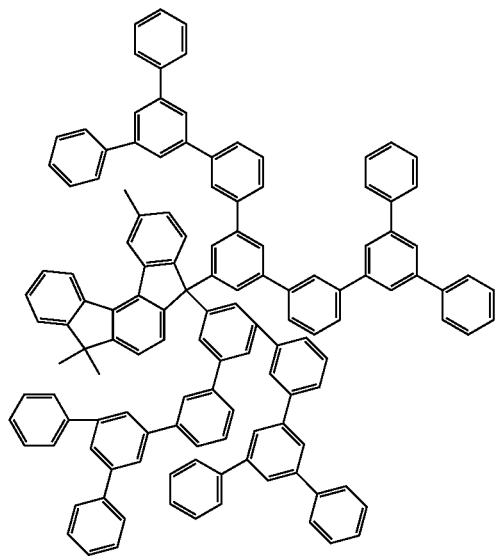
BB-162 + BB-180
M-0255
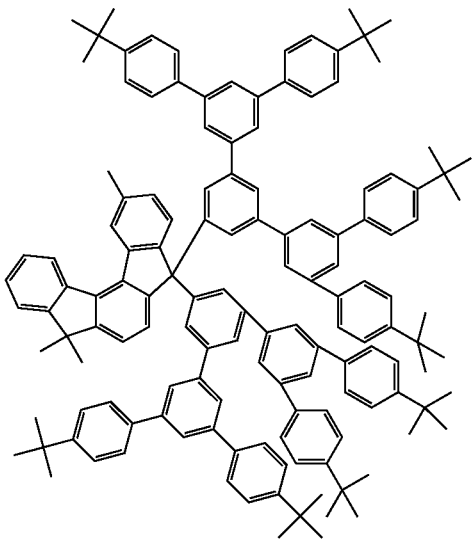
BB-162 + BB-181
M-0256
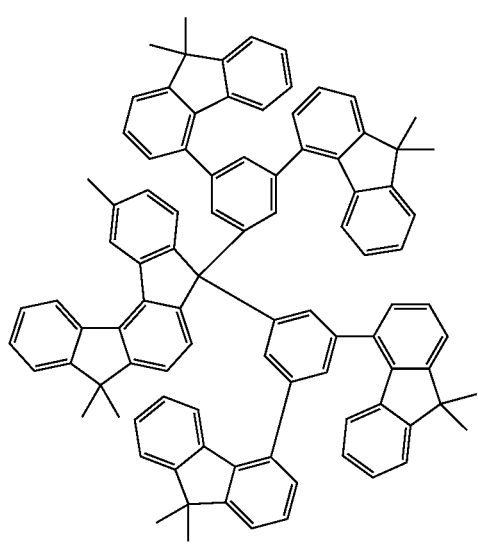
BB-162 + BB-182
M-0257
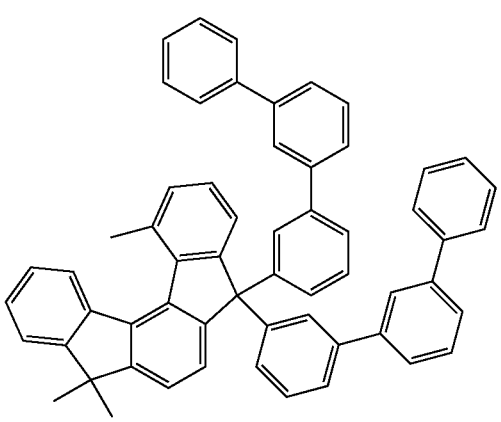
BB-163 + BB-179

-continued
M-0258
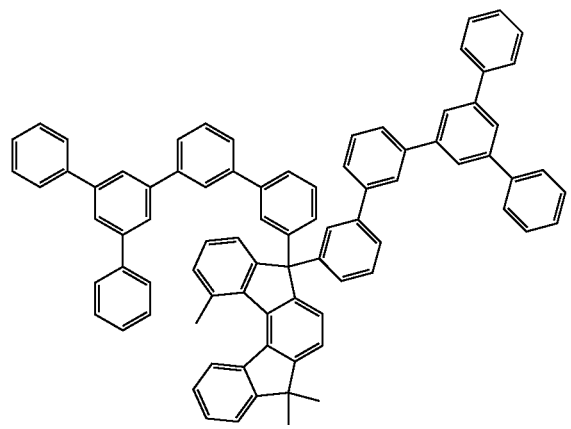
BB-163 + BB-180
M-0259
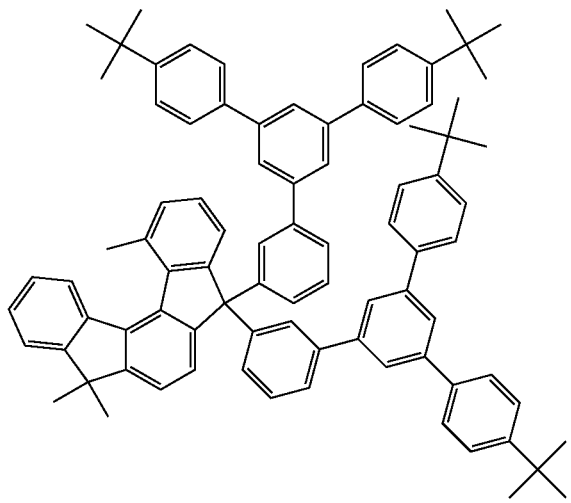
BB-163 + BB-181
M-0260
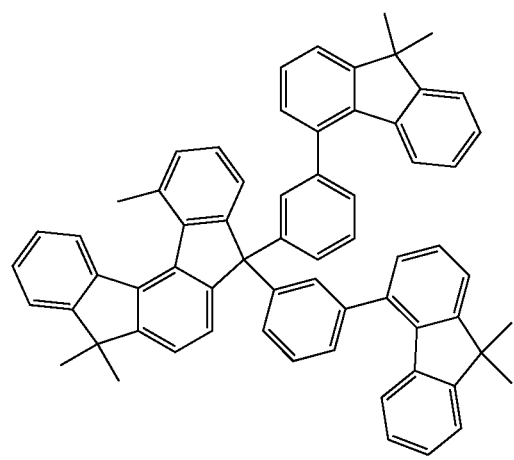
BB-163 + BB-182
M-0261
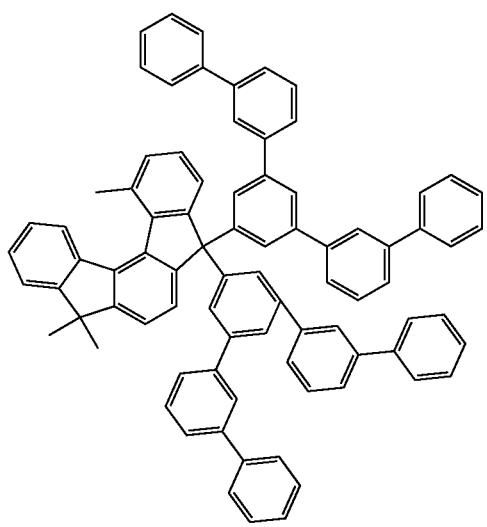
BB-164 + BB-179

-continued
M-0262
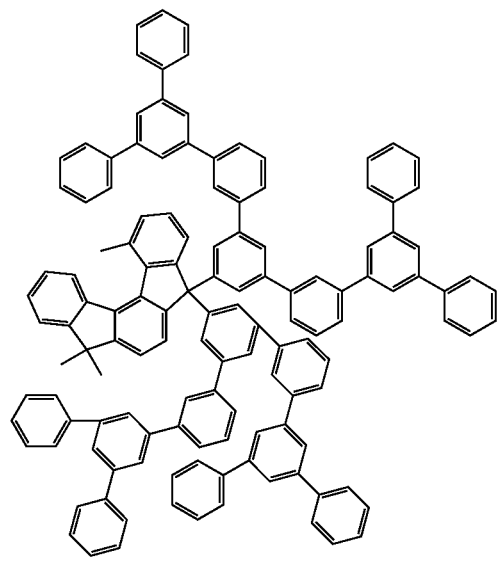
BB-164 + BB-180
M-0263
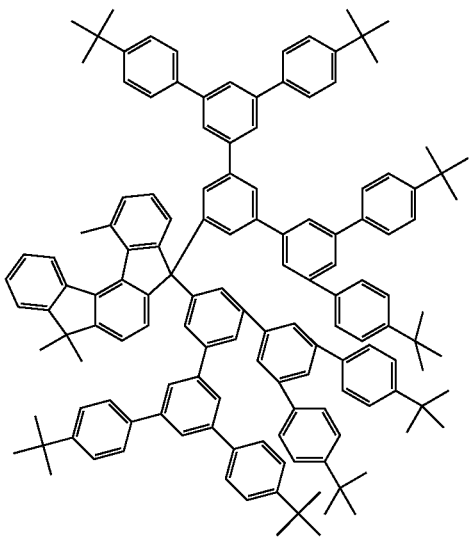
BB-164 + BB-181
M-0264
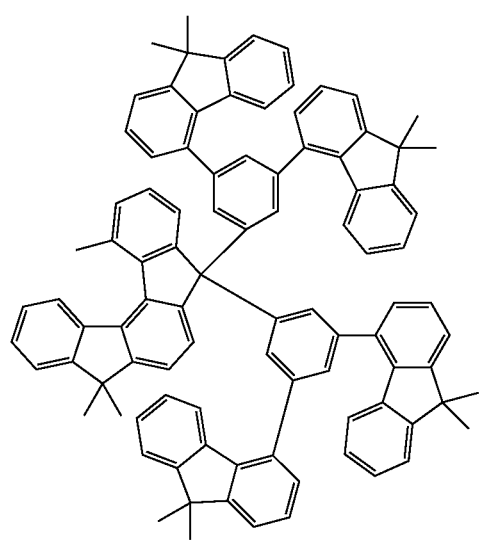
BB-164 + BB-182
M-0265
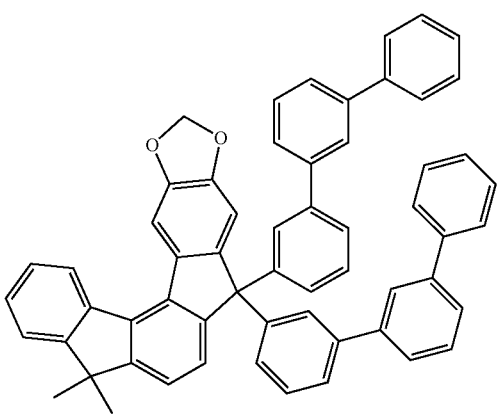
BB-165 + BB-179

M-0266
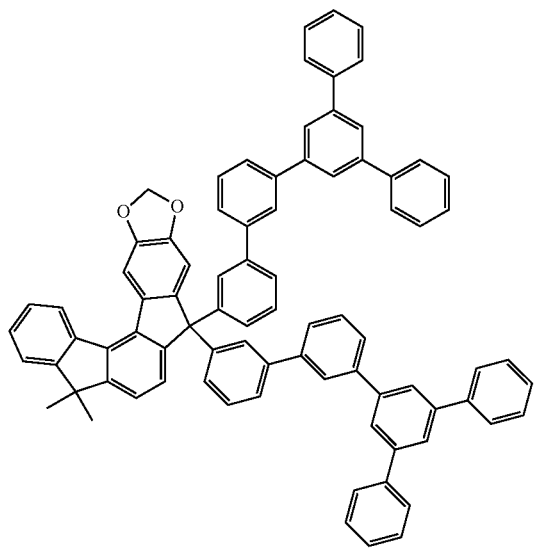
BB-165 + BB-180
M-0267
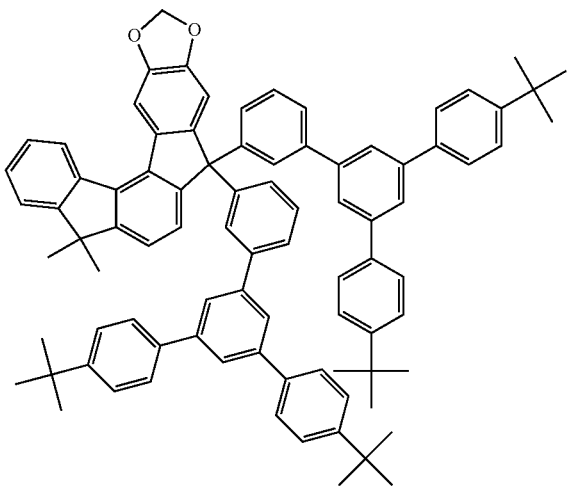
BB-165 + BB-181
M-0268
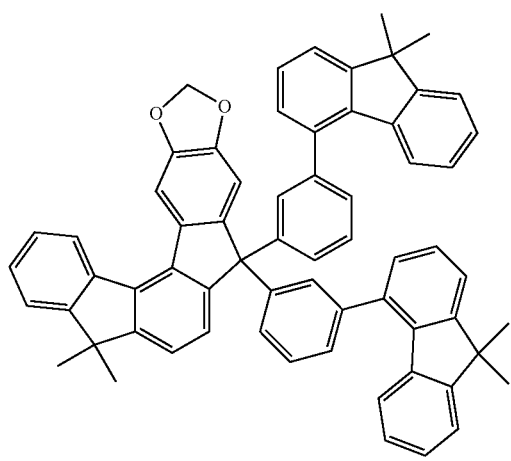
BB-165 + BB-182
M-0269
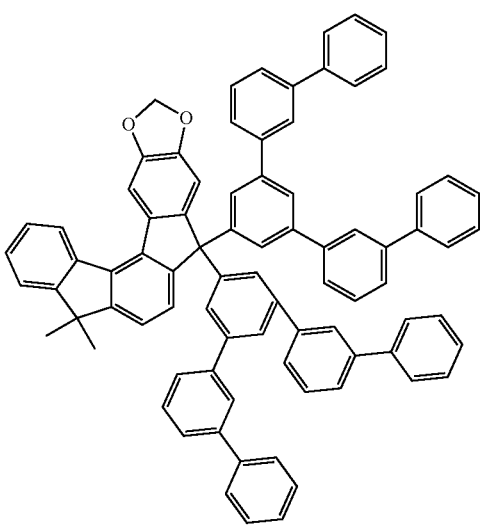
BB-166 + BB-179

-continued
M-0270
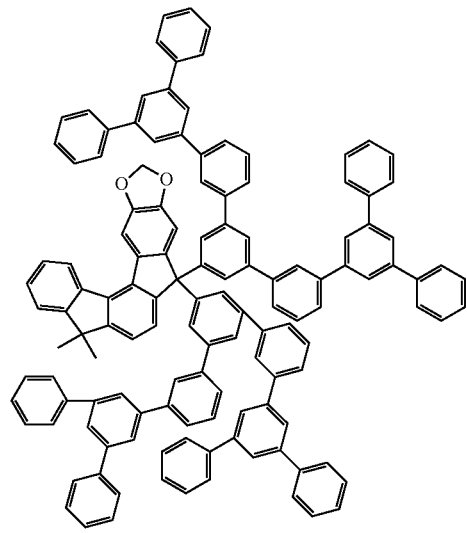
BB-166 + BB-180
M-0271
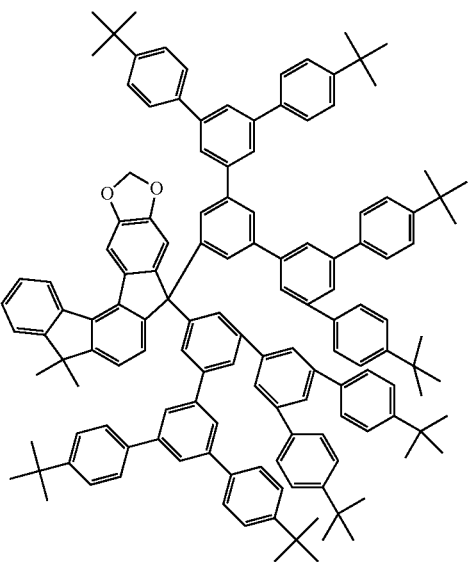
BB-166 + BB-181
M-0272
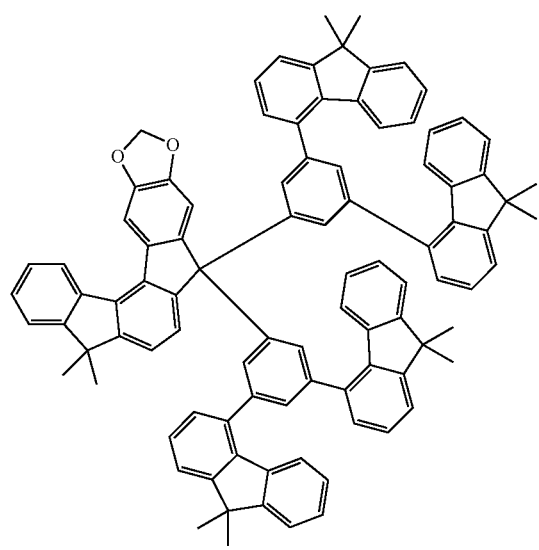
BB-166 + BB-182
M-0273
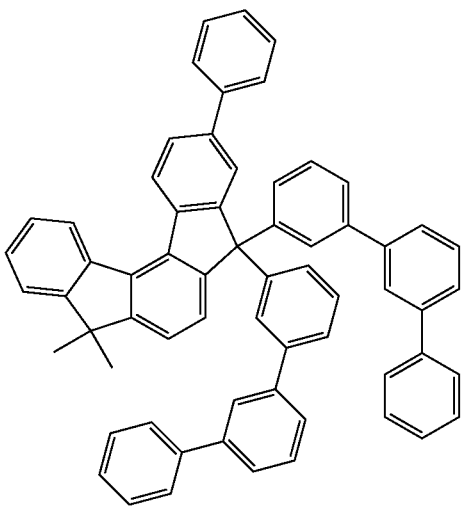
BB-167 + BB-179

M-0274
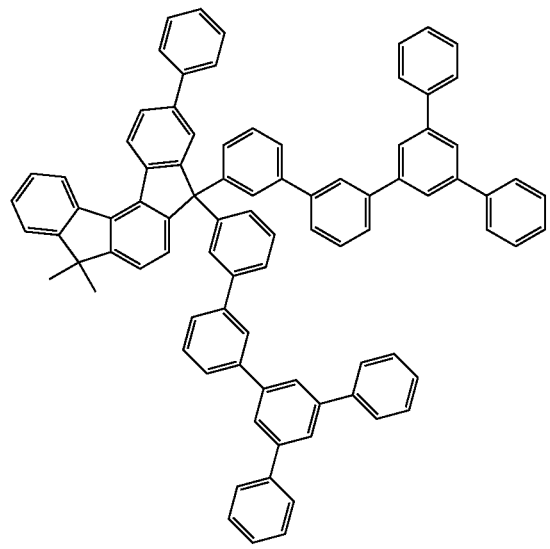
BB-167 + BB-180
M-0275
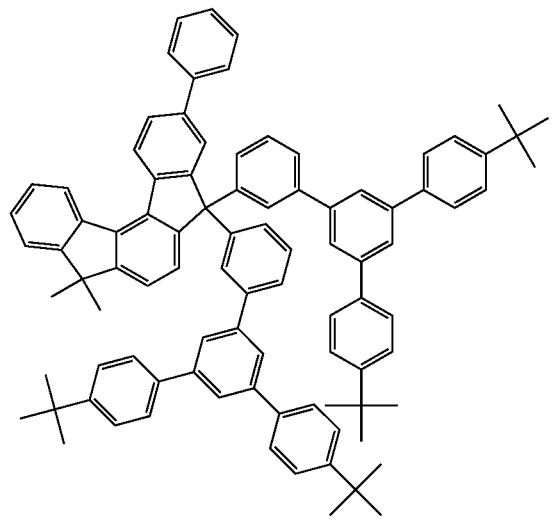
BB-167 + BB-181
M-0276
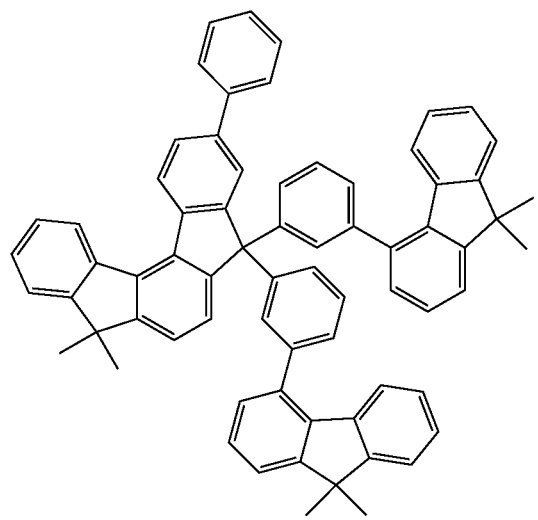
BB-167 + BB-182
M-0277
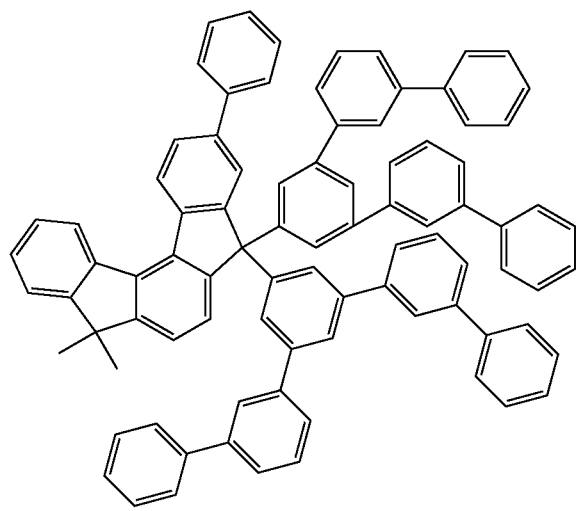
BB-168 + BB-179

-continued
M-0278
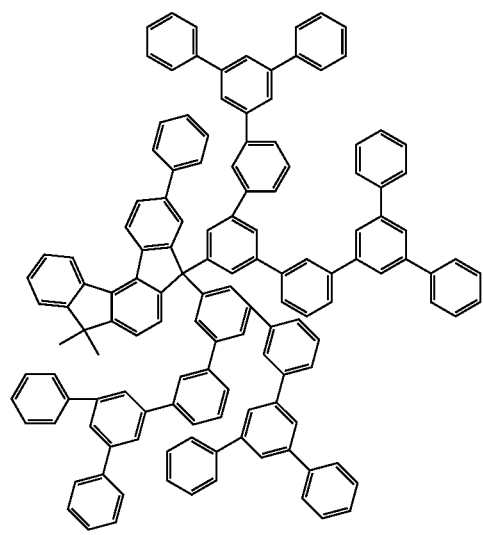
BB-168 + BB-180
M-0279
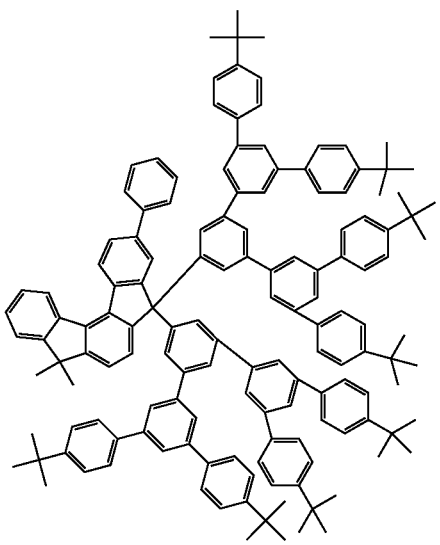
BB-168 + BB-181
M-0280
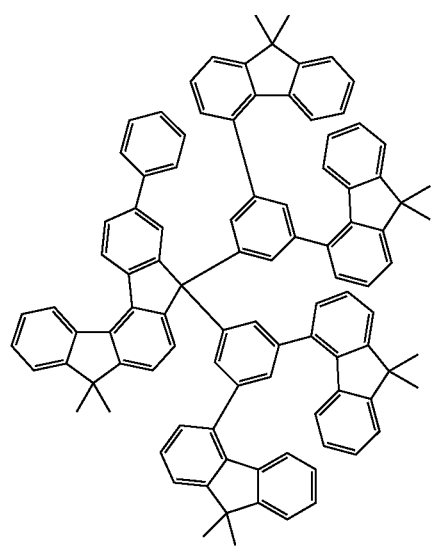
BB-168 + BB-182
M-0281
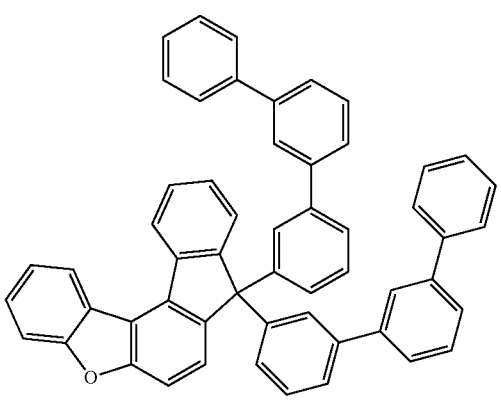
BB-169 + BB-179

-continued
M-0282
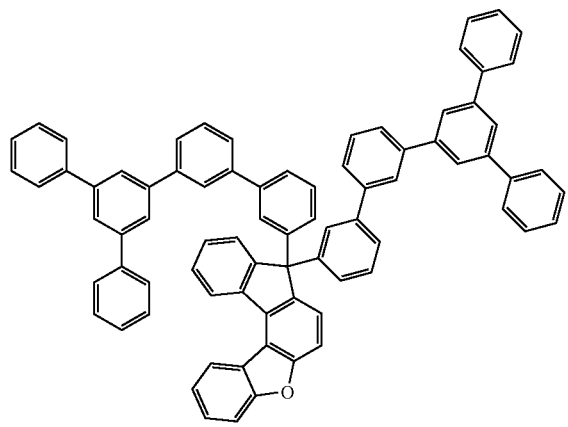
BB-169 + BB-180
M-0283
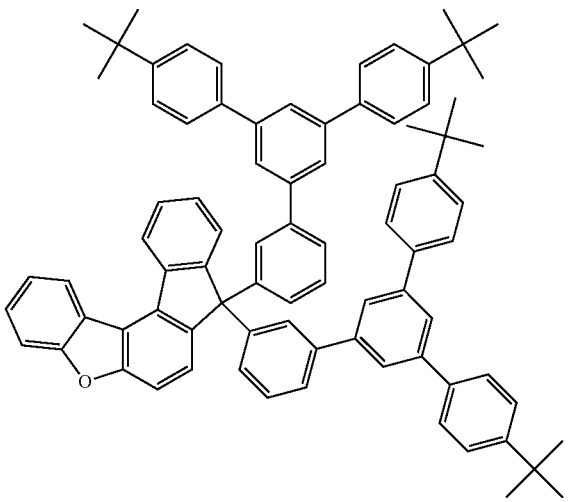
BB-169 + BB-181
M-0284
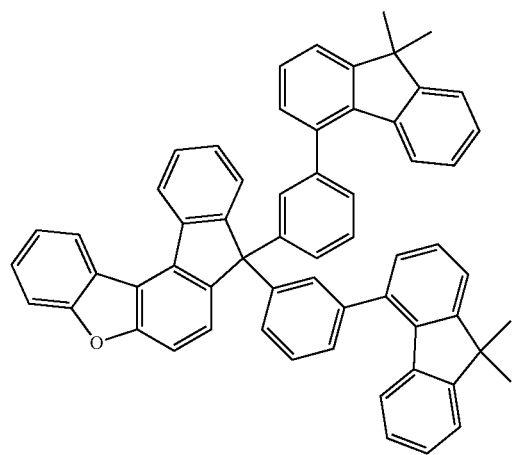
BB-169 + BB-182
M-0285
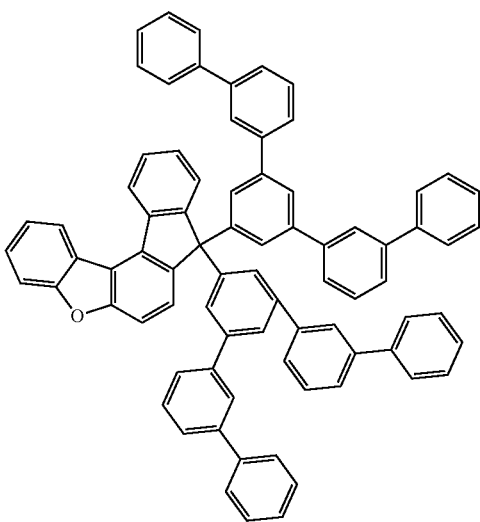
BB-170 + BB-179

-continued
M-0286
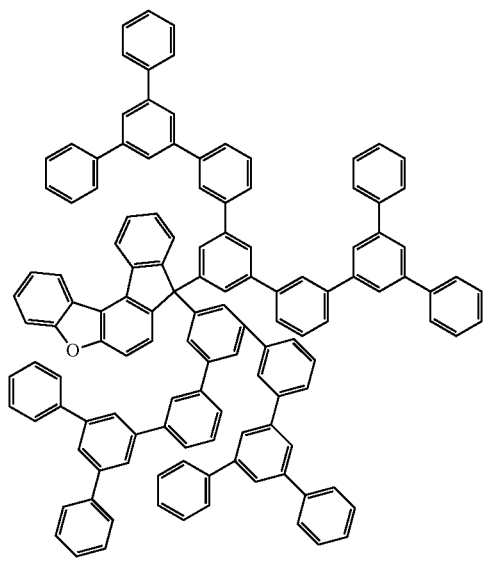
BB-170 + BB-180
M-0287
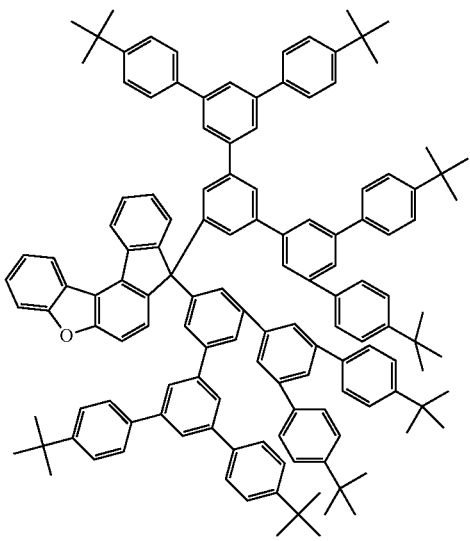
BB-170 + BB-181
M-0288
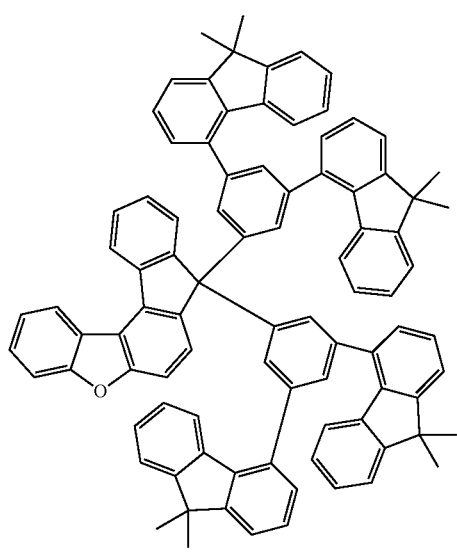
BB-170 + BB-182
M-0289
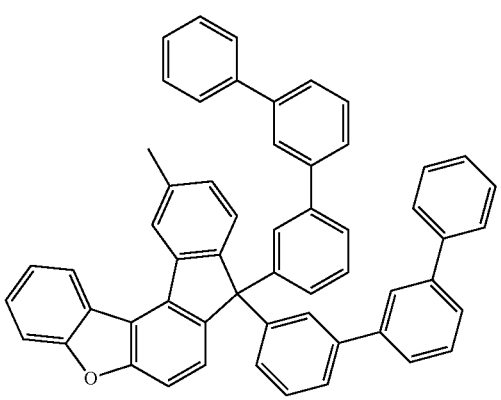
BB-171 + BB-179

-continued
M-0290
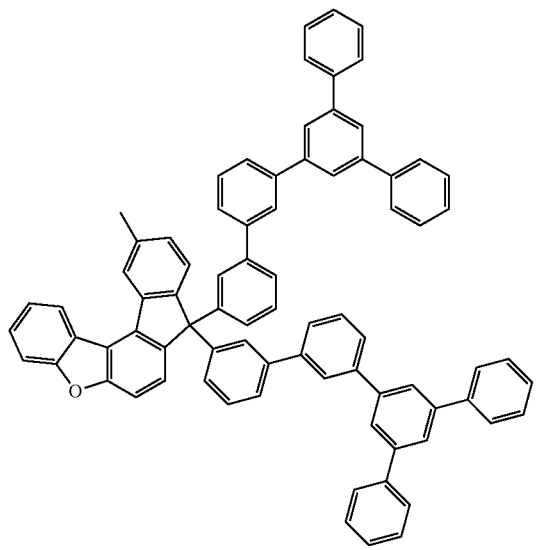
BB-171 + BB-180
M-0291
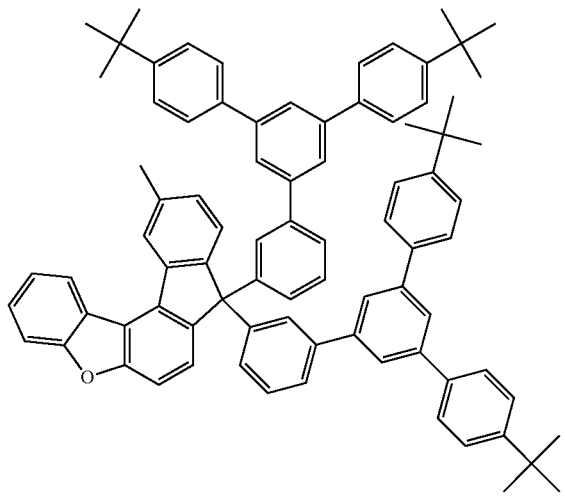
BB-171 + BB-181
M-0292
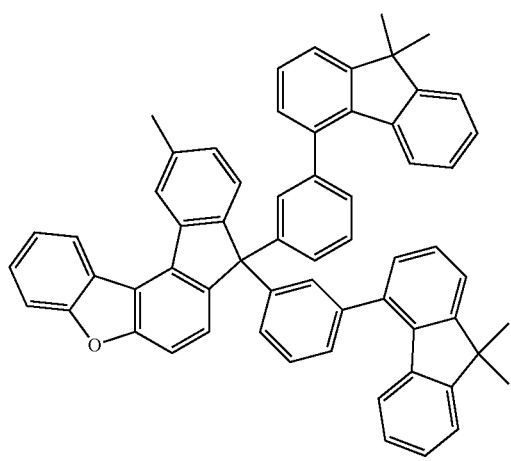
BB-171 + BB-182
M-0293
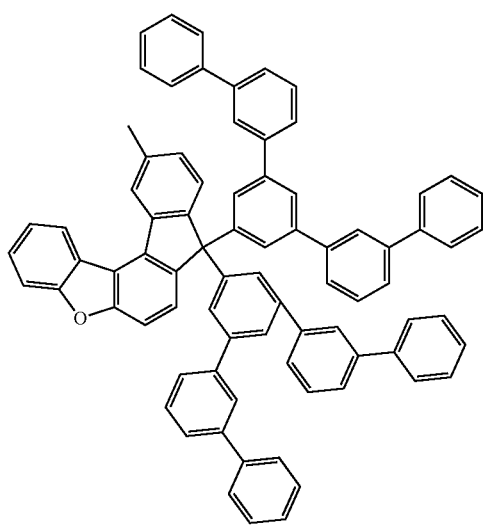
BB-172 + BB-179

-continued
M-0294
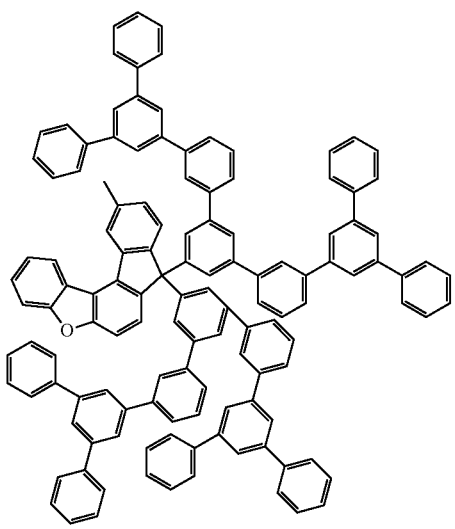
BB-172 + BB-180
M-0295
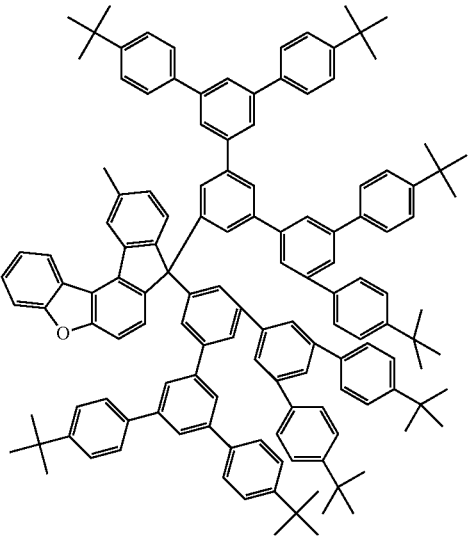
BB-172 + BB-181
M-0296
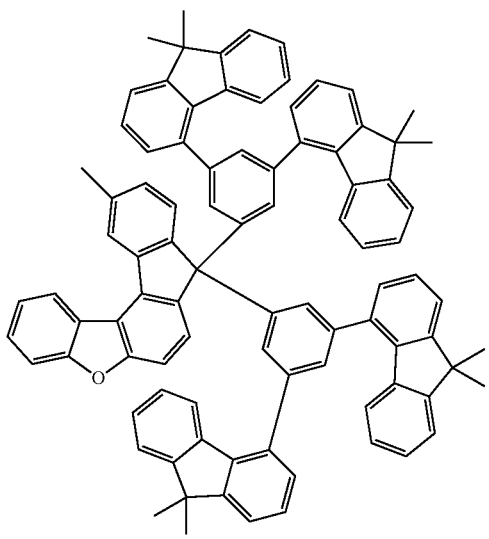
BB-172 + BB-182
M-0297
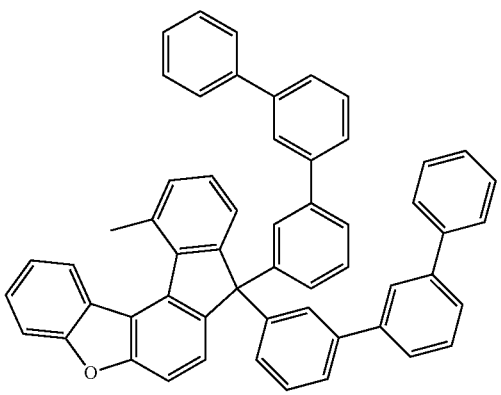
BB-173 + BB-179

-continued
M-0298
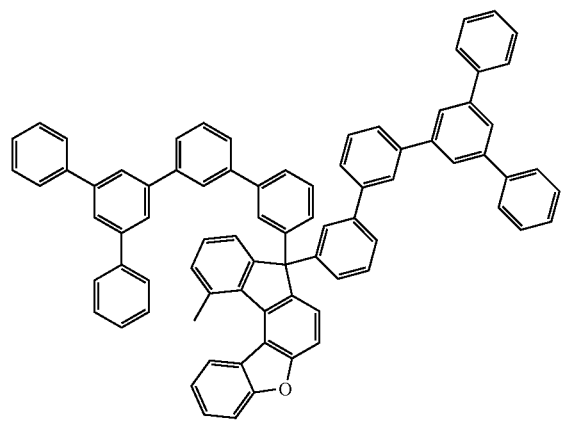
BB-173 + BB-180
M-0299
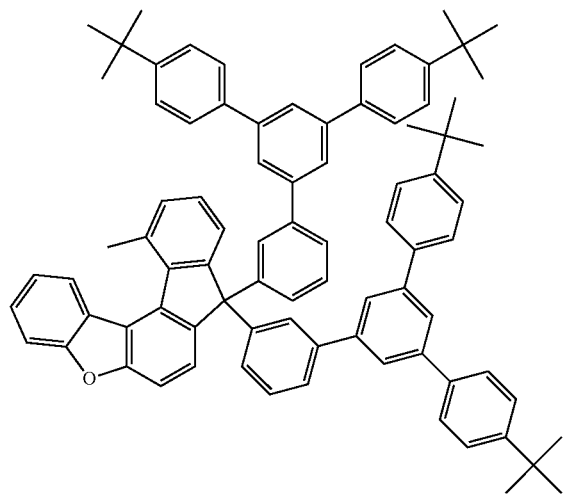
BB-173 + BB-181
M-0300
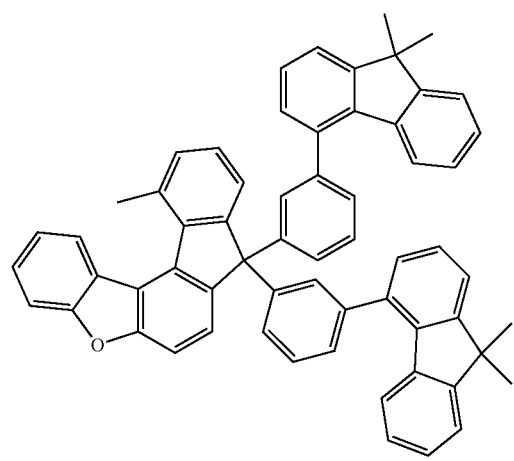
BB-173 + BB-182
M-0301
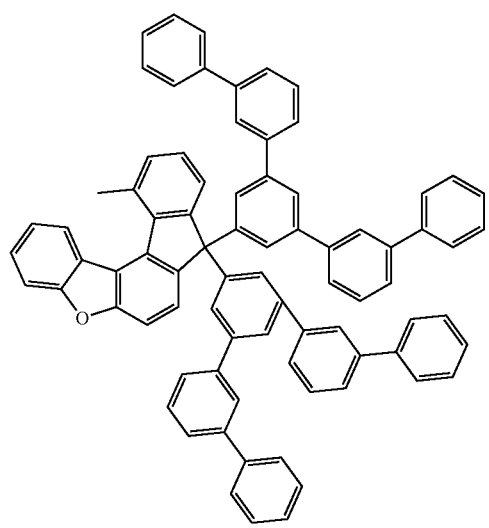
BB-174 + BB-179

-continued
M-0302
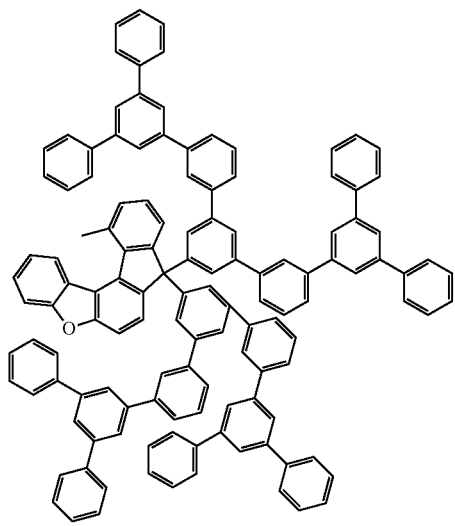
BB-174 + BB-180
M-0303
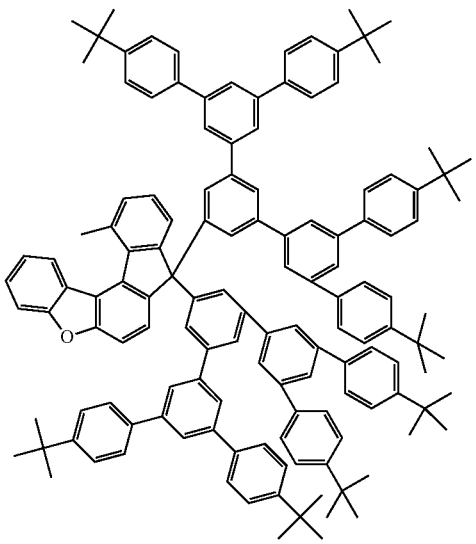
BB-174 + BB-181
M-0304
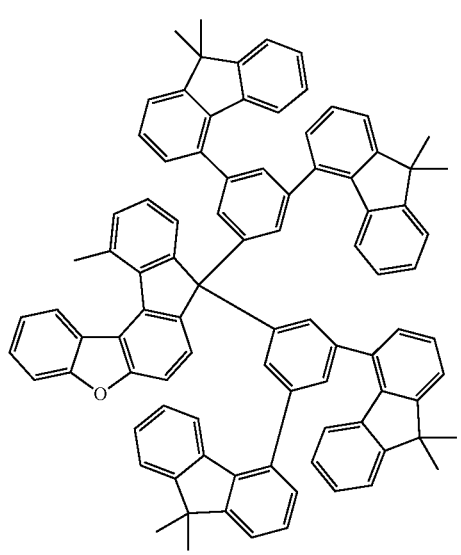
BB-174 + BB-182
M-0305
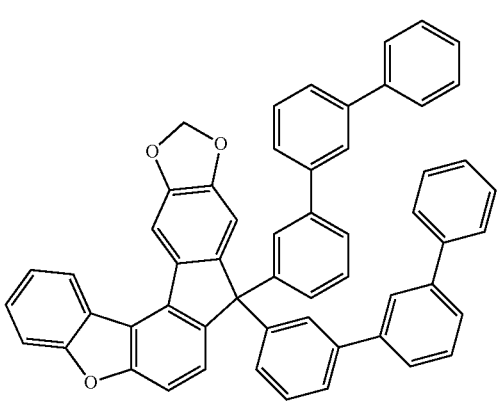
BB-175 + BB-179

-continued
M-0306
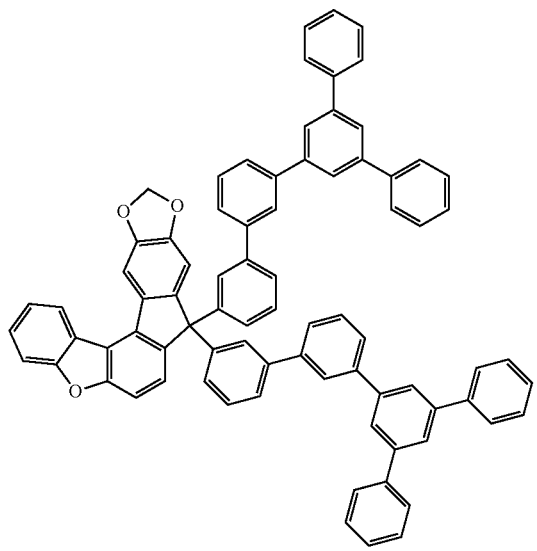
BB-175 + BB-180
M-0307
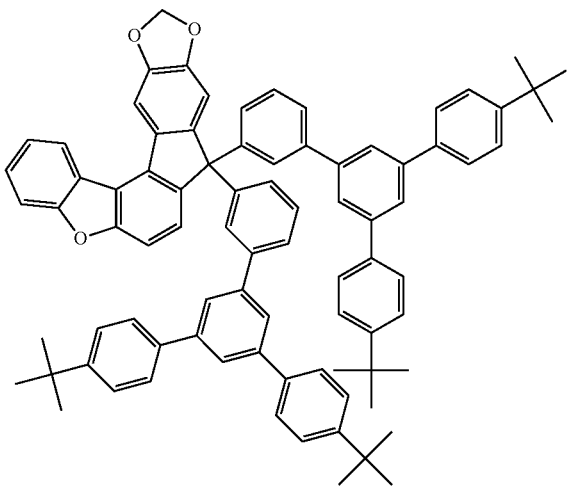
BB-175 + BB-181
M-0308
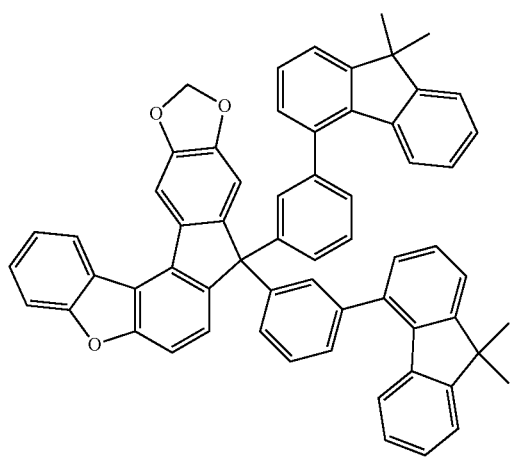
BB-175 + BB-182
M-0309
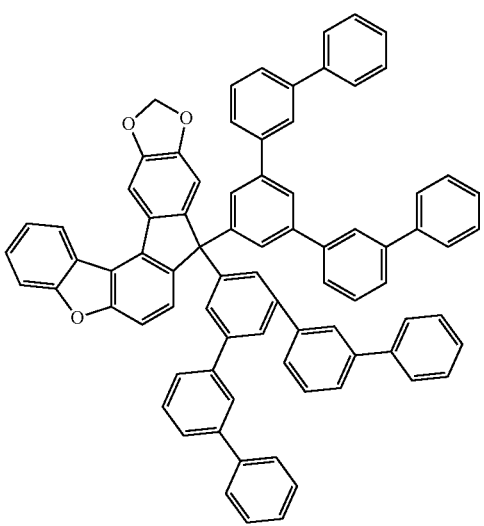
BB-176 + BB-179

-continued
M-0310
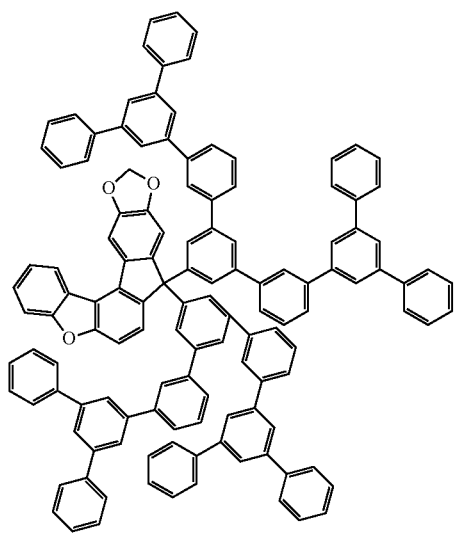
BB-176 + BB-180
M-0311
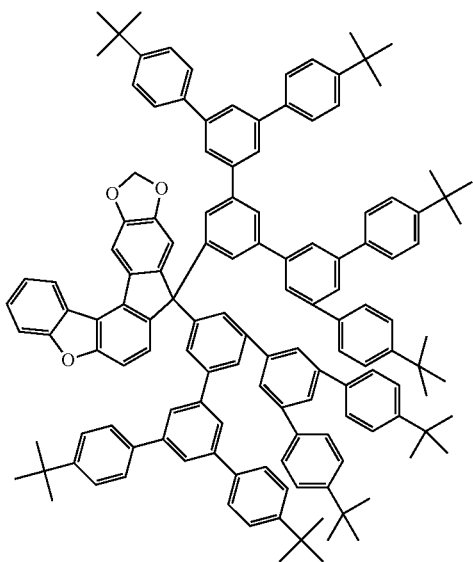
BB-176 + BB-181
M-0312
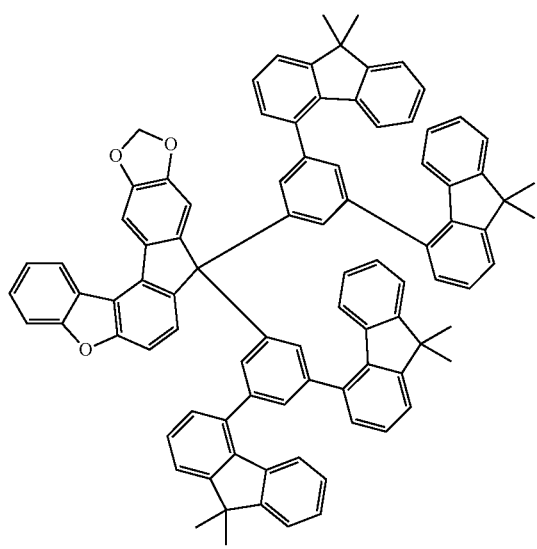
BB-176 + BB-182
M-0313
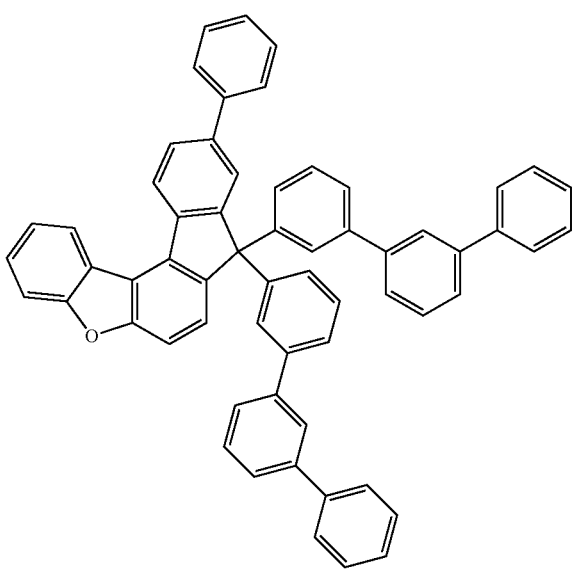
BB-177 + BB-179

M-0314
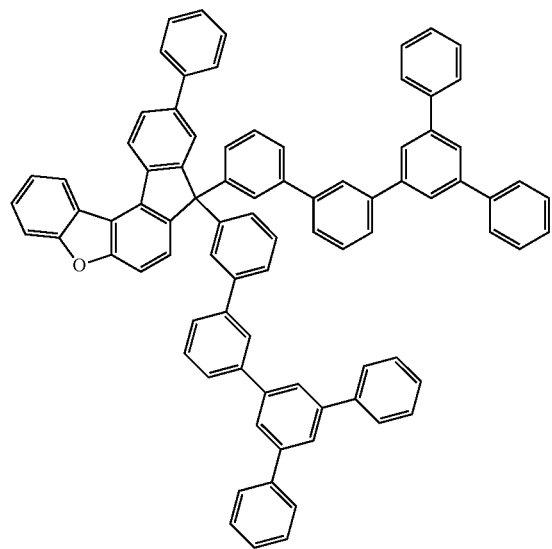
BB-177 + BB-180
M-0315
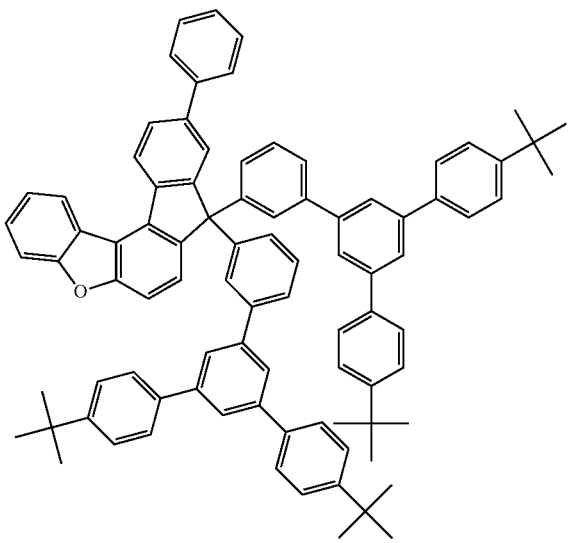
BB-177 + BB-181
M-0316
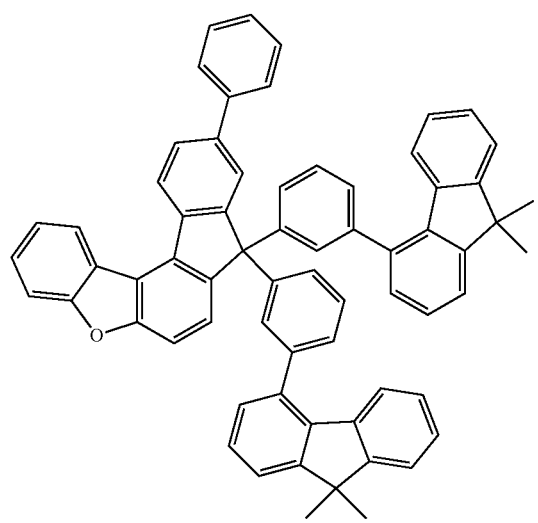
BB-177 + BB-182
M-0317
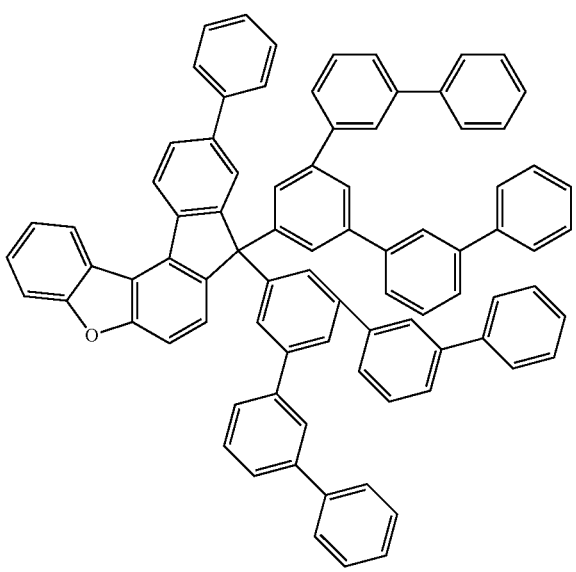
BB-178 + BB-179

-continued

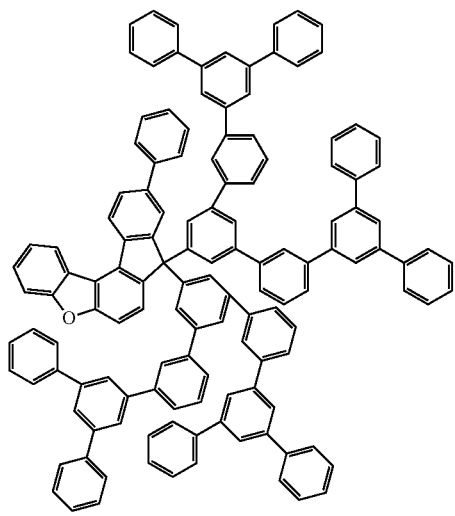

BB-178 + BB-180

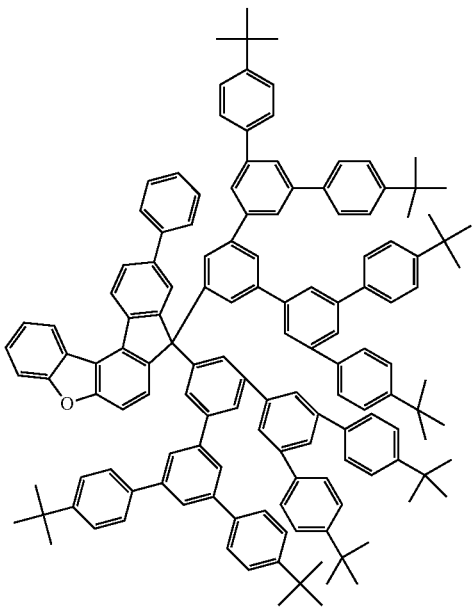

BB-178 + BB-181

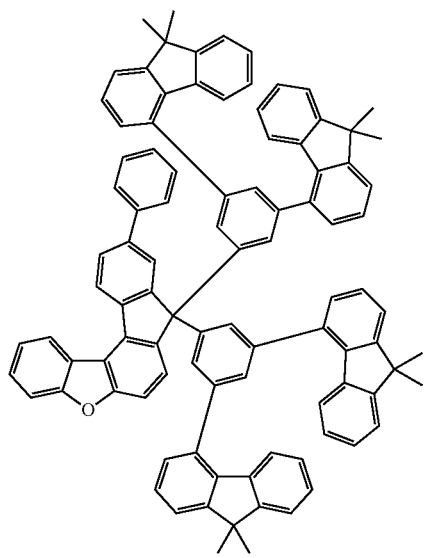

BB-178 + BB-182

Device Examples

Example 1: Processibility

One way of processing the materials of the invention is from solution. They are notable here for elevated solubility compared to symmetric comparative compounds, as shown in Table 1. In addition, it is a feature of materials of the invention that their shade stability is elevated, as apparent from the long-term solubility data in Table 1.

The inventive compound M-0005 is directly comparable to compound B-1 and differs merely by the presence or absence of the Ar group on the fluorene. It can be seen that the solubility of M-0005 in cyclohexylbenzene is significantly better than the solubility of B-1. In addition, the long-term stability of the solution of M-0005 in mesitylene is significantly better than that of B-1 in mesitylene.

The inventive compounds M-0002, M-0097 and M-0226 are directly comparable to compound B-2 and differ merely or essentially by the presence or absence of the Ar group on the fluorene. It can be seen that the solubility of the inventive compounds M-0097 and M-0226 in toluene and mesitylene is significantly better than the solubility of B-2. In addition, the long-term stability of the solutions of M-0097 and M-0226 is significantly better than that of B-2.

TABLE 1

Solubility

| Ex. | Material | Solubility after 24 hours [g/l] | | | | Solubility after 7 days [g/l] | | | |
|---|---|---|---|---|---|---|---|---|---|
| | | Cyclohexylbenzene | Tetralin | Toluene | Mesitylene | Cyclohexylbenzene | Tetralin | Toluene | Mesitylene |
| C1.1 | B-1 | <20 | >50 | >50 | >50 | <20 | >50 | >50 | <40 |
| C1.2 | B-2 | >50 | >50 | <1 | <1 | <1 | <20 | <1 | <1 |
| C1.3 | B-3 | >50 | <50 | >50 | <50 | >50 | <50 | >50 | <40 |
| I1.1 | M-0005 | >50 | >50 | >50 | >50 | >50 | <50 | >50 | >50 |
| I1.2 | M-0002 | <1 | >50 | >50 | >50 | <1 | >50 | >50 | 50 |
| I1.3 | M-0008 | <50 | <30 | >50 | >50 | <50 | <30 | >50 | >50 |
| I1.4 | M-0026 | >50 | >50 | >50 | >50 | >50 | >50 | >50 | >50 |
| I1.5 | M-0033 | >50 | >50 | >50 | >50 | >50 | >50 | >50 | >50 |
| I1.6 | M-0043 | <50 | >50 | <50 | <50 | <50 | >50 | <50 | <50 |
| I1.7 | M-0086 | >50 | >50 | >50 | >50 | >50 | >50 | >50 | >50 |
| I1.8 | M-0097 | >50 | >50 | <20 | <20 | <25 | <25 | <20 | <20 |
| I1.9 | M-0162 | <50 | >50 | >50 | >50 | <50 | >50 | >50 | >50 |
| I1.10 | M-0172 | <40 | <40 | <30 | <30 | <40 | <40 | <30 | <30 |
| I1.11 | M-0203 | <40 | <40 | <20 | <20 | <40 | <40 | <20 | <20 |
| I1.12 | M-0226 | <30 | <30 | <20 | <20 | <25 | <25 | <20 | <20 |
| I1.13 | M-0244 | <50 | <50 | <20 | <20 | <40 | <40 | <20 | <20 |
| I1.14 | M-0281 | <50 | <50 | <50 | <50 | <50 | <50 | <50 | <50 |
| I1.15 | M-0315 | <50 | >50 | <50 | <50 | <50 | >50 | <50 | <50 |

Method of Determining Solubility Via HPTLC

Sample preparation: The material is weighed out in two 25 mg portions (W1, W2), 0.5 ml of solvent is added, and the mixture is shaken at 60° C. for 60 minutes and then at 25° C. and 600 rpm for 24 h. When the solution is clear, more solid material is added until a saturated solution is formed. After being cooled to room temperature, the samples are filtered through a syringe filter (0.2 μm). The solutions are stored in glass vials at room temperature for 7 days, and the solubility is determined by HPTLC on days 1 and 7. For this purpose, the filtered solutions are diluted.

Calibration: Making up a standard solution: about 6 mg of substance are dissolved in 20 ml of 2-methyl-THF. If it is not possible to dissolve the material under these conditions, the concentration can be reduced. The stock solution is diluted for the calibration (standardization).

Chromatographic conditions (HPTLC): plate: HPTLC RP 18 F254, 10×20 cm eluent: methanol/2-methyl-THF 70/30 (V/V)

Migration distance: 5 cm

Recognition: 366 nm

Use volume: standard: 1, 3, 6, 10, 15, 20, 25, 30 μl

HPTLC measurement: The HPTLC plate is scanned by a TLC scanner, peaks are integrated and a calibration function is determined.

Furthermore, materials of the invention are notable in that, as shown in Table 2, films containing these materials can be baked at higher temperatures without turning cloudy and, when used in OLED components, leading to lower efficiency. The production of the corresponding OLED components is described below. The EML mixtures and structures of the OLED components examined are shown in tables 5 and 6.

For example, compound M-0002 is directly comparable to compound B-2 and differs merely by the absence of the Ar group on the fluorene. It can be seen that the layer comprising M-0002 can be baked at higher temperature without cloudiness and with a significantly smaller loss of efficiency.

TABLE 2

Baking at elevated temperature

| Ex. | Material | Ref. temp. | Elevated temp. | State of film after baking at elevated temp. | Loss of efficiency after baking at elevated temperature |
|---|---|---|---|---|---|
| C2.1 | B-2 | 160 | 180 | slightly cloudy | ≥10% |
| C2.2 | B-1 | 160 | 180 | cloudy | ≥70% |
| I2.1 | M-0002 | 160 | 180 | clear | ≤5% |
| C2.3 | B-1 | 160 | 170 | slightly cloudy | ≥10% |
| I2.2 | M-0005 | 160 | 170 | clear | ≤5% |
| C2.4 | B-4 | 150 | 180 | slightly cloudy | ≥10% |
| C2.5 | B-1 | 150 | 180 | cloudy | ≥70% |
| I2.3 | M-0002 | 150 | 180 | clear | ≤5% |
| I2.4 | M-0005 | 150 | 170 | clear | ≤5% |
| I2.5 | M-0172 | 150 | 170 | clear | ≤5% |
| I2.6 | M-0008 | 150 | 180 | clear | ≤5% |
| I2.7 | M-0026 | 150 | 180 | clear | ≤5% |
| I2.8 | M-0033 | 150 | 180 | clear | ≤5% |
| I2.9 | M-0043 | 150 | 180 | clear | ≤5% |
| I2.10 | M-0086 | 150 | 180 | clear | ≤5% |
| I2.11 | M-0097 | 150 | 180 | clear | ≤5% |
| I2.12 | M-0162 | 150 | 180 | clear | ≤5% |
| I2.13 | M-0203 | 150 | 180 | clear | ≤5% |
| I2.14 | M-0226 | 150 | 180 | clear | ≤5% |
| I2.15 | M-0315 | 150 | 180 | clear | ≤5% |

Example 2: OLED Components

One way of processing the matrix materials of the invention is from solution. There are already many descriptions of the production of completely solution-based OLEDs in the literature, for example in WO 2004/037887 by means of spin coating. There have likewise been many previous descriptions of the production of vacuum-based OLEDs, including in WO 2004/058911. In the examples discussed hereinafter, layers applied in a solution-based and vacuum-based manner are combined within an OLED, and so the processing up to and including the emission layer is effected from solution and in the subsequent layers (hole blocker layer and electron transport layer) from vacuum. For this purpose, the previously described general methods are matched to the circumstances described here (layer thickness variation, materials) and combined as follows. The general structure is as follows: substrate/ITO (50 nm)/hole injection layer (HIL)/hole transport layer (HTL)/emission layer (EML)/optional hole blocker layer (HBL)/electron transport layer (ETL)/optional electron injection layer/cathode (aluminium, 100 nm). Substrates used are glass plates coated with structured ITO (indium tin oxide) of thickness 50 nm. For better processing, they are coated with PEDOT:PSS (poly(3,4-ethylenedioxy-2,5-thiophene) polystyrenesulfonate, purchased from Heraeus Precious Metals GmbH & Co. KG, Germany). PEDOT:PSS is spun on from water under air and subsequently baked under air at 180° C. for 10 minutes in order to remove residual water. The hole transport layer and the emission layer are applied to these coated glass plates. The hole transport layer used is crosslinkable. A polymer of the structures depicted below is used, which can be synthesized according to WO 2010/097155 or WO 2013/156130:

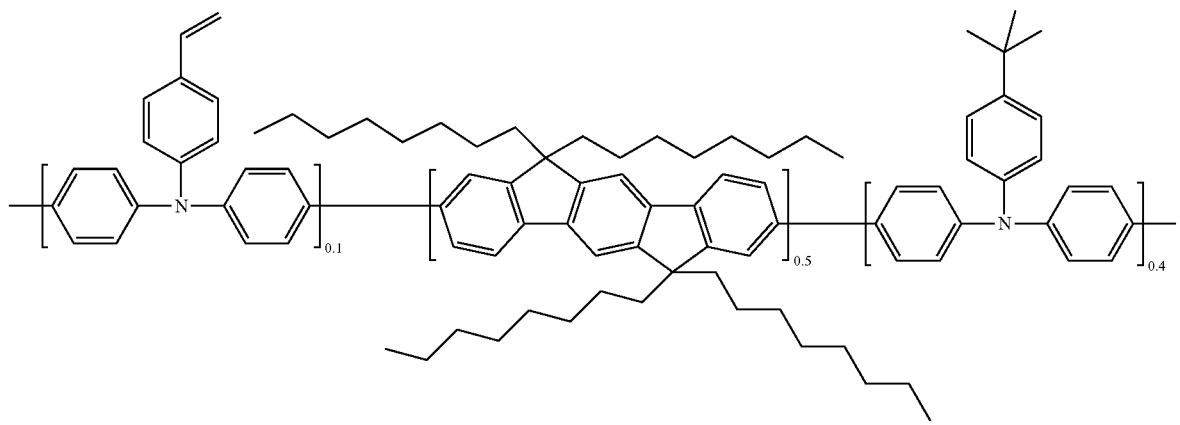

HTL-1

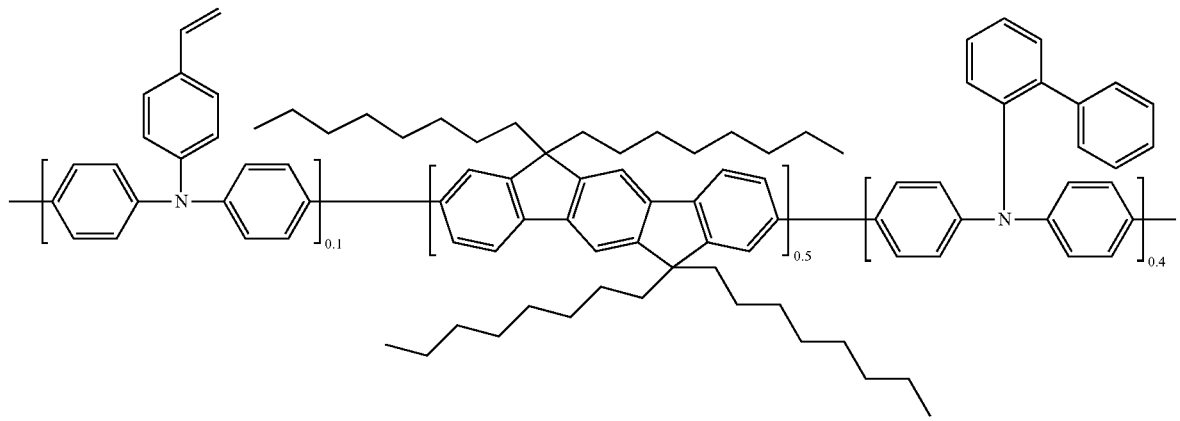

HTL-2

The hole transport polymer is dissolved in toluene. The typical solids content of such solutions is about 5 g/l when, as here, the layer thickness of 20-60 nm which is typical of a device is to be achieved by means of spin-coating. The layers are spun on in an inert gas atmosphere, argon in the present case, and baked at 180° C. for 60 minutes.

The emission layer is composed of at least one matrix material (host material) and an emitting dopant (emitter). In addition, it is possible to use mixtures of a plurality of matrix materials and co-dopants. Details given in such a form as TMM-A (92%):dopant (8%) mean here that the material TMM-A is present in the emission layer in a proportion by weight of 92% and dopant in a proportion by weight of 8%. The mixture for the emission layer is dissolved in toluene or optionally chlorobenzene. The typical solids content of such solutions is about 17 g/l when, as here, the layer thickness of 60 nm which is typical of a device is to be achieved by means of spin-coating. The layers are spun on in an inert gas atmosphere, argon in the present case, and baked for 10 minutes. The materials used in the present case are shown in Table 3.

417 418
TABLE 3
EML materials used
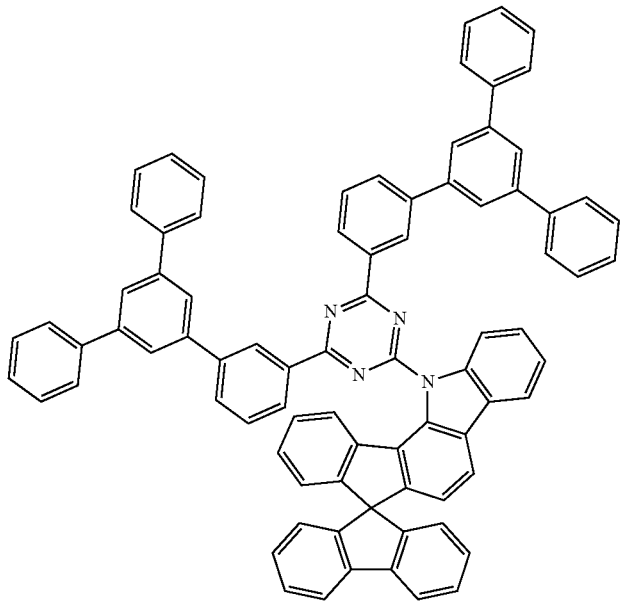
see WO 2014/094963
A-1
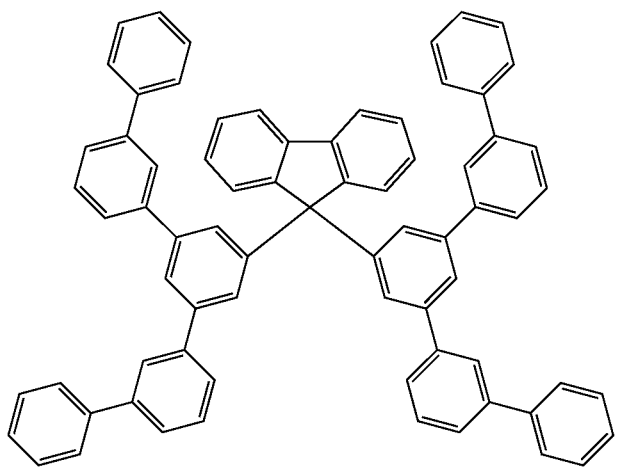
[1246496-85-4]
B-1
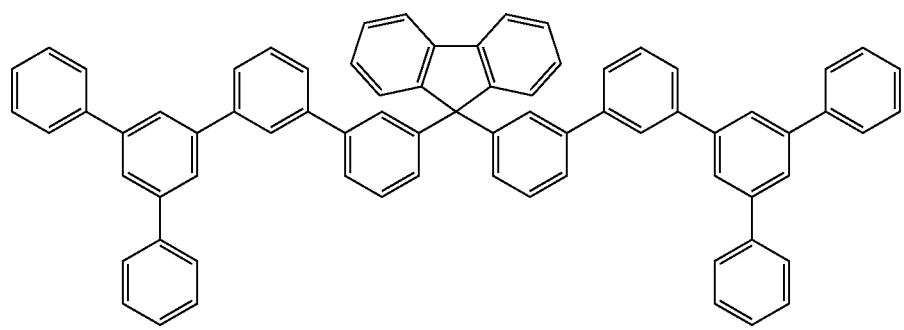
[2047361-36-2]
B-2

TABLE 3-continued
EML materials used
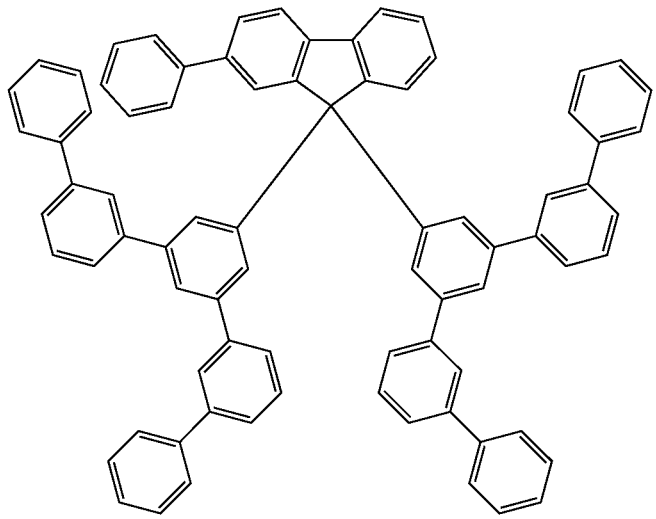
B-3
see WO 2016/184540
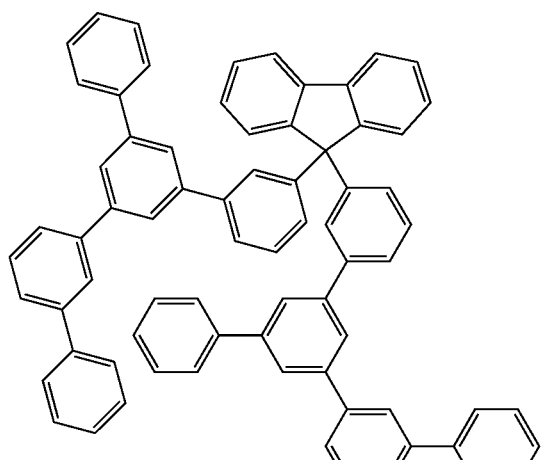
B-4
[2231029-69-7]
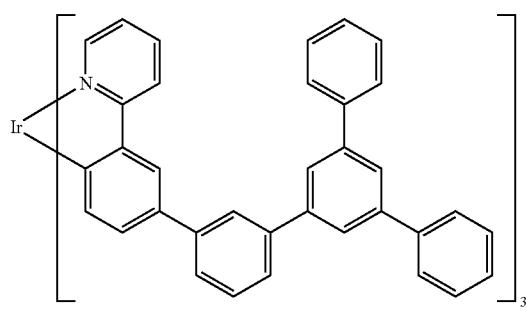
C-1
[1269508-30-6]

TABLE 3-continued
EML materials used
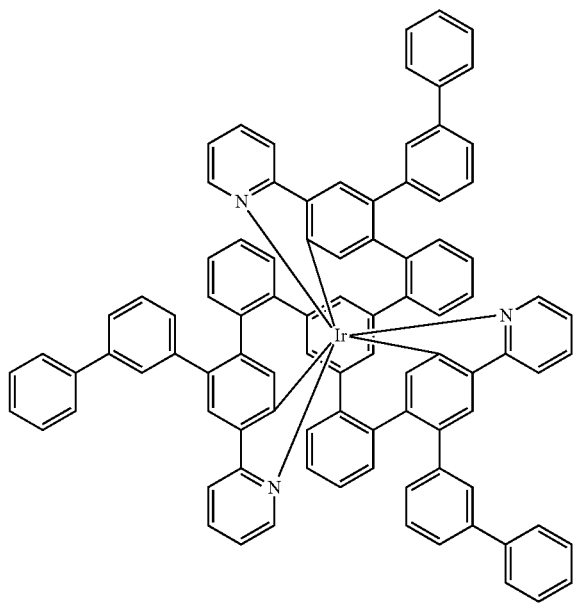
C-2
see WO 2016/124304
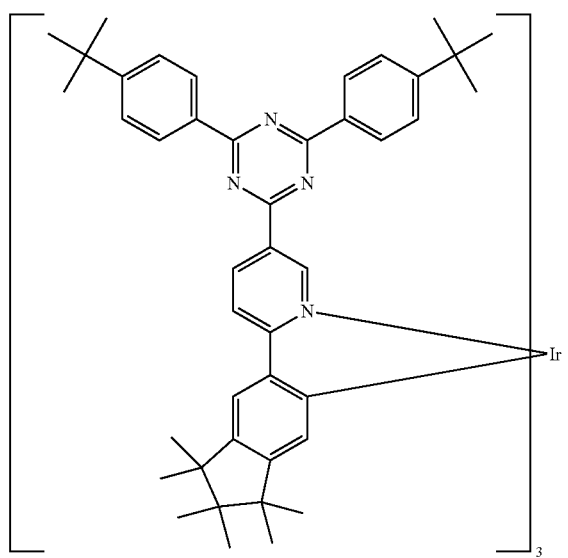
D-1
[1870013-87-8]

TABLE 3-continued

EML materials used

D-2

[2202715-38-4]

The materials for the hole blocker layer, electron transport layer and electron injection layer are applied by thermal vapour deposition in a vacuum chamber. The electron transport layer, for example, may consist of more than one material, the materials being added to one another by co-evaporation in a particular proportion by volume. Details given in such a form as ETM1:ETM2 (50%:50%) mean here that the ETM1 and ETM2 materials are present in the layer in a proportion by volume of 50% each. The materials used in the present case are shown in Table 4.

TABLE 4

HBL and ETL materials used

ETM1

[1233200-52-6]

TABLE 4-continued

HBL and ETL materials used

ETM2

[25387-93-3]

The cathode is formed by the thermal evaporation of an aluminium layer of thickness 100 nm. The OLEDs are characterized in a standard manner. For this purpose, the electroluminescence spectra, current-voltage-luminance characteristics (IUL characteristics) assuming Lambertian radiation characteristics and the (operating) lifetime are determined. The IUL characteristics are used to determine indices such as, for example, external quantum efficiency at a particular brightness. LT97 @ 60 mA/cm² is the lifetime before the OLED, given a constant current density of 60 mA/cm², has fallen to 97% of the starting luminance.

The EML mixtures and structures of the OLED components examined are shown in Tables 5 and 6. The corresponding results can be found in Table 7.

TABLE 5

EML mixtures of the PLED components examined

| Ex. | Matrix A | | Co-matrix B | | Co-dopant C | | Dopant D | |
|---|---|---|---|---|---|---|---|---|
| | Material | % | Material | % | Material | % | Material | % |
| C2.1 | A-1 | 20 | B-2 | 60 | C-1 | 20 | — | — |
| C2.2 | A-1 | 20 | B-1 | 60 | C-1 | 20 | — | — |

TABLE 5-continued

EML mixtures of the PLED components examined

| Ex. | Matrix A Material | % | Co-matrix B Material | % | Co-dopant C Material | % | Dopant D Material | % |
|---|---|---|---|---|---|---|---|---|
| I2.1 | A-1 | 20 | M-0002 | 60 | C-1 | 20 | — | — |
| C2.3 | A-1 | 25 | B-1 | 53 | C-2 | 22 | — | — |
| I2.2 | A-1 | 25 | M-0005 | 53 | C-2 | 22 | — | — |
| C2.4 | A-1 | 30 | B-4 | 34 | C-1 | 30 | D-1 | 6 |
| C2.5 | A-1 | 30 | B-1 | 34 | C-1 | 30 | D-1 | 6 |
| I2.3 | A-1 | 30 | M-0002 | 34 | C-1 | 30 | D-1 | 6 |
| I2.4 | A-1 | 30 | M-0005 | 34 | C-1 | 30 | D-2 | 6 |
| I2.5 | A-1 | 30 | M-0172 | 34 | C-1 | 30 | D-1 | 6 |
| I2.6 | A-1 | 30 | M-0008 | 34 | C-1 | 30 | D-1 | 6 |
| I2.7 | A-1 | 30 | M-0026 | 34 | C-1 | 30 | D-1 | 6 |
| I2.8 | A-1 | 30 | M-0033 | 34 | C-1 | 30 | D-2 | 6 |
| I2.9 | A-1 | 30 | M-0043 | 34 | C-1 | 30 | D-2 | 6 |
| I2.10 | A-1 | 30 | M-0086 | 34 | C-1 | 30 | D-2 | 6 |
| I2.11 | A-1 | 30 | M-0097 | 34 | C-1 | 30 | D-1 | 6 |
| I2.12 | A-1 | 30 | M-0162 | 34 | C-1 | 30 | D-1 | 6 |
| I2.13 | A-1 | 30 | M-0203 | 34 | C-1 | 30 | D-1 | 6 |
| I2.14 | A-1 | 30 | M-0226 | 34 | C-1 | 30 | D-1 | 6 |
| I2.15 | A-1 | 30 | M-0315 | 34 | C-1 | 30 | D-1 | 6 |
| C3.1 | A-1 | 40 | B-3 | 37 | C-2 | 15 | D-2 | 8 |
| I3.1 | A-1 | 40 | M-0005 | 37 | C-2 | 15 | D-2 | 8 |
| C3.2 | A-1 | 40 | B-3 | 37 | C-2 | 15 | D-2 | 8 |
| I3.2 | A-1 | 40 | M-0005 | 37 | C-2 | 15 | D-2 | 8 |
| C3.3 | A-1 | 30 | B-1 | 34 | C-1 | 30 | D-1 | 6 |
| C3.4 | A-1 | 30 | B-2 | 34 | C-1 | 30 | D-1 | 6 |
| I3.3 | A-1 | 30 | M-0002 | 34 | C-1 | 30 | D-1 | 6 |
| C3.5 | A-1 | 20 | B-4 | 60 | C-1 | 20 | — | — |
| I3.4 | A-1 | 20 | M-0002 | 60 | C-1 | 20 | — | — |
| C3.6 | A-1 | 20 | B-4 | 60 | C-1 | 20 | — | — |
| I3.5 | A-1 | 20 | M-0002 | 60 | C-1 | 20 | — | — |

TABLE 6

Structure of the OLED components examined

| Ex. | HIL (thickness) | HTL (thickness) | EML thickness | EML baking temperature | HBL (thickness) | ETL (thickness) | EIL (thickness) |
|---|---|---|---|---|---|---|---|
| C2.1 | PEDOT (20 nm) | HTL-1 (20 nm) | 60 nm | see Tab. 2 | ETM-1 (10 nm) | ETM-1:ETM-2 (50:50) (40 nm) | — |
| C2.2 | PEDOT (20 nm) | HTL-1 (20 nm) | 60 nm | see Tab. 2 | ETM-1 (10 nm) | ETM-1:ETM-2 (50:50) (40 nm) | — |
| I2.1 | PEDOT (20 nm) | HTL-2 (20 nm) | 60 nm | see Tab. 2 | ETM-1 (10 nm) | ETM-1:ETM-2 (50:50) (40 nm) | — |
| C2.3 | PEDOT (20 nm) | HTL-2 (20 nm) | 60 nm | see Tab. 2 | ETM-1 (10 nm) | ETM-1:ETM-2 (50:50) (40 nm) | — |
| I2.2 | PEDOT (20 nm) | HTL-2 (20 nm) | 60 nm | see Tab. 2 | ETM-1 (10 nm) | ETM-1:ETM-2 (50:50) (40 nm) | — |
| C2.4 | PEDOT (60 nm) | HTL-2 (20 nm) | 60 nm | see Tab. 2 | ETM-1 (10 nm) | ETM-1:ETM-2 (50:50) (40 nm) | — |
| C2.5 | PEDOT (60 nm) | HTL-2 (20 nm) | 60 nm | see Tab. 2 | ETM-1 (10 nm) | ETM-1:ETM-2 (50:50) (40 nm) | — |
| I2.3 | PEDOT (60 nm) | HTL-2 (20 nm) | 60 nm | see Tab. 2 | ETM-1 (10 nm) | ETM-1:ETM-2 (50:50) (40 nm) | — |
| I2.4 | PEDOT (60 nm) | HTL-2 (20 nm) | 60 nm | see Tab. 2 | ETM-1 (10 nm) | ETM-1:ETM-2 (50:50) (40 nm) | — |
| I2.5 | PEDOT (60 nm) | HTL-2 (20 nm) | 60 nm | see Tab. 2 | ETM-1 (10 nm) | ETM-1:ETM-2 (50:50) (40 nm) | — |
| I2.6 | PEDOT (60 nm) | HTL-2 (20 nm) | 60 nm | see Tab. 2 | ETM-1 (10 nm) | ETM-1:ETM-2 (50:50) (40 nm) | — |
| I2.7 | PEDOT (60 nm) | HTL-2 (20 nm) | 60 nm | see Tab. 2 | ETM-1 (10 nm) | ETM-1:ETM-2 (50:50) (40 nm) | — |
| I2.8 | PEDOT (60 nm) | HTL-2 (20 nm) | 60 nm | see Tab. 2 | ETM-1 (10 nm) | ETM-1:ETM-2 (50:50) (40 nm) | — |
| I2.9 | PEDOT (60 nm) | HTL-2 (20 nm) | 60 nm | see Tab. 2 | ETM-1 (10 nm) | ETM-1:ETM-2 (50:50) (40 nm) | — |
| I2.10 | PEDOT (60 nm) | HTL-2 (20 nm) | 60 nm | see Tab. 2 | ETM-1 (10 nm) | ETM-1:ETM-2 (50:50) (40 nm) | — |
| I2.11 | PEDOT (60 nm) | HTL-2 (20 nm) | 60 nm | see Tab. 2 | ETM-1 (10 nm) | ETM-1:ETM-2 (50:50) (40 nm) | — |
| I2.12 | PEDOT (60 nm) | HTL-2 (20 nm) | 60 nm | see Tab. 2 | ETM-1 (10 nm) | ETM-1:ETM-2 (50:50) (40 nm) | — |
| I2.13 | PEDOT (60 nm) | HTL-2 (20 nm) | 60 nm | see Tab. 2 | ETM-1 (10 nm) | ETM-1:ETM-2 (50:50) (40 nm) | — |
| I2.14 | PEDOT (60 nm) | HTL-2 (20 nm) | 60 nm | see Tab. 2 | ETM-1 (10 nm) | ETM-1:ETM-2 (50:50) (40 nm) | — |
| I2.15 | PEDOT (60 nm) | HTL-2 (20 nm) | 60 nm | see Tab. 2 | ETM-1 (10 nm) | ETM-1:ETM-2 (50:50) (40 nm) | — |
| C3.1 | PEDOT (80 nm) | HTL-2 (20 nm) | 90 nm | 150 | — | ETM-1 (20 nm) | ETM-2 (3 nm) |
| I3.1 | PEDOT (80 nm) | HTL-2 (20 nm) | 90 nm | 150 | — | ETM-1 (20 nm) | ETM-2 (3 nm) |
| C3.2 | PEDOT (80 nm) | HTL-2 (20 nm) | 90 nm | 160 | — | ETM-1 (20 nm) | ETM-2 (3 nm) |

TABLE 6-continued

Structure of the OLED components examined

| Ex. | HIL (thickness) | HTL (thickness) | EML thickness | EML baking temperature | HBL (thickness) | ETL (thickness) | EIL (thickness) |
|---|---|---|---|---|---|---|---|
| I3.2 | PEDOT (80 nm) | HTL-2 (20 nm) | 90 nm | 160 | — | ETM-1 (20 nm) | ETM-2 (3 nm) |
| C3.3 | PEDOT (60 nm) | HTL-2 (20 nm) | 60 nm | 150 | ETM-1 (10 nm) | ETM-1:ETM-2 (50:50) (40 nm) | — |
| C3.4 | PEDOT (60 nm) | HTL-2 (20 nm) | 60 nm | 150 | ETM-1 (10 nm) | ETM-1:ETM-2 (50:50) (40 nm) | — |
| I3.3 | PEDOT (60 nm) | HTL-2 (20 nm) | 60 nm | 170 | ETM-1 (10 nm) | ETM-1:ETM-2 (50:50) (40 nm) | — |
| C3.5 | PEDOT (20 nm) | HTL-2 (20 nm) | 60 nm | 160 | ETM-1 (10 nm) | ETM-1:ETM-2 (50:50) (40 nm) | — |
| I3.4 | PEDOT (20 nm) | HTL-2 (20 nm) | 60 nm | 160 | ETM-1 (10 nm) | ETM-1:ETM-2 (50:50) (40 nm) | — |
| C3.6 | PEDOT (20 nm) | HTL-2 (20 nm) | 60 nm | 150 | ETM-1 (10 nm) | ETM-1:ETM-2 (50:50) (40 nm) | — |
| I3.5 | PEDOT (20 nm) | HTL-2 (20 nm) | 60 nm | 150 | ETM-1 (10 nm) | ETM-1:ETM-2 (50:50) (40 nm) | — |

TABLE 7

Results for solution-processed OLEDs

| Ex. | EQE [%] @1000 cd/m² | LT97 | @x mA/cm² |
|---|---|---|---|
| C3.1 | 18.4 | 27 | 60 |
| I3.1 | 18.6 | 36 | 60 |
| C3.2 | 18.9 | 31 | 60 |
| I3.2 | 19.0 | 46 | 60 |
| C3.3 | 16.5 | 81 | 60 |
| C3.4 | 16.4 | 86 | 60 |
| I3.3 | 16.4 | 131 | 60 |
| C3.5 | 19.4 | 7 | 40 |
| I3.4 | 20.3 | 16 | 40 |
| C3.6 | 21.0 | 8 | 40 |
| I3.5 | 21.0 | 12 | 40 |

As apparent from the OLED component data shown above, the materials of the invention lead to good performance data in relation to lifetime and efficiency. They offer an improvement here compared to existing comparative materials. In addition, it is found that the larger process window in relation to baking temperatures not only has practical advantages in the industrial manufacture of components but also facilitates the attainment of high component lifetimes.

For example, compound M-0005 is directly comparable with compound B-3 and differs merely by the position of the Ar group on the fluorene. It can be seen that the substitution pattern of the invention has a positive effect on the component lifetime.

Compound M-0002 is likewise directly comparable with compounds B-2 and B-4, from which it differs by the presence of the Ar group on the fluorene. It is otherwise identical to B-2; it otherwise differs from compound B-4 merely by the linkage of the phenyl rings in the 9 position of the fluorene. In both cases, M-0002 leads to improved component lifetimes, and in Example I3.4 by comparison with C3.5 additionally to an improvement in efficiency.

By comparison with comparative compound B-1 known from the prior art as well, M-0002 leads to an improvement in component lifetime.

The invention claimed is:
1. A compound of the formula (3a)

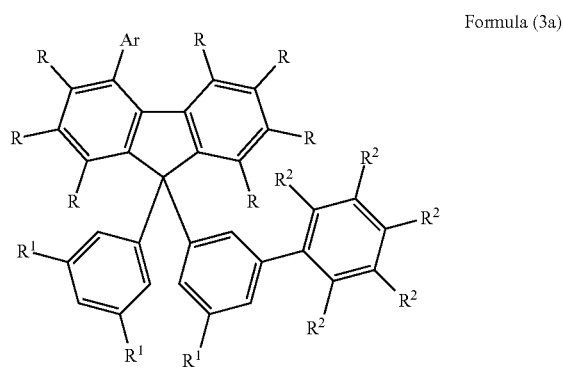

Formula (3a)

where the symbols used are as follows:
Ar is an aromatic ring system which has 6 to 30 aromatic ring atoms and may be substituted by one or more $R^3$ radicals, or a dibenzofuran or dibenzothiophene group, each of which may be substituted by one or more $R^3$ radicals, or a combination of an aromatic ring system having 6 to 18 aromatic ring atoms and a dibenzofuran or dibenzothiophene group, where these groups may each be substituted by one or more $R^3$ radicals; Ar here may form a ring system together with the adjacent substituent R, which is bound on the same ring as Ar;
R is the same or different at each instance and is H, D, a straight-chain alkyl or alkoxy group having 1 to 20 carbon atoms or a branched or cyclic alkyl or alkoxy group having 3 to 20 carbon atoms or an alkenyl group having 2 to 20 carbon atoms, where the alkyl, alkoxy or alkenyl group may in each case be substituted by one or more $R^3$ radicals, where one or more hydrogen atoms may be replaced by D, or an aromatic ring system which has 6 to 30 aromatic ring atoms and may be substituted by one or more $R^3$ radicals, or a dibenzofuran or dibenzothiophene group, each of which may be substituted by one or more $R^3$ radicals; it is also possible here for two or more adjacent substituents R together to form a mono- or polycyclic aliphatic ring system; in addition, it is possible for R, which is bound on the same ring as Ar, with an adjacent Ar group to form a ring system;

$R^1$ is the same or different at each instance and is an aromatic ring system which has 6 to 30 aromatic ring atoms and may be substituted by one or more $R^3$ radicals, or a dibenzofuran or dibenzothiophene group, each of which may be substituted by one or more $R^3$ radicals;

$R^2$ is the same or different at each instance and is H, D, a straight-chain alkyl or alkoxy group having 1 to 20 carbon atoms or a branched or cyclic alkyl or alkoxy group having 3 to 20 carbon atoms or an alkenyl group having 2 to 20 carbon atoms, where the alkyl, alkoxy or alkenyl group may in each case be substituted by one or more $R^3$ radicals, where one or more hydrogen atoms may be replaced by D, or an aromatic ring system which has 6 to 30 aromatic ring atoms and may be substituted by one or more $R^3$ radicals, or a dibenzofuran or dibenzothiophene group, each of which may be substituted by one or more $R^3$ radicals; in addition, it is possible for multiple adjacent substituents $R^2$ together to form a ring system;

$R^3$ is the same or different at each instance and is H, D, a straight-chain alkyl or alkoxy group having 1 to 20 carbon atoms or a branched or cyclic alkyl or alkoxy group having 3 to 20 carbon atoms, where the alkyl or alkoxy group may in each case be substituted by one or more $R^4$ radicals, where one or more hydrogen atoms may be replaced by D, or an aromatic ring system which has 6 to 30 aromatic ring atoms and may be substituted by one or more $R^4$ radicals, or a dibenzofuran or dibenzothiophene group, each of which may be substituted by one or more $R^4$ radicals; it is also possible here for two or more adjacent substituents $R^3$ together to form a ring system;

$R^4$ is the same or different at each instance and is H, D or an aliphatic and/or aromatic hydrocarbyl radical having 1 to 20 carbon atoms.

2. The compound according to claim 1, wherein the compound is selected from the compounds of the formulae (2a*), (2b*) and (2c*)

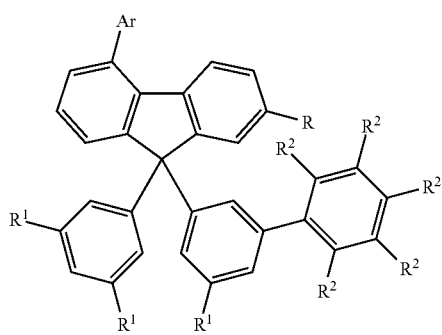

Formula (2a*)

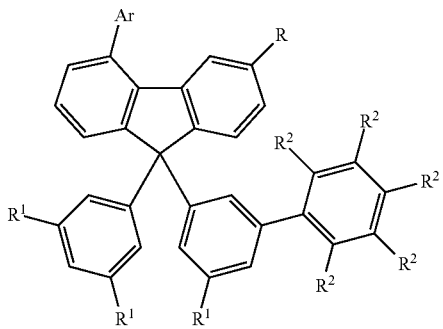

Formula (2b*)

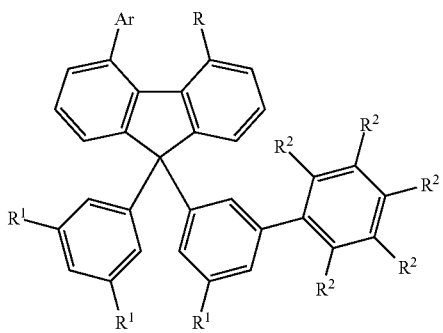

Formula (2c*)

where the symbols used have the definitions given in claim 1.

3. The compound according to claim 1, wherein the compound is selected from the compounds of the formulae (4a), (4c) and (4e)

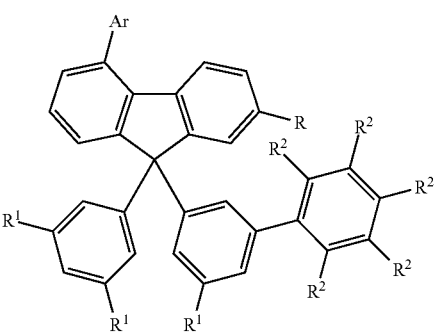

Formula (4a)

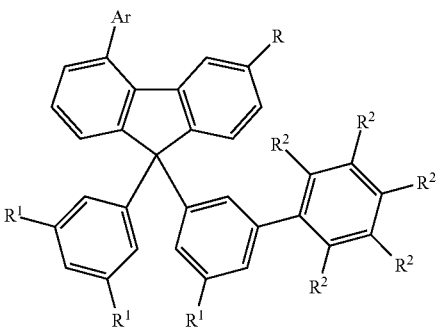

Formula (4c)

-continued

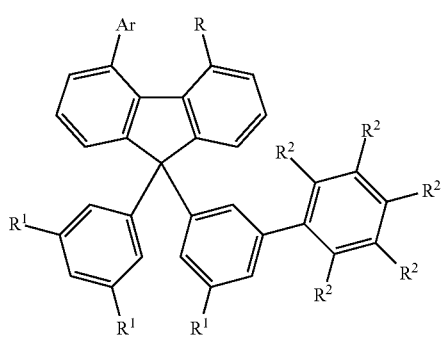

Formula (4e)

where the symbols used have the definitions given in claim 1.

4. The compound according to claim 1, wherein the compound is selected from the compounds of the formulae (6a) (6c) and (6e)

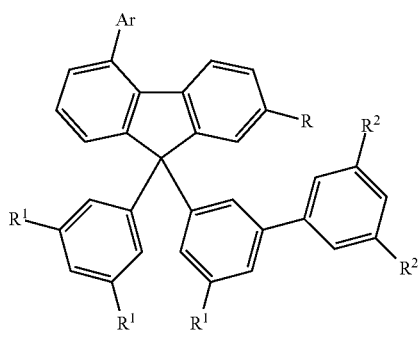

Formula (6a)

Formula (6c)

Formula (6e)

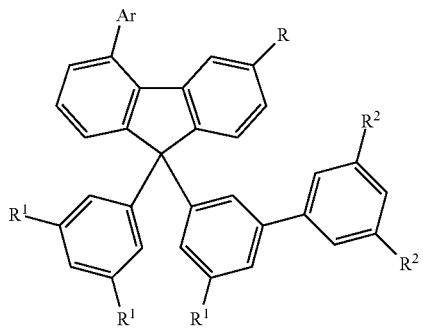

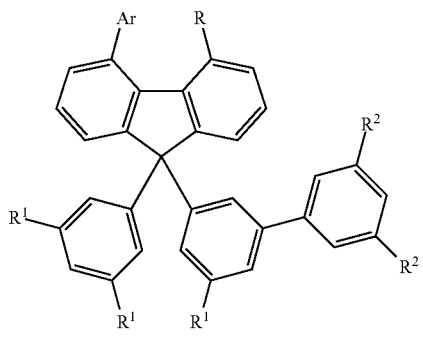

where the symbols used have the definitions given in claim 1.

5. The compound according to claim 1, wherein Ar is selected from the group consisting of phenyl, biphenyl, terphenyl, quaterphenyl, fluorene, spirobifluorene, naphthalene, dibenzofuran, dibenzothiophene, phenanthrene, triphenylene or a combination of these groups, each of which may be substituted by one or more $R^3$ radicals.

6. The compound according to claim 1, wherein the compound is selected from the compounds of the formulae (2d*) and (6g)

Formula (2d*)

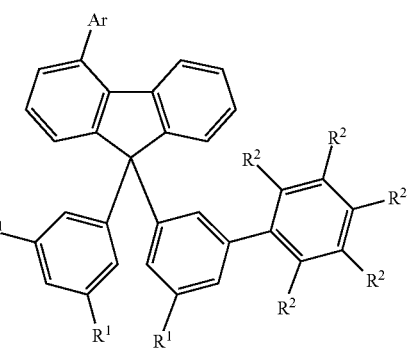

Formula (6g)

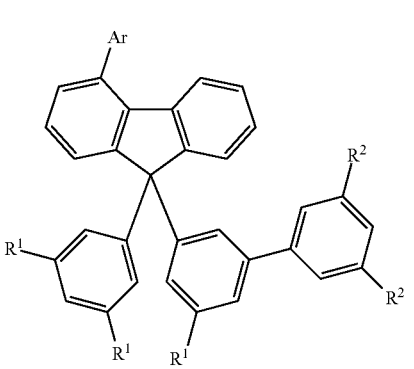

where the symbols used have the definitions given in claim 1.

7. The compound according to claim 1, wherein the compound is selected from the compounds of the formulae (8a), and (9a)

Formula (8a)

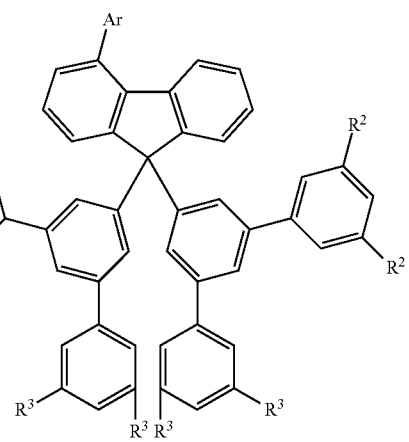

Formula (9a)

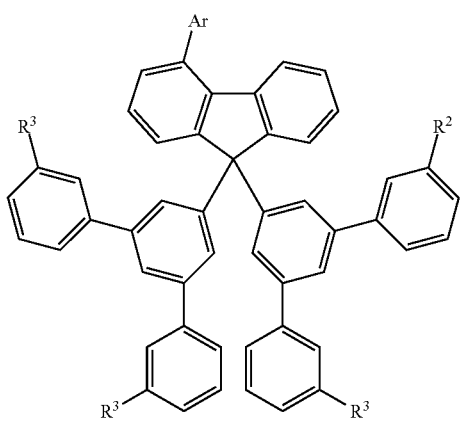

where the symbols used have the definitions given in claim 1.

8. A composition comprising at least one compound according to claim 1 and at least one further functional material, wherein the further functional material is selected from a phosphorescent emitter, an emitter that exhibits TADF, and/or a matrix material selected from the group consisting of electron transport materials, hole transport materials and bipolar materials.

9. A formulation comprising at least one compound according to claim 1 and at least one organic solvent.

10. An electronic device comprising at least one compound according to claim 1.

11. The electronic device according to claim 10 which is an organic electroluminescent device, comprising an emitting layer, wherein the emitting layer comprises said at least one compound.

12. The electronic device according to claim 11, wherein in the emitting layer contains at least one triazine, quinazoline or pyrimidine derivative of one of the formulae (10), (11) and (12)

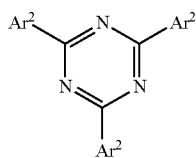
Formula (10)

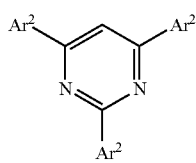
Formula (11)

Formula (12)

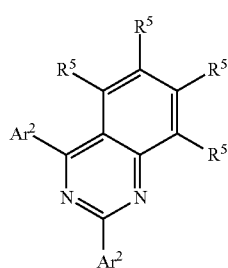

where $R^3$ is the same or different at each instance and is H, D, a straight-chain alkyl or alkoxy group having 1 to 20 carbon atoms or a branched or cyclic alkyl or alkoxy group having 3 to 20 carbon atoms, where the alkyl or alkoxy group may in each case be substituted by one or more $R^4$ radicals, where one or more hydrogen atoms may be replaced by D, or an aromatic ring system which has 6 to 30 aromatic ring atoms and may be substituted by one or more $R^4$ radicals, or a dibenzofuran or dibenzothiophene group, each of which may be substituted by one or more $R^4$ radicals; it is also possible here for two or more adjacent substituents $R^3$ together to form a ring system;

$R^4$ is the same or different at each instance and is H, D or an aliphatic and/or aromatic hydrocarbyl radical having 1 to 20 carbon atoms $Ar^2$ is the same or different at each instance and is an aromatic or heteroaromatic ring system which has 5 to 40 aromatic ring atoms and may be substituted by one or more $R^5$ radicals;

$R^5$ is the same or different at each instance and is H, D, F, Cl, Br, I, CN, $NO_2$, $N(R^3)_2$, $OR^3$, $SR^3$, $COOR^3$, $C(=O)N(R^3)_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl or alkoxy group having 1 to 20 carbon atoms or an alkenyl or alkynyl group having 2 to 20 carbon atoms or a branched or cyclic alkyl or alkoxy group having 3 to 20 carbon atoms, where the alkyl, alkoxy, alkenyl or alkynyl group may in each case be substituted by one or more $R^3$ radicals, where one or more nonadjacent $CH_2$ groups may be replaced by $Si(R^3)_2$, C=O, $NR^3$, O, S or $CONR^3$, or an aromatic or heteroaromatic ring system which has 5 to 30 aromatic ring atoms and may be substituted in each case by one or more $R^3$ radicals; at the same time, two $R^5$ radicals together may also form an aliphatic, heteroaliphatic, aromatic or heteroaromatic ring system.

13. A formulation comprising the composition according to claim 8 and at least one organic solvent.

14. An electronic device comprising the composition according to claim 8.

15. An electronic device which is an organic electroluminescent device comprising an emitting layer which comprises at least one compound according to claim 1.

16. The electronic device according to claim 15, wherein the emitting layer contains at least one triazine, quinazoline or pyrimidine derivative of one of the formulae (10), (11) and (12)

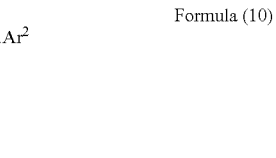
Formula (10)

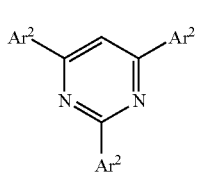
Formula (11)

-continued

Formula (12)

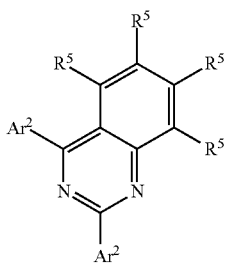

where

R³ is the same or different at each instance and is H, D, a straight-chain alkyl or alkoxy group having 1 to 20 carbon atoms or a branched or cyclic alkyl or alkoxy group having 3 to 20 carbon atoms, where the alkyl or alkoxy group may in each case be substituted by one or more R⁴ radicals, where one or more hydrogen atoms may be replaced by D, or an aromatic ring system which has 6 to 30 aromatic ring atoms and may be substituted by one or more R⁴ radicals, or a dibenzofuran or dibenzothiophene group, each of which may be substituted by one or more R⁴ radicals; it is also possible here for two or more adjacent substituents R³ together to form a ring system;

R⁴ is the same or different at each instance and is H, D or an aliphatic and/or aromatic hydrocarbyl radical having 1 to 20 carbon atoms;

Ar² is the same or different at each instance and is an aromatic or heteroaromatic ring system which has 5 to 40 aromatic ring atoms and may be substituted by one or more R⁵ radicals;

R⁵ is the same or different at each instance and is H, D, F, Cl, Br, I, CN, NO₂, N(R³)₂, OR³, SR³, COOR³, C(=O)N(R³)₂, Si(R³)₃, B(OR³)₂, C(=O)R³, P(=O)(R³)₂, S(=O)R³, S(=O)₂R³, OSO₂R³, a straight-chain alkyl or alkoxy group having 1 to 20 carbon atoms or an alkenyl or alkynyl group having 2 to 20 carbon atoms or a branched or cyclic alkyl or alkoxy group having 3 to 20 carbon atoms, where the alkyl, alkoxy, alkenyl or alkynyl group may in each case be substituted by one or more R³ radicals, where one or more nonadjacent CH₂ groups may be replaced by Si(R³)₂, C=O, NR³, O, S or CONR³, or an aromatic or heteroaromatic ring system which has 5 to 30 aromatic ring atoms and may be substituted in each case by one or more R³ radicals; at the same time, two R⁵ radicals together may also form an aliphatic, heteroaliphatic, aromatic or heteroaromatic ring system.

17. A composition comprising at least one compound according to claim 1 and at least one further functional material, wherein the further functional material is selected from a phosphorescent emitter, an emitter that exhibits TADF, and/or a matrix material selected from the group consisting of electron transport materials, hole transport materials and bipolar materials.

* * * * *